(12) United States Patent
Targan et al.

(10) Patent No.: US 12,110,555 B2
(45) Date of Patent: Oct. 8, 2024

(54) DIAGNOSIS AND TREATMENT OF INFLAMMATORY BOWEL DISEASE

(71) Applicant: CEDARS-SINAI MEDICAL CENTER, Los Angeles, CA (US)

(72) Inventors: Stephan R. Targan, Santa Monica, CA (US); Marla C. Dubinsky, Los Angeles, CA (US); Carol J. Landers, Los Angeles, CA (US); Ling Mei, Pasadena, CA (US); Jerome I. Rotter, Los Angeles, CA (US); Kent D. Taylor, Ventura, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 17/588,089

(22) Filed: Jan. 28, 2022

(65) Prior Publication Data

US 2022/0290235 A1 Sep. 15, 2022

Related U.S. Application Data

(60) Continuation of application No. 16/683,141, filed on Nov. 13, 2019, now Pat. No. 11,268,149, which is a continuation of application No. 14/726,343, filed on May 29, 2015, now Pat. No. 10,544,459, which is a continuation-in-part of application No. 11/720,785, filed as application No. PCT/US2005/044335 on Dec. 8, 2005, now abandoned, said application No. 14/726,343 is a continuation-in-part of application No. 12/527,376, filed as application No. PCT/US2008/054033 on Feb. 14, 2008, now abandoned, said application No. 14/726,343 is a continuation-in-part of application No. 12/529,106, filed as application No. PCT/US2008/056103 on Mar. 6, 2008, now abandoned, said application No. 14/726,343 is a continuation-in-part of application No. 13/124,311, filed as application No. PCT/US2009/061698 on Oct. 22, 2009, now abandoned, said application No. 14/726,343 is a continuation-in-part of application No. 13/410,881, filed on Mar. 2, 2012, now abandoned, which is a division of application No. 12/599,549, filed as application No. PCT/US2008/063202 on May 9, 2008, now Pat. No. 8,153,443, said application No. 14/726,343 is a continuation-in-part of application No. 12/196,505, filed on Aug. 22, 2008, now abandoned, which is a continuation of application No. 12/032,442, filed on Feb. 15, 2008, now abandoned.

(60) Provisional application No. 61/107,590, filed on Oct. 22, 2008, provisional application No. 60/917,254, filed on May 10, 2007, provisional application No. 60/893,308, filed on Mar. 6, 2007, provisional application No. 60/890,429, filed on Feb. 16, 2007, provisional application No. 60/889,806, filed on Feb. 14, 2007, provisional application No. 60/634,339, filed on Dec. 8, 2004.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/156* (2013.01); *G01N 2800/065* (2013.01); *G01N 2800/50* (2013.01)

(58) Field of Classification Search
None
See application file for complete search history.

(56) References Cited

U.S. PATENT DOCUMENTS 5,840,300 A 11/1998 Williams et al.
5,937,862 A 8/1999 Targan et al.
(Continued)

FOREIGN PATENT DOCUMENTS

AU 2005314089 B2 3/2011
AU 2011202664 B2 4/2012
(Continued)

OTHER PUBLICATIONS

Bene et al.: Prevalence of SLC22A4, SLC22A6 and CARD15 Gene Mutations in Hungarian Pediatric Patients with Crohn's Disease. World J. Gastroenterol; 12(34:5550-5553 (2006).
(Continued)

*Primary Examiner* — Kenneth R Horlick
(74) *Attorney, Agent, or Firm* — Wilson Sonsini Goodrich & Rosati

(57) ABSTRACT

This invention provides methods of diagnosis, predicting and diagnosing susceptibility to, predicting disease progression and treatment of inflammatory bowel disease (IBD), including Crohn's disease and/or subtypes of Crohn's disease (CD) and/or Ulcerative Colitis (UC). In one embodiment, a method of the invention is practiced by determining the presence or absence of the genetic variants NOD2, TLR8, TLR2, CARD8, CARD15 and/or JAK3 to diagnose, predict and diagnose susceptibility and predict disease progression in an individual. In another embodiment, a method of the invention is practiced by determining the presence or absence of anti-Cbir1, anti-OmpC, ASCA, anti-I2 and/or pANCA in an individual. In another embodiment, the invention further associates the presence or absence of the risk variants with the expression of anti-Cbir1, anti-OmpC, ASCA, anti-I2 and/or pANCA for the diagnosis, prediction of susceptibility, prediction of disease progression and/or treatment of IBD, including CD and/or UC.

2 Claims, 37 Drawing Sheets
Specification includes a Sequence Listing.

(56) References Cited

U.S. PATENT DOCUMENTS

| | | | |
|---|---|---|---|
| 6,218,129 | B1 | 4/2001 | Walsh et al. |
| 6,320,037 | B2 | 11/2001 | Braun et al. |
| 6,348,316 | B1 | 2/2002 | Taylor et al. |
| 6,348,452 | B1 | 2/2002 | Brown et al. |
| 6,607,879 | B1 | 8/2003 | Cocks et al. |
| 6,759,530 | B2 | 7/2004 | Braun et al. |
| 6,812,339 | B1 | 11/2004 | Venter et al. |
| 6,858,391 | B2 | 2/2005 | Nunez et al. |
| 6,869,762 | B1 | 3/2005 | Daly et al. |
| 7,138,237 | B1 | 11/2006 | Targan et al. |
| 7,361,733 | B2 | 4/2008 | Hershberg et al. |
| 7,557,194 | B2 | 7/2009 | Braun et al. |
| 7,759,079 | B2 | 7/2010 | Oh et al. |
| 7,803,535 | B2 | 9/2010 | Klein |
| 7,993,865 | B2 | 8/2011 | Targan et al. |
| 7,993,866 | B2 | 8/2011 | Targan et al. |
| 7,993,867 | B2 | 8/2011 | Targan et al. |
| 8,137,915 | B2 | 3/2012 | Hugot et al. |
| 8,153,443 | B2 | 4/2012 | Taylor et al. |
| 8,318,901 | B2 | 11/2012 | Hershberg et al. |
| 9,175,046 | B2 | 11/2015 | Hershberg et al. |
| 9,290,543 | B2 | 3/2016 | Hershberg et al. |
| 9,732,385 | B2 | 8/2017 | Barken et al. |
| 9,868,779 | B2 | 1/2018 | Hershberg et al. |
| 10,011,650 | B2 | 7/2018 | Hershberg et al. |
| 10,322,174 | B2 | 6/2019 | Bilsborough et al. |
| 10,457,722 | B2 | 10/2019 | Hershberg et al. |
| 10,544,459 | B2 | 1/2020 | Targan et al. |
| 10,981,978 | B2 | 4/2021 | Hershberg et al. |
| 11,268,149 | B2 | 3/2022 | Targan et al. |
| 2002/0150939 | A1 | 10/2002 | Taylor et al. |
| 2002/0197616 | A1 | 12/2002 | Nunez et al. |
| 2003/0092019 | A1 | 5/2003 | Meyer et al. |
| 2004/0043931 | A1 | 3/2004 | Hersberg et al. |
| 2004/0053263 | A1 | 3/2004 | Abreu et al. |
| 2004/0076960 | A1 | 4/2004 | Taylor et al. |
| 2004/0203076 | A1 | 10/2004 | Targan et al. |
| 2005/0054021 | A1 | 3/2005 | Targan et al. |
| 2005/0163764 | A1 | 7/2005 | Medzhitov et al. |
| 2006/0003392 | A1 | 1/2006 | Oh et al. |
| 2006/0141478 | A1 | 6/2006 | Brant et al. |
| 2006/0154276 | A1 | 7/2006 | Lois et al. |
| 2006/0194265 | A1 | 8/2006 | Morris et al. |
| 2006/0211020 | A1 | 9/2006 | Farrer et al. |
| 2006/0280741 | A1 | 12/2006 | Mohler et al. |
| 2007/0037165 | A1 | 2/2007 | Venter et al. |
| 2007/0072180 | A1 | 3/2007 | Abreu |
| 2007/0275424 | A1 | 11/2007 | Gewirtz et al. |
| 2009/0253133 | A1 | 10/2009 | Mitsuhashi et al. |
| 2009/0258848 | A1 | 10/2009 | Chakravarti et al. |
| 2009/0297563 | A1 | 12/2009 | Borglum et al. |
| 2010/0015156 | A1 | 1/2010 | Dubinsky et al. |
| 2010/0021455 | A1 | 1/2010 | Targan et al. |
| 2010/0021917 | A1 | 1/2010 | Rotter et al. |
| 2010/0055700 | A1 | 3/2010 | Targan et al. |
| 2010/0105044 | A1 | 4/2010 | Fleshner et al. |
| 2010/0144903 | A1 | 6/2010 | Taylor et al. |
| 2010/0184050 | A1 | 7/2010 | Rotter et al. |
| 2010/0190162 | A1 | 7/2010 | Rotter et al. |
| 2010/0240043 | A1 | 9/2010 | Rotter et al. |
| 2010/0284999 | A1 | 11/2010 | Taylor et al. |
| 2011/0124644 | A1 | 5/2011 | Targan et al. |
| 2011/0177969 | A1 | 7/2011 | Rotter et al. |
| 2011/0189685 | A1 | 8/2011 | Taylor et al. |
| 2011/0229471 | A1 | 9/2011 | Rotter et al. |
| 2012/0171672 | A1 | 7/2012 | Barken et al. |
| 2012/0208212 | A1 | 8/2012 | Targan et al. |
| 2012/0225427 | A1 | 9/2012 | Mallat et al. |
| 2013/0015282 | A1 | 1/2013 | Thole |
| 2013/0035260 | A1 | 2/2013 | Hugot et al. |
| 2013/0058953 | A1 | 3/2013 | Taylor et al. |

FOREIGN PATENT DOCUMENTS

| | | |
|---|---|---|
| AU | 2012203956 A1 | 7/2012 |
| CA | 2476755 A1 | 7/2003 |
| CA | 2589746 A1 | 6/2006 |
| EP | 1285271 B1 | 8/2005 |
| EP | 1819827 B1 | 8/2010 |
| EP | 2270512 B1 | 3/2016 |
| TW | 201105662 A | 2/2011 |
| WO | WO-03046141 A2 | 6/2003 |
| WO | WO-03053220 A2 | 7/2003 |
| WO | WO-2004048600 A2 | 6/2004 |
| WO | WO-2006063093 A2 | 6/2006 |
| WO | WO-2007025989 A2 | 3/2007 |
| WO | WO-2008101133 A2 | 8/2008 |
| WO | WO-2008109782 A2 | 9/2008 |
| WO | WO-2008116150 A2 | 9/2008 |
| WO | WO-2008141148 A2 | 11/2008 |
| WO | WO-2010048415 A1 | 4/2010 |

OTHER PUBLICATIONS

Dubinsky et al., Serum immune responses predict rapid disease progression among children with Crohn's disease: immune responses predict disease progression. Am J. Gastroenterology 101:360-367 (2006).

Dubinsky et al. Synergism of NOD2 and ASCA (Anti-*Saccharomyces* Cerevisiac Antibodies) Contributes to Disease Behavior in Pediatric Crohn's Disease (CD) Patients. Gastroenterology (2003): 124 (Suppl): M1556.

Duerr et al., A genome-wide association study identifies IL23R as an inflammatory bowel disease gene. Science 314:1461-1463 (2006).

Ferguson et al., IL23R and IL12B SNPs and haplotypes strongly associate with Crohn's disease risk in a New Zealand population. Gastroenterology Research and Practice, 2010:12 pages, 2010.

Ferrairis et al.: Analysis of CARD15 Gene Variants in Italian Pediatric Patients with Inflammatory Bowel Disease. Journal of Pediatrics; pp. 272-273 (2005).

GenBank Accession No. AF513860 (12 pgs.) Jul. 9, 2002).

Gewirtz et al., Dominant-negative TLR5 polymorphism reduces adaptive immune response to flagellin and negatively associates with Crohn's disease. Am J Physiol Gastrointest Liver Physiol. 290:G1157-G1163 (2006).

Heresbach et al., NOD2/CARD15 gene polymorphisms in Crohn's disease: a genotype-phenotype analysis. Eur J Gastroenterology and Hepatology 16:55-62 (2004).

Hirschhorn et al., A comprehensive review of genetic association studies. Genetics in Medicine, 4(2):45-61, 2002.

Hugot et al., GenBank Accession No. AX259776.1 retrieved from: http://www.ncbi.nlm.nih.gov/nuccore/16508849 on Apr. 6, 2010.

IL17RD GeneCard retrieved from: http://www.genecard.org.cgi-bin/carddisp.pl?gene=IL17RD&search=il17rd on May 14, 2013.

Ilumina Press Release dated Jan. 12, 2006, retrieved from: http://investor.illumina.com/phoenix.zhtml?=121278.

International Preliminary Report on Patentability for PCT/2008/054033 dated Aug. 19, 2009, 8 pages.

International Preliminary Report on Patentability for PCT/US2005/044335 dated Jun. 13, 2007, 7 pages.

International Preliminary Report on Patentability for PCT/US2008/056103 dated Nov. 24, 2009, 5 pages.

International Preliminary Report on Patentability for PCT/US2008/057820 dated Sep. 22, 2009, 4 pages.

International Preliminary Report on Patentability for PCT/US2008/063202 dated Nov. 10, 2009, 6 pages.

International Preliminary Report on Patentability for PCT/US2009/061698 dated Apr. 26, 2011, 6 pages.

International Search Report and Written Opinion for PCT/US2005/044335 dated Sep. 22, 2006, 10 pages.

International Search Report and Written Opinion for PCT/US2008/054033 dated Aug. 21, 2008, 13 pages.

International Search Report and Written Opinion for PCT/US2008/056103 dated Sep. 3, 2008, 8 pages.

(56) References Cited

OTHER PUBLICATIONS

International Search Report and Written Opinion for PCT/US2008/057820 dated Sep. 11, 2008, 5 pages.
International Search Report and Written Opinion for PCT/US2008/063202 dated Nov. 18, 2008, 9 pages.
International Search Report and Written Opinion for PCT/US2009/061698 dated Mar. 16, 2010, 8 pages.
Ioannidis et al., Replication validity of genetic association studies Nature Genetics 29:306-309 (2001).
Janus Kinase 3 GeneCard retrieved from http://www.genecards.org/cgi-bin/carddisp.pl?gene=JAP3 on Jan. 19, 2017.
Jaskowski et al.: Analysis of Serum Antibodies in Patients Suspected of Having Inflammatory Bowel Disease. Clinical and Vaccine Immunology; 13(6):655-660 (2006).
Kugathasan et al.: Comparative Phenotypic and CARD 15 Mutational Analysis Among African American, Hispanic and White Children with Crohn's Disease. Inflammatory Bowel Disease; 11(7):631-638 (2005).
Li et al., New serological biomarkers of inflammatory bowel disease. World J of Gastroenterology14:5115-5124 (2008).
Livak. Allelic discrimination using fluorogenic probes and the 5' nuclease assay. Genetic Analysis 14:143-149 (1999).
Lodes et al., Bacterial flagellin is a dominant antigen in Crohn disease. Journal of Clinical Investigation 113:1296-1306 (2004).
Lovato et al.: Constitutive STAT3 Activation in Intestinal T Cells from Patients with Crohn's Disease. The Journal of Biological Chemistry; 278(19):16777-16781 (2003).
Mow et al., Association of antibody responses to microbial antigens and complications of small bowel Crohn's disease. Gastroenterology 126:414-424 (2004).
Murata et al.: The Conversation of Redox Status of Peritoneal Macrophages During Pathological Progression of Spontaneous Inflammatory Bowel Disease in Janus Family Tyrosine Kinase 3 and IL-2 Receptor Mice. International Immunology; 4(6):627-636 (2002).
Murray et al., GenBank Accession No. G08322 (Feb. 5, 1997).
NCBI SNP ID No. rs2066844 retrieved from http://www.ncbi.nlm.nih.gove/projects/SNP/snp_ref.cgi?rs=2066844 on Apr. 6, 2010.
NCBI SNP ID No. rs2066845 retrieved from http://www.ncbi.nlm.nih.gov/projects/SNP/snp_ref.cgi?rs=2066845 on Apr. 6, 2010.
NCBI SNP ID No. rs2066847 retrieved from http://www.ncbi.nlm.nih.gov/projects/SNP/snp_ref.cgi?rs=2066847 on Apr. 6, 2010.
NCBI SNP ID No. rs2302600 retrieved from https://www.ncbi.nlm.nih.gov/projects/SNP/snp_ref.cgi?rs=2302600 on Jun. 6, 2017.
NCBI SNP ID No. ss4473198 retrieved from http://www.ncbi.nlm.nih.gov/projects/SNP/snp_ss.cgi?subsnp_id=4473198 on Dec. 3, 2014.
NOD2 Genecard retrieved from http://www.genecards.org/cgi-bin/carddisp.pl?gene=NOD2&search=not2 on Feb. 12, 2010.
Ogura et al., A frameshift mutation in NOD2 associates with susceptibility to Crohn's disease. Nature 411:603-606 (2001).
Ogura et al.: GenBank Accession No. AF385089.1 retrieved from http:www.ncbi.nlm.nih.gov/nuccore/14595635 on Apr. 6, 2010.

Papadakis et al., Anti-Flagellin (Cbir1) phenotypic and genetic Crohn's Disease associations. Inflamm Bowel Dis 13(5):524-530 (2007).
Prometheus Biosciences, Inc. Form S-1 Registration Statement as filed with the Securities and Exchange Commission on Feb. 19, 2021 (246 pages).
Redon et al. Global variation in copy number in the human genome. Nature. 444(7118): 444-54 (2006).
Rioux et al., Genome-wide association study identifies new susceptibility loci for Crohn disease and implicates autophagy in disease pathogenesis. Nature Genetics 39(5):596-604 (2007).
Rotter et al., TLR5 polymorphisms are associated with OmpC and CBir1 expression and with severity of Crohn's disease in Ashkenazi Jews. Abstract only (2004). Journal unknown.
Saruta et al., High frequency haplotypes in the X-chromosome locus TLR8 are associated with both CD and UC in females. Inflammatory Bowel Disease. 15(3):321-327 (2009).
Shanahan: Crohn's Disease. The Lancet; 359:62-69 (2002).
Sitaraman et al., Elevated flagellin-specific immunoglobulins in Crohn's disease. Am J Physiol Gastrointest Liver Physiol 288:G403-G406 (2005).
Targan et al., Antibodies to a novel flagellin (CBir1) define a unique serologic response in Crohn's disease (CD). Gastroenterology Abstract only 126(4), Suppl 2:A113 (2004).
Targan et al., Antibodies to CBir1 flagellin define a unique response that is associated independently with complicated Crohn's disease. Gastroenterology 128:2020-2028 (2005).
Taylor et al., Genes regulating the expression of antibody to C8ir1 flagellin in humans are located within a syntenic region to the major mouse colitogenic locus Cdcs1. AGA Institute Abstract #444 p. A-64 (2006).
Taylor et al., IL23R haplotypes provide a large population attributable risk for Crohn's disease. Inflammatory Bowel 14:1185-1191 (2008).
Thisteda. What is a P-value. Departments of Statistics and Health Studies. The University of Chicago. (May 25, 1988).
U.S. Appl. No. 16/683,141 Office Action dated Jul. 15, 2021.
U.S. Appl. No. 16/683,141 Office Action dated Mar. 23, 2021.
Vasiliauskas et al., Marker antibody expression stratifies Crohn's disease into immunologically homogeneous subgroups with distinct clinical characteristics. Gut 47:487-496 (2000).
Vermiere et al.: Current Status of Genetics Research in Inflammatory Bowel Disease. Genes and Immunity; 6:637-645 (2005).
Weiss et al.: NOD2/CARD16 Mutation Analysis and Genotype-Phenotype Correlation in Jewish Pediatric Patients Compared with Adults with Crohn's Disease. The Journal of Pediatrics; 145:208-212 (2004).
Yamazaki et al., Association analysis of genetic variants in IL23R, ATG16L 1 and 5p13.1 loci with Crohn's disease in Japanese patients. J Hum Genet 52:575-582 (2007).
Zaahl et al., Analysis of the three common mutations in the CARD15 gene (R702W, G908R and 1007fs) in South African colored patients with inflammatory bowel disease. Molecular and Cellular Probes 19:278-281 (2005).

"1" is the minor allele

"2" is the major allele

Figure 27:

| Demographic | |
|---|---|
| Males | 56% |
| Median duration of disease | 32 months |
| Median age at Diagnosis | 12 years |

| Antibody | % |
|---|---|
| pANCA | 19 |
| ASCA | 45 |
| OmpC | 18 |
| CBir1 | 52 |
| CARD15 | % |
| R702W | 17 |
| G908R | 10 |
| 1007fs | 14 |
| ANY SNP | 32 |

| Location | % |
|---|---|
| Small Bowel | 68 |
| Large Bowel | 85 |
| Upper GI | 36 |
| Perianal | 21 |
| Behavior | % |
| Non-penetrating Non stricturing | 70 |
| Stricturing | 15 |
| Internal Penetrating | 9 |
| Perianal Penetrating | 15 |
| Any Surgery | 16 |

Figure 28:

|  | Small Bowel OR P value | Large Bowel OR P value | Perianal OR P value |
|---|---|---|---|
| ASCA | 2.9 < 0.0001 | 0.67 0.04 | 1.5 < 0.02 |
| OmpC | NS | NS | NS |
| CBir1 | 1.6 0.002 | NS | NS |
| pANCA | 0.44 < 0.0001 | 4.0 < 0.0001 | NS |
| CARD15 | 1.9 < 0.0001 | NS | NS |

Figure 29:

| | NPNS OR P value | IP OR P value | S OR P value | Surgery OR P value |
|---|---|---|---|---|
| ASCA | 0.45 0.0001 | 2.3 0.002 | 2.4 0.0001 | 2.2 0.0001 |
| OmpC | 0.37 0.001 | 3.7 0.0001 | 2.7 0.0001 | 4 0.0001 |
| CBir1 | 0.56 0.001 | 2.3 0.003 | 2.0 0.002 | 2.0 0.001 |
| pANCA | 1.8 0.01 | NS | 0.45 0.02 | NS |
| CARD15 | NS | NS | NS | NS |

Figure 33:

|  | NPNS OR P value | IP OR P value | S OR P value | Surgery OR P value |
|---|---|---|---|---|
| OmpC | NS | NS | NS | 2.6 0.0002 |
| pANCA | 2.0 0.005 | NS | 0.37 0.007 | NS |
| Δ OR/Unit of Quartile Sum Δ | 0.8 < 0.0001 | 1.3 < 0.0001 | 1.3 < 0.0001 | 1.2 0.0015 |
| QS increase from 3 to 12 (OR)[a] | 0.13 | 10.6 | 10.6 | 5.2 |

Figure 37:

|  | IP/S Hazard Ratio | Surgery Hazard Ratio |
|---|---|---|
| Antibody Sum (Baseline risk = 0) | | |
| 1 | 1.1 NS | 3.4 <0.03 |
| 2 | 5.5 0.005 | 7.5 0.0002 |
| 3 | 6.0 <0.005 | 10.3 <0.0001 |
| Quartile Sum Group (Baseline risk = 1) | | |
| 2 | 3.4 NS | 7.2 <0.009 |
| 3 | 5.2 0.03 | 7.7 0.0006 |
| 4 | 10.0 0.002 | 13.1 0.0005 |

DIAGNOSIS AND TREATMENT OF INFLAMMATORY BOWEL DISEASE

CROSS-REFERENCE TO RELATED APPLICATIONS

This application is a continuation of U.S. Ser. No. 16/683,141 filed on Nov. 13, 2019, now issued as U.S. Pat. No. 11,268,149 on Mar. 8, 2022, which is a continuation of U.S. Ser. No. 14/726,343 filed on May 29, 2015, now issued as U.S. Pat. No. 10,544,459 on Jan. 28, 2020, which is a continuation-in-part of U.S. Ser. No. 11/720,785 filed on Sep. 17, 2007, now abandoned, which is a U.S. national stage application of PCT/US2005/044335 filed on Dec. 8, 2005, which claim s priority to U.S. Ser. No. 60/634,339 filed on Dec. 8, 2004; and U.S. Ser. No. 14/726,343 is a continuation-in-part of U.S. Ser. No. 12/527,376 filed on Sep. 1, 2009, now abandoned, which is a U.S. national stage application of PCT/US2008/054033 filed on Feb. 14, 2008, which claims priority to U.S. Ser. No. 60/889,806 filed on Feb. 14, 2007; and U.S. Ser. No. 14/726,343 is a continuation-in-part of U.S. Ser. No. 12/529,106 filed on Aug. 28, 2009, now abandoned, which is a U.S. national stage application of PCT/US2008/056103 filed on Mar. 6, 2008, which claims priority to U.S. Ser. No. 60/893,308 filed on Mar. 6, 2007; and U.S. Ser. No. 14/726,343 is a continuation-in-part of U.S. Ser. No. 13/124,311 filed on Apr. 14, 2011, now abandoned, which is a U.S. national stage application of PCT/US2009/061698 filed on Oct. 22, 2009, which claims priority to U.S. Ser. No. 61/107,590 filed on Oct. 22, 2008; and U.S. Ser. No. 14/726,343 is a continuation-in-part of U.S. Ser. No. 13/410,881 filed on Mar. 2, 2012, now abandoned, which is a U.S. divisional application of U.S. Ser. No. 12/599,549 filed on Dec. 18, 2009 and issued as U.S. Pat. No. 8,153,443 on Apr. 10, 2012, which is a national stage application of PCT/US2008/63202 filed on May 9, 2008, which claims priority to U.S. Ser. No. 60/917,254 filed on May 10, 2007; and U.S. Ser. No. 14/726,343 is a continuation-in-part of U.S. Ser. No. 12/196,505 filed on Aug. 22, 2008, now abandoned, which is a U.S. continuation application of U.S. Ser. No. 12/032,442 filed on Feb. 15, 2008, now abandoned, which claims priority to U.S. Ser. No. 60/890,429 filed on Feb. 16, 2007, the contents of each of which are herein incorporated by reference in their entirety.

GOVERNMENT RIGHTS

This invention was made with government support under Grant Nos. DK046763, DK071176 and DK066248 awarded by the National Institutes of Health. The U.S. Government may have certain rights in this invention.

SEQUENCE LISTING

The instant application contains a Sequence Listing which has been submitted electronically in ASCII format and is hereby incorporated by reference in its entirety. Said ASCII copy, created on Jan. 28, 2022, is named 56884-732_302_SL.txt and is 118,944 bytes in size.

FIELD OF THE INVENTION

This invention relates to methods useful in the medical arts. In particular, various embodiments of the present invention relate to methods for diagnosis and treatment of Inflammatory Bowel Disease (IBD).

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), collectively referred to as inflammatory bowel disease (IBD), are relatively common inflammatory diseases of the gastrointestinal (GI) tract, which are chronic, relapsing inflammatory disorders. Histopathologically and anatomically, these two conditions are distinct, with CD characterized by transmural inflammation that can occur throughout the GI tract, and UC characterized by more superficial inflammation confined to the colon and rectum. Interestingly, both diseases are dependent upon factors present within the complex intestinal microbiota. Indeed, a unifying hypothesis has emerged that proposes that IBD results from a dysregulated mucosal immune response to the intestinal microbiota in genetically susceptible individuals (Strober W, Fuss I J, Blumberg R S. The immunology of mucosal models of inflammation. Annu. Rev. Immunol. 2002; 20:495-549. Bouma G, Strober W. The immunological and genetic basis of inflammatory bowel disease. Nat. Rev. Immunol. 2003; 3:521-533.).

While the dependence of IBD on intestinal microbes is increasingly clear, the molecular mechanisms underlying this dependence are not. The intestinal mucosa is exposed to the largest concentration of foreign bacterial antigens of any tissue in the body, estimated to be up to 1012 organisms per gram of stool in the normal colon. An emerging concept is that there is an active "dialogue" between the microbiota, intestinal epithelial cells, and mucosal immune cells, with each partner communicating with the others (McCracken V J, Lorenz R G. The gastrointestinal ecosystem: a precarious alliance among epithelium, immunity and microbiota. Cell. Microbiol. 2001; 3:1-11.). In this context, "innate" immune responses, which recognize conserved microbial products such as lipopolysaccharide (LPS) and peptidoglycan (PG), are likely to be important in these microbial-host interactions and intestinal homeostasis. Critical to the host's "sensing" of microbes are members of the Toll-like receptor (TLR) family that, alone or in combination, recognize a wide array of microbe-associated molecular patterns on either pathogens or commensals (Kopp E, Medzhitov R. Recognition of microbial infection by Toll-like receptors. Curr. Opin. Immunol. 2003; 15:396-401. Akira S. Mammalian Toll-like receptors. Curr. Opin. Immunol. 2003; 15:5-11. Sieling P A, Modlin R L. Toll-like receptors: mammalian 'taste receptors' for a smorgasbord of microbial invaders. Current Opin. Microbiol. 2002; 5:70-75.). Various TLRs are expressed on intestinal epithelial cells (Cario E, Podolsky D K. Differential alteration in intestinal epithelial cell expression of toll-like receptor 3 (TLR3) and TLR4 in inflammatory bowel disease. Infect. Immunol. 2000; 68:7010-7017. Gewirtz A T, Navas T A, Lyons S, Godowski P J, Madara J L. Cutting Edge: Bacterial flagellin activates basolaterally expressed TLR5 to induce epithelial proinflammatory gene expression. J. Immunol. 2001; 167:1882-1885. Abreu M T, et al. TLR4 and MD-2 expression is regulated by immune-mediated signals in human intestinal epithelial cells. J. Biol. Chem. 2002; 277:20431-20437. Hershberg R M. The epithelial cell cytoskeleton and intracellular trafficking V.

Polarized compartmentalization of antigen processing and Toll-like receptor signaling in intestinal epithelial cells. Am. J. Physiol. Gastrointest. Liver Physiol. 2002; 283: G833-G839.) and more broadly on macrophages and dendritic cells in the lamina propria.

Given the involvement of innate immune mechanisms in the modulation of T cell responses, the bacterial dependence of IBD is likely to involve both bacterial products such as LPS, PG, and other TLR ligands, and specific bacterial antigens capable of stimulating CD4+ T cell responses. CD4+T lymphocytes have been identified as the crucial effector cells in experimental models of IBD (Berg D J, et al. Enterocolitis and colon cancer in interleukin-10-deficient mice are associated with aberrant cytokine production and CD4+TH1-like responses. J. Clin. Invest. 1996; 98:1010-1020. Powrie F, et al. Inhibition of Th1 responses prevents inflammatory bowel disease in scid mice reconstituted with CD45RBhi CD4+ T cells. Immunity. 1994; 1:553-562. Cong Y, et al. CD4+ T cells reactive to enteric bacterial antigens in spontaneously colitic C3H/HeJBir mice: increased T helper cell Type 1 response and ability to transfer disease. J. Exp. Med. 1998; 187:855-864.), and these pathogenic CD4+ T cell responses are directed against the enteric microbiota. Enteric bacterial antigen—reactive CD4+ T cells are able to induce colitis when adoptively transferred into immunodeficient recipients (Cong Y, et al. CD4+ T cells reactive to enteric bacterial antigens in spontaneously colitic C3H/HeJBir mice: increased T helper cell Type 1 response and ability to transfer disease. J. Exp. Med. 1998; 187:855-864.). The in vitro data suggest that there is a relatively small number of immunodominant antigens that stimulate the pathogenic T cell responses (Brandwein S L, et al. Spontaneously colitic C3H/HeJBir mice demonstrate selective antibody reactivity to antigens of the enteric bacterial flora. J. Immunol. 1997; 159:44-52), but the complexity of the intestinal microflora has posed a significant challenge to their identification.

In humans, specific associations between particular bacterial species and the development of disease or its characteristics have not been established. Immune responses to commensal enteric organisms have been investigated in CD. It was been shown that CD patients have antibodies to specific bacterial antigens and that patients can be clustered into 4 groups depending on their antibody response patterns (Landers C J, Cohavy O, Misra R, Yang H, Lin Y C, Braun J, Targan S R. Selected loss of tolerance evidenced by Crohn's disease-associated immune responses to auto- and microbial antigens. Gastroenterology 2002; 123:689-99.). These clusters are (1) antibody responses against oligomannan (anti-*Saccharomyces cerevisiae*; ASCA), (2) antibody responses to both *Escherichia coli* outer membrane protein C (anti-OmpC) and a CD-related protein from *Pseudomonas fluorescens* (anti-CD-related bacterial sequence {I2}), (3) antibody responses to nuclear antigens (perinuclear antineutrophil cytoplasmic antibody; pANCA), or (4) low or no serological response to any of the tested antigens. These distinct antibody response patterns may indicate unique pathophysiological mechanisms in the progression of this complicated disease. In addition, phenotypic associations with specific serological response patterns have been discovered (Landers C J, Cohavy O, Misra R, Yang H, Lin Y C, Braun J, Targan S R. Selected loss of tolerance evidenced by Crohn's disease-associated immune responses to auto- and microbial antigens. Gastroenterology 2002; 123:689-99. Vasiliauskas E A, Plevy S E, Landers C J, Binder S W, Ferguson D M, Yang H, Rotter J I, Vidrich A, Targan S R. Perinuclear antineutrophil cytoplasmic antibodies in patients with Crohn's disease define a clinical subgroup. Gastroenterology 1996; 110:1810-9. Vasiliauskas E A, Kam L Y, Karp L C, Gaiennie J, Yang H, Targan S R. Marker antibody expression stratifies Crohn's disease into immunologically homogeneous subgroups with distinct clinical characteristics. Gut 2000; 47:487-96. Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.).

Immunologic responses to bacterial products are key to the induction of inflammatory bowel disease in humans and in experimental models. The relationship of these immune responses to the underlying genetic and clinical phenotypes is just beginning to emerge. Thus, among patients with Crohn's disease, immune responses to different microbial antigens may be related to different pathophysiologic mechanisms, and may represent distinct genotypes and phenotypes.

Thus, there is need in the art to associate clinical phenotypes of Crohn's disease with various antigens, as such determination can enable more appropriate treatments for the disease. Furthermore, there exists a need for the diagnosis and treatment of Crohn's disease and subtypes of Crohn's disease.

The two common forms of IBD, CD and UC, are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). Moreover, genetic analyses have linked IBD to specific genetic variants, especially CARD15 variants on chromosome 16q12 and the IBD5 haplotype (spanning the organic cation transporters, SLC22A4 and SLC22A5, and other genes) on chromosome 5q31 (S. Vermeire, P. Rutgeerts, Genes Immun 6, 637 (2005); J. P. Hugot et al., Nature 411, 599 (2001); Y. Ogura et al., Nature 411, 603 (2001); J. D. Rioux et al., Nat Genet 29, 223 (2001); V. D. Peltekova et al., Nat Genet 36, 471 (2004)). CD and UC are thought to be related disorders that share some genetic susceptibility loci but differ at others.

The replicated associations between CD and variants in CARD15 and the IBD5 haplotype do not fully explain the genetic risk for CD. Thus, there is need in the art to determine other markers, genes, allelic variants and/or haplotypes that may assist in explaining the genetic risk, predicting disease progression, diagnosing, and/or predicting susceptibility for or protection against inflammatory bowel disease including but not limited to CD and/or UC.

SUMMARY OF THE INVENTION

The following embodiments and aspects thereof are described and illustrated in conjunction with compositions and methods which are meant to be exemplary and illustrative, not limiting in scope.

Various embodiments of the present invention provide for methods for diagnosing Crohn's disease in a mammal. Additional embodiments provide for determining a subtype of Crohn's disease, such as a phenotypic feature associated with Crohn's disease. Further embodiments provide for treating Crohn's disease. In one embodiment, the mammal is a human.

In particular embodiments, diagnosing Crohn's disease may be performed by determining the presence of anti-CBir1 expression, where the presence of anti-CBir1 expression indicates that the mammal has Crohn's disease. Determining a subtype of Crohn's disease, such as a phenotypic feature associated with Crohn's disease may also be performed by determining the presence of anti-CBir1 expression, where the presence of anti-CBir1 indicates that the mammal has small bowel disease, internal penetrating/perforating disease or fibrostenosing disease.

Determining the presence of anti-CBir1 expression may be accomplished by various techniques. For example, determining the presence of anti-CBir1 expression may be performed by determining the presence of an RNA sequence or a fragment of an RNA sequence that encodes an anti-CBir1 antibody; for example, using Northern blot analysis or reverse transcription-polymerase chain reaction (RT-PCR). Determining the presence of anti-CBir1 expression may also be performed by determining the presence of anti-CBir1 antibodies; for example IgG anti-CBir1. Anti-CBir1 antibodies are not limited to IgG, as IgA, IgM, IgD and IgE are also contemplated in connection with various embodiments of the present invention. These examples are not intended to be limiting, as one skilled in the art will recognize other appropriate means for determining the presence of anti-CBir1 expression.

Determining the presence of anti-CBir1 antibodies may be accomplished by a number of ways. For example, the determination may be made by an enzyme-linked immunosorbent assay (ELISA), sodium dodecyl sulfate polyacrylamide gel electrophoresis (SDS-PAGE), Western blot analysis, and mass spectrometric analysis.

In other embodiments of the invention, an immune complex can be detected with a labeled secondary antibody, for example, that has specificity for a class determining portion of an anti-CBir1 antibody. A signal from a detectable secondary antibody can be analyzed, and positive results indicate the presence of anti-CBir1 antibodies.

Additional embodiments of the present invention provide for methods of treating Crohn's disease by the use of antigen-directed therapy. The target antigen in this therapy may be flagellin, and particularly CBir1 or an immunoreactive fragment thereof.

In other embodiments, methods are provided to define a subset of CD patients that may have colitic disease, and/or colitic and small bowel disease. Defining this subset of CD patients may be performed by determining the presence of anti-CBir1 expression and determining the presence of perinuclear antineutrophil cytoplasmic antibodies (pANCA), where the presence of both is diagnostic of Crohn's disease with properties of colitic disease and/or colitic and small bowel disease. Determination of the presence of pANCA may also be accomplished using ELISA, SDS-PAGE, Western blot analysis, or mass spectrometric analysis. These examples are not intended to be limiting, as one skilled in the art will recognize other appropriate means for determining the presence of pANCA.

Further embodiments of the present invention provide for methods of treating the subset of CD patients with colitic disease and/or colitic and small bowel disease. Treating colitic disease and/or colitic and small bowel disease may be performed by manipulating the bacterial flora in the colon and/or colon and small bowel. Manipulation of the bacterial flora may be performed by administering antibiotics and/or probiotics.

Samples useful in various embodiments of the present invention can be obtained from any biological fluid having antibodies or RNA sequences or fragments of RNA sequences; for example, whole blood, plasma, serum, saliva, or other bodily fluid or tissue. The sample used in connection with various embodiments of the present invention may be removed from the mammal; for example, from drawn blood, aspirated fluids, or biopsies. Alternatively, the sample may be in situ; for example a tool or device may be used to obtain a sample and perform a diagnosis while the tool or device is still in the mammal.

A CBir1 antigen, or immunoreactive fragment thereof, useful in the invention can be produced by any appropriate method for protein or peptide synthesis.

Other embodiments of the present invention use anti-idiotypic antibodies specific to the anti-CBir1 antibody or other antibody of interest.

The present invention is also directed to kits for diagnosing and/or treating Crohn's disease and/or subtypes of Crohn's disease. The exact nature of the components configured in the inventive kits depends on their intended purpose. For instance, a quantity of CBir1 antigen may be included in the kit for determining the presence of anti-CBir1 antibodies. Instructions for use may be included in the kit.

Various embodiments provide methods of diagnosing susceptibility to Crohn's Disease in an individual, comprising determining the presence or absence of at least one risk variant at the NOD2 locus selected from the group consisting of R702W, G908R and 1007fs, and determining the presence or absence of at least one risk serological marker, where the presence of at least one risk variant and at least one risk serological marker is diagnostic of susceptibility to Crohn's Disease.

In other embodiments, the presence of three of the risk variants at the NOD2 locus present a greater susceptibility than the presence of two, one or none of the risk variants at the NOD2 locus, and the presence of two of the risk variants at the NOD2 locus presents a greater susceptibility than the presence of one or none of the risk variants at the NOD2 locus but less than the presence of three risk variants at the NOD2 locus, and the presence of one of the risk variants at the NOD2 locus presents a greater susceptibility than the presence of none of the risk variants at the NOD2 locus but less than the presence of three or two of the risk variants at the NOD2 locus.

In other embodiments, the risk serological markers are selected from the group consisting of ASCA, I2, OmpC and Cbir. In another embodiment, the presence of four of the risk serological markers presents a greater susceptibility than the presence of three or two or one or none of the risk serological markers, and the presence of three of the risk serological markers presents a greater susceptibility than the presence of two or one or none of the risk serological markers but less than the presence of four risk serological markers, and the presence of two of the risk serological markers presents a greater susceptibility than the presence of one or none of the risk serological markers but less than the presence of four or three risk serological markers, and the presence of one of the risk serological markers presents a greater susceptibility than the presence of none of the risk serological markers but less than the presence of four or three or two of the risk serological markers.

In another embodiment, the invention further comprises the step of determining the presence or absence of one or more risk haplotypes at the TLR8 locus, wherein the presence of one or more risk haplotypes at the TLR8 locus is diagnostic of susceptibility to Crohn's Disease.

In another embodiment, the invention comprises the step of determining the presence or absence of one or more risk haplotypes at the TLR2 locus, wherein the presence of one or more risk haplotypes at the TLR2 locus is diagnostic of susceptibility to Crohn's Disease.

Other various embodiments provide methods of diagnosing susceptibility to Crohn's Disease in an individual comprising determining the presence or absence of one or more risk haplotypes at the TLR8 locus in the individual, where the presence of one or more risk haplotypes is diagnostic of susceptibility to Crohn's Disease. In other embodiments, the individual is a female. In another embodiment, the method further comprises determining the presence of H3.

Other various embodiments provide methods of determining a low probability relative to a healthy individual of developing Crohn's Disease and/or ulcerative colitis in an individual, the method comprising determining the presence or absence of one or more protective haplotypes at the TLR8 locus in the individual, where the presence of one or more said protective haplotypes is diagnostic of a low probability relative to a healthy individual of developing Crohn's Disease and/or ulcerative colitis. In other embodiments, the individual is a female. In other embodiments, the method further comprises determining the presence of H2.

Further embodiments provide methods of diagnosing susceptibility to Crohn's Disease in an individual comprising determining the presence or absence of one or more risk variants at the TLR2 locus in the individual, where the presence of one or more risk variants is diagnostic of susceptibility to Crohn's Disease. In another embodiment, the individual is Jewish. In another embodiment, the invention further comprises determining the presence of P631H at the TLR2 locus.

Various embodiments provide methods of diagnosing susceptibility to a subtype of Crohn's Disease in a child, comprising determining the presence or absence of at least one risk variant at the CARD15 locus selected from the group consisting of SNP8, SNP12, and SNP13, and determining the presence or absence of at least one risk serological marker, selected from the group consisting of Cbir1, OmpC, and ASCA, where the presence of at least one variant and at least one risk serological marker is diagnostic of susceptibility to the subtype of Crohn's Disease in a child. In another embodiment, the subtype of Crohn's Disease in a child comprises an aggressive complicating phenotype, a small bowel disease phenotype, and/or an internal penetrating and/or fibrostenosing disease phenotype. In another embodiment, the presence of three of the risk serological markers presents a greater susceptibility than the presence of two, one or none of the risk serological markers, and the presence of two of the risk serological markers presents a greater susceptibility than the presence of one or none of the risk serological markers but less than the presence of three of the risk serological markers, and the presence of one of the risk serological markers presents a greater susceptibility than the presence of none of the risk serological markers but less than the presence of three or two of the risk serological markers. In another embodiment, the SNP8 comprises SEQ ID NO: 18. In another embodiment, the SNP12 comprises SEQ ID NO: 19. And in another embodiment, the SNP13 comprises SEQ ID NO: 20.

Other embodiments provide for methods of diagnosing susceptibility to a subtype of Crohn's Disease in a child, comprising determining the presence or absence of a high immune reactivity relative to a healthy individual for at least one risk serological marker, selected from the group consisting of Cbir1, OmpC, ASCA, I2, and pANCA, where the presence of a high immune reactivity relative to a healthy individual to at least one risk serological marker is diagnostic of susceptibility to the subtype of Crohn's Disease in a child. In another embodiment, the subtype of Crohn's Disease in a child comprises an aggressive complicating phenotype. In another embodiment, a high immune reactivity comprises a high magnitude of expression for the risk serological marker. In another embodiment, the presence of four of the risk serological markers presents a greater susceptibility than the presence of three, two, one or none of the risk serological markers, and the presence of three of the risk serological markers presents a greater susceptibility than the presence of two, one or none of the risk serological markers but less than the presence of four of the risk serological markers, and the presence of two of the risk serological markers presents a greater susceptibility than the presence of one or none of the risk serological markers but less than the presence of four or three of the risk serological markers, and the presence of one of the risk serological markers presents a greater susceptibility than the presence of none of the risk serological markers but less than the presence of four or three or two of the risk serological markers.

Various embodiments also provide methods of treating Crohn's Disease in a child, comprising determining the presence of a high immune reactivity to a risk serological marker relative to a healthy individual, and administering a therapeutically effective amount of Crohn's Disease treatment.

Other embodiments provide methods of diagnosing ulcerative colitis in an individual, comprising determining the presence or absence of a risk variant at the CARD8 locus, where the presence of the risk variant at the CARD8 locus is diagnostic of susceptibility to ulcerative colitis. In other embodiments, the risk variant at the CARD8 locus comprises SEQ ID NO: 36. In other embodiments, the individual is a child.

Various embodiments provide methods of determining the prognosis of Crohn's Disease in an individual, comprising determining the presence or absence of a high immune reactivity relative to a healthy individual for at least one risk serological marker, selected from the group consisting of Cbir1, OmpC, ASCA, and pANCA, where the presence of a high immune reactivity relative to a healthy individual to at least one risk serological marker is indicative of a prognosis of an aggressive form of Crohn's Disease. In other embodiments, the individual is a child. In other embodiments, the prognosis of an aggressive form of Crohn's Disease further comprises a rapid complicating internal penetrating and/or fibrostenosing disease phenotype.

Other embodiments provide methods of determining the prognosis of Crohn's Disease in a pediatric subject, comprising determining the presence or absence of a high immune reactivity of Cbir1, OmpC, ASCA, and pANCA in the pediatric subject relative to a child who has and maintains a non-aggressive form of Crohn's Disease, where the presence of the high immune reactivity relative to a child who has and maintains a non-aggressive Crohn's Disease is indicative of a prognosis of an aggressive form of Crohn's Disease in the pediatric subject. In other embodiments, the aggressive form of Crohn's Disease further comprises a rapid complicating internal penetrating and/or structuring disease phenotype.

Other embodiments provide methods of treating an aggressive form of Crohn's Disease in a pediatric subject, comprising determining the presence of a high immune reactivity of Cbir1, OmpC, ASCA and pANCA relative to a child who has and maintains a non-aggressive form of Crohn's Disease to prognose the aggressive form of Crohn's Disease, and treating the aggressive form of Crohn's Disease.

Other embodiments provide methods of determining the prognosis of Crohn's Disease in a subject, comprising determining the presence or absence of a high immune reactivity in the subject relative to an individual who has and maintains a non-aggressive form of Crohn's Disease for at least one risk serological marker, selected from the group consisting of Cbir1, OmpC, ASCA, and pANCA, where the presence of the high immune reactivity relative to an individual who has and maintains a non-aggressive form of Crohn's Disease is indicative of a prognosis of an aggressive form of Crohn's Disease. In other embodiments, the subject is a pediatric subject. In other embodiments, the individual who has and maintains a non-aggressive form of Crohn's Disease is a child. In other embodiments, the aggressive form of Crohn's Disease further comprises a rapid complicating internal penetrating and/or fibrostenosing disease phenotype.

Various embodiments also provide methods of treating an aggressive form of Crohn's Disease in a subject, comprising determining the presence of a high immune reactivity relative to an individual who has and maintains a non-aggressive form of Crohn's Disease to prognose the aggressive form of Crohn's Disease, and treating the aggressive form of Crohn's Disease. In other embodiments, the subject is a pediatric subject. In other embodiments, the individual who has and maintains a non-aggressive form of Crohn's Disease is a child. In other embodiments, the aggressive form of Crohn's Disease further comprises a rapid complicating internal penetrating and/or fibrostenosing disease phenotype.

Various embodiments include a method of diagnosing susceptibility to a subtype of Crohn's disease in an individual, comprising determining the presence or absence of one or more risk variants at the Janus kinases 3 (JAK3) genetic locus in the individual, and determining the presence or absence of a positive expression of ASCA and/or anti-I2, where the presence of one or more risk variants at the JAK3 locus and the presence of ASCA and/or anti-I2 expression is indicative of susceptibility in the individual to the subtype of Crohn's Disease. In another embodiment, one of the one or more risk variants at the JAK3 locus comprises SEQ ID NO: 37. In another embodiment, one of the one or more risk variants at the JAK3 locus comprises SEQ ID NO: 38. In another embodiment, positive expression of ASCA and/or anti-I2 comprises a high level of expression relative to a healthy subject.

Other embodiments include a method of diagnosing a subtype of Crohn's disease in an individual, comprising obtaining a sample from the individual, assaying the sample for the presence or absence of a risk variant at the Janus kinases 3 (JAK3) genetic locus in the individual, and diagnosing the subtype of Crohn's disease based upon the presence of the risk variant at the JAK3 genetic locus. In another embodiment, the risk variant comprises SEQ ID NO: 37 and/or SEQ ID NO: 38. In another embodiment, the presence of the risk variant is associated with a positive expression of ASCA and/or anti-I2. In another embodiment, the positive expression of ASCA and/or anti-I2 comprises a high level of expression relative to a healthy subject.

Various embodiment of the present invention provide for a method of diagnosing Inflammatory Bowel Disease (IBD) in a subject, comprising: providing a sample from the subject; assaying the sample to detect risk and/or protective variants in genes selected from the group consisting of: NOD2, CARD15, CARD 8, TLR8, TLR2 and JAK3; optionally, assaying the sample to detect risk serological factors selected from the group consisting of: anti-Cbir1 antibody, pANCA, anti-OmpC, ASCA and anti-I2; and determining that the subject has IBD if one or more risk variants and/or risk serological factors are present and the protective variants are absent or determining that the subject does not have IBD if one or more protective variants are present and the risk variants and/or risk serological factors are absent. In other embodiments, IBD comprises Crohn's disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38, or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In other embodiments, TLR8 comprises a protective variant and the protective variant located at the TLR8 locus is H2 and comprises SEQ ID NOs: 23-31. In other embodiments, the detection of the TLR8 risk variant in a female subject indicates an IBD diagnosis. In another embodiment, the detection of the TLR2 risk variant in a Jewish subject indicates an IBD diagnosis. In other embodiments, the detection of the NOD2 and/or CARD15 risk variants and/or risk serological factors in a pediatric subject indicates an IBD diagnosis associated with a subtype of CD. In other embodiments, a subtype of CD comprises aggressive complicating phenotype, small bowel disease phenotype, internal penetrating and/or fibrostenosing disease phenotype.

In various other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In various other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of risk variants, risk serological factors and protective variants is relative to that detected in a healthy subject.

In yet other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention provide for a process for predicting IBD susceptibility in a subject, comprising: providing a sample from the subject; assaying the sample to detect risk and/or protective variants in genes selected from the group consisting of: NOD2, CARD15, CARD 8, TLR8, TLR2 and JAK3; optionally, assaying the sample to detect risk serological factors selected from the group consisting of: anti-CBir1, pANCA, anti-OmpC, ASCA and anti-I2; and determining that the subject has increased susceptibility to IBD if one or more risk variants and/or risk serological factors are present and the protective variants are absent or determining that the subject has a decreased susceptibility to IBD if one or more protective variants are present and the risk variants and/or risk serological factors are absent. In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, IBD comprises Crohn's disease (CD) and ulcerative colitis (UC). In other embodiments, the risk variants are NOD2, CARD15, CARD 8, TLR2, TLR 8 and JAK3, wherein the TLR8 locus is H3 and comprises SEQ ID Nos: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38 or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii). In other embodiments, TLR8 comprises a protective variant and the protective variant located at the TLR8 locus is H2 and comprises SEQ ID NOs: 23-31. In other embodiments, the detection of the TLR8 risk variant in a female subject indicates an increased susceptibility to IBD. In other embodiments, the detection of the TLR2 risk variant in a Jewish subject indicates an increased susceptibility to IBD. In other embodiments, the detection of the NOD2 and/or CARD15 risk variants and/or risk serological factors in a pediatric subject indicates an increased susceptibility to IBD associated with a subtype of CD. In other embodiments, a subtype of Crohn's disease comprises aggressive complicating phenotype, small bowel disease phenotype, internal penetrating and/or fibrostenosing disease phenotype.

In yet other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In yet other embodiment, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In another embodiment, the detection of risk variants, risk serological factors and protective variants is relative to that detected in a healthy subject.

In other embodiments, there is a greater susceptibility to IBD when an increased number of risk variants and/or risk serological factors and a decreased number of protective variants are present and a decreased susceptibility when an increased number of protective variants and a decreased number of risk variants are present. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention also provide for a method for treating a subject with IBD, comprising: providing a sample from the subject; assaying the sample to detect risk and/or protective variants selected from the group consisting of: NOD2, CARD15, CARD8, TLR8, TLR2 and JAK3; assaying the sample to detect risk serological factors selected from the group consisting of: anti-CBir1, pANCA, anti-OmpC, ASCA and anti-I2; determining that the subject has IBD if one or more risk variants and/or risk serological factors are present and the protective variants are absent or determining that the subject does not have IBD if one or more protective variants are present and the risk variants and/or risk serological factors are absent; and prescribing a therapy to treat the subject diagnosed with IBD. In other embodiments, IBD comprises Crohn's Disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38 or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In yet other embodiments, TLR8 comprises a protective variant and the protective variant located at the TLR8 locus is H2 and comprises SEQ ID NOs: 23-31. In other embodiments, the therapy is an antigen-directed therapy that targets Cbir-1 flagellin or an immunoreactive fragment thereof. In other embodiments, the therapy consists of manipulation of bacteria in the colon and/or small intestine.

In yet other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In yet other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In other embodiments, the detection of risk variants, risk serological factors and protective variants is relative to that detected in a healthy subject. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention also provide for a process for selecting a therapy for a subject with IBD comprising: providing a sample from the subject; assaying the sample to detect risk and/or protective variants selected from the group consisting of: NOD2, CARD15, CARD8, TLR8, TLR2 and JAK3; optionally, assaying the sample to detect risk serological factors selected from the group consisting of: anti-CBir1, pANCA, anti-OmpC, ASCA and anti-I2; and determining that the subject has IBD if one or more risk variants and/or risk serological factors are present and the protective variants are absent or determining that the subject does not have IBD if one or more protective variants are present and the risk variants and/or risk serological factors are absent; and selecting a therapy for the subject with IBD. In other embodiments, IBD comprises Crohn's Disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38, or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In yet other embodiments, TLR8 comprises a protective variant and the protective variant located at the TLR8 locus is H2 and comprises SEQ ID NOs: 23-31. In other embodiments, the therapy selected for a subject with IBD is an antigen-directed therapy. In other embodiments, the antigen-directed therapy targets Cbir-1 flagellin or an immunoreactive fragment thereof. In other embodiments, the therapy consists of manipulation of bacteria in the colon and/or small intestine. In other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In yet other embodiments, the detection of risk variants, risk serological factors and protective variants is relative to that detected in a healthy subject. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various other embodiments of the present invention also provide for a method of diagnosing susceptibility to IBD in a female subject comprising: providing a sample from the female subject; assaying the sample to detect the risk and/or protective variants of TLR8, wherein TLR8 H3 is the risk variant and TLR8 H2 is the protective variant; and determining that the female subject has increased susceptibility to IBD if the TLR8 H3 risk variant is present and/or the TLR8 H2 protective variant is absent or determining that the subject has a decreased susceptibility to IBD if the TLR8 H2 protective variant is present and/or the TLR8 H3 risk variant is absent. In other embodiments, IBD comprises Crohn's Disease (CD) and ulcerative colitis (UC). In other embodiments, there is a greater susceptibility to IBD when an increased number of risk variants and a decreased number of protective variants are present and a decreased susceptibility when an increased number of protective variants and a decreased number of risk variants are present. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of risk variants and protective variants is relative to that detected in a healthy subject.

Various other embodiments of the present invention also provide for a method of diagnosing susceptibility to IBD in a Jewish subject comprising: providing a sample from the Jewish subject; assaying the sample to detect the TLR2 risk variant, wherein P631H is the risk variant at the TLR2 locus; and determining that the Jewish subject has increased susceptibility to IBD if the P631H risk variant is present or determining that the subject has a decreased susceptibility to IBD if the P631H risk variant is absent. In other embodiments, the P631H risk variant comprises SEQ ID NO: 33. In other embodiments, IBD comprises Crohn's Disease (CD) and ulcerative colitis (UC). In other embodiments, there is a greater susceptibility to IBD when an increased number of risk variants and a decreased number of protective variants are present and a decreased susceptibility when an increased number of protective variants and a decreased number of risk variants are present. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of the risk variants is relative to that detected in a healthy subject.

Various embodiments of the present invention also provide for a method of diagnosing susceptibility to IBD in a pediatric subject comprising: providing a sample from the pediatric subject; assaying the sample to detect the NOD2 and/or CARD15 risk variants; optionally, assaying the sample to detect risk serological factors selected from the group consisting of: anti-CBir1, pANCA, anti-OmpC, ASCA and anti-I2; and determining that the pediatric subject has increased susceptibility to IBD if one or more risk variants and/or risk serological factors are present or determining that the subject has a decreased susceptibility to IBD if the risk variants and/or risk serological factors are absent. In other embodiments, the risk variants at the NOD2 locus are R702W, G908R and 1007insC and comprise SEQ ID NO: 18, 19 and 20, respectively, and at the CARD15 locus are R675W, G881R and 3020insC and comprise SEQ ID NO: 18, 19 and 20, respectively. In other embodiments, IBD comprises Crohn's disease (CD) and ulcerative colitis (UC). In other embodiments, the detection of the NOD2 and/or CARD15 risk variants and/or risk serological factors in a pediatric subject indicates an IBD diagnosis associated with a subtype of CD. In other embodiments, a subtype of Crohn's disease comprises aggressive complicating phenotype, small bowel disease phenotype, internal penetrating and/or fibrostenosing disease phenotype. In other embodiments, there is a greater susceptibility to IBD when an increased number of risk variants and/or risk serological factors and a decreased number of protective variants are present and a decreased susceptibility when an increased number of protective variants and a decreased number of risk variants are present. In other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In other embodiments, the detection of risk variants, risk serological factors and protective variants is relative to that detected in a healthy subject.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts the Flagellin clone identity and similarity to known flagellin sequences, in accordance with an embodiment of the present invention. (A) Schematic of CBir flagellin clones from serological expression screening. The predicted amino acid sequences from the flagellin expression clones (CBir1-CBir15) are mapped in relation to the representation of the *B. fibrisolvens* sequence at the top. Ruler length equals 500 amino acids. Similarity in the $NH_2$ conserved sequence between these flagellin clones and *B. fibrisolvens* sequences ranged from 45 to 84% (mean, 60.3%). Breaks in the lines representing clones CBir1 and CBir2 indicate differences in sequence length in the hypervariable region. $NH_2$-conserved, conserved $NH_2$ sequence; $CO_2H$-conserved, conserved carboxy sequence. (B) Phylogenetic tree showing relatedness at the conserved $NH_2$ termini of CBir1-CBir15 clones to flagellin sequences in the GenBank database. The dendrogram was constructed using the Clustal program in DNAStar and reflects similarity at the amino acid level. The approximate location of the *Clostridium* subphylum cluster XIVa is indicated with a bracket.

FIG. 27 depicts results of patient demographics from 796 well characterized pediatric Crohn's Disease patients as part of a study that demonstrates an increased immune reactivity predicts aggressive complicating Crohn's Disease in children.

FIG. 28 depicts results demonstrating an association of immune reactivity and CARD15 with disease location through univariate analysis.

FIG. 29 depicts results demonstrating an association of immune reactivity and CARD15 with disease behavior through univariate analysis.

FIG. 33 depicts results demonstrating an association of immune reactivity with disease behavior using multivariate analysis.

FIG. 37 depicts a chart describing hazard ratios, with immune response prediction of complications and surgery.

DESCRIPTION OF THE INVENTION

Figure 2:
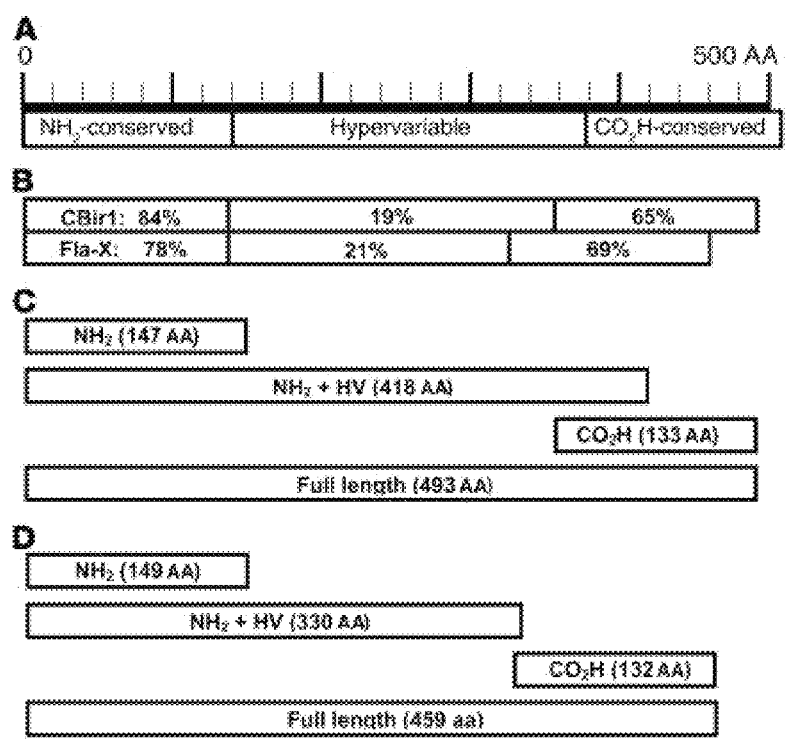
FIG. 2 depicts the schematic of recombinant flagellin constructs with percent similarity to related flagellin B from the anaerobe *B. fibrisolvens* (GenBank accession number AAB82613), in accordance with an embodiment of the present invention. (A) Structure of *B. fibrisolvens* flagellin B showing conserved $NH_2$ and carboxy ($CO_2H$-conserved) regions and the hypervariable central domain. (B) Diagram of the full-length amino acid sequence of mouse cecal bacteria flagellins CBir1 and Fla-X, indicating the similarity of the three domains with the respective *B. fibrisolvens* domains. (C and D) Schematics of recombinant flagellin proteins and fragments for CBir1 (C) and Fla-X (D) expressed in *E. coli* and purified by six-histidine tag affinity to nickel-nitrilotriacetic acid columns.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, NY 1994); March, *Advanced Organic Chemistry Reactions, Mechanisms and Structure* 4th ed., J. Wiley & Sons (New York, NY 1992); Sambrook and Russel, *Molecular Cloning: A Laboratory Manual* 3rd ed., Cold Spring Harbor Laboratory Press (Cold Spring Harbor, NY 2001); and D. Lane, *Antibodies: A Laboratory Manual* (Cold Spring Harbor Press, Cold Spring Harbor NY, 1988), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Fibrostenosis" as used herein refers to a classification of Crohn's disease characterized by one or more accepted characteristics of fibrostenosing disease. Such characteristics of fibrostenosing disease include, for example, documented persistent intestinal obstruction or intestinal resection for an intestinal obstruction. The fibrostenosis can be accompanied by other symptoms such as perforations, abscesses or fistulae, and can be further characterized by persistent symptoms of intestinal blockage such as nausea, vomiting, abdominal distention and inability to eat solid food.

"Immune complex" and "complex" as used herein refer to an aggregate of two or more molecules that result from specific binding between an antigen and an antibody.

"Secondary antibody" means an antibody or combination of antibodies, which binds to the antibody of interest (i.e., the primary antibody); for example an antibody that binds to a pANCA or binds an antibody that specifically binds a CBir1 flagellin antigen, or an immunoreactive fragment thereof.

"Labeled secondary antibody" means a secondary antibody, as defined above, that can be detected or measured by analytical methods. Thus, the term labeled secondary antibody includes an antibody labeled directly or indirectly with a detectable marker that can be detected or measured and used in an assay such as an enzyme-linked immunosorbent assay (ELISA), fluorescent assay, radioimmunoassay, radial immunodiffusion assay or Western blotting assay. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to the CBir1 antigen.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Treatment" and "treating," as used herein refer to both therapeutic treatment and prophylactic or preventative measures, wherein the object is to prevent, slow down and/or lessen the disease even if the treatment is ultimately unsuccessful.

"CD" and "UC" as used herein refer to Crohn's Disease and Ulcerative colitis, respectively.

"Haplotype" as used herein refers to a set of single nucleotide polymorphisms (SNPs) on a gene or chromatid that are statistically associated.

"Risk" as used herein refers to an increase in susceptibility to IBD, including but not limited to CD and UC.

"Protective" and "protection" as used herein refer to a decrease in susceptibility to IBD, including but not limited to CD and UC.

"Risk variant" as used herein refers to an allele whose presence is associated with an increase in susceptibility to IBD, including but not limited to CD and UC, relative to a healthy individual.

"Protective variant" as used herein refers to an allele whose presence is associated with a decrease/low probability in susceptibility to IBD, including but not limited to CD and UC, relative to an individual diagnosed with IBD.

"Risk haplotype" as used herein refers to a haplotype sequence whose presence is associated with an increase in susceptibility to IBD, including but not limited to CD and UC, relative to a healthy individual, who does not have the risk haplotype.

"Protective haplotype" as used herein refers to a haplotype sequence whose presence is associated with a decrease in susceptibility to IBD, including but not limited to CD and UC, relative to an individual diagnosed with IBD.

"Risk serological marker" as used herein refers to a serological marker whose expression is associated with an increase in susceptibility to and/or risk for rapid disease progression of inflammatory bowel disease, including but not limited to Crohn's Disease and ulcerative colitis, relative to a healthy individual.

As used herein, the term "sero-reactivity" means positive expression of an antibody.

As used herein, "antibody sum (AS)" means the number of positive antibodies per individual, such as 0, or 1 or 2, or 3 positive.

As used herein, "antibody quartile score" means the quartile score for each antibody level (<25%=1, 25-50%=2, 51%-<75%=3, 75%-100%=4).

As used herein, "quartile sum score (QSS)" means the sum of quartiles score for all of the antibodies.

As described herein, the inventors regrouped patients based on a range of quartile sum scores, defined as "Quartile Sum Score (QSS) Group." For example, quartile sum score 3-5=group 1, 6-7=group 2, 8-9=group 3 and 10-12=group 4.

As used herein, "ASCA" means anti-*Saccharomyces cerevisiae* antibodies.

As used herein, "pANCA" means perinuclear anti-neutrophil cytoplasmic antibodies.

As used herein, "OmpC" means outer membrane protein C.

As used herein, "I2" means *Pseudomonas fluorescens*-associated sequence.

As used herein, "OR" is an abbreviation for odds ratio.

As used herein, "CI" is an abbreviation for confidence interval.

As used herein, "OCTN" is an abbreviation for organic cation transporter.

As used herein, "IP" is an abbreviation for internal penetrating disease.

As used herein, "S" is an abbreviation of stricturing disease.

As used herein, "NPNS" is an abbreviation of non-penetrating, non-stricturing disease.

As used herein, "PP" is an abbreviation of perianal penetrating.

"Jak3" as used herein refers to Janus kinase 3.

As used herein, "CARD15" also means NOD2. As disclosed herein, an example of CARD15 is described as SEQ ID NO: 16.

As used herein, SNP 8, 12, and 13, are also described as R702W, G908R, and 1007fs, respectively, as well as R675W, G881R, and 3020insC, respectively. Examples of SNP 8, 12, and 13, are described herein as SEQ ID NO: 18, SEQ ID NO: 19, SEQ ID NO: 20, respectively.

An example of CARD8 is described herein as SEQ ID NO: 35.

An example of T10C variant at the CARD8 locus is described herein as SEQ ID NO: 36.

Figure 24:
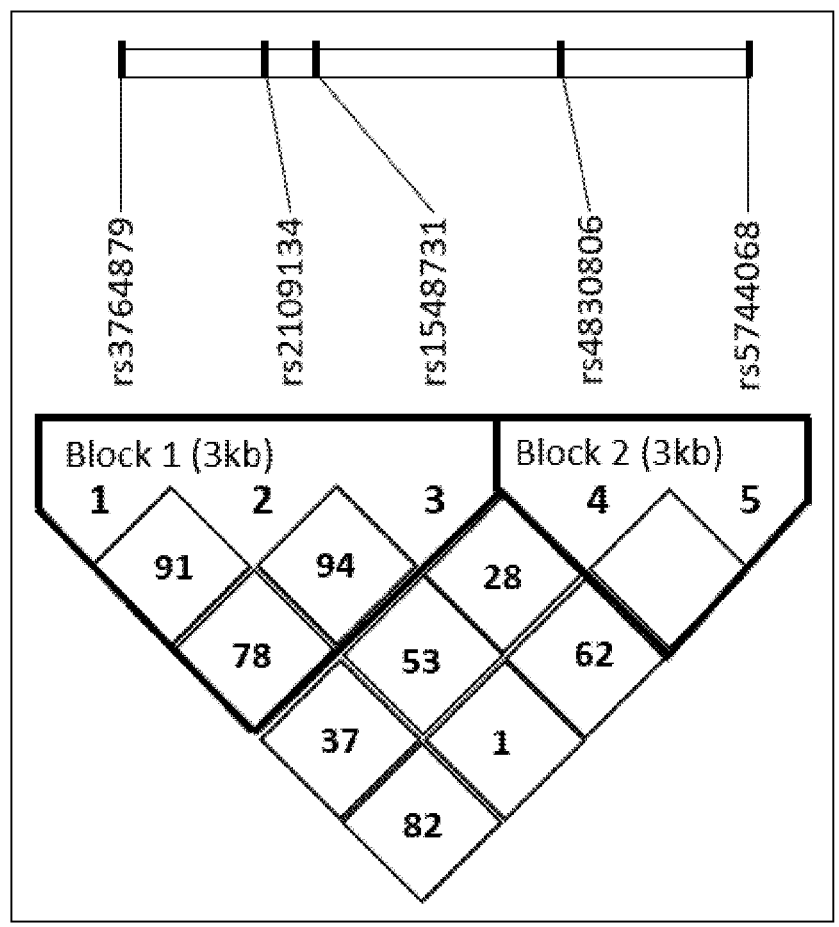
FIG. 24 depicts TLR8 haplotype associations with corresponding SNPs. As described herein, the data demonstrates that H3 ("211") is a risk haplotype associated with Crohn's Disease in females, and H2 ("222") is a protective haplotype against Crohn's Disease in females. "2" is the major allele, and "1" is the minor allele.
Figure 25:
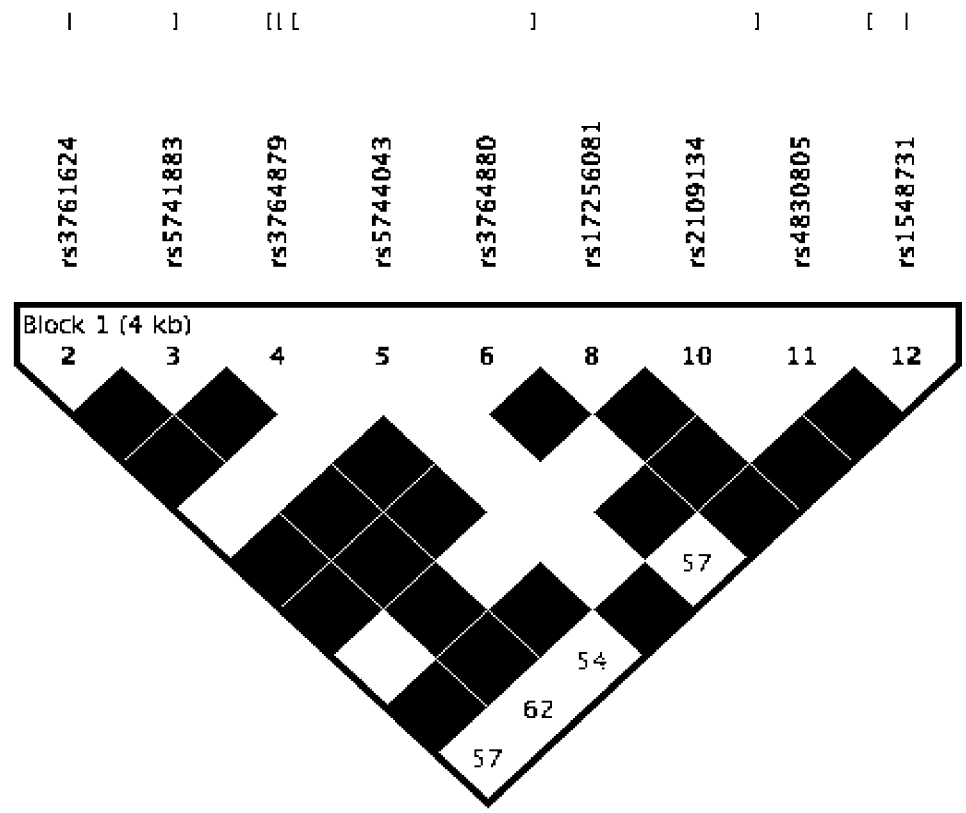
FIG. 25 depicts TLR8 haplotype associations with corresponding SNPs. It should be noted that Haplotype H3 spans two listings from HapMap data, and H1 has a minor component noted as 0.
Figure 26:
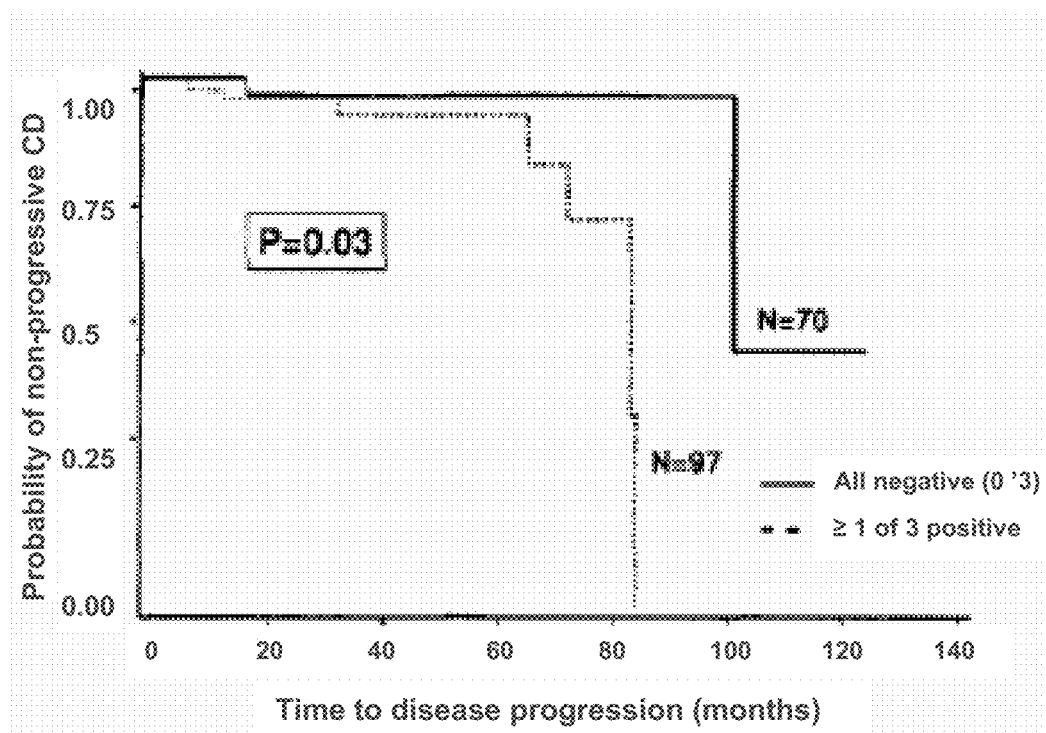
FIG. 26 depicts Kaplan-Meier survival analysis. Comparison of time to progression from noncomplicating to complicating disease behaviors between patients positive for ≥1 immune response to ASCA, I2, and OmpC (n=97) ( . . . ) and those negative for all three (n=70) (_____).
Figure 30:
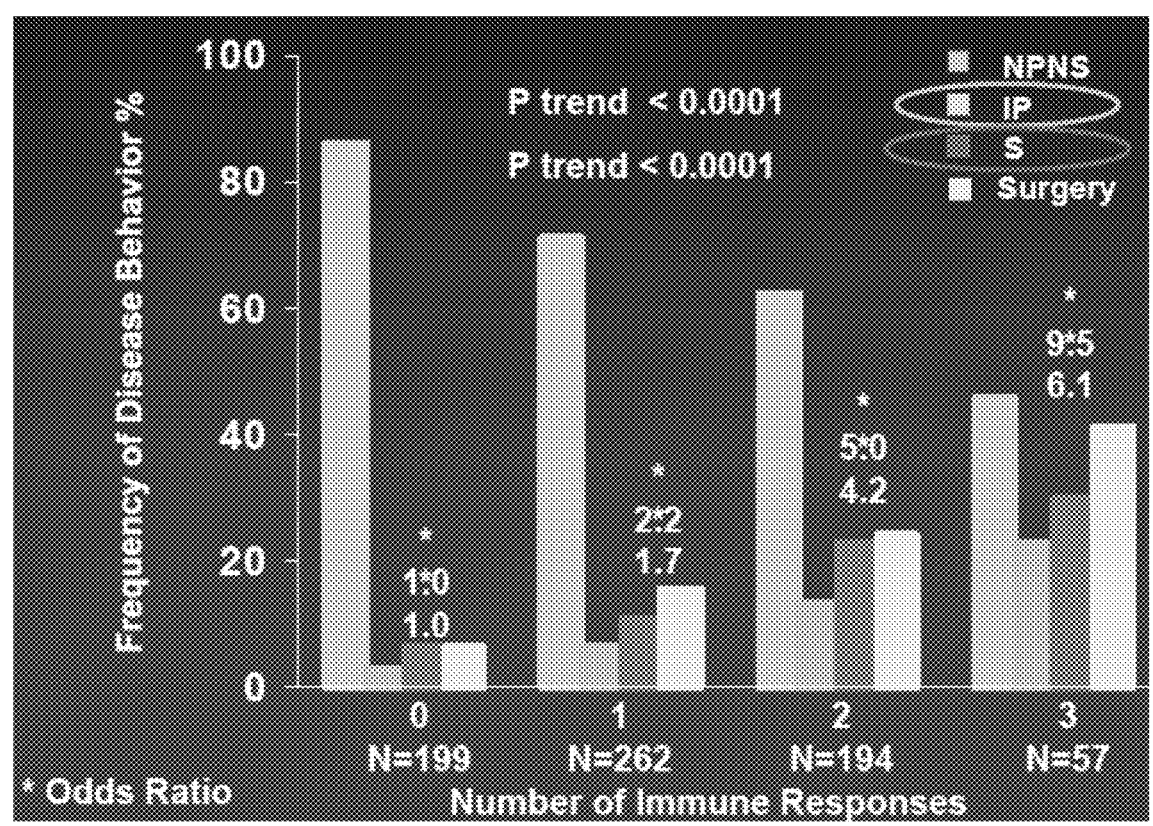
FIG. 30 depicts a chart of antibody sum and disease behavior.
Figure 31:
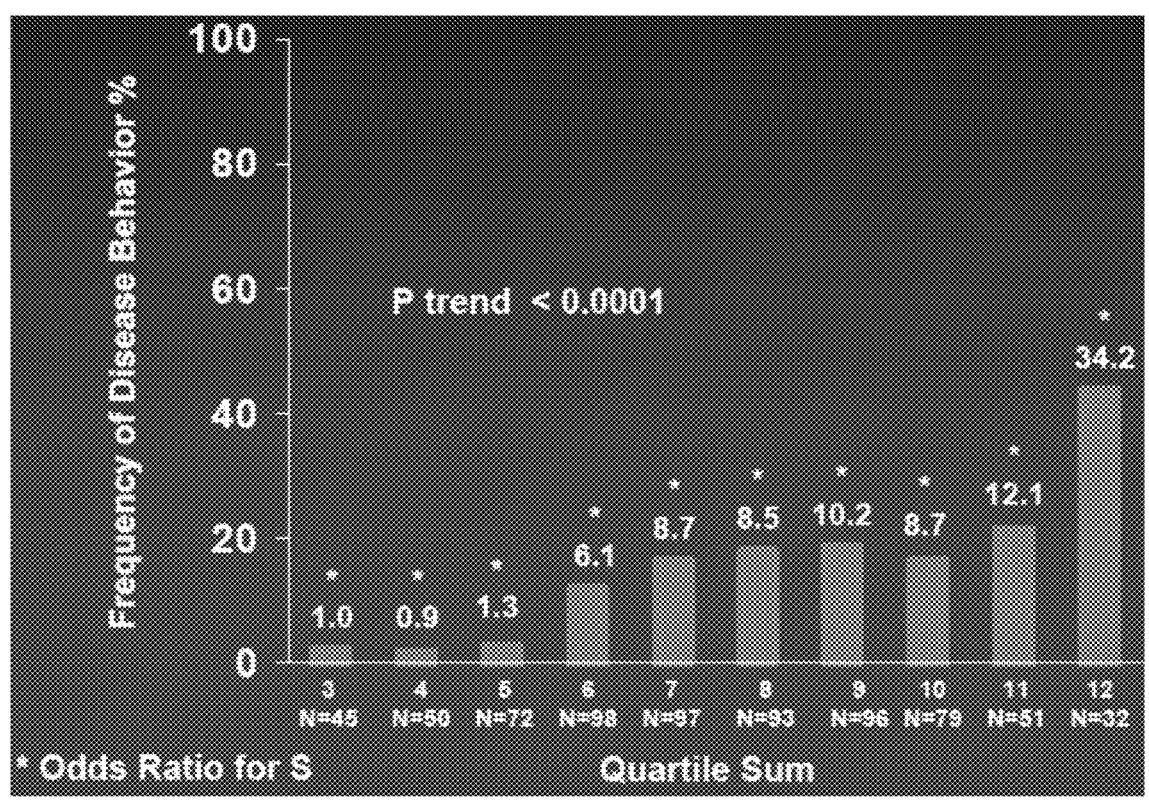
FIG. 31 depicts a chart of quartile sum and structuring disease.
Figure 32:
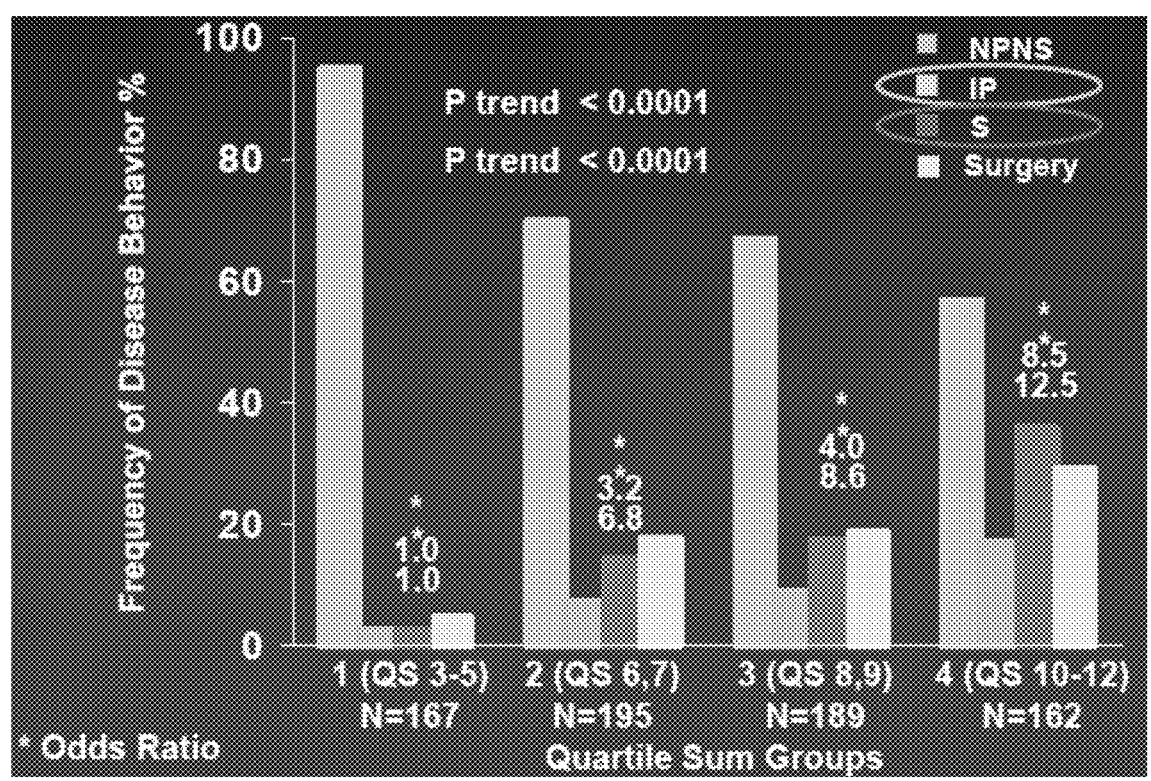
FIG. 32 depicts a chart of quartile sum groups and disease behavior.
Figure 34:
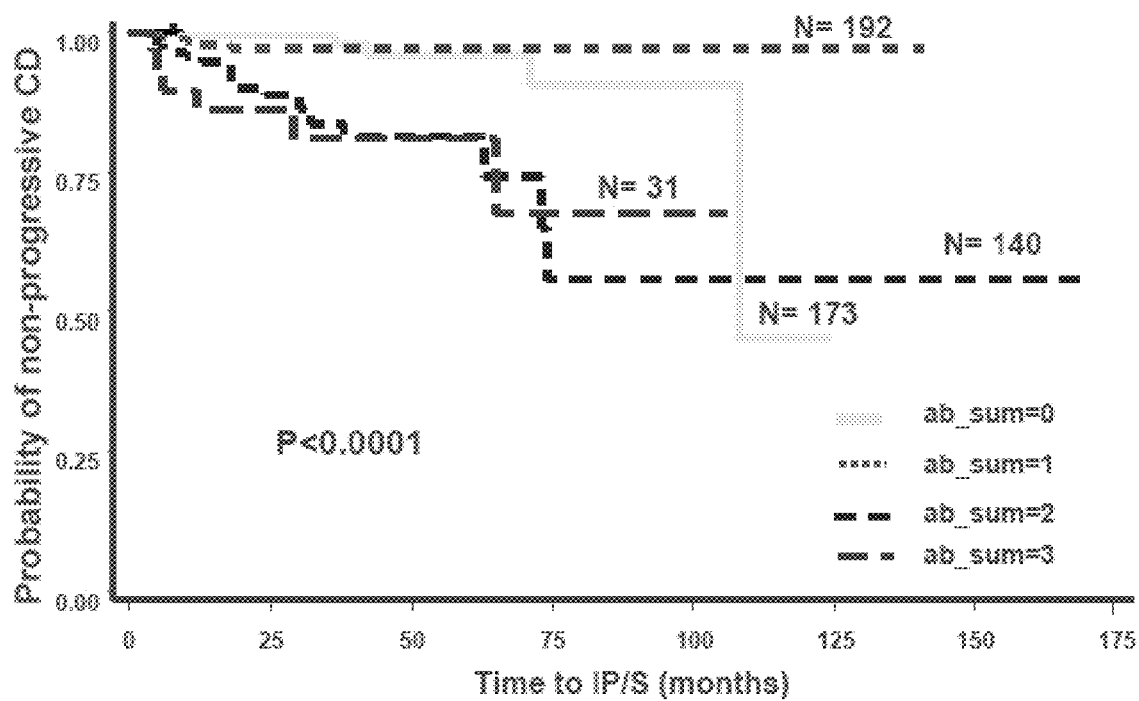
FIG. 34 depicts a chart demonstrating predictors of disease progression. The chart describes antibody sum and disease progression.
Figure 35:
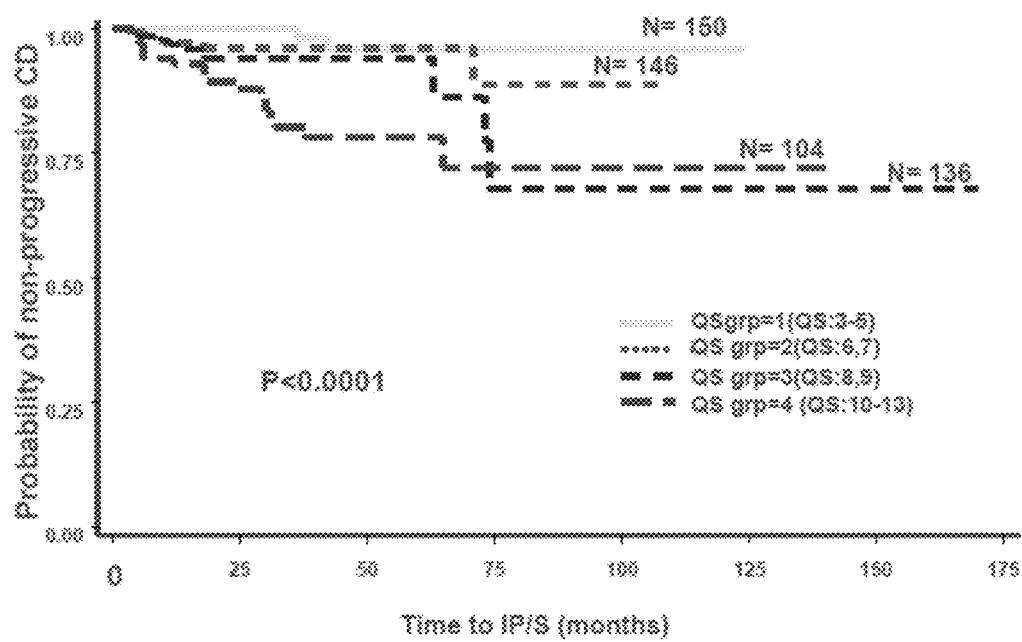
FIG. 35 depicts a chart describing predictors of disease progression. The chart describes quartile sum groups and disease progression.
Figure 36:
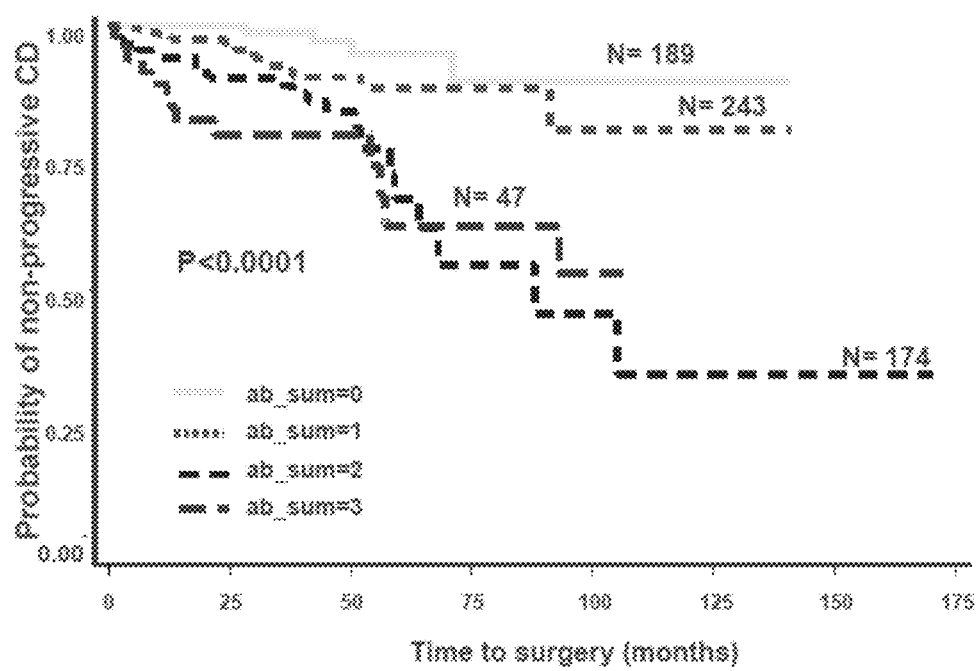
FIG. 36 depicts a chart describing predictors of disease progression. The chart describes antibody sum and surgery.

As used herein, the term of "TLR8 H3" is further described in FIGS. 24 and 25 herein.

As used herein, the term of "TLR8 H2" is further described in FIGS. 24 and 25 herein.

As used herein, examples of SNP variants at the Jak3 genetic locus are rs2302600 (SEQ ID NO: 37) and rs3212741 (SEQ ID NO: 38). However, as understood by one of skill in the art, additional risk variants the Jak2 genetic locus may be readily apparent to one of skill in the art and Jak3 risk variants are not limited to these specific SNP sequences. Similarly, SNP variants rs2302600 and rs3212741 themselves may also come in many additional versions, including for example, nucleotide probes encoding the complementary strands.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

As known to one of ordinary skill in the art, there are presently various treatments and therapies available for those diagnosed with Inflammatory Bowel Disease, including but not limited to surgery, anti-inflammatory medications, steroids, and immunosuppressants.

Serological Factors

Various embodiments of the present invention provide for methods for diagnosing Crohn's disease in a mammal. Additional embodiments provide for determining a subtype of Crohn's disease, such as a phenotypic feature associated with Crohn's disease. Further embodiments provide for treating Crohn's disease. In a one embodiment, the mammal is a human.

In particular embodiments, diagnosing Crohn's disease may be performed by determining the presence of anti-CBir1 expression, where the presence of anti-CBir1 expression indicates that the mammal has Crohn's disease. Determining a subtype of Crohn's disease, such as a phenotypic feature associated with Crohn's disease may also be performed by determining the presence of anti-CBir1 expression, where the presence of anti-CBir1 indicates that the mammal has small bowel disease, internal penetrating/perforating disease or fibrostenosing disease.

Determining the presence of anti-CBir1 expression may be accomplished by various means. For example, determining the presence of anti-CBir1 expression may be performed by determining the presence of an RNA sequence or a fragment of an RNA sequence that encodes an anti-CBir1 antibody; for example, using Northern blot analysis or reverse transcription-polymerase chain reaction (RT-PCR). Determining the presence of anti-CBir1 expression may also be performed by determining the presence of anti-CBir1 antibodies; for example IgG anti-CBir1. Anti-CBir1 antibodies are not limited to IgG, as IgA, IgM, IgD and IgE are also included in various embodiments of the present invention. These examples are not intended to be limiting, as one skilled in the art will recognize other appropriate techniques for determining the presence of anti-CBir1 expression.

Determining the presence of anti-CBir1 antibodies may be accomplished by a number of ways. For example, the determination may be made by an enzyme-linked immunosorbent assay (ELISA), sodium dodecyl sulfate polyacrylamide gel electrophoresis (SDS-PAGE), Western blot analysis, and mass spectrometric analysis.

In other embodiments for the determination of the presence of anti-CBir1 antibodies, an immune complex can be detected with a labeled secondary antibody, for example, that has specificity for a class determining portion of an anti-CBir1 antibody. One skilled in the art understands that, preferably, a secondary antibody does not compete with the CBir1 flagellin antigen for binding to the primary antibody. A secondary antibody can bind any epitope of an anti-CBir1 antibody.

It is understood that a useful secondary antibody is specific for the species from which the sample was obtained. For example, if human serum is the sample to be assayed, mouse anti-human IgG can be a useful secondary antibody. A combination of different antibodies, which can be useful in the methods of the invention, also is encompassed within the meaning of the term secondary antibody, provided that at least one antibody of the combination reacts with an antibody that specifically binds a CBir1 antigen.

A secondary antibody can be rendered detectable by labeling with an enzyme such as horseradish peroxidase (HRP), alkaline phosphatase (AP), beta-galactosidase or urease. A secondary antibody also can be rendered detectable by labeling with a fluorochrome (such a fluorochrome emits light of ultraviolet or visible wavelength after excitation by light or another energy source), a chemiluminescent marker or a radioisotope.

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis can be made using a spectrophotometer. If desired, the assays of the invention can be automated or performed robotically, and the signal from multiple samples can be detected simultaneously.

These examples are not intended to be limiting, as one skilled in the art will recognize other appropriate techniques for determining the presence of anti-CBir1 antibodies.

Additional embodiments of the present invention provide for methods of treating Crohn's disease in a human by the use of antigen-directed therapy. The target antigen in this antigen-therapy may be flagellin, and particularly CBir1 or an immunoreactive fragment thereof.

In other embodiments, methods are provided to diagnose a subset of CD patients that may have colitic disease, and/or colitic and small bowel disease. Defining this subset of CD patients may be performed by determining the presence of anti-CBir1 expression and determining the presence of perinuclear antineutrophil cytoplasmic antibodies (pANCA), where the presence of both is diagnostic of Crohn's disease with properties of colitic disease and/or colitic and small bowel disease. Determination of the presence of pANCA may also be accomplished using ELISA, SDS-PAGE, Western blot analysis, or mass spectrometric analysis. These examples are not intended to be limiting, as one skilled in the art will recognize other appropriate means for determining the presence of pANCA.

Further embodiments of the present invention provide for methods of treating the subset of CD patients with colitic disease and/or colitic and small bowel disease. Treating colitic disease and/or colitic and small bowel disease may be performed by manipulating the bacterial flora in the colon and/or colon and small bowel. Manipulation of the bacterial flora may be performed by administering antibiotics and/or probiotics. Examples of probiotics include but are not limited to *Bifidobacterium*, including, *B. bifidum, B. breve, B. infantis*, and *B. longum; Lactobacillus*, including, *L. acidophilus, L. bulgaricus, L. casei, L. plantarum, L. rhamnosus, L. reuiteri*, and *L. paracasei*.

Samples useful in various embodiments of the present invention can be obtained from any biological fluid having antibodies or RNA sequences or fragments of RNA sequences; for example, whole blood, plasma, serum, saliva, or other bodily fluid or tissue. It is understood that a sample to be assayed according to the various embodiments of the present invention may be a fresh or preserved sample obtained from a subject to be diagnosed. Furthermore, the sample used in connection with various embodiments of the present invention may be removed from the mammal; for example, from drawn blood, aspirated fluids, or biopsies. Alternatively, the sample may be in situ; for example a tool or device may be used to obtain a sample and perform a diagnosis while the tool or device is still in the mammal.

A CBir1 antigen, or immunoreactive fragment thereof, useful in the invention can be produced by any appropriate method for protein or peptide synthesis.

Other embodiments of the present invention use anti-idiotypic antibodies specific to the anti-CBir1 antibody or other antibody of interest. An anti-idiotypic antibody contains an internal image of the antigen used to create the antibody of interest. Therefore, an anti-idiotypic antibody can bind to an anti-CBir1 antibody or other marker antibody of interest. One skilled in the art will know and appreciate appropriate methods of making, selecting and using anti-idiotype antibodies.

The present invention is also directed to kits for diagnosing and/or treating Crohn's disease and/or subtypes of Crohn's disease. The kit is useful for practicing the inventive methods of diagnosing and/or treating Crohn's disease and/or subtypes of Crohn's disease. The kit is an assemblage of materials or components.

The exact nature of the components configured in the inventive kit depends on its intended purpose. For example, some embodiments are configured for the purpose of diagnosing Crohn's disease or subtypes of Crohn's disease. Subtypes include small bowel disease, internal perforating disease, fibrostenosing disease, colitic disease and colitic and small bowel disease. For instance, a quantity of CBir1 antigen may be included in the kit for determining the presence of anti-CBir1 antibodies in accordance with various embodiments of the present invention. Additional embodiments are configured for treating Crohn's disease or subtypes of Crohn's disease. Further embodiments are configured for treating Crohn's disease patients with colitic disease and/or colitic and small bowel disease. In one embodiment, the kit is configured particularly for the purpose of diagnosing human subjects. In another embodiment, the kit is configured particularly for the purpose of treating human subjects.

Instructions for use may be included in the kit. "Instructions for use" typically include a tangible expression describing the technique to be employed in using the components of the kit to effect a desired outcome, such as to diagnose or treat Crohn's disease and/or subtypes of Crohn's disease. Optionally, the kit also contains other useful components, such as, secondary antibodies, enzymes (e.g., horseradish peroxidase (HRP), alkaline phosphatase (AP), beta-galactosidase or urease), fluorochrome, chemiluminescent markers, radioisotopes, labeled secondary antibodies, tetramethylbenzidine substrates, multiple well plates, diluents, buffers, pharmaceutically acceptable carriers, syringes, catheters, applicators, pipetting or measuring tools, or other useful paraphernalia as will be readily recognized by those of skill in the art.

In one embodiment, a subject is diagnosed with IBD if the subject has the presence of anti-CBir1 and/or pANCA.

In one embodiment, Crohn's Disease is diagnosed when anti-CBir-1 is detected in the subject. In another embodiment, ulcerative colitis is diagnosed when pANCA is detected in the subject.

In one embodiment, antigen-directed therapy targeting CBir-1 flagellinis used to treat the subject diagnosed with IBD, CD and/or UC. In a\\nother embodiment, bacterial manipulation is used to treat the subject diagnosed with IBD, CD and/or UC.

Embodiments of the present invention provide for methods of diagnosing and/or predicting susceptibility for or protection against inflammatory bowel disease including but not limited to Crohn's Disease and/or ulcerative colitis. Other embodiments provide for methods of prognosing inflammatory bowel disease including but not limited to Crohn's Disease and/or ulcerative colitis. Other embodiments provide for methods of treating inflammatory bowel disease including but not limited to Crohn's Disease and/or ulcerative colitis.

The methods may include the steps of obtaining a biological sample containing nucleic acid from the individual and determining the presence or absence of a SNP and/or a haplotype in the biological sample. The methods may further include correlating the presence or absence of the SNP and/or the haplotype to a genetic risk, a susceptibility for inflammatory bowel disease including but not limited to Crohn's Disease and ulcerative colitis, as described herein. The methods may also further include recording whether a genetic risk, susceptibility for inflammatory bowel disease including but not limited to Crohn's Disease and ulcerative colitis exists in the individual. The methods may also further include a prognosis of inflammatory bowel disease based upon the presence or absence of the SNP and/or haplotype. The methods may also further include a treatment of inflammatory bowel disease based upon the presence or absence of the SNP and/or haplotype.

In one embodiment, a method of the invention is practiced with whole blood, which can be obtained readily by non-invasive means and used to prepare genomic DNA, for example, for enzymatic amplification or automated sequencing. In another embodiment, a method of the invention is practiced with tissue obtained from an individual such as tissue obtained during surgery or biopsy procedures.

NOD2 Variants

In one embodiment, the present invention provides methods of diagnosing and/or predicting susceptibility to Crohn's Disease in an individual by determining the presence or absence in the individual of R702W, G908, and/or 1000fs in the NOD2 gene. In another embodiment, the present invention provides methods of prognosis of Crohn's Disease in an individual by determining the presence or absence in the individual of R702W, G908, and/or 1000fs in the NOD2 gene. In another embodiment, the present invention provides methods of treatment of Crohn's Disease in an individual by determining the presence or absence in the individual of R702W, G908, and/or 1000fs in the NOD2 gene.

In another embodiment, sero-reactivity associated with NOD2 variants is diagnostic or predictive of susceptibility of Crohn's Disease. In another embodiment, the association of sero-reactivity of ASCA, I2, OmpC, or Cbir to variants R702W, G908R, or 1000fs, is diagnostic or predictive of susceptibility of Crohn's Disease. In another embodiment, the association of sero-reactivity of ASCA, I2, OmpC, or Cbir to variants R702W, G908R, or 1000fs provides methods of prognosis of Crohn's Disease. In another embodiment, the association of sero-reactivity of ASCA, I2, OmpC, or Cbir to variants R702W, G908R, or 1000fs provides methods of treatment of Crohn's Disease.

In another embodiment, the presence of R702W, G908R, or 1000fs NOD2 variant is diagnostic or predictive of an increased adaptive immune response.

TLR8 Variants

As disclosed herein, an example of a TLR8 genetic sequence is described as SEQ ID NO: 21. An example of a TLR8 peptide sequence is described herein as SEQ ID NO: 22.

H2 and H3 are further described herein by FIGS. 24 and 25, noting which A, C, G, and T variant corresponds to the listed reference number. These aforementioned listed reference numbers rs3761624, rs5741883, rs3764879, rs5744043, rs3764880, rs17256081, rs2109134, rs4830805, and rs1548731, are also described herein as SEQ ID NOS: 23-31, respectively, wherein the position of the variant allele within the sequence listing is marked as a letter other than A, C, G or T.

In one embodiment, the present invention provides methods of diagnosing and/or predicting susceptibility for or protection against inflammatory bowel disease in an individual by determining the presence or absence in the individual of a haplotype in the TLR8 gene.

In one embodiment, the present invention provides a method of determining susceptibility and/or diagnosing Crohn's Disease in an individual by determining the presence or absence of a TLR8 risk haplotype. In another embodiment, the TLR8 risk haplotype includes H3. In another embodiment, the individual is a female.

In another embodiment, the present invention provides a method of determining protection against Crohn's Disease in an individual by determining the presence or absence of a TLR8 protective haplotype. In another embodiment, the TLR8 protective haplotype includes H2. In another embodiment, the individual is a female. In another embodiment, the presence of a H2 determines protection against ulcerative colitis.

In another embodiment, the presence of H3 and/or H2 may provide methods of prognosis of inflammatory bowel disease. In another embodiment, the presence of H3 and/or H2 may provide methods of treatment of inflammatory bowel disease.

TLR2 Variants

As disclosed herein, an example of a TLR2 genetic sequence is described as SEQ ID NO: 32. An example of a TLR2 peptide sequence is described herein as SEQ ID NO: 34.

The P631H variant of TLR2 is also described herein as SEQ ID NO: 33, wherein the position of the variant allele within the sequence listing is marked as M.

In one embodiment, the present invention provides methods of diagnosing and/or predicting susceptibility for or protection against Crohn's Disease in an individual by determining the presence or absence in the individual of a variant in the TLR2 gene.

In another embodiment, the P631H variant of the TLR2 gene is diagnostic or predictive of susceptibility to Crohn's Disease.

In another embodiment, sero-reactivity associated with TLR2 variants is diagnostic or predictive of susceptibility of Crohn's Disease. In another embodiment, the association of sero-reactivity of ASCA, I2, OmpC, or Cbir to the P631H variant of the TLR2 gene is diagnostic or predictive of susceptibility of Crohn's Disease. In another embodiment, the association of sero-reactivity of ASCA, I2, OmpC, or Cbir to the P631H variant of the TLR2 gene is diagnostic or predictive of susceptibility of Crohn's Disease in Jewish individuals.

In one embodiment, a subject is diagnosed with IBD if the subject has the presence of R702W, G908R, 1007insC or a combination thereof in NOD2.

In one embodiment, a subject is diagnosed with IBD if the subject has the presence of R675W, G881R, 3020incC or a combination thereof in CARD15.

In one embodiment, a subject is diagnosed with IBD if the subject has the presence of Haplotype 3 (H3) in TLR8. In another embodiment, a subject is not diagnosed with IBD if the subject has the presence of Haplotype 2 (H2) in TLR8.

In one embodiment, a subject is diagnosed with IBD if the subject has the presence of P631H in TLR2.

In one embodiment, a subject is diagnosed with IBD if the subject has (i) the presence of R702W, G908R, 1007insC or a combination thereof in NOD2; (ii) the presence of R675W, G881R, 3020incC or a combination thereof in CARD15; (iii) the presence of Haplotype 3 (H3) in TLR8 and the absence of Haplotype 2 (H2); and (iv) the presence of P631H in TLR2 and/or a combination thereof.

In one embodiment, a subject is at an increased risk of IBD if the subject has the presence of R702W, G908R, 1007insC or a combination thereof in NOD2.

In one embodiment, a subject is at an increased risk of IBD if the subject has the presence of R675W, G881R, 3020incC or a combination thereof in CARD15.

In one embodiment, a subject is at an increased risk of IBD if the subject has the presence of Haplotype 3 (H3) in TLR8 and the absence of Haplotype 2 (H2).

In one embodiment, a subject is at an increased risk of IBD if the subject has the presence of P631H in TLR2.

In one embodiment, a subject is at an increased risk of IBD if the subject has (i) the presence of R702W, G908R, 1007insC or a combination thereof in NOD2; (ii) the presence of R675W, G881R, 3020incC or a combination thereof in CARD15; (iii) the presence of Haplotype 3 (H3) in TLR8 and the absence of Haplotype 2 (H2) in TLR8; and (iv) the presence of P631H in TLR2 and/or a combination thereof.

In one embodiment, a subject is at a decreased risk of IBD if the subject has (i) the absence of R702W, G908R, 1007insC or a combination thereof in NOD2; (ii) the absence of R675W, G881R, 3020incC or a combination thereof in CARD15; (iii) the absence of Haplotype 3 (H3) in TLR8 and the presence of Haplotype 2 (H2); (iv) the absence of P631H in TLR2 and/or a combination thereof.

In one embodiment, a female subject is at an increased risk of IBD if the subject has the presence of Haplotype 3 (H3) in TLR8 and the absence of Haplotype 2 (H2) in TLR8. In one embodiment, a female subject is at a decreased risk of IBD if the subject has the absence of Haplotype 3 (H3) in TLR8 and the presence of Haplotype 2 (H2) in TLR8.

In one embodiment, a Jewish subject is at an increased risk of CD if the subject has the presence of P631H in TLR2.

CARD 15 and CARD 8 Variants

As used herein, SNP's 8, 12, 13 are also referred to as R702W, G908R, 1007insC.

In one embodiment, the present invention provides methods of diagnosing and/or predicting susceptibility to a subtype of Crohn's Disease in an individual by determining the presence or absence of immune reactivity in the individual, where the presence of immune reactivity is diagnostic of the subtype of Crohn's Disease. In another embodiment, the present invention provides methods of prognosis of Crohn's Disease in an individual by determining the presence or absence of immune reactivity, wherein the presence of immune reactivity is indicative of a complicating Crohn's Disease prognosis. In another embodiment, the present invention provides methods of treatment of Crohn's Disease by administering a therapeutically effective amount of Crohn's Disease treatment wherein there is a presence of immune reactivity in the individual. In another embodiment, the subtype is complicating Crohn's Disease. In another embodiment, the subtype is small bowel disease, internal penetrating and/or fibrostenosing. In another embodiment, immune reactivity is a high expression of ASCA, OmpC, and/or Cbir1, relative to levels found in a healthy individual. In another embodiment, the individual is a child.

In one embodiment, the present invention provides a method of diagnosing susceptibility to a subytpe of Crohn's Disease by determining the presence of immune reactivity, and determining the presence of CARD15 variants, wherein the presence of immune reactivity and one or more CARD15 variants is diagnostic of susceptibility to the subtype of Crohn's Disease. In another embodiment, the present invention provides a method of prognosis of Crohn's Disease in an individual by determining the presence of immune reactivity, and determining the presence of CARD15 variants, wherein the presence of immune reactivity and one or more CARD15 variants is indicative of a complicating Crohn's Disease prognosis. In another embodiment, the present invention provides a method of treatment of Crohn's Disease by administering a therapeutically effective amount of Crohn's Disease treatment wherein there is a presence of immune reactivity and CARD15 variants in the individual. In another embodiment, the CARD15 variants comprise SNPs 8, 12, and/or 13. In another embodiment, immune reactivity is a high expression of ASCA, OmpC, and/or Cbir1, relative to levels found in a healthy individual. In another embodiment, the individual is a child. In another embodiment, the subtype of Crohn's Disease is small bowel disease, internal penetrating and/or fibrostenosis.

In one embodiment, the present invention provides methods of diagnosing and/or predicting susceptibility to a subtype of Crohn's Disease in an individual by determining the presence or absence of immune reactivity in the individual, where the presence of immune reactivity is diagnostic of the subtype of Crohn's Disease. In another embodiment, the present invention provides methods of prognosis of Crohn's Disease in an individual by determining the presence or absence of immune reactivity, wherein the presence of immune reactivity is indicative of a complicating Crohn's Disease prognosis. In another embodiment, the present invention provides methods of treatment of Crohn's Disease by administering a therapeutically effective amount of Crohn's Disease treatment wherein there is a presence of immune reactivity in the individual. In another embodiment, the subtype is complicating Crohn's Disease. In another embodiment, the subtype is small bowel disease, internal penetrating and/or fibrostenosing. In another embodiment, immune reactivity is a high expression of ASCA, OmpC, Cbir1, and/or 12 relative to levels found in a healthy individual. In another embodiment, the individual is a child.

In one embodiment, the present invention provides methods of diagnosing and/or predicting susceptibility to ulcerative colitis in an individual by determining the presence or absence of a CARD8 risk variant in the individual, where the presence of the CARD8 risk variant is diagnostic of ulcerative colitis. In another embodiment, the present invention provides methods of treatment of ulcerative colitis by administering a therapeutically effective amount of ulcerative colitis treatment wherein there is a presence of a CARD8 risk variant in the individual. In another embodiment, the CARD8 variant is T10C. In another embodiment, the individual is a child.

In one embodiment, the present invention provides methods of diagnosing and/or predicting susceptibility to inflammatory bowel disease in a child by determining the presence or absence of high expression of anti-Cbir1 relative to a healthy individual, wherein the presence of the high expression of anti-Cbir1 relative to a healthy individual is indicative of susceptibility to inflammatory bowel disease in the child. In another embodiment, the present invention provides methods of treatment for inflammatory bowel disease in a child by administering a therapeutically effective amount of inflammatory bowel disease treatment in a child with a high expression of anti-Cbir1 relative to a healthy individual.

In one embodiment, the present invention provides a method of predicting Crohn's Disease progression in an individual by determining the presence or absence of a high immune reactivity relative to a healthy individual. In another embodiment, the present invention provides a method of treatment of Crohn's Disease by administering a therapeutically effective amount of Crohn's Disease treatment in an individual with immune reactivity relative to a healthy individual. In another embodiment, the present invention provides a method of treating an aggressive form of Crohn's Disease in a pediatric subject by determining the presence of a high immune reactivity and treating the aggressive form of Crohn's Disease. In another embodiment, the present invention provides a method of determining the prognosis of Crohn's Disease in a subject by determining the presence or absence of a high immune reactivity relative to a child with a non-aggressive form of Crohn's Disease. In another embodiment, immune reactivity includes OmpC, ASCA, Cbir1 and/or pANCA. In another embodiment, the individual is a child. In another embodiment, the subject is a pediatric subject. In another embodiment, immune reactivity is determined by time to complication or surgery. In another embodiment, the immune reactivity is associated with disease phenotype, such as disease location, behavior and/or surgery. In another embodiment, the presence of the high immune reactivity is indicative of a prognosis of an aggressive form of Crohn's Disease.

As described herein, various embodiments provide methods of prognosis of Crohn's Disease by determining a high immune reactivity of various markers, such as OmpC, ASCA, Cbir1 and/or pANCA, where a high immune reactivity of one or more markers is associated with a prognosis of developing an aggressive form of Crohn's Disease. Immune reactivity is determined by comparing both the presence and magnitude of markers to a standard set by those marker levels found in a subject who has and maintains a non-aggressive form of Crohn's Disease.

In one embodiment, a subject is diagnosed with IBD if the subject has the presence of R702W, G908R, 1007insC or a combination thereof in NOD2.

In one embodiment, a subject is diagnosed with IBD if the subject has the presence of R675W, G881R, 3020incC or a combination thereof in CARD15.

In one embodiment, a subject is diagnosed with IBD if the subject has the presence of T10C in CARD8.

In one embodiment, a subject is diagnosed with IBD if the subject has the presence of anti-CBir1, pANCA, anti-OmpC, ASCA and/or anti-I2.

In one embodiment, a subject is diagnosed with IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8 and/or a combination thereof.

In one embodiment, a subject is diagnosed with IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8 and/or a combination thereof, (vi) the presence of anti-CBir1, pANCA, anti-OmpC, ASCA and/or a combination thereof.

In one embodiment, a subject is at an increased risk of IBD if the subject has the presence of R702W, G908R, 1007insC or a combination thereof in NOD2.

In one embodiment, a subject is at an increased risk of IBD if the subject has the presence of R675W, G881R, 3020incC or a combination thereof in CARD15.

In one embodiment, a subject is at an increased risk of IBD if the subject has the presence of T10C in CARD8.

In one embodiment, a subject is at an increased risk for IBD if the subject has the presence of anti-CBir1, pANCA, anti-OmpC and/or ASCA.

In one embodiment, a subject is at an increased risk of IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8 and/or a combination thereof.

In one embodiment, a subject is at an increased risk of IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8; the presence of anti-CBir1, pANCA, anti-OmpC, ASCA, and/or a combination thereof.

In one embodiment, a subject is at a decreased risk of IBD if the subject has (i) the absence of R702W, G908R, 1007insC or a combination thereof in NOD2; (ii) the absence of R675W, G881R, 3020incC or a combination thereof in CARD15; (iii) the absence of T10C in CARD8 and/or a combination thereof.

JAK3 Variants

In one embodiment, the present invention provides a method of diagnosing susceptibility to a subtype of Crohn's Disease by determining the presence or absence of a risk variant at the JAK3 locus, where the presence of the risk variant at the JAK3 locus is indicative of susceptibility to the subtype of Crohn's Disease. In another embodiment, the risk variant is associated with ASCA and/or anti-I2 expression. In another embodiment, the risk variant at the JAK3 locus comprises SEQ ID NO: 37. In another embodiment, the risk variant at the JAK3 locus comprises SEQ ID NO: 38.

In one embodiment, the present invention provides a method of diagnosing Crohn's Disease by determining the presence or absence of a risk variant at the JAK3 locus, where the presence of the risk variant at the JAK3 locus is indicative of Crohn's Disease. In another embodiment, the risk variant is associated with ASCA and/or anti-I2 expression. In another embodiment, the risk variant at the JAK3 locus comprises SEQ ID NO: 37. In another embodiment, the risk variant at the JAK3 locus comprises SEQ ID NO: 38.

In another embodiment, the present invention provides a method of treating Crohn's Disease by determining the presence of a risk variant at the JAK3 locus and treating the Crohn's Disease.

In one embodiment, the present invention provides a method of determining protection against inflammatory bowel disease in an individual by determining the presence or absence of a protective haplotype at the JAK3 locus, where the presence of a protective haplotype at the JAK3 locus is indicative of a decreased likelihood of inflammatory bowel disease.

In one embodiment, a subject is diagnosed with IBD if the subject has the presence of JAK3 risk variants.

In one embodiment, a subject is diagnosed with IBD if the subject has the presence of ASCA and/or anti-I2.

In one embodiment, a subject is diagnosed with IBD if the subject has (i) the presence of JAK3 risk variants; and (ii) ASCA, anti-I2 and/or a combination thereof.

In one embodiment, a subject is at an increased risk for IBD if the subject has the presence of JAK3 risk variants.

In one embodiment, a subject is at an increased risk for IBD if the subject has the presence of ASCA and/or anti-I2.

In one embodiment, a subject is at an increased risk for IBD if the subject has (i) the presence of JAK3 risk variants; and (ii) ASCA, anti-I2 and/or a combination thereof.

In one embodiment, a subject is diagnosed with IBD if the subject has the presence of R702W, G908R, 1007insC or a combination thereof in NOD2.

In one embodiment, a subject is diagnosed with IBD if the subject has the presence of R675W, G881R, 3020incC or a combination thereof in CARD15.

In one embodiment, a subject is diagnosed with IBD if the subject has the presence of T10C in CARD8.

In one embodiment, a subject is diagnosed with IBD if the subject has the presence of Haplotype 3 (H3) in TLR8. In another embodiment, a subject is not diagnosed with IBD if the subject has the presence of Haplotype 2 (H2) in TLR8.

In one embodiment, a subject is diagnosed with IBD if the subject has the presence of P631H in TLR2.

In one embodiment, a subject is diagnosed with IBD if the subject has the presence of JAK3 risk variants.

In one embodiment, a subject is diagnosed with IBD if the subject has the presence of anti-CBir1, pANCA, anti-OmpC, ASCA and/or anti-I2.

In one embodiment, a subject is diagnosed with IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8; (iv) the presence of Haplotype 3 (H3) in TLR8 and the absence of Haplotype 2 (H2); (v) the presence of P631H in TLR2; (vi) the presence of JAK3 risk variants and/or a combination thereof.

In one embodiment, a subject is diagnosed with IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8; (iv) the presence of Haplotype 3 (H3) in TLR8 and the absence of Haplotype 2 (H2); (v) the presence of P631H in TLR2; (vi) the presence of JAK3 risk variants; (vi) the presence of anti-CBir1, pANCA, anti-OmpC, ASCA, anti-I2 and/or a combination thereof.

In one embodiment, a subject is at an increased risk of IBD if the subject has the presence of R702W, G908R, 1007insC or a combination thereof in NOD2.

In one embodiment, a subject is at an increased risk of IBD if the subject has the presence of R675W, G881R, 3020incC or a combination thereof in CARD15.

In one embodiment, a subject is at an increased risk of IBD if the subject has the presence of T10C in CARD8.

In one embodiment, a subject is at an increased risk of IBD if the subject has the presence of Haplotype 3 (H3) in TLR8 and the absence of Haplotype 2 (H2).

In one embodiment, a subject is at an increased risk of IBD if the subject has the presence of P631H in TLR2.

In one embodiment, a subject is diagnosed with IBD if the subject has the presence of JAK3 risk variants.

In one embodiment, a subject is at an increased risk for IBD if the subject has the presence of anti-CBir1, pANCA, anti-OmpC, ASCA and/or anti-I2.

In one embodiment, a subject is at an increased risk of IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8; (iv) the presence of Haplotype 3 (H3) in TLR8 and the absence of Haplotype 2 (H2); (v) the presence of JAK3 risk variants; (vi) the presence of P631H in TLR2 and/or a combination thereof.

In one embodiment, a subject is at an increased risk of IBD if the subject has (i) the presence of R702W, G908R, 1007insC or a combination thereof in NOD2; (ii) the presence of R675W, G881R, 3020incC or a combination thereof in CARD15; (iii) the presence of T10C in CARD8; (iv) the presence of Haplotype 3 (H3) in TLR8 and the absence of Haplotype 2 (H2); (v) the presence of JAK3 risk variants; (vi) the presence of P631H in TLR2 and/or a combination thereof; (vi) the presence of anti-CBir1, pANCA, anti-OmpC, ASCA, anti-I2 and/or a combination thereof.

In one embodiment, a subject is at a decreased risk of IBD if the subject has (i) the absence of R702W, G908R, 1007insC or a combination thereof in NOD2; (ii) the absence of R675W, G881R, 3020incC or a combination thereof in CARD15; (iii) the absence of T10C in CARD8; (iv) the absence of Haplotype 3 (H3) in TLR8 and the presence of Haplotype 2 (H2); (v) the absence of P631H in TLR2 and/or a combination thereof.

Various embodiments of the present invention provide for methods for diagnosing Crohn's disease in a mammal. Additional embodiments provide for determining a subtype of Crohn's disease, such as a phenotypic feature associated with Crohn's disease. Further embodiments provide for treating Crohn's disease. In one embodiment, the mammal is a human.

In particular embodiments, diagnosing Crohn's disease may be performed by determining the presence of anti-CBir1 expression, where the presence of anti-CBir1 expression indicates that the mammal has Crohn's disease. Determining a subtype of Crohn's disease, such as a phenotypic feature associated with Crohn's disease may also be performed by determining the presence of anti-CBir1 expression, where the presence of anti-CBir1 indicates that the mammal has small bowel disease, internal penetrating/perforating disease or fibrostenosing disease.

Determining the presence of anti-CBir1 expression may be accomplished by various techniques. For example, determining the presence of anti-CBir1 expression may be performed by determining the presence of an RNA sequence or a fragment of an RNA sequence that encodes an anti-CBir1 antibody; for example, using Northern blot analysis or reverse transcription-polymerase chain reaction (RT-PCR). Determining the presence of anti-CBir1 expression may also be performed by determining the presence of anti-CBir1 antibodies; for example IgG anti-CBir1. Anti-CBir1 antibodies are not limited to IgG, as IgA, IgM, IgD and IgE are also contemplated in connection with various embodiments of the present invention. These examples are not intended to be limiting, as one skilled in the art will recognize other appropriate means for determining the presence of anti-CBir1 expression.

Determining the presence of anti-CBir1 antibodies may be accomplished by a number of ways. For example, the determination may be made by an enzyme-linked immunosorbent assay (ELISA), sodium dodecyl sulfate polyacrylamide gel electrophoresis (SDS-PAGE), Western blot analysis, and mass spectrometric analysis.

In other embodiments of the invention, an immune complex can be detected with a labeled secondary antibody, for example, that has specificity for a class determining portion of an anti-CBir1 antibody. A signal from a detectable secondary antibody can be analyzed, and positive results indicate the presence of anti-CBir1 antibodies.

Additional embodiments of the present invention provide for methods of treating Crohn's disease by the use of antigen-directed therapy. The target antigen in this therapy may be flagellin, and particularly CBir1 or an immunoreactive fragment thereof.

In other embodiments, methods are provided to define a subset of CD patients that may have colitic disease, and/or colitic and small bowel disease. Defining this subset of CD patients may be performed by determining the presence of anti-CBir1 expression and determining the presence of perinuclear antineutrophil cytoplasmic antibodies (pANCA), where the presence of both is diagnostic of Crohn's disease with properties of colitic disease and/or colitic and small bowel disease. Determination of the presence of pANCA may also be accomplished using ELISA, SDS-PAGE, Western blot analysis, or mass spectrometric analysis. These examples are not intended to be limiting, as one skilled in the art will recognize other appropriate means for determining the presence of pANCA.

Further embodiments of the present invention provide for methods of treating the subset of CD patients with colitic disease and/or colitic and small bowel disease. Treating colitic disease and/or colitic and small bowel disease may be performed by manipulating the bacterial flora in the colon and/or colon and small bowel. Manipulation of the bacterial flora may be performed by administering antibiotics and/or probiotics.

Samples useful in various embodiments of the present invention can be obtained from any biological fluid having antibodies or RNA sequences or fragments of RNA sequences; for example, whole blood, plasma, serum, saliva, or other bodily fluid or tissue. The sample used in connection with various embodiments of the present invention may be removed from the mammal; for example, from drawn blood, aspirated fluids, or biopsies. Alternatively, the sample may be in situ; for example a tool or device may be used to obtain a sample and perform a diagnosis while the tool or device is still in the mammal.

A CBir1 antigen, or immunoreactive fragment thereof, useful in the invention can be produced by any appropriate method for protein or peptide synthesis.

Other embodiments of the present invention use anti-idiotypic antibodies specific to the anti-CBir1 antibody or other antibody of interest.

The present invention is also directed to kits for diagnosing and/or treating Crohn's disease and/or subtypes of Crohn's disease. The exact nature of the components configured in the inventive kits depends on their intended purpose. For instance, a quantity of CBir1 antigen may be included in the kit for determining the presence of anti-CBir1 antibodies. Instructions for use may be included in the kit.

Various embodiments provide methods of diagnosing susceptibility to Crohn's Disease in an individual, comprising determining the presence or absence of at least one risk variant at the NOD2 locus selected from the group consisting of R702W, G908R and 1007fs, and determining the presence or absence of at least one risk serological marker, where the presence of at least one risk variant and at least one risk serological marker is diagnostic of susceptibility to Crohn's Disease.

In other embodiments, the presence of three of the risk variants at the NOD2 locus present a greater susceptibility than the presence of two, one or none of the risk variants at the NOD2 locus, and the presence of two of the risk variants at the NOD2 locus presents a greater susceptibility than the presence of one or none of the risk variants at the NOD2 locus but less than the presence of three risk variants at the NOD2 locus, and the presence of one of the risk variants at the NOD2 locus presents a greater susceptibility than the presence of none of the risk variants at the NOD2 locus but less than the presence of three or two of the risk variants at the NOD2 locus.

In other embodiments, the risk serological markers are selected from the group consisting of ASCA, I2, OmpC and Cbir. In another embodiment, the presence of four of the risk serological markers presents a greater susceptibility than the presence of three or two or one or none of the risk serological markers, and the presence of three of the risk serological markers presents a greater susceptibility than the presence of two or one or none of the risk serological markers but less than the presence of four risk serological markers, and the presence of two of the risk serological markers presents a greater susceptibility than the presence of one or none of the risk serological markers but less than the presence of four or three risk serological markers, and the presence of one of the risk serological markers presents a greater susceptibility than the presence of none of the risk serological markers but less than the presence of four or three or two of the risk serological markers.

In another embodiment, the invention further comprises the step of determining the presence or absence of one or more risk haplotypes at the TLR8 locus, wherein the presence of one or more risk haplotypes at the TLR8 locus is diagnostic of susceptibility to Crohn's Disease.

In another embodiment, the invention comprises the step of determining the presence or absence of one or more risk haplotypes at the TLR2 locus, wherein the presence of one or more risk haplotypes at the TLR2 locus is diagnostic of susceptibility to Crohn's Disease.

Other various embodiments provide methods of diagnosing susceptibility to Crohn's Disease in an individual comprising determining the presence or absence of one or more risk haplotypes at the TLR8 locus in the individual, where the presence of one or more risk haplotypes is diagnostic of susceptibility to Crohn's Disease. In other embodiments, the individual is a female. In another embodiment, the method further comprises determining the presence of H3.

Other various embodiments provide methods of determining a low probability relative to a healthy individual of developing Crohn's Disease and/or ulcerative colitis in an individual, the method comprising determining the presence or absence of one or more protective haplotypes at the TLR8 locus in the individual, where the presence of one or more said protective haplotypes is diagnostic of a low probability relative to a healthy individual of developing Crohn's Disease and/or ulcerative colitis. In other embodiments, the individual is a female. In other embodiments, the method further comprises determining the presence of H2.

Further embodiments provide methods of diagnosing susceptibility to Crohn's Disease in an individual comprising determining the presence or absence of one or more risk variants at the TLR2 locus in the individual, where the presence of one or more risk variants is diagnostic of susceptibility to Crohn's Disease. In another embodiment, the individual is Jewish. In another embodiment, the invention further comprises determining the presence of P631H at the TLR2 locus.

Various embodiments provide methods of diagnosing susceptibility to a subtype of Crohn's Disease in a child, comprising determining the presence or absence of at least one risk variant at the CARD15 locus selected from the group consisting of SNP8, SNP12, and SNP13, and determining the presence or absence of at least one risk serological marker, selected from the group consisting of Cbir1, OmpC, and ASCA, where the presence of at least one variant and at least one risk serological marker is diagnostic of susceptibility to the subtype of Crohn's Disease in a child. In another embodiment, the subtype of Crohn's Disease in a child comprises an aggressive complicating phenotype, a small bowel disease phenotype, and/or an internal penetrating and/or fibrostenosing disease phenotype. In another embodiment, the presence of three of the risk serological markers presents a greater susceptibility than the presence of two, one or none of the risk serological markers, and the presence of two of the risk serological markers presents a greater susceptibility than the presence of one or none of the risk serological markers but less than the presence of three of the risk serological markers, and the presence of one of the risk serological markers presents a greater susceptibility than the presence of none of the risk serological markers but less than the presence of three or two of the risk serological markers. In another embodiment, the SNP8 comprises SEQ ID NO: 18. In another embodiment, the SNP12 comprises SEQ ID NO: 19. And in another embodiment, the SNP13 comprises SEQ ID NO: 20.

Other embodiments provide for methods of diagnosing susceptibility to a subtype of Crohn's Disease in a child, comprising determining the presence or absence of a high immune reactivity relative to a healthy individual for at least one risk serological marker, selected from the group consisting of Cbir1, OmpC, ASCA, I2, and pANCA, where the presence of a high immune reactivity relative to a healthy individual to at least one risk serological marker is diagnostic of susceptibility to the subtype of Crohn's Disease in a child. In another embodiment, the subtype of Crohn's Disease in a child comprises an aggressive complicating phenotype. In another embodiment, a high immune reactivity comprises a high magnitude of expression for the risk serological marker. In another embodiment, the presence of four of the risk serological markers presents a greater susceptibility than the presence of three, two, one or none of the risk serological markers, and the presence of three of the risk serological markers presents a greater susceptibility than the presence of two, one or none of the risk serological markers but less than the presence of four of the risk serological markers, and the presence of two of the risk serological markers presents a greater susceptibility than the presence of one or none of the risk serological markers but less than the presence of four or three of the risk serological markers, and the presence of one of the risk serological markers presents a greater susceptibility than the presence of none of the risk serological markers but less than the presence of four or three or two of the risk serological markers.

Various embodiments also provide methods of treating Crohn's Disease in a child, comprising determining the presence of a high immune reactivity to a risk serological marker relative to a healthy individual, and administering a therapeutically effective amount of Crohn's Disease treatment.

Other embodiments provide methods of diagnosing ulcerative colitis in an individual, comprising determining the presence or absence of a risk variant at the CARD8 locus, where the presence of the risk variant at the CARD8 locus is diagnostic of susceptibility to ulcerative colitis. In other embodiments, the risk variant at the CARD8 locus comprises SEQ ID NO: 36. In other embodiments, the individual is a child.

Various embodiments provide methods of determining the prognosis of Crohn's Disease in an individual, comprising determining the presence or absence of a high immune reactivity relative to a healthy individual for at least one risk serological marker, selected from the group consisting of Cbir1, OmpC, ASCA, and pANCA, where the presence of a high immune reactivity relative to a healthy individual to at least one risk serological marker is indicative of a prognosis of an aggressive form of Crohn's Disease. In other embodiments, the individual is a child. In other embodiments, the prognosis of an aggressive form of Crohn's Disease further comprises a rapid complicating internal penetrating and/or fibrostenosing disease phenotype.

Other embodiments provide methods of determining the prognosis of Crohn's Disease in a pediatric subject, comprising determining the presence or absence of a high immune reactivity of Cbir1, OmpC, ASCA, and pANCA in the pediatric subject relative to a child who has and maintains a non-aggressive form of Crohn's Disease, where the presence of the high immune reactivity relative to a child who has and maintains a non-aggressive Crohn's Disease is indicative of a prognosis of an aggressive form of Crohn's Disease in the pediatric subject. In other embodiments, the aggressive form of Crohn's Disease further comprises a rapid complicating internal penetrating and/or stricturing disease phenotype.

Other embodiments provide methods of treating an aggressive form of Crohn's Disease in a pediatric subject, comprising determining the presence of a high immune reactivity of Cbir1, OmpC, ASCA and pANCA relative to a child who has and maintains a non-aggressive form of Crohn's Disease to prognose the aggressive form of Crohn's Disease, and treating the aggressive form of Crohn's Disease.

Other embodiments provide methods of determining the prognosis of Crohn's Disease in a subject, comprising determining the presence or absence of a high immune reactivity in the subject relative to an individual who has and maintains a non-aggressive form of Crohn's Disease for at least one risk serological marker, selected from the group consisting of Cbir1, OmpC, ASCA, and pANCA, where the presence of the high immune reactivity relative to an individual who has and maintains a non-aggressive form of Crohn's Disease is indicative of a prognosis of an aggressive form of Crohn's Disease. In other embodiments, the subject is a pediatric subject. In other embodiments, the individual who has and maintains a non-aggressive form of Crohn's Disease is a child. In other embodiments, the aggressive form of Crohn's Disease further comprises a rapid complicating internal penetrating and/or fibrostenosing disease phenotype.

Various embodiments also provide methods of treating an aggressive form of Crohn's Disease in a subject, comprising determining the presence of a high immune reactivity relative to an individual who has and maintains a non-aggressive form of Crohn's Disease to prognose the aggressive form of Crohn's Disease, and treating the aggressive form of Crohn's Disease. In other embodiments, the subject is a pediatric subject. In other embodiments, the individual who has and maintains a non-aggressive form of Crohn's Disease is a child. In other embodiments, the aggressive form of Crohn's Disease further comprises a rapid complicating internal penetrating and/or fibrostenosing disease phenotype.

Various embodiments include a method of diagnosing susceptibility to a subtype of Crohn's disease in an individual, comprising determining the presence or absence of one or more risk variants at the Janus kinases 3 (JAK3) genetic locus in the individual, and determining the presence or absence of a positive expression of ASCA and/or anti-I2, where the presence of one or more risk variants at the JAK3 locus and the presence of ASCA and/or anti-I2 expression is indicative of susceptibility in the individual to the subtype of Crohn's Disease. In another embodiment, one of the one or more risk variants at the JAK3 locus comprises SEQ ID NO: 37. In another embodiment, one of the one or more risk variants at the JAK3 locus comprises SEQ ID NO: 38. In another embodiment, positive expression of ASCA and/or anti-I2 comprises a high level of expression relative to a healthy subject.

Other embodiments include a method of diagnosing a subtype of Crohn's disease in an individual, comprising obtaining a sample from the individual, assaying the sample for the presence or absence of a risk variant at the Janus kinases 3 (JAK3) genetic locus in the individual, and diagnosing the subtype of Crohn's disease based upon the presence of the risk variant at the JAK3 genetic locus. In another embodiment, the risk variant comprises SEQ ID NO: 37 and/or SEQ ID NO: 38. In another embodiment, the presence of the risk variant is associated with a positive expression of ASCA and/or anti-I2. In another embodiment, the positive expression of ASCA and/or anti-I2 comprises a high level of expression relative to a healthy subject.

Various embodiment of the present invention provide for a method of diagnosing Inflammatory Bowel Disease (IBD) in a subject, comprising: providing a sample from the subject; assaying the sample to detect risk and/or protective variants in genes selected from the group consisting of: NOD2, CARD15, CARD 8, TLR8, TLR2 and JAK3; optionally, assaying the sample to detect risk serological factors selected from the group consisting of: anti-Cbir1 antibody, pANCA, anti-OmpC, ASCA and anti-I2; and determining that the subject has IBD if one or more risk variants and/or risk serological factors are present and the protective variants are absent or determining that the subject does not have IBD if one or more protective variants are present and the risk variants and/or risk serological factors are absent. In other embodiments, IBD comprises Crohn's disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38, or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In other embodiments, TLR8 comprises a protective variant and the protective variant located at the TLR8 locus is H2 and comprises SEQ ID NOs: 23-31. In other embodiments, the detection of the TLR8 risk variant in a female subject indicates an IBD diagnosis. In another embodiment, the detection of the TLR2 risk variant in a Jewish subject indicates an IBD diagnosis. In other embodiments, the detection of the NOD2 and/or CARD15 risk variants and/or risk serological factors in a pediatric subject indicates an IBD diagnosis associated with a subtype of CD. In other embodiments, a subtype of CD comprises aggressive complicating phenotype, small bowel disease phenotype, internal penetrating and/or fibrostenosing disease phenotype.

In various other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In various other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of risk variants, risk serological factors and protective variants is relative to that detected in a healthy subject.

In yet other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention provide for a process for predicting IBD susceptibility in a subject, comprising: providing a sample from the subject; assaying the sample to detect risk and/or protective variants in genes selected from the group consisting of: NOD2, CARD15, CARD 8, TLR8, TLR2 and JAK3; optionally, assaying the sample to detect risk serological factors selected from the group consisting of: anti-CBir1, pANCA, anti-OmpC, ASCA and anti-I2; and determining that the subject has increased susceptibility to IBD if one or more risk variants and/or risk serological factors are present and the protective variants are absent or determining that the subject has a decreased susceptibility to IBD if one or more protective variants are present and the risk variants and/or risk serological factors are absent. In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, IBD comprises Crohn's disease (CD) and ulcerative colitis (UC). In other embodiments, the risk variants are NOD2, CARD15, CARD 8, TLR2, TLR 8 and JAK3, wherein the TLR8 locus is H3 and comprises SEQ ID Nos: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38 or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii). In other embodiments, TLR8 comprises a protective variant and the protective variant located at the TLR8 locus is H2 and comprises SEQ ID NOs: 23-31. In other embodiments, the detection of the TLR8 risk variant in a female subject indicates an increased susceptibility to IBD. In other embodiments, the detection of the TLR2 risk variant in a Jewish subject indicates an increased susceptibility to IBD. In other embodiments, the detection of the NOD2 and/or CARD15 risk variants and/or risk serological factors in a pediatric subject indicates an increased susceptibility to IBD associated with a subtype of CD. In other embodiments, a subtype of Crohn's disease comprises aggressive complicating phenotype, small bowel disease phenotype, internal penetrating and/or fibrostenosing disease phenotype.

In yet other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In yet other embodiment, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In another embodiment, the detection of risk variants, risk serological factors and protective variants is relative to that detected in a healthy subject.

In other embodiments, there is a greater susceptibility to IBD when an increased number of risk variants and/or risk serological factors and a decreased number of protective variants are present and a decreased susceptibility when an increased number of protective variants and a decreased number of risk variants are present. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention also provide for a method for treating a subject with IBD, comprising: providing a sample from the subject; assaying the sample to detect risk and/or protective variants selected from the group consisting of: NOD2, CARD15, CARD8, TLR8, TLR2 and JAK3; assaying the sample to detect risk serological factors selected from the group consisting of: anti-CBir1, pANCA, anti-OmpC, ASCA and anti-I2; determining that the subject has IBD if one or more risk variants and/or risk serological factors are present and the protective variants are absent or determining that the subject does not have IBD if one or more protective variants are present and the risk variants and/or risk serological factors are absent; and prescribing a therapy to treat the subject diagnosed with IBD. In other embodiments, IBD comprises Crohn's Disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38 or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In yet other embodiments, TLR8 comprises a protective variant and the protective variant located at the TLR8 locus is H2 and comprises SEQ ID NOs: 23-31. In other embodiments, the therapy is an antigen-directed therapy that targets Cbir-1 flagellin or an immunoreactive fragment thereof. In other embodiments, the therapy consists of manipulation of bacteria in the colon and/or small intestine.

In yet other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In yet other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In other embodiments, the detection of risk variants, risk serological factors and protective variants is relative to that detected in a healthy subject. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various embodiments of the present invention also provide for a process for selecting a therapy for a subject with IBD comprising: providing a sample from the subject; assaying the sample to detect risk and/or protective variants selected from the group consisting of: NOD2, CARD15, CARD8, TLR8, TLR2 and JAK3; optionally, assaying the sample to detect risk serological factors selected from the group consisting of: anti-CBir1, pANCA, anti-OmpC, ASCA and anti-I2; and determining that the subject has IBD if one or more risk variants and/or risk serological factors are present and the protective variants are absent or determining that the subject does not have IBD if one or more protective variants are present and the risk variants and/or risk serological factors are absent; and selecting a therapy for the subject with IBD. In other embodiments, IBD comprises Crohn's Disease (CD) and ulcerative colitis (UC). In other embodiments, expression of any one or more of anti-CBir1, NOD2, TLR2 or a combination thereof is indicative of CD and wherein expression of any one or more of pANCA, CARD8 or a combination thereof is indicative of UC.

In other embodiments, the risk variants are NOD2, CARD15, CARD 8, TLR2, TLR 8 and JAK3, wherein the TLR8 locus is H3 and comprises SEQ ID NOs: 23-31. In other embodiments, the risk variants located at the: NOD2 locus are R702W, G908R and 1007insC and comprise SEQ ID NO: 18, 19 and 20, respectively, CARD15 locus are R675W, G881R and 3020insC and comprise SEQ ID NO: 18, 19 and 20, respectively, CARD8 locus is T10C and comprises SEQ ID NO: 36, TLR8 locus is H3 and comprises SEQ ID NOs: 23-31, TLR2 locus is P631H and comprises SEQ ID NO: 33, and JAK3 comprises SEQ ID NO: 37, SEQ ID NO: 38, or a combination thereof. In other embodiments, the subject is diagnosed with IBD if the subject expresses any one or more of (i) NOD2, CARD15, CARD 8, TLR8, TLR2, JAK3 risk variants or a combination thereof or if the subject expresses any one or more of (ii) anti-Cbir1 antibody, pANCA, anti-OmpC, ASCA, anti-I2 serological risk factors or a combination thereof or (iii) if the subject expresses the combination of (i) and (ii).

In yet other embodiments, TLR8 comprises a protective variant and the protective variant located at the TLR8 locus is H2 and comprises SEQ ID NOs: 23-31. In other embodiments, the therapy selected for a subject with IBD is an antigen-directed therapy. In other embodiments, the antigen-directed therapy targets Cbir-1 flagellin or an immunoreactive fragment thereof. In other embodiments, the therapy consists of manipulation of bacteria in the colon and/or small intestine. In other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In yet other embodiments, the detection of risk variants, risk serological factors and protective variants is relative to that detected in a healthy subject. In other embodiments, the presence of twelve risk haplotypes presents a greater susceptibility than the presence of eleven, ten, nine, eight, seven, six, five, four, three, two, one or none of the risk haplotypes, and the presence of eleven risk haplotypes presents a greater susceptibility than the presence of ten, nine, eight, seven, six, five, four, three, two, one or none of the risk haplotypes, wherein the presence of ten risk haplotypes presents a greater susceptibility than the presence of nine, eight, seven, six, five, four, three, two, one or none of the risk haplotypes, and the presence of nine risk haplotypes presents a greater susceptibility than the presence of eight, seven, six, five, four, three, two, one or none of the risk haplotypes, and the presence of eight risk haplotypes presents a greater susceptibility than the presence of seven, six, five, four, three, two, one or none of the risk haplotypes, and the presence of seven risk haplotypes presents a greater susceptibility than the presence of six, five, four, three, two, one or none of the risk haplotypes, and the presence of six risk haplotypes presents a greater susceptibility than the presence of five, four, three, two, one or none of the risk haplotypes, and the presence of five risk haplotypes presents a greater susceptibility than the presence of four, three, two, one or none of the risk haplotypes, and the presence of four risk haplotypes presents a greater susceptibility than the presence of three, two, one or none of the risk haplotypes, and the presence of three risk haplotypes presents a greater susceptibility than the presence of two, one or none of the risk haplotypes, and the presence of two risk haplotypes presents a greater susceptibility than the presence of one or none of the risk haplotypes, and the presence of one risk haplotype presents a greater susceptibility than the presence of none of the risk haplotypes.

Various other embodiments of the present invention also provide for a method of diagnosing susceptibility to IBD in a female subject comprising: providing a sample from the female subject; assaying the sample to detect the risk and/or protective variants of TLR8, wherein TLR8 H3 is the risk variant and TLR8 H2 is the protective variant; and determining that the female subject has increased susceptibility to IBD if the TLR8 H3 risk variant is present and/or the TLR8 H2 protective variant is absent or determining that the subject has a decreased susceptibility to IBD if the TLR8 H2 protective variant is present and/or the TLR8 H3 risk variant is absent. In other embodiments, IBD comprises Crohn's Disease (CD) and ulcerative colitis (UC). In other embodiments, there is a greater susceptibility to IBD when an increased number of risk variants and a decreased number of protective variants are present and a decreased susceptibility when an increased number of protective variants and a decreased number of risk variants are present. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of risk variants and protective variants is relative to that detected in a healthy subject.

Various other embodiments of the present invention also provide for a method of diagnosing susceptibility to IBD in a Jewish subject comprising: providing a sample from the Jewish subject; assaying the sample to detect the TLR2 risk variant, wherein P631H is the risk variant at the TLR2 locus; and determining that the Jewish subject has increased susceptibility to IBD if the P631H risk variant is present or determining that the subject has a decreased susceptibility to IBD if the P631H risk variant is absent. In other embodiments, the P631H risk variant comprises SEQ ID NO: 33. In other embodiments, IBD comprises Crohn's Disease (CD) and ulcerative colitis (UC). In other embodiments, there is a greater susceptibility to IBD when an increased number of risk variants and a decreased number of protective variants are present and a decreased susceptibility when an increased number of protective variants and a decreased number of risk variants are present. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE). In other embodiments, the detection of the risk variants is relative to that detected in a healthy subject.

Various embodiments of the present invention also provide for a method of diagnosing susceptibility to IBD in a pediatric subject comprising: providing a sample from the pediatric subject; assaying the sample to detect the NOD2 and/or CARD15 risk variants; optionally, assaying the sample to detect risk serological factors selected from the group consisting of: anti-CBir1, pANCA, anti-OmpC, ASCA and anti-I2; and determining that the pediatric subject has increased susceptibility to IBD if one or more risk variants and/or risk serological factors are present or determining that the subject has a decreased susceptibility to IBD if the risk variants and/or risk serological factors are absent. In other embodiments, the risk variants at the NOD2 locus are R702W, G908R and 1007insC and comprise SEQ ID NO: 18, 19 and 20, respectively, and at the CARD15 locus are R675W, G881R and 3020insC and comprise SEQ ID NO: 18, 19 and 20, respectively. In other embodiments, IBD comprises Crohn's disease (CD) and ulcerative colitis (UC). In other embodiments, the detection of the NOD2 and/or CARD15 risk variants and/or risk serological factors in a pediatric subject indicates an IBD diagnosis associated with a subtype of CD. In other embodiments, a subtype of Crohn's disease comprises aggressive complicating phenotype, small bowel disease phenotype, internal penetrating and/or fibrostenosing disease phenotype. In other embodiments, there is a greater susceptibility to IBD when an increased number of risk variants and/or risk serological factors and a decreased number of protective variants are present and a decreased susceptibility when an increased number of protective variants and a decreased number of risk variants are present. In other embodiments, the detection of risk serological factors comprises using a technique selected from the group consisting of Northern blot, reverse transcription-polymerase chain reaction (RT-PCR), enzyme-linked immunosorbant assay (ELISA), sodium dodecyl sulfate polyacrylamide gel electrophoresis (SDS-PAGE), Western Blot and mass spectrometric analysis. In other embodiments, the detection of risk variants comprises using a technique selected from the group consisting of allelic discrimination assay, sequence analysis, allele-specific oligonucleotide hybridization assay, heteroplex mobility assay (HMA), single strand conformational polymorphism (SSCP) and denaturing gradient gel electrophoresis (DGGE).

In other embodiments, the detection of risk variants, risk serological factors and protective variants is relative to that detected in a healthy subject.

Variety of Methods and Materials

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of an IL23R variant allele. In a TaqmanB allelic discrimination assay, a specific, fluorescent, dye-labeled probe for each allele is constructed. The probes contain different fluorescent reporter dyes such as FAM and VIC™ to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature, "Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of an IL23R variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD in an individual may be practiced using one or any combination of the well known assays described above or another art-recognized genetic assay.

There are many techniques readily available in the field for detecting the presence or absence of antibodies, polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate antibodies or protein biomarkers. For example, a biomarker and/or antibody may be captured using biospecific capture reagents, such as aptamers or other antibodies that recognize the antibody and/or protein biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides and antibodies may be detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, antibodies and/or biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Chronic intestinal inflammation, as seen in inflammatory bowel disease (IBD), results from an aberrant and poorly understood mucosal immune response to the microbiota of the gastrointestinal tract in genetically susceptible individuals. Serological expression cloning to identify commensal bacterial proteins that could contribute to the pathogenesis of IBD was used. The dominant antigens identified were flagellins, molecules known to activate innate immunity via Toll-like receptor 5 (TLR5), and critical targets of the acquired immune system in host defense. Multiple strains of colitic mice had elevated serum anti-flagellin IgG2a responses and Th1 T cell responses to flagellin. In addition, flagellin-specific CD4$^+$ T cells induced severe colitis when adoptively transferred into naive SCID mice. Serum IgG to these flagellins, but not to the dissimilar *Salmonella muenchen* flagellin, was elevated in patients with Crohn's disease, but not in patients with ulcerative colitis or in controls. These results identify flagellins as a class of immunodominant antigens that stimulate pathogenic intestinal immune reactions in genetically diverse hosts and suggest new avenues for the diagnosis and antigen-directed therapy of patients with IBD.

A molecular technique known as serological expression cloning (SEC) was used to identify specific bacterial antigens driving experimental IBD. SEC involves the screening of DNA expression libraries in lambda phage with defined antisera.

Molecular cloning of antigens by SEC using sera from colitic C3H/HeJBir mice is described. The dominant antigens identified were a family of related, novel flagellins. Strong reactivity against specific flagellins was seen in multiple models of experimental colitis across several distinct MHC haplotypes. There was a clear IgG2a predominance to the anti-flagellin response, suggesting a concurrent Th1-biased T cell response against flagellin. Indeed, marked reactivity against flagellin was seen in mesenteric and splenic T cell cultures from colitic animals, and flagellin-specific T cells were able to induce colitis when adoptively transferred into immunodeficient animals. Surprisingly, the reactivity against these flagellins (but not against the dissimilar *Salmonella* flagellin) was also seen in human IBD sera, with significant reactivity in patients with CD but not UC or control patients.

Using an unbiased molecular screen to search for bacterial antigens relevant to IBD, the dominant antigens identified were a family of related, novel flagellins. A strong, IgG2a-biased serological response to these specific flagellins was seen in multiple models of experimental colitis across several distinct MHC haplotypes. In addition, marked reactivity against these flagellins was seen at the T cell level, and flagellin-specific T cells were able to induce colitis when adoptively transferred into immunodeficient animals. Interestingly, while these flagellins were identified from mouse cecal bacteria, there was clear, specific reactivity against these molecules in patients with CD (but not in patients with UC or in NCs).

It has been observed that full-length flagellin Fla-X (endotoxin free) is capable of stimulating TNF-α production by human macrophages in vitro (M. J. Lodes and R. M. Hershberg). It is tempting to speculate that the intrinsic "adjuvanticity" of flagellin is likely to contribute to its antigenicity. While flagellin molecules clearly have the capacity to stimulate the production of proinflammatory cytokines via TLR5, and while not wishing to be bound to any particular theory, it is believed that the B and T cell responses to flagellin contribute more directly to the chronic intestinal inflammation seen in IBD.

Figure 1:
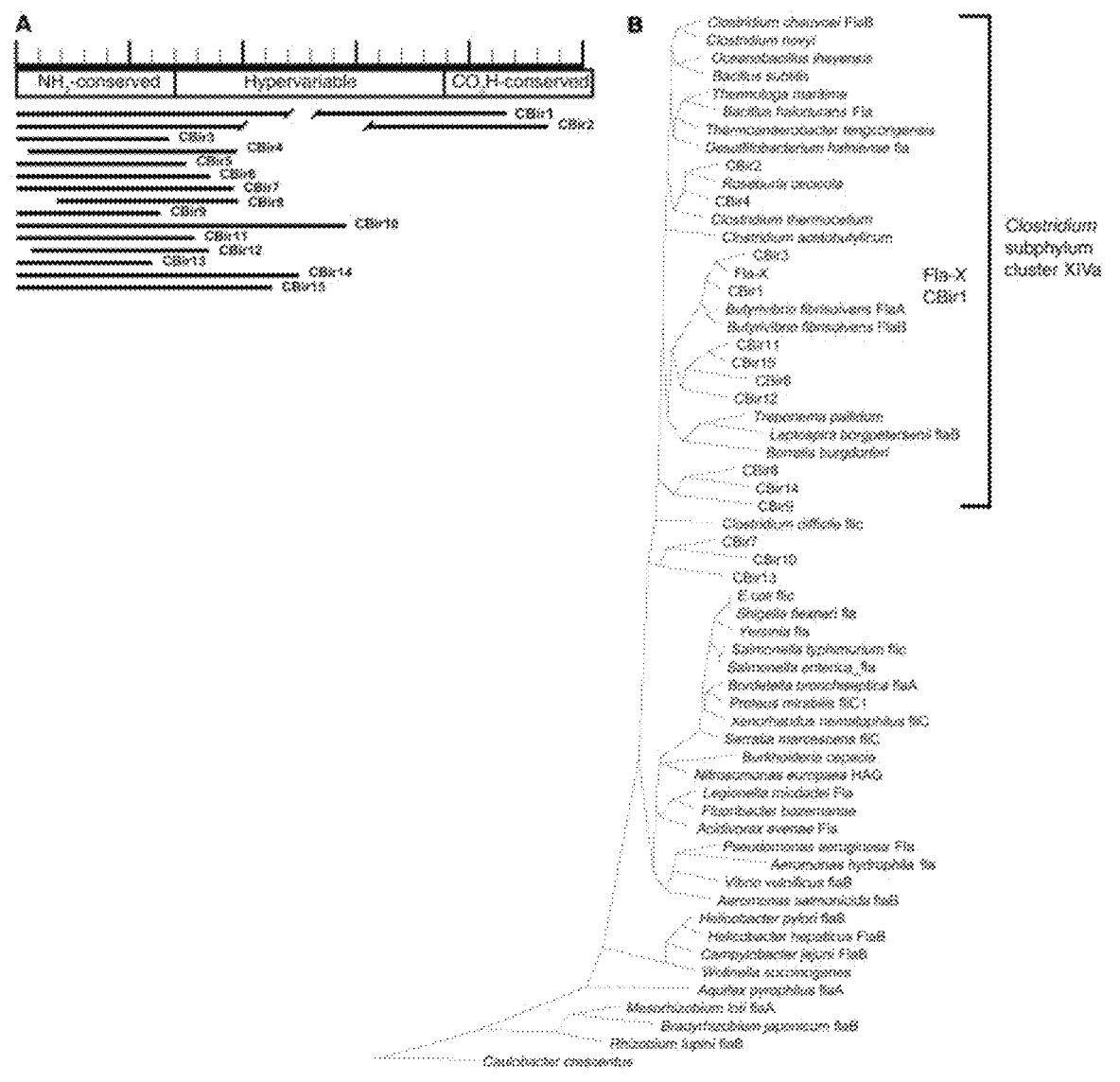
Figure 6:
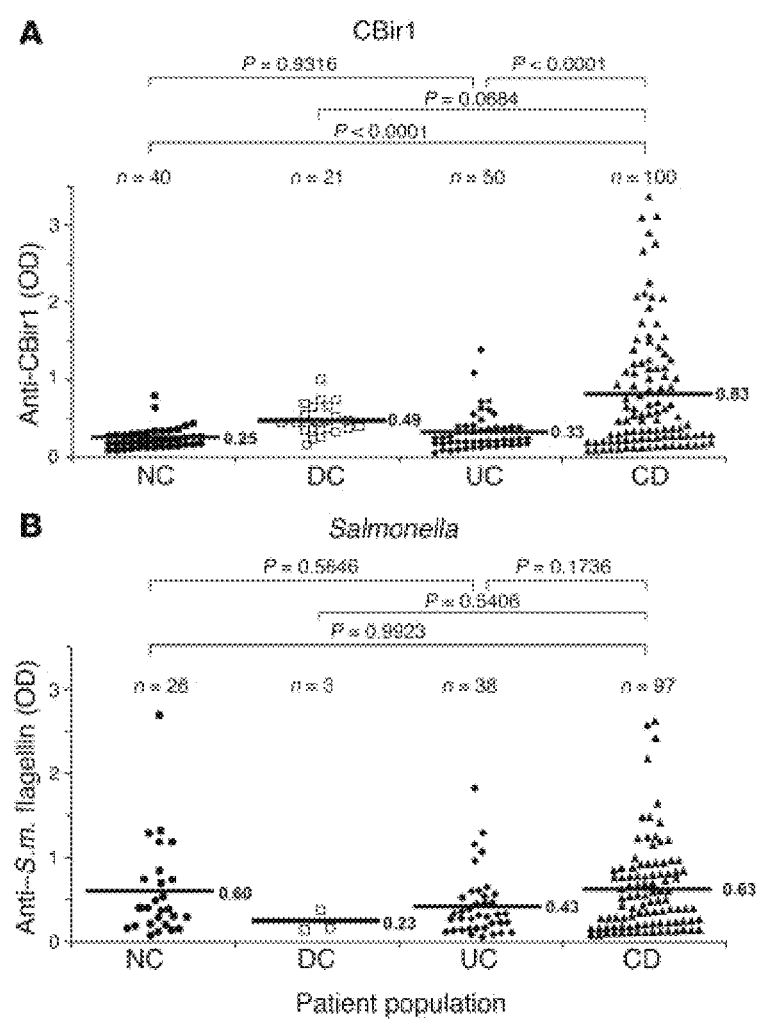
FIG. 6 depicts the association of anti-flagellin antibodies with human IBDs, in accordance with an embodiment of the present invention. Human sera, well characterized for CD and UC, were tested by ELISA for reactivity to flagellin CBir1 (A) and *Salmonella muenchen* (S.m.) flagellin (B). Statistical analysis was performed with the Tukey-Kramer test; the resulting statistics (P values) as well as population size (n) are shown above the graphs. Mean $OD_{450}$ values are indicated by horizontal bars.

The clinical data (FIG. 6) are consistent with the fact that the aberrant response in patients with CD is specific to the subgroup of flagellins identified in the inventive molecular screen. Specifically, there was no correlation between IBD and a response to flagellin from *Salmonella muenchen*, which is very similar (84-91%) in the NH$_2$ conserved region to the flagellin from the commensal organism *Escherichia coli*. It must be emphasized that the flagellins identified were from a source of material devoid of known bacterial pathogens. The bacteria with genes that "encode" the flagellins CBir1 and Fla-X (the two dominant flagellins tested) are unknown; however, preliminary phylogenetic data suggest that these flagellins are most closely related to the flagellins of bacteria in the genera *Butyrivibrio, Rosburia, Thermotoga*, and *Clostridium* and fall within the *Clostridium* subphylum XIVa cluster of Gram-positive bacteria (FIG. 1B). While not wishing to be bound to any particular theory, it is believed that the aberrant response to the flagellin molecule (s) from these organisms is related to a combination of the intrinsic property of the molecules themselves (as immunogens and adjuvants) and an underlying genetic susceptibility. Using monoclonal antibodies directed against CBir1, the inventors have demonstrated that this antigen is present in the stool of wild-type strains (FVB, C57BL/6, BALB/c, and C3H/HeJ) and colitic strains (mdr1a$^{-/-}$, B6.IL-10$^{-/-}$, and C3H/HeJBir). These data indicate that the presence of the antigen itself does not strictly correlate with colitis. Still, the widespread presence of these antigens does not preclude the possibility of enhanced colonization of organisms expressing these flagellins in CD lesions.

In general, the data are consistent with the belief that IBD is associated with a defect in tolerance to commensal organisms (Duchmann R, et al. Tolerance exists towards resident intestinal flora but is broken in active inflammatory bowel disease. *Clin. Exp. Immunol.* 1995; 102:448-455.). The IgG2a-biased antibody against Fla-X and CBir1 highlights the Th1 bias of the T cell responses seen. The broad recognition of these flagellins in several different mouse models and in humans with CD indicates that these flagellins are among the immunodominant antigens of the microbiota. However, the exact role of these flagellins in the pathogenesis of IBD (e.g., whether they are predominant or obligatory for disease) compared with that of other microbial antigens remains to be defined. While not wishing to be bound to any particular theory, it is believed that a T cell regulatory response to specific flagellins (and/or other bacterial antigens) may be selectively impaired in IBD. In this context, specific flagellin molecules may represent novel targets for antigen-directed therapy in IBD.

As observed with the specific flagellins identified here, only a subset of patients with CD show specific seroreactivity against 12 (an antigen derived from *Pseudomonas fluorescens*).

Antibody responses to certain microbial antigens define heterogeneous groups of Crohn's patients; multiple and high-level responses to these antigens are associated with aggressive clinical phenotypes. The flagellin, CBir1, identified by the inventors in the C3H/HeJBir mouse model, is a dominant antigen capable of inducing colitis in mice and eliciting antibody responses in a subpopulation of patients with Crohn's disease. Serum response to CBir1 flagellin in Crohn's disease patients was evaluated and compared to previously defined responses to oligomannan (ASCA), 12, OmpC and neutrophil nuclear autoantigens (pANCA), and to determine anti-CBir1 associated phenotypes.

It was found that the presence and level of IgG anti-CBir1 were associated with Crohn's disease, independently. Anti-CBir1 was present in all antibody subgroups and expression increases in parallel with increases in the number of antibody responses. pANCA+ Crohn's patients were more reactive to CBir1 than were pANCA+ ulcerative colitis patients. Anti-CBir1 expression is independently associated with small bowel, internal-penetrating and fibrostenosing disease features.

Thus, serum responses to CBir1 independently identify a unique subset of patients with complicated Crohn's disease. This is the first bacterial antigen identified in a murine model with a similar pattern of aberrant reactivity in a subset of Crohn's disease patients.

Serologic expression cloning was used to identify an immunodominant antigen, CBir1 flagellin, to which strong B cell and CD4+ T cell responses occur in colitic mice. Transfer of CBir1 specific CD4+ Th1 T cells to C3H/SCID mice generated a severe colitis dependent on endogenous expression of CBir1 flagellin in the cecum and colon. These findings prove that CBir1 flagellin is an immunodominant antigen of the enteric microbial flora. Of note, approximately 50% of patients with CD had serum reactivity to CBir1, whereas patients with ulcerative colitis, patients with other inflammatory GI diseases, and control subjects had little or no reactivity to this flagellin. The inventors determined the relationship of serum reactivity to CBir1 and the previously defined responses to oligomannan (ASCA), OmpC, 12 and pANCA in patients with CD and to define distinct clinical phenotypes. Results show that antibodies to CBir1 are independently associated with CD, have no correlation to levels of previously defined antibodies, are expressed in ASCA-negative and pANCA+ CD patients and are independently associated with aspects of complicated CD.

Investigations have yielded compelling evidence that serum antibody to CBir1 flagellin, marks for an independent subset of patients with CD. It is shown that the level of response can vary widely, that these responses are relatively stable over time and do not correspond with active or remission disease states. It is believed that anti-CBir1 expression is independent of serologic responses to previously defined bacterial antigens and is independently associated with complicated CD. It is also the first antigen to be discovered with a role as ligand for activation of the innate immune response via Toll-like receptors and a strong immunogen for adaptive immunity. This dual effect provides a focus for investigations of the role of anti-CBir1 in the pathogenesis of this subset of patients with CD.

It has been previously shown that groups of patients with unique disease characteristics can be distinguished by the presence and level of serum antibodies to one, two or all of the following antigens: oligomannan (ASCA); the novel Crohn's related bacterial sequence, 12; and *E. coli* outer-membrane porin-C(OmpC). While each of these reactivities may serve to subclassify phenotypes within CD, none of them have yet been shown to have any direct pathophysiologic significance. The dominant serologic immune response to CBir1 flagellin was found by serologic expression cloning using sera from colitic mice to screen a DNA phage library derived from mouse cecal bacteria. CBir1 flagellin was then used to generate a specific CD4+ Th1 cell line. Transfer of this Th1 cell line into SCID mice induced a colitis due to reactivity to endogenous CBir1 flagellin in the microbial flora indicating that CBir1 is an immunodominant antigen in mouse colitis. CBir1 is the first bacterial antigen capable of inducing colitis in animals that demonstrates a similar aberrant immune response in patients with CD.

Interesting findings resulted from the examination of the relationship of anti-CBir1 to the previously defined antibodies to microbial antigens in patients with CD. The level of response to CBir1 is greater in patients who have increasing levels of reactivity to ASCA, OmpC, and 12 (with a peak occurring in those who respond to all three), which is consistent with the concept that this subset of patients has a propensity to respond to multiple bacterial antigens. However, high CBir1 reactivity was seen across all antibody-defined subsets, which is consistent with it being independent of the other antibody responses.

The data presented herein show that the serotypic and phenotypic associations with anti-CBir1 expression, (small bowel, internal penetrating, and fibrostenosing disease) differ from those associated with any or a combination of responses to 12, OmpC, oligomannan, or neutrophil nuclear antibodies. The lack of relationship to small bowel surgery and to ulcerative colitis-like suggest that to define the true phenotype associated with this antibody response may require further more precise clinical groupings.

Another seroreactivity that defines a subgroup of patients is pANCA, which is predominantly associated with ulcerative colitis and may reflect cross reactivity to bacteria (Seibold F, Brandwein S, Simpson S, Terhorst C, Elson C O. pANCA represents a cross-reactivity to enteric bacterial antigens. J Clin Immunol 1998; 18:153-60.); however, there is a subset of patients with CD who also express pANCA (Vasiliauskas E A, Plevy S E, Landers C J, Binder S W, Ferguson D M, Yang H, Rotter J I, Vidrich A, Targan S R. Perinuclear antineutrophil cytoplasmic antibodies in patients with Crohn's disease define a clinical subgroup. Gastroenterology 1996; 110:1810-9. Vasiliauskas E A, Kam L Y, Karp L C, Gaiennie J, Yang H, Targan S R. Marker antibody expression stratifies Crohn's disease into immunologically homogeneous subgroups with distinct clinical characteristics. Gut 2000; 47:487-96.). pANCA+ CD patients have both colitic and left-sided disease with features similar to ulcerative colitis. Among the population of CD patients who express pANCA but do not react to the other known antigens, 40-44% expressed anti-CBir1, while anti-CBir1 expression was found in only 4% of pANCA+ ulcerative colitis patients. Because anti-CBir1 expression appears to be associated with a specific CD subtype, it may prove to be useful in distinguishing among patients with indeterminate colitis; i.e, those that may be more Crohn's-like compared to those that may be more ulcerative colitis-like. Used in combination with pANCA, anti-CBir1 expression may also be used diagnose a subset of patients with colitic and/or colitic and small bowel disease, perhaps defining those patients potentially likely to respond to manipulation of bacteria using either antibiotics or probiotics.

The expression of antibodies to CBir1 is indicative of an adaptive immune response to this antigen. Antibody reactivity to flagellin may provide an important tool to define potential differences in pathophysiologic immune mechanisms in innate and adaptive immunity in a subset of patients with CD. Anti-CBir expression defines a subgroup of CD patients not previously recognized by other serologic responses and is independently associated with aspects of the complicated CD phenotype. These results represent the first example of discovery from animal models having direct correlates in human disease.

Isolation of Genomic DNA of Mouse Cecal Bacterium

Pelleted bacteria from C3H/HeJBir mouse ceca were inactivated at 80° C. for 20 minutes and then were treated with 2 ml lysozyme (20 mg/ml in Tris-EDTA [TE] buffer) for 1 hour at 37° C. This solution was rocked at room temperature for 10 minutes with 40 µl proteinase K (10 mg/ml) and 140 µl 20% SDS (Sigma-Aldrich, St. Louis, Missouri, USA) and then incubated for 15 minutes at 65° C., then 0.4 ml of 5 M NaCl and 0.32 ml of a 10% cetyltrimethylammonium bromide (CTAB) solution (1 g CTAB [Sigma-Aldrich], 1.4 ml 5M NaCl, and 8.6 ml distilled $H_2O$) was added, followed by incubation at 65° C. for 10 minutes. DNA was then extracted twice with phenol, followed by extraction with phenol/chloroform/isoamyl alcohol (24:24:2), and then with chloroform. Finally the DNA was precipitated with 0.6 volumes of isopropanol and resuspended in TE buffer.

Genomic Expression Library Construction

A detailed description of library construction can be found in the following references: Lodes, M. J., Dillon, D. C., Houghton, R. L., and Skeiky, Y. A. W. 2004. Expression cloning. In Molecular diagnosis of infectious diseases. 2nd edition. J. Walker, series editor; J. Decker and U. Reischl, volume editors. Humana Press. Totowa, New Jersey, USA. 91-106. Briefly, 20 of genomic DNA of mouse cecal bacterium was resuspended in 400 µl of TE buffer and was sonicated for five seconds at 30% continuous power with a Sonic Dismembrator (Fisher Scientific, Pittsburgh, Pennsylvania, USA) to generate fragments of approximately 0.5-5.0 kb. DNA fragments were blunted with T4 DNA polymerase (Invitrogen, Carlsbad, California, USA) and were ligated to EcoRI adaptors (Stratagene, La Jolla, California, USA) with T4 DNA ligase (Stratagene). Adapted inserts were then phosphorylated with T4 polynucleotide kinase (Stratagene) and were selected by size with a Sephacryl 400-HR column (Sigma-Aldrich). Approximately 0.25 µg of insert was ligated to 1.0 µg Lambda ZAP Express Vector treated with EcoRI and calf intestinal alkaline phosphatase (Stratagene), and the ligation mix was packaged with Gigapack III Gold packaging extract (Stratagene) following the manufacturer's instructions.

Expression Screening

Immunoreactive proteins were screened from approximately $6 \times 10^5$ plaque-forming units (PFU) of the unamplified cecal bacterium expression lambda library. Briefly, twenty 150-mm petri dishes were plated with *E. coli* XL1-Blue MRF' host cells (Stratagene) and approximately $3 \times 10^4$ PFU of the unamplified library and were incubated at 42° C. until plaques formed. Dry nitrocellulose filters (Schleicher and Schuell, Keene, New Hampshire, USA), pre-wet with 10 mM isopropyl β-thiogalactopyranoside (IPTG), were placed on the plates, which were then incubated overnight at 37° C. Filters were removed and washed three times with PBS containing 0.1% Tween 20 (PBST) (Sigma-Aldrich), blocked with 1.0% BSA (Sigma-Aldrich) in PBST, and washed three times with PBST. Filters were next incubated overnight with *E. coli* lysate— adsorbed C3H/HeJ Bir mouse serum (1:200 dilution in PBST), washed three times with PBST, and incubated with a goat anti-mouse IgG+IgA+IgM (heavy and light chain) alkaline phosphatase—conjugated secondary antibody (diluted 1:10,000 with PBST; Jackson Laboratories, West Grove, Pennsylvania, USA) for 1 hour. Filters were finally washed three times with PBST and two times with alkaline phosphatase buffer (pH 9.5) and were developed with nitroblue tetrazolium chloride/5-bromo-4-chloro-3-indolylphosphate p-toluidine salt (Invitrogen). Reactive plaques were then isolated and a second or third plaque purification was performed. Excision of phagemid followed the Stratagene Lambda ZAP Express protocol, and the resulting plasmid DNA was sequenced with an automated sequencer (ABI, Foster City, California, USA) using M13 forward, reverse, and sequence-specific internal DNA sequencing primers. Nucleic acid and predicted protein sequences were used to search the GenBank nucleotide and translated databases. Protein analysis was performed with the PSORT program (National Institute for Basic Biology, Okazaki, Japan) and with the IDENTIFY program of EMOTIF (Department of Biochemistry, Stanford University). Sequence alignments were produced with the MegAlign program (Clustal) of DNAStar (Madison, Wisconsin, USA). Note that 20 random clones from the lambda library were picked and sequenced prior to serolological expression cloning. None of the 20 were found to be derived from mouse DNA and no flagellins were identified.

Cloning of Full-Length Flagellins Representing Clones CBir1 and Fla-X

Clone CBir1 contains the conserved $NH_2$ and variable regions of an unknown immunoreactive flagellin. The full-length sequence was obtained by first amplifying the unknown CBir1 carboxy terminus from total genomic cecal bacterium DNA with Expand polymerase (Roche, Indianapolis, Indiana, USA) and the primers CBir1var1 (designed from the variable region of CBir1; CACAATCACAA-CATCTACCCAG; SEQ ID NO: 1) and CBir1 Carb Z (designed from the carboxy terminus of the related flagellin B of *Butyrivibrio* fibrisolvens, GenBank accession number AF026812; 5'-TTACTGTAAGAGCTGAAGTA-CACCCTG-3; SEQ ID NO: 2). This PCR product was cloned with a Zero Blunt TOPO PCR Cloning Kit (Invitrogen), digested with EcoRI, and gel-isolated (carboxy end of CBir1). Clone CBir1 plasmid DNA, which represents the $NH_2$ terminus plus flagellin central variable region and overlaps with the cloned carboxy region, was digested with ScaI and then gel-isolated. Both overlapping (181-bp) DNA fragments (approximately 20 ng each) were added to a PCR reaction with the primers CBir1 HIS and CBir1 TERMX (see below), and the amplification product was cloned and expressed as described below.

Fla-X is an immunoreactive full-length flagellin sequence with no known identity in the public databases. Full-length flagellin Fla-X was cloned from total cecal bacterium genomic DNA by PCR amplification with the primers CBir Fla-X HIS (5'-CAATTACATATGCATCACCATCACCAT-CACGTAGTACAGCACAATC-3; SEQ ID NO: 3) and CBir1 TERMX (5'-ATAGACTAAGCT-TACTGTAAGAGCTGAAGTACACCCTG-3; SEQ ID NO: 4), and was expressed as described below. The amplification product was cloned with a Zero Blunt TOPO PCR Cloning Kit (Invitrogen), and several clones were sequenced.

Recombinant Protein

Recombinant *Salmonella* muenchen flagellin (≥95% pure by SDS-PAGE) was obtained from Calbiochem (La Jolla, California, USA). Expression of other recombinant flagellin proteins and deletion constructs was accomplished by amplification from the cloned plasmid or genomic DNA (full length Fla-X) with Pfu polymerase (Stratagene) and the following primer pairs: for full-length CBir1, CBir1 HIS (5'-CAATTACATATGCATCACCATCACCAT-CACGTAGTACAGCACAATTTACAGGC-3; SEQ ID NO: 5) and CBir1 TERMX (5'-ATAGACTAAGCT-TACTGTAAGAGCTGAAGTACACCCTG-3; SEQ ID NO: 6); for the CBir1 $NH_2$ plus variable regions, CBir1 HIS and CBir1 AV TERM (5'-ATAGACTAAGCT-TAAGAAACCTTCTTGATAGCGCCAG-3; SEQ ID NO: 7); for the CBir1 $NH_2$ terminus, CBir1 HIS and CBir1 A TERM (5'-TAGACTGAATTCTAGTCCATAGCGT-CAACGTTCTTTGTGTC-3; SEQ ID NO: 8); for the CBir1 carboxy terminus, CBir1 C HIS (5'-CAATTACATATGCA TCACCATCACCATCACAAGATGAACTTC-CATGTAGGTGC-3; SEQ ID NO: 9) and CBir1 TERMX; for full-length Fla-X, CBir Fla-X HIS (5'-CAATTA- CATATGCATCACCATCACCATCACGTAGTA-CAGCACAATC-3; SEQ ID NO: 10) and CBir1 TERMX (ATAGACTAAGCTTACTGTAAGAGCTGAAGTA-CACCCTG-3; SEQ ID NO: 11); for the Fla-X $NH_2$ plus variable regions, Fla-X HIS (5'-CAATTACATATGCAT-CACCATCACCATCACGTAGTACAGCACAATCT-TAGAGC-3; SEQ ID NO: 12) and Fla-X AV TERM (5'-ATAGACTAAGCTTAGAGGCTGAAATCAATGTCCTCG-3; SEQ ID NO: 13); for the Fla-X $NH_2$ terminus, Fla-X HIS and Fla-X A TERM (5'-ATAGACTAAGCTTAATGTGCT-GAAAGATATCTTGTCAC-3; SEQ ID NO: 14); and for the Fla-X carboxy terminus, Fla-X C HIS (5'-CAATTA-CATATGCATCACCATCACCATCACTTCAGCCTC-CATGTAGGTGCAGATGC-3; SEQ ID NO: 15) and CBir1 TERMX. Primers contained restriction sites for cloning (in bold) and a six-histidine tag (in italics) for protein purification ($NH_2$ terminus). The amplification products were digested with the restriction enzymes NdeI and HindIII or EcoRI, depending on the primer set used, gel-isolated, and ligated to a pET 17b plasmid vector (Novagen, Madison, Wisconsin, USA) previously cut with NdeI and with HindIII or EcoRI and dephosphorylated with alkaline phosphatase (MB grade; Roche). The ligation mix was transformed into XL1 Blue competent cells (Stratagene) and plasmid DNA was prepared for sequencing (Qiagen, Valencia, California, USA). Recombinant protein was expressed by transformation of plasmid DNA into BL21 pLysS competent cells (Novagen) and induction of a single-colony cell culture with 2 mM IPTG (Sigma-Aldrich). Recombinant protein was recovered from cell lysate with nickel-nitrilotriacetic acid agarose beads (Qiagen), following the manufacturer's instructions, and was dialyzed in 10 mM Tris, pH 4-11 depending on predicted recombinant pI characteristics. Recombinant proteins were "quality-checked" for purity by SDS-PAGE followed by staining with Coomassie blue and by $NH_2$-terminal protein sequencing, and were quantified with a Micro BCA assay (Pierce, Rockford, Illinois, USA). Recombinants were assayed for endotoxin contamination with the Limulus assay (Bio Whittaker, Walkersville, Maryland, USA). Production of the *Mycobacterium tuberculosis* 38-kDa protein has been described previously (Lodes M J, et al. Serodiagnosis of human granulocytic ehrlichiosis by using novel combinations of immunoreactive recombinant proteins. *J. Clin. Microbiol.* 2001; 39:2466-2476.).

ELISA

Ninety-six-well EIA/RIA microtiter plates (3369; Corning Costar, Cambridge, Massachusetts, USA) were coated overnight at 4° C. with 100 ng/well of the recombinant proteins. Solutions were then aspirated from the plates, which were then blocked for 2 hours at room temperature with PBS containing 1% (weight/volume) BSA. This was followed by washing in PBST. Serum diluted in PBS containing 0.1% BSA was added to wells and incubated for 30 minutes at room temperature, followed by washing six times with PBST and then incubation with secondary antibody—HRP conjugate (1:10,000 dilution) for 30 minutes. Plates were then washed six times in PBST and then were incubated with tetramethylbenzidine (TMB) substrate (Kirkegaard and Perry, Gaithersburg, Maryland, USA) for 15 minutes. The reaction was stopped by the addition of 1 N sulfuric acid, and plates were "read" at 450 nm using an ELISA plate reader (Biotek instrument EL311, Hyland Park VA). Background values were determined by reading of reactions that lacked the primary antibody step.

Western Blot Analysis

Recombinant antigens (50-200 ng/lane) were subjected to SDS-PAGE analysis using 15% polyacrylamide "minigels." The antigens were transferred to nitrocellulose BA-85 (Schleicher & Schuell, Keene, New Hampshire, USA) and were blocked for 1 hour at room temperature with PBS containing 1% Tween 20. Blots were then washed three times, 10 minutes each wash, in PBST. Next, blots were probed for 1 hour at room temperature with serum diluted 1:500 in PBST followed by washing three times, 10 minutes each wash, in PBST. Blots were then incubated for 30 minutes at room temperature with secondary antibody—HRP diluted 1:10,000 in wash buffer and were again washed three times for 10 minutes each wash in PBST containing 0.5 M sodium chloride. Finally, blots were incubated in chemiluminescent substrate for ECL (Amersham Plc, Little Charlton, UK) for about 1 minute and then were exposed to X-ray film (XARS) for 10-60 seconds, as required.

$CD4^+$ T Cell Isolation and Culture, and Generation of a Cbir1-Specific T Cell Line $CD4^+$ T cells were isolated from mesenteric lymph nodes (MLNs) of mice with BD IMAG anti-mouse CD4 beads according to the manufacturer's instructions (BD Biosciences Pharmingen, San Diego, California, USA). Briefly, MLN cells were labeled with anti-CD4 beads and then were placed within the magnetic field of the BD Imagnet. The unlabeled cells in suspension were removed and the cells binding to beads were washed and used in the $CD4^+$ T cell culture. More than 99% of cells were $CD4^+$, as shown by flow cytometry. For the generation of a T cell line reactive to CBir1, $CD4^+$ T cells were isolated from MLNs of C3H/HeJBir mice as described above and were cultured with splenic APCs that were pulsed with CBir1 (100 mg/ml) overnight. The cells were restimulated every 10-14 days.

Antigen-Specific Proliferation of T Cells

Spleen and MLN $CD4^+$ T cells, isolated as described above, or a CBir1 flagellin—specific T cell line ($4\times10^5$ cells/well) were incubated in triplicate in the presence of antigen-pulsed, irradiated APCs ($4\times10^5$ cells per well; treated with 1-100 µg/ml antigen for 18 hours at 37° C.) in 96-well flat-bottomed tissue culture plates (Falcon, Lincoln Park, New Jersey, USA) at 37° C. in 5% $CO_2$ humidified air. [$^3$H]thymidine (0.5 (New England Nuclear, Boston, Massachusetts, USA) was added at day 3 of culture and the cells were harvested at 16 hours after the pulse. The cells were harvested on glass fiber filters on a PHD cell harvester (Cambridge Technology Inc., Watertown, Massachusetts, USA), washed with distilled water, and dried. Proliferation was assessed as the amount of incorporation of [$^3$H]thymidine into cell DNA, as measured by beta scintillation counting (Beckman Instruments, Palo Alto, California, USA) of the harvested samples, and was expressed as cpm±SD. The preparation of epithelial cell proteins and food antigens has been described previously (Cong Y, et al. CD4+ T cells reactive to enteric bacterial antigens in spontaneously colitic C3H/HeJBir mice: increased T helper cell Type 1 response and ability to transfer disease. *J. Exp. Med.* 1998; 187:855-864.). Ethical approval for animal studies was obtained from the Institutional Animal Care and Use Committee at the University of Alabama (Birmingham, Alabama) and from Corixa Corporation.

Specificity of $CD4^+$ T Cell Stimulation

APCs were BALB/c spleen cells that were pulsed for 24 hours with nothing, OVA peptide at 2 µg/ml, CBir1 at 100 µg/ml, or Fla-X at 100 µg/ml, alone or in combinations as shown in Table 5. These APCs were washed and irradiated with 3,000 rads prior to culture. $CD4^+$ T cells were isolated from DO11.10 mice and were cultured at a density of $1\times10^5$ with $4\times10^5$ prepulsed APCs. [$^3$H]TdR was added at day 3 of culture and the cells were harvested after 16 hours.

Adoptive Transfer

CD4+ T cells were cultured with cecal bacterial antigen—pulsed and irradiated C3H/HeJ splenic cells in complete medium at 37° C. for 4 days in 5% $CO_2$ air before being transferred intravenously into C3H/HeSnJ scid/scid recipients. Three months later, the recipients were killed and then the cecum and the proximal, medial, and distal portions of the colon were fixed in formalin. Fixed tissues were embedded in paraffin, and sections were stained with hematoxylin and eosin for histological examination. All slides were "read" by an experienced pathologist (A. Lazenby, Department of Pathology, University of Alabama at Birmingham) without knowledge of their origin.

Human Subjects

Serum samples from 212 subjects (50 UC patients, 100 CD patients, 22 DCs, and 40 NCs) were obtained from the serum archive of the Cedars-Sinai IBD Research Center. Sera were produced from standard phlebotomy blood specimens and were given an "anonymous" number code, divided into aliquots, and stored at −80° C. until use. The UC and CD patient specimens were obtained from a genetic case-control study (Toyoda H, et al. Distinct associations of HLA class II genes with inflammatory bowel disease. Gastroenterology. 1993; 104:741-748. Yang H-Y, et al. Ulcerative colitis: a genetically heterogeneous disorder defined by genetic (HLA class II) and subclinical (antineutrophil cytoplasmic antibodies) markers. *J. Clin. Invest.* 1993; 92:1080-1084.). Each patient's diagnosis was confirmed by clinical history, endoscopic and radiologic examination, and histopathology findings. The NC group is a collection of environmental controls that contain sera from individuals with no symptoms/signs of disease (i.e., spouses). DC samples include sera from patients with presumed infectious enteritis (stool culture negative for specific pathogens), *blastocystis*, celiac disease, collagenous colitis, irritable bowel syndrome, radiation proctitis, and acute schistosomiasis. The UC group includes both pANCA-positive and -negative specimens, while the CD group contains samples that are marker-negative, ASCA+; I2+; OmpC+(I2-positive); OmpC+, I2+, and ASCA+; and pANCA+. Ethical approval for human studies was obtained from the institution review board at Cedars-Sinai Medical Center.

Nucleotide Sequence Accession Numbers

The nucleotide sequence data for the flagellins CBir1 and Fla-X have been assigned GenBank accession numbers AY551005 and AY551006, respectively.

Seroreactivity in Mice is Directed Mainly Against a Specific Group of Flagellins Serologic expression cloning resulted in 55 clones that were sequenced and identified. Using the basic local alignment search tool to search the GenBank databases demonstrated that 15 (26.8%) of these clones were flagellin-like sequences. None of the sequences directly matched any flagellin in the GenBank database, and all flagellin sequences identified represented unique clones. Given the average insert size of 0.8 kb in the library, no full-length flagellin clones were identified. However, all of the flagellin clones contained sequences derived from the conserved $NH_2$ terminus, with varying amounts of the hypervariable central domain, and only two clones contained partial sequence from the conserved carboxy domain. Sequences from the 15 flagellin clones identified (CBir1-CBir15) were aligned at the protein level to flagellin sequences available in the public domain using the Clustal program in DNAStar. As shown in FIG. 1B, these flagellins are most closely related to flagellins from *Butyrivibrio, Roseburia, Thermotoga,* and *Clostridium* species and appear to align, by similarity, in the *Clostridium* subphylum cluster XIVa of Gram-positive bacteria. Sequences from the remaining 40 clones (see Table 1) were also unique and were either related to known proteins (33 clones) or without significant homology to known proteins (7 clones).

TABLE 1

Identity of serological expression clones

| No. Clones | Homology |
|---|---|
| 15 | Flagellins |
| 6 | Ribosomal proteins |
| 4 | Elongation factors |
| 3 | Chemotaxis proteins |
| 2 | Transcription regulators |
| 1 | Motility protein A |
| 1 | Surface Ag BspA |
| 1 | ABC transport protein |
| 1 | ParB protein |
| 1 | Multimeric flavodoxin WrbA |
| 1 | Toprim domain protein |
| 1 | dnaA |
| 1 | Two-component sensor protein |
| 10 | Enzymes |
| 7 | Novel/hypothetical |

Number of clones with a similar homology (No. clones). BspA, *bacteroides* surface protein A; ParB, chromosome partitioning protein B; WrbA, tryptophan-repressor—binding protein A; dnaA, chromosome replication initiator A.

Because of strong serum antibody reactivity to one particular flagellin clone, called CBir1, it was cloned and expressed its full-length gene. During this effort, the inventors also cloned a second, highly homologous and reactive flagellin (83.5% similarity to CBir1 at the $NH_2$ conserved domain) and refer to it here as Fla-X (FIG. 2B). Recombinant proteins representing full-length sequence and $NH_2$ and carboxy fragments of both CBir1 and Fla-X were subsequently expressed in *E. coli* with a six-histidine tag to aid in protein purification (FIGS. 2, C and D, respectively).

Figure 3:
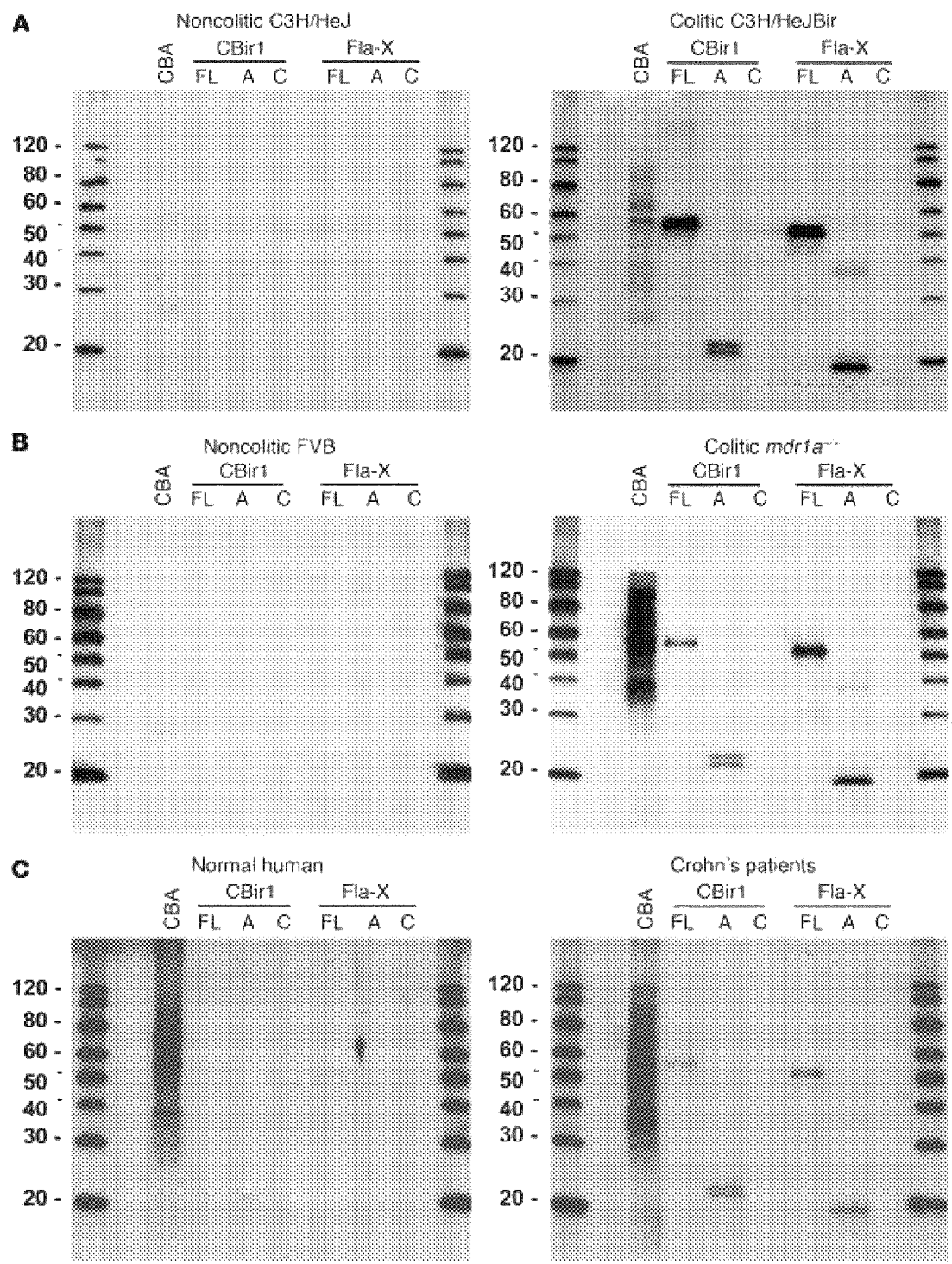
FIG. 3 depicts the Western blot analysis of the serum antibody response to recombinant flagellins CBir1 and Fla-X and their fragments, in accordance with an embodiment of the present invention. (A) Noncolitic C3H/HeJ (pool of two) versus colitic C3H/HdBir (pool of five) mice. (B) Noncolitic FVB (pool of five) versus colitic mdr1a$^{-/-}$ (pool of five) mice. (C) Random human blood donor (Normal human) versus a pool of CD patients with severe disease. Protein samples include mouse CBA, full-length recombinant proteins (FL), the $NH_2$ conserved region (A) and the conserved carboxy region (C) of flagellin (see FIGS. 2, C and D).

Antibody Reactivity to Flagellin Directed Against the $NH_2$ Terminus is of the IgG2a Subclass and Correlates with Disease Western blot analyses using these purified recombinant flagellins and fragments with sera from the diseased C3H/HeJBir mice demonstrated the strong reactivity to flagellin, predominantly to the $NH_2$-terminal fragments (FIG. 3A). Little or no antibody reactivity was seen to the carboxy-terminal CBir1 or Fla-X recombinant fragments in the sera tested (FIG. 3). This selective reactivity to the $NH_2$ domain is consistent with the presence of an $NH_2$ domain in all flagellin clones identified in the initial serological screen (FIG. 1). In addition, strong reactivity to both flagellins was seen using sera from two additional experimental models of colitis: mdr1a$^{-/-}$ mice (FIG. 3B) and B6.IL-10$^{-/-}$ mice. These last two models are on strains with different haplotypes from each other (H-2$^s$ and H-2$^b$, respectively) and from the C3H/HeJBir strain (H-2$^k$), and the sera were obtained from mice from geographically different mouse facilities. In addition, these additional colitic strains have very different mechanisms underlying the genetic predisposition to develop IBD; that is, epithelial barrier dysfunction in the mdr1a$^{-/-}$ mice and a defect in regulatory T cells in the B6.IL-10$^{-/-}$ mice. Little or no reactivity was seen to CBir1 or Fla-X in noncolitic mouse serum from control WIC haplotype—matched noncolitic mice (FIGS. 3, A and B). Interestingly, the inventors also saw a similar pattern of reactivity to the NH₂ termini of both CBir1 and Fla-X with a serum pool from patients with CD (FIG. 3C).

Figure 4:
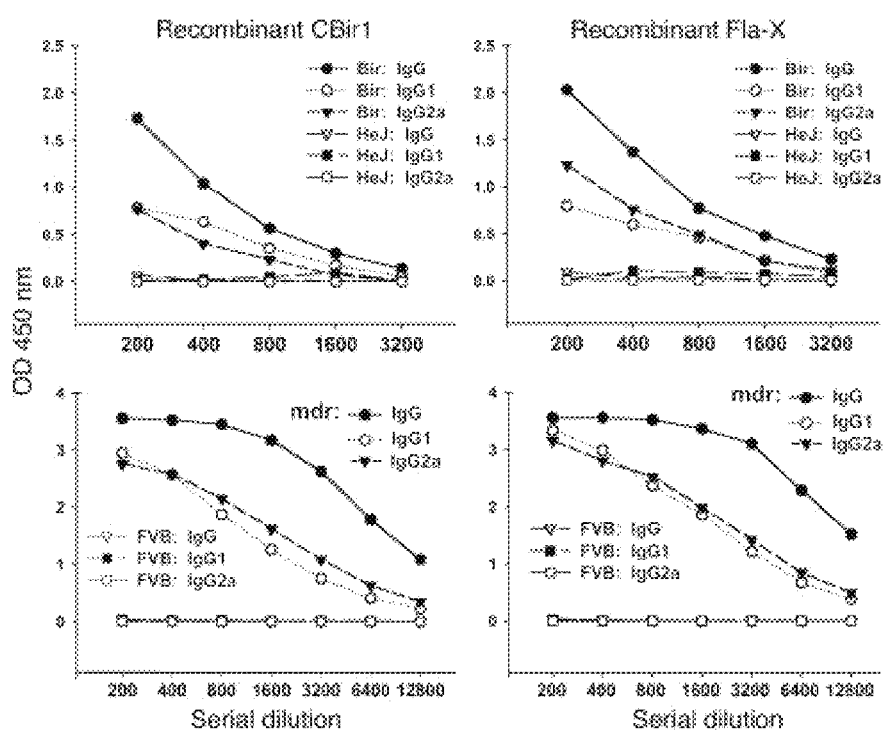
FIG. 4 depicts the ELISA titration of mouse serum anti-flagellin against recombinant flagellins CBir1 and Fla-X with secondary antibodies specific for mouse IgG, IgG1, and IgG2a antibodies, in accordance with an embodiment of the present invention. Colitic C3H/HeJBir serum (pool of five) versus noncolitic C3H/HeJ serum (pool of two) was used in the upper panel and colitic mdr1a$^{-/-}$ serum (pool of five) versus noncolitic FVB serum (pool of five) was used in the lower panel.
Figure 5:
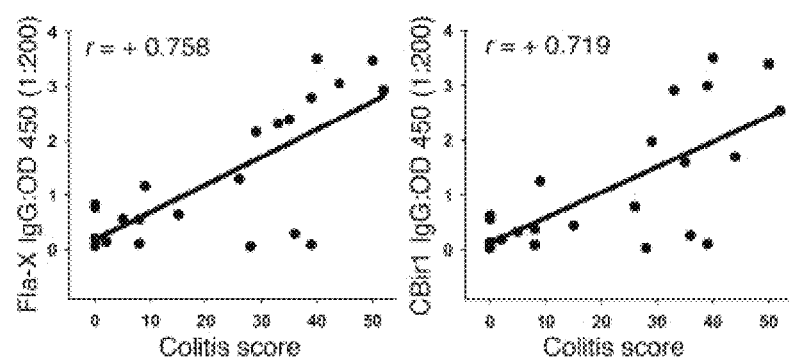
FIG. 5 depicts the correlation of colitis histopathology score (0-60) with serum anti-Fla-X and anti-CBir1, in accordance with an embodiment of the present invention. Twenty-three mdr1a$^{-/-}$ mice, ranging in age from 6 to 13 weeks, were randomly chosen for assignment of quantitative histopathology scores. Serum anti-flagellin from these mice was quantified by ELISA. Colitis scores of 0-2 represent no disease; 3-15, mild disease, 16-35, moderate disease, and more than 35, severe disease (Winstanley C, Morgan J A W. The bacterial flagellin gene as a biomarker for detection, population genetics and epidemiological analysis. *Microbiology*. 1997; 143:3071-3084.). Similar results were obtained for both recombinant flagellins: Fla-X (left panel) and CBir1 (right panel).

In order to generate more quantitative data with multiple IBD models at various time points in the course of disease, an antibody subclass ELISA against full-length or fragments of CBir1 or Fla-X was developed (FIGS. 2, C and D). This assay confirmed Western blot data showing that the antibody reactivity observed was predominantly to the $NH_2$ terminus (data not shown) and of the IgG2a subclass. High titers of anti-flagellin antibody were seen in the four genetically distinct models of IBD tested (colitic mice: C3H/HdBir [FIG. 4], mdr1a$^{-/-}$ [FIG. 4], BALB/c.IL-10$^{-/-}$ [not shown] and B6.IL-10$^{-/-}$ [not shown]), while minimal to no reactivity was seen in serum from the H-2-matched, control, noncolitic mouse strains. Given the nonuniform incidence of colitis in the mdr1a$^{-/-}$ colony at varying time points, the inventors randomly chose 23 animals in the colony and assigned quantitative histopathological scores using a scale (from 0 to 60) that incorporates both the degree and extent of inflammation in the large intestine (Burich A, et al. *Helicobacter*-induced inflammatory bowel disease in IL-10- and T cell-deficient mice. *Am. J. Physiol. Gastrointest. Liver Physiol.* 2001; 281:G764-G778.). The inventors measured antibodies against Fla-X and CBir1 by ELISA in a "blinded" manner using sera from these animals and found that an increased titer of anti-flagellin IgG correlated positively with worsening IBD histopathology (r=+0.758 and +0.719, respectively; FIG. 5). Weak correlations were found between antibody and mouse age (r=+0.325) and between colitis score and mouse age (r=+0.372).

Anti-CBir1 Reactivity in CD Patient Sera but not Normal or UC Patient Sera

Subsequently, a large panel of sera from controls and patients with IBD for reactivity against CBir1 and Fla-X using antigen-specific ELISAs was tested. It was found that a significantly higher level of serum anti-CBir1/Fla-X flagellin in CD patients than in NCs, disease controls (DCs), and UC patients (FIG. 6A). It should be noted that more than 50% of the UC sera were from patients with a modified Truelove and Witts severity index greater than 7, indicating moderate to active disease. The observation of serum responses to flagellins CBir1 and Fla-X in a group of CD patients, but not UC patients (FIG. 6A), highlights the possibility that anti-flagellin responses may be valuable in the diagnosis of IBD, in particular with regards to the more precise discrimination between UC and CD, and the definition of CD patient subsets.

Reactivity to the *Salmonella muenchen* flagellin (which is highly similar to the flagellin of *Eschericia coli* [84-91% at the conserved $NH_2$ end]), however, showed no significant correlation to disease (FIG. 6B). As shown in FIG. 6B, the mean values for the anti-*Salmonella* response were nearly identical in the control, CD, and UC populations. In all populations, there appeared to be a minority of samples without significant reactivity and a majority of samples that were "positive." While these data may reflect the random exposure to *Salmonella* in humans due to prior infection (possibly subclinical) or a cross-reactivity to an undefined but closely related flagellin (probably from the Enterobacteriaceae family), it is clear that the serological response to the *Salmonella* flagellin molecule does not correlate with IBD. Similarly, there was no correlation between reactivity to *Salmonella* flagellin and colitis in the C3H/HeJBir or mdr1a$^{-/-}$ strains compared with the MHC haplotype—matched controls.

Figure 7:
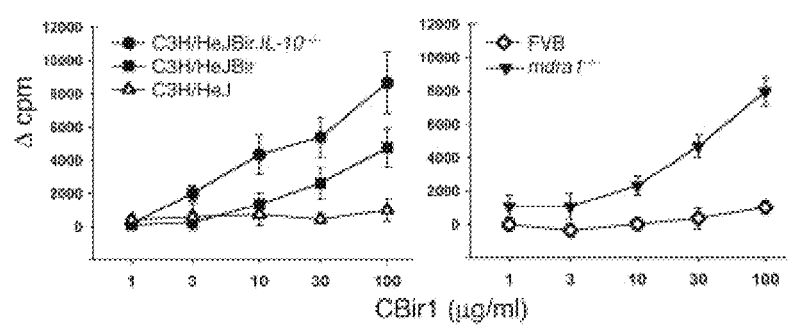
FIG. 7 depicts the dose response of CD4$^+$ T cell proliferation to CBir1 and Fla-X in multiple strains of mice, in accordance with an embodiment of the present invention. Left panel: C3H/HeJ (open triangles), C3H/HeJBir (squares), and C3H/HeJBir.IL-10$^{-/-}$ (circles). Right panel: FVB (diamonds) and mdr1a$^{-/-}$ (filled triangles). The y axes indicate sample counts per minute (cpm) minus control T cell plus APC cpm ($\Delta$ cpm) for each experimental group. The x axes indicate the dose (μg/ml) of recombinant flagellin used in each assay. Vertical bars indicate plus or minus one standard deviation of the mean value.

Marked reactivity against flagellin is seen at the T cell level, and flagellin-specific T cells are able to induce colitis when adoptively transferred. Given the strong IgG2a bias seen in the antibody response in the mouse IBD strains, and while not wishing to be bound by any particular theory, it is believed that flagellin-specific Th1 T cells would be present in mice with IBD. To address this possibility, CD4$^+$ T cells from pooled spleens and mesenteric lymph nodes from colitic mdr1a$^{-/-}$, C3H/HeJBir, and C3H/HeJ.IL-10$^{-/-}$ mice (and haplotype-matched, noncolitic FVB and C3H/HeJ mice) were purified and tested the cells for reactivity against purified CBir1 and Fla-X in vitro in the presence of antigen-presenting cells (APCs). CD4$^+$ T cells from the colitic mdr1a$^{-/-}$, C3H/HeJBir, and C3H/HeJ.IL-10$^{-/-}$ mice, but not from age-matched control FVB or C3H/HeJ mice raised in the same mouse facility, responded to CBir1, as assessed by proliferation (FIG. 7). It was possible that the responses seen were due to the fact that the flagellin molecule was nonspecifically activating the cultured T cells via TLR5 or TLR4 activation (through endotoxin contamination of the recombinant protein). This possibility was excluded by the lack of stimulation in both the noncolitic T cell cultures (FIG. 7) and in an independent T cell culture system that showed no influence of Fla-X or CBir1 on the ovalbumin-specific proliferation of CD4$^+$ T cells from DO11.10 ovalbumin-specific T cell receptor—transgenic animals (Table 2).

TABLE 2

Specificity of T cell activation

| CD4$^+$ T cells | APC | Antigen | Mean cpm ± SD |
| --- | --- | --- | --- |
| DO11.10 | None | None | 232 ± 48 |
| DO11.10 | + | None | 223 ± 37 |
| DO11.10 | + | OVA | 63,104 ± 6,379 |
| DO11.10 | + | CBir1 | 1,036 ± 150 |
| DO11.10 | + | Fla-X | 876 ± 1,045 |
| DO11.10 | + | OVA + CBir1 | 58,831 ± 4,684 |
| DO11.10 | + | OVA + Fla-X | 64,300 ± 1,314 |

OVA-specific T cell line DO11.10 proliferates specifically in the presence of OVA peptide, but not nonspecifically in the presence of recombinant proteins CBir1 or Fla-X.

Figure 8:
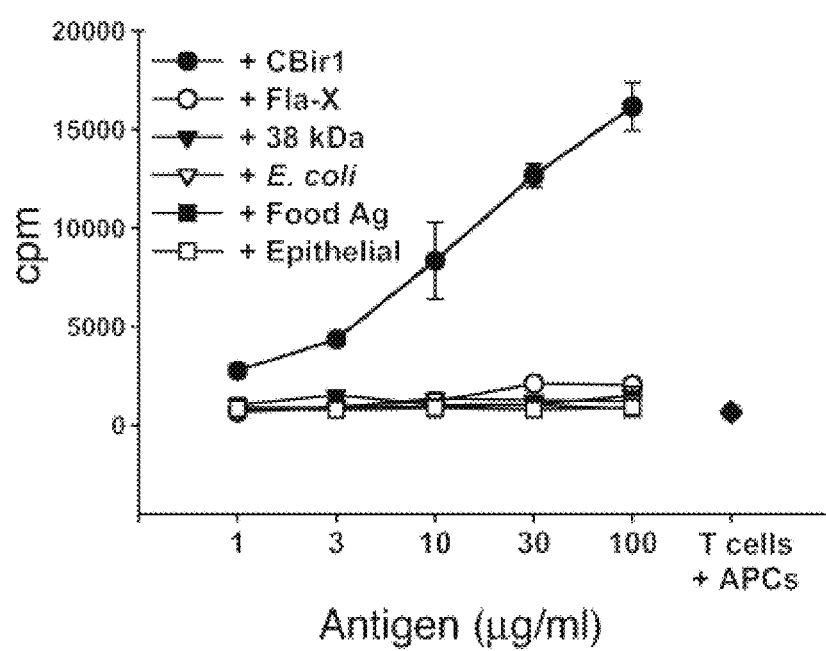
FIG. 8 depicts the dose response and specificity of C3H/HeJBir CD4+ CBir1-specific T cell line, in accordance with an embodiment of the present invention. T cell line CBir-1B1 proliferated specifically in response to recombinant flagellin protein CBir1. Antigens used in the assay include recombinant flagellins CBir1 (filled circles) and Fla-X (open circles); the 38-kDa antigen of *M. tuberculosis* (p38 antigen; 38 kDa: filled triangles); lysate of *E. coli* antigens (*E. coli*; open triangles); protein antigens extracted from mouse food pellets (Food Ag; filled squares); and a lysate of the ModeK epithelial cell line, of C3H origin (epithelial: open squares). Several randomly expressed recombinant commensal bacterial antigens were also tested and were negative (including randomly cloned C3H/HeJ mouse cecal bacterial antigens 99 [rIB99] and 32 [rIB32]). T cells plus APCs only are indicated by a filled diamond.
Figure 9:
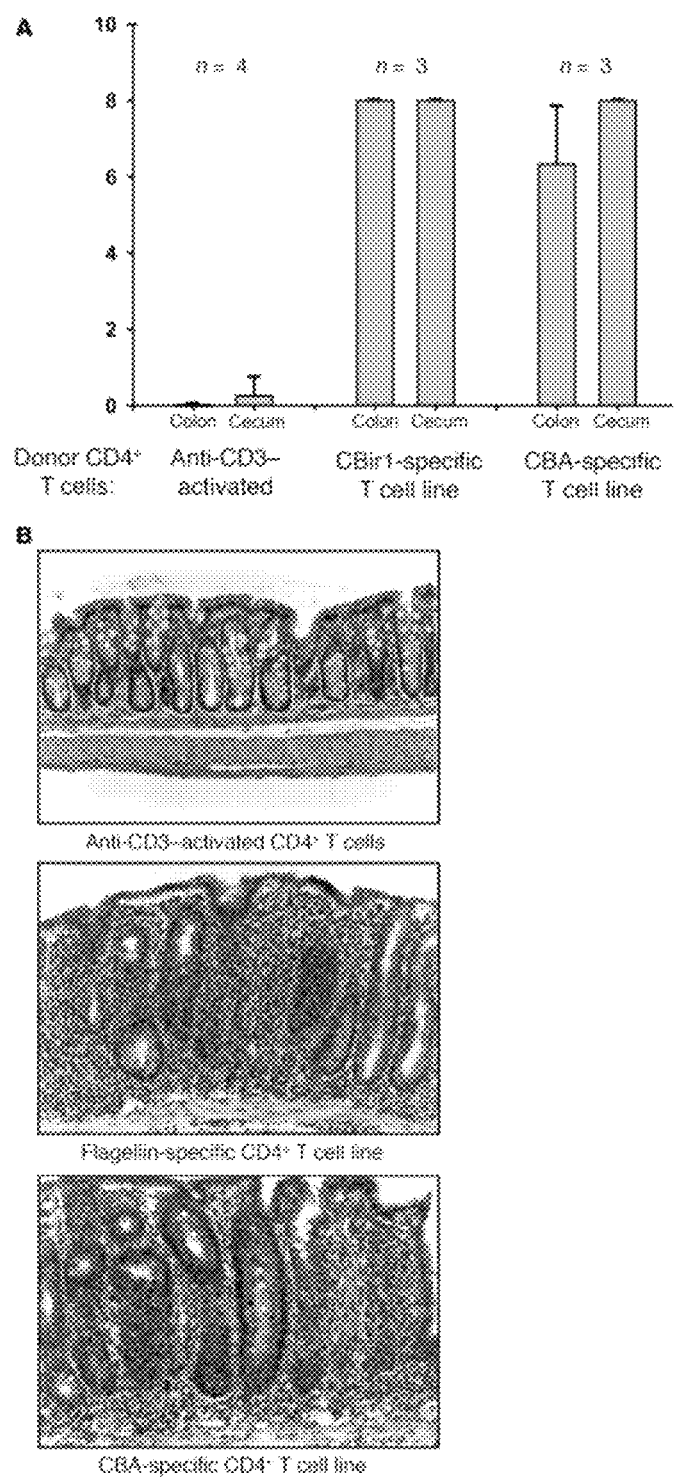
FIG. 9 depicts the adoptive transfer of C3H/HeJBir CD4+ CBir1-specific T cell line into C3H/HeJ scid/scid recipients, in accordance with an embodiment of the present invention. (A) Two months after transfer, cecal and colon histopathology was assigned scores with a quantitative system (Cong Y, et al. CD4+ T cells reactive to enteric bacterial antigens in spontaneously colitic C3H/HeJBir mice: increased T helper cell Type 1 response and ability to transfer disease. *J. Exp. Med.* 1998; 187:855-864.). CD4+ T cells activated polyclonally with mAb against CD3 prior to transfer were used as a negative control (Anti-CD3-activated). A CBA-specific CD4+ T cell line reactive with unselected cecal bacterial antigens was used as a positive control (CBA-specific T cell line); the CBir1-specific CD4+ T cell line corresponds to the flagellin-specific T cell line in FIG. 8. Sample size (n) is indicated at the top. (B) Representative histopathology of the groups shown in A: Anti-CD3-activated CD4+ T cells (top panel), CBir1 flagellin-specific CD4+ T cells (middle panel), and CBA-specific CD4+ T cells (bottom panel). Magnification, x200.

It has been previously shown that a T cell line specific for cecal bacterial protein/antigen (CBA), but not CD4$^+$ T cells polyclonally activated by anti-CD3, could induce mucosal inflammation when adoptively transferred into H-2-matched immunodeficient scid/scid mice (Cong Y, et al. CD4+ T cells reactive to enteric bacterial antigens in spontaneously colitic C3H/HeJBir mice: increased T helper cell Type 1 response and ability to transfer disease. *J. Exp. Med.* 1998; 187:855-864.). To address the potentially pathogenic role of flagellin-specific T cells in the initiation of mucosal inflammation, a CD4$^+$ T cell line reactive with CBir1 flagellin from C3H/HeJBir mice was generated by repeated stimulation with antigen and APCs. This CD4$^+$ T cell line strongly responded to CBir1 but not to Fla-X or a variety of other microbial, food, and epithelial antigens (FIG. 8). These CBir1-specific CD4$^+$ T cells were adoptively transferred into C3H/HeJ-scid/scid recipients. Control SCID mice received anti-CD3-activated CD4$^+$ T cells as a negative control or a CD4$^+$ T cell line reactive to CBA as a positive control. Quantitative histopathological scores were assigned at 8 weeks after transfer (FIG. 9A). The CBir1-specific CD4$^+$ T cell line induced colitis in all recipients of an intensity that was similar to or greater than that induced by the CBA-specific CD4$^+$ T cell line, whereas none of the recipients given anti-CD3-activated C3H/HeJBir CD4$^+$ T cells developed disease (representative histology is shown in FIG. 9B).

Human Subjects

Serum samples from 484 subjects (40 normal controls (NC), 21 disease controls (DC), 50 UC patients, and 373 CD patients) were selected from the serum archive of the Cedars-Sinai IBD Research Center. All research related activities were approved by the Cedars-Sinai Medical Center, Institutional Review Board. Diagnosis for each patient was based on standard endoscopic, histologic, and radiographic features. The normal control (NC) group is a collection of environmental controls that contain sera from individuals with no symptoms/signs of disease (i.e. spouses of patients). Disease controls (DC) include sera from patients with presumed infectious enteritis (stool culture negative for specific pathogens), blastocystis, celiac disease, collagenous colitis, irritable bowel syndrome, radiation proctitis, and acute schistosomiasis. For UC, groups chosen were pANCA– (n=25, seronegative) and pANCA$^+$ (n=25, pANCA EU>45, no other antibody reactivity present). For CD, two cohorts were chosen: Cohort 1 (Lodes M J, Cong Y, Elson C O, Mohamath R, Landers C J, Targan S R, Fort M, Hershberg R M. Bacterial flagellin is a dominant antigen in Crohn disease. J Clin Invest 2004; 113:1296-306.) (n=100) was comprised of patients with select antibody expression to test CBir-1's specificity for CD and its relationship with other CD associated antibodies, Cohort 2 (n=303) was unbiased, previously well clinically and serologically characterized (Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.), with an overlap of 30 patients between the two. Within Cohort 1, groups chosen were seronegative (n=40), ASCA$^+$ (n=15, IgG ASCA EU>40, IgA ASCA EU>45, and no other antibody reactivity present), I2$^+$ (n=15, anti-I2 EU>40, and no other antibody reactivity present), I2$^+$/OmpC$^+$ (n=15, OmpC EU>30, and anti-I2 reactivity present), I2$^+$/OmpC$^+$/ASCA$^+$ (n=15, anti-I2, anti-OmpC, IgG and IgA ASCA all positive, but no ANCA reactivity allowed), and pANCA$^+$ (n=25, ANCA EU>35, no other antibody reactivity present). Cohort 2 was used for determining antibody groups as well as for phenotype analysis using definitions of clinical subgroup previously reported (Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.). Serum samples from 44 CD patients diagnosed as above were analyzed for changes in antibody expression. Twenty of these patients were under treatment with infliximab and had experienced a CD Activity Index (CDAI) change of at least 70 (mean=$\Delta$181) at time points at least 4 months apart with serum drawn at both times. The other 24 patients were drawn at the time of surgery and once at least 6 months following surgery.

ELISA

ELISA analysis of anti-CBir1 was performed as described in Lodes, et al. (Lodes M J, Cong Y, Elson C O, Mohamath R, Landers C J, Targan S R, Fort M, Hershberg R M. Bacterial flagellin is a dominant antigen in Crohn disease. J Clin Invest 2004; 113:1296-306.) but using $NH_2$-terminal fragment of of CBir1 (147aa) without knowledge of diagnosis or other serology results. Briefly, ELISA plates were coated overnight with 100 ng/well of CBir1, then blocked with 1% BSA in PBS for 2 hours. Plates were washed and serum was added at a 1:200 dilution in 1% BSA-PBS for a 30 minute incubation. After washing, horseradish peroxidase conjugated anti-human IgG at a 1:10,000 dilution was added and incubated for 30 minutes. After another wash, the plates were incubated with tetramethylbenzidine substrate for 15 minutes. The reaction was stopped with 1 N sulfuric acid and read at 450 nm. Positive was defined as the mean+2 SD of the healthy controls. For Cohort 2 and the longitudinal cohorts and phenotype cohorts, this assay was modified to be more similar to the ANCA, OmpC and I2 protocols: alkaline phosphatase was substituted as the secondary conjugate and incubated for 1 hour followed by paranitrophenyl phosphate as substrate for 30 minutes.

Statistical Analysis

Differences between disease groups were tested with non-parametric (Wilcoxon signed rank) statistics for quantitative levels. To determine the associations between antibody responses (positivity) toward microbial antigens, autoantigens, and disease phenotype characteristics, univariate analyses utilizing $\chi^2$ tests were performed. The Cochran-Armitage test for trend was utilized to test if there is a linear trend in the proportion of patients with positive anti-CBir 1 expression as the number of antibody responses increased. A p-value (p trend)<=0.05 suggests that the linear trend is statistically significant. A stratified Cochran-Mantel-Haenszel test was used to determine the association between anti-CBir1 and disease phenotypes. Multivariate analysis with logistic regression modeling was also performed to determine the primary associations among qualitative serological responses with disease phenotypes. All statistic tests were preformed using Statistical Analysis Software (Version 8.02; SAS Institute, Inc., Cary, NC).

Serum Reactivity to CBir1 Defines a Subset of Patients with Crohn's Disease

Figure 10:
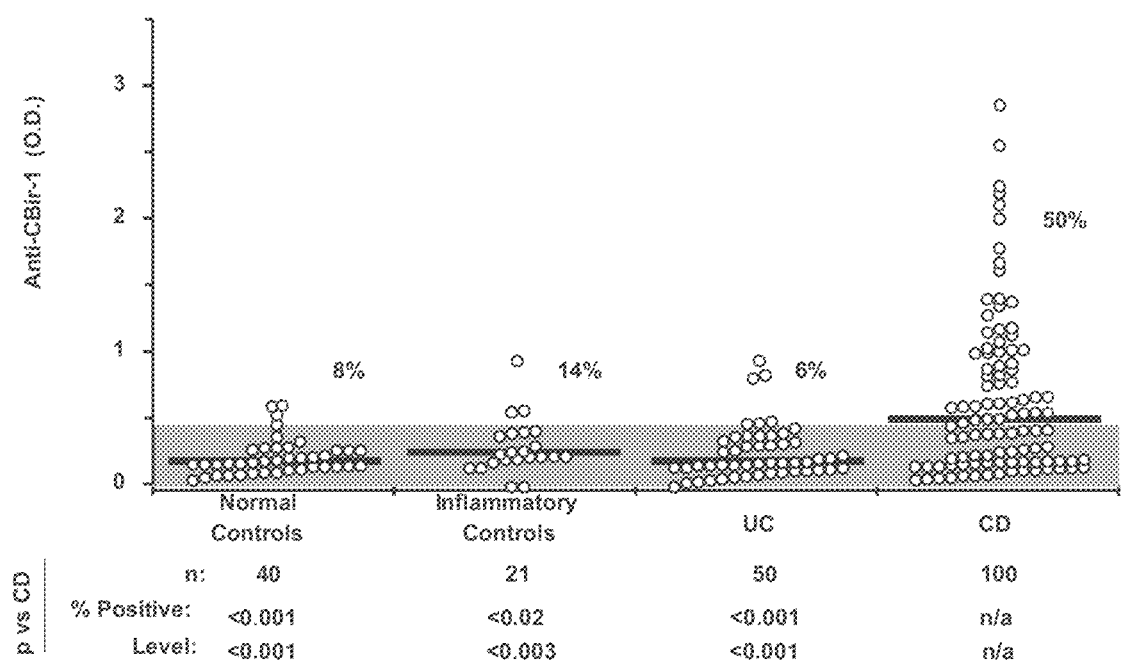
FIG. 10 shows fifty percent of patients with Crohn's disease have antibodies to CBir1 and depicts the level of antibody response in Cohort 1 to CBir1 flagellin, in accordance with an embodiment of the present invention. The gray area indicates the negative range as defined by <2 SD above the mean of the normal controls, lines indicate the median level for each group. The percentage of positive samples for each group is shown. Wilcoxon signed rank test was used for assessing significance of number of positive samples, chi square analysis was used for significance of OD levels of positivity.

Serologic expression cloning of a cecal bacterial antigen phage library identified the flagellin, CBir1, as an immunodominant antigen recognized by colitic mice and by approximately half of patients with CD. Serum from two separate cohorts was used to investigate subgroups of CD patients. Cohort 1 consisted of sera from 100 CD patients selected on the basis of antibody profile. Newly tested sera from a group of 303 unselected patients that were studied and reported on in Mow et al (Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.) comprised Cohort 2. For antigen, the amino domain of CBir1 flagellin was used because most of the IgG reactivity was to this region of the molecule. In addition, this form of CBir1 had a lower baseline reactivity among inflammatory controls, patients with UC or CD, and healthy control subjects, compared to the full length construct. As shown in FIG. 10, 50% of CD patients from the Cohort 1 had serologic responses to this CBir1 construct, as compared to very low numbers and low levels of response among inflammatory controls, patients with UC, or healthy control subjects. Among the control subjects who did respond to CBir1, the level of response was much lower than that of the patients with CD. In the unselected cohort, Cohort 2, 55% (167 of 303) of sera were positive for antibodies to CBir1. Approximately half of CD patients, whether selected serologically or not, are reactive to CBir1.

Levels of Antibodies to CBir1 do not Correlate with Disease Activity

Figure 11:
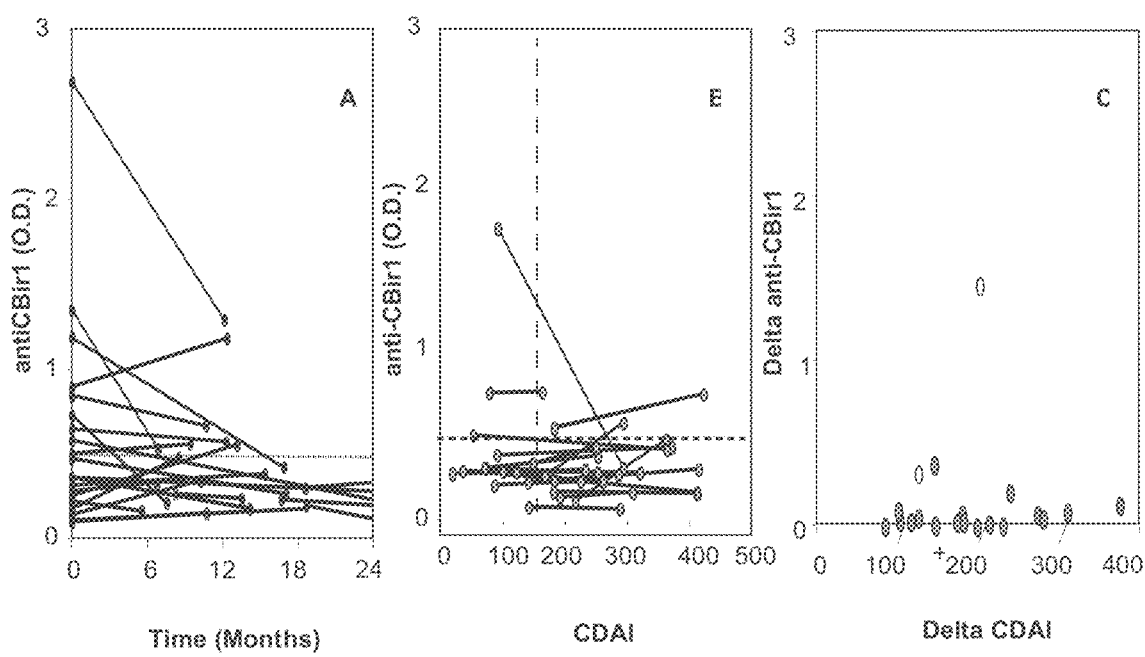
FIG. 11 shows the change in antibody levels following surgery or infliximab therapy and depicts the relation of CBir1 antibody expression level to disease activity over time, in accordance with an embodiment of the present invention. A. Serologic responses towards CBir1 in 24 surgical CD patients at time of small bowel surgery (time 0) and at least 6 months or more after surgery. Dashed lines represent the demarcation between positive and negative values. B. CDAI and antibody expression levels for infliximab treated patients at two connected time points. C. Change in CDAI score and antibody expression level between the time points shown in B. The median change in CDAI and antibody expression level is depicted by a cross, ○ (open circle)=change in antibody expression from negative to positive or vice versa; • (filled circle)=no change.
Figure 12:
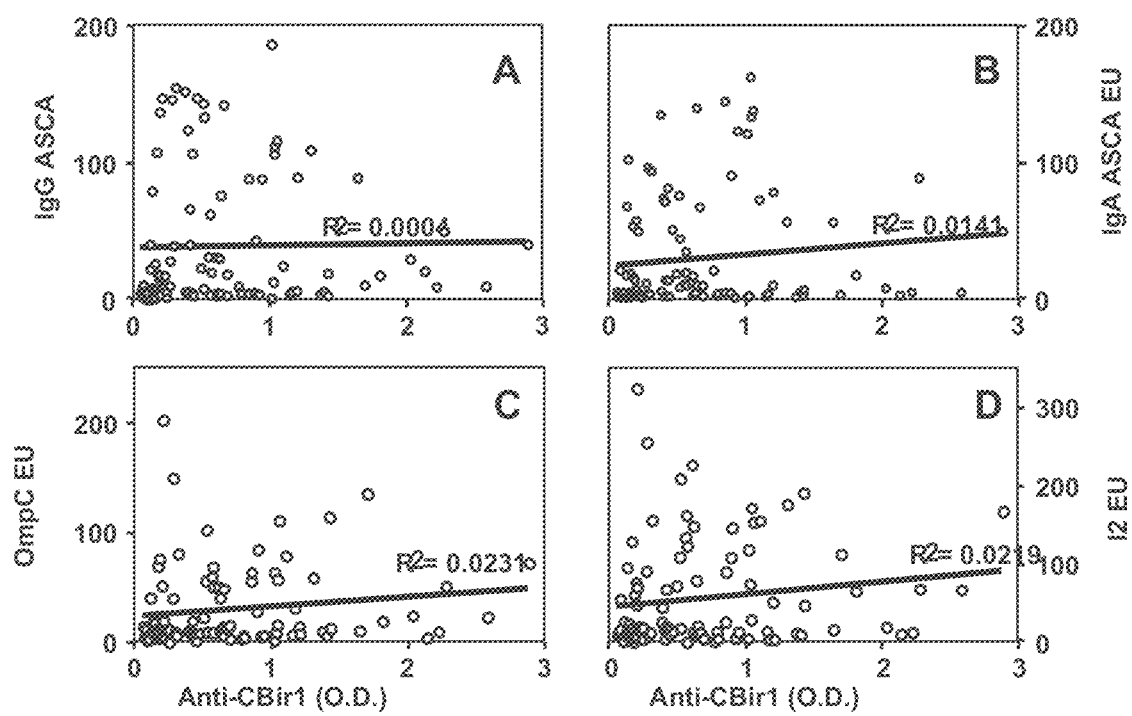
FIG. 12 shows that the level of anti-CBir1 is independent of other serum markers and depicts the relationship between marker antibodies in CD by level of response, in accordance with an embodiment of the present invention. Correlation coefficients for linear fits are shown, p for all $R^2<0.05$.

As had been done with the previously defined CD-related antigens (I2/OmpC, oligomannan; Landers C J, Cohavy O, Misra R, Yang H, Lin Y C, Braun J, Targan S R. Selected loss of tolerance evidenced by Crohn's disease-associated immune responses to auto- and microbial antigens. Gastroenterology 2002; 123:689-99. Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.), determining whether the level of anti-CBir1 expression changed in association with disease activity was sought. Serum samples from medically-resistant patients with CD, who were undergoing surgical removal of active disease were collected. Samples were taken again 6 months post-operatively and analyzed for differences in response. In general, there was very little change before and 6 months post surgery, when patients were in clinical and endoscopic remission (FIG. 11A). The same analysis was performed before, and 4 months after, treatment of CD with infliximab (FIG. 11B, C). Among patients who achieved complete remission as evidenced by mucosal changes and healing, similar stability in anti-CBir1 expression is seen (FIG. 11B, C). These findings are consistent with antibody responses to other microbial antigens (Landers C J, Cohavy O, Misra R, Yang H, Lin Y C, Braun J, Targan S R. Selected loss of tolerance evidenced by Crohn's disease-associated immune responses to auto- and microbial antigens. Gastroenterology 2002; 123:689-99. Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24.).

Antibody Response to CBir1 and Other Crohn's Disease-Associated Anti-Microbial Immune Responses To determine the relationship of expression and level of anti-CBir1 expression to the previously defined antibodies to microbial antigens (anti-I2, anti-OmpC, ASCA), multiple logistic regression analysis with Cohort 1 was used, it was found that anti-CBir1 relates independently to CD when controlled for anti-I2, anti-OmpC and ASCA (p<0.001). In addition, there is no relationship between the level of response to CBir1 and any one of the other four antibodies (FIG. 12A-D). Thus, reactivity to CBir1 defines another potentially pathophysiogically distinct subgroup of CD.

Figure 13:
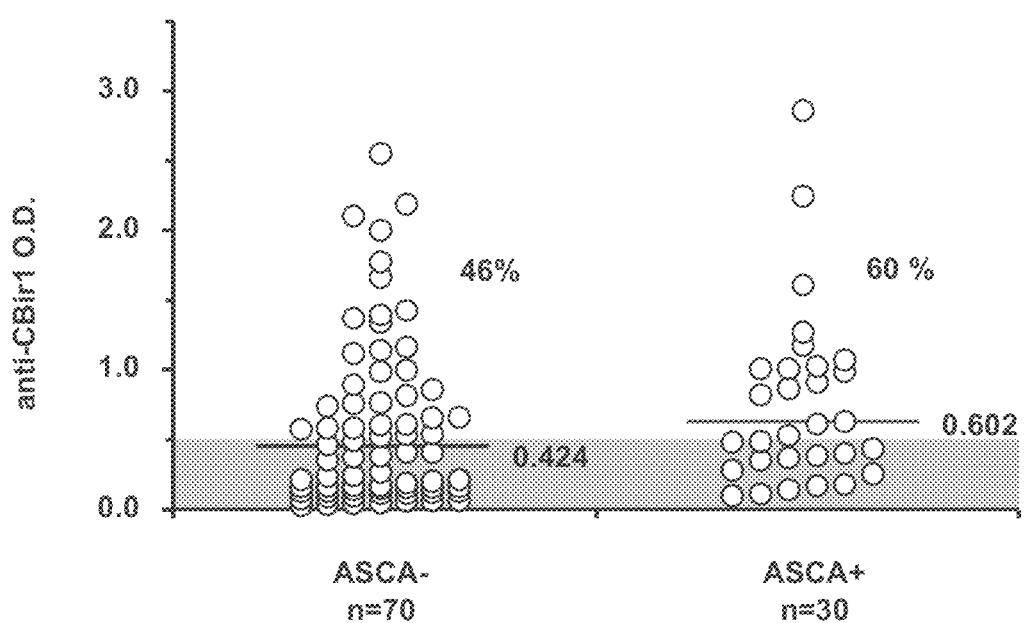
FIG. 13 shows that anti-CBir1 is expressed in approximately 50% of ASCA-negative patients with Crohn's disease and depicts the level of antibody response in ASCA+ and ASCA− subsets of CD to CBir1 flagellin, in accordance with an embodiment of the present invention. The gray area indicates the negative range as defined by 2SD above the mean of the normal controls; lines indicate the median level for each group. The percentage of positive samples for each group is shown.
Figure 14:
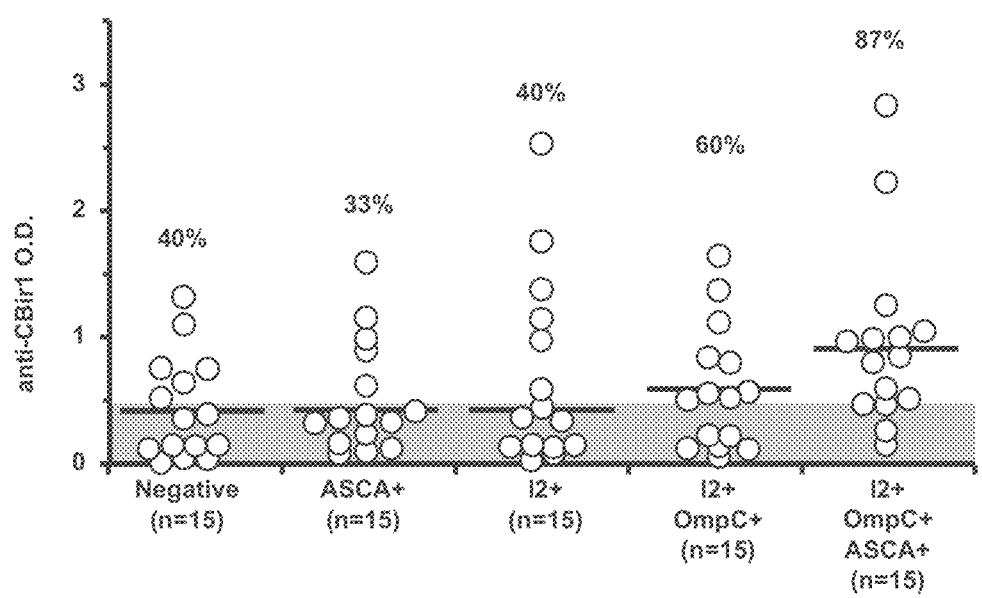
FIG. 14 shows that anti-CBir1 is found in all Crohn's disease serologic subtypes, but is most prevalent in I2+/OmpC+/ASCA+ patients and depicts the level of antibody response in defined subsets of CD to CBir1 flagellin, in accordance with an embodiment of the present invention. Subsets are negative for all antibodies other than those listed. The gray area indicates the negative range as defined by 2SD above the mean of the normal controls; lines indicate the median level for each group. The percentage of positive samples for each group is shown.
Figure 15:
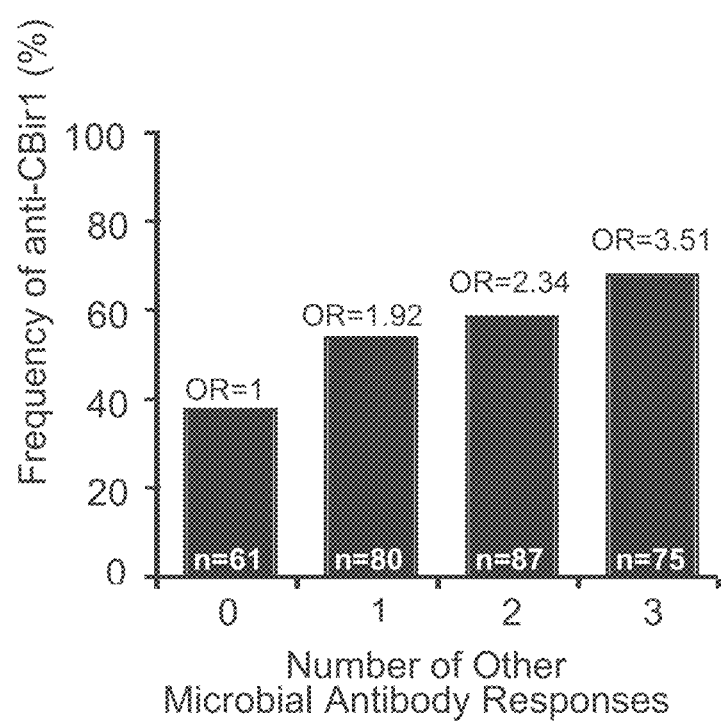
FIG. 15 shows that the frequency of anti-CBir1 expression increases with multiple microbial antibody expression and depicts the frequency of anti-CBir expression in patients with no other microbial antibodies and those expressing 1, 2, or 3 other microbial antibodies (p trend<0.0005), in accordance with an embodiment of the present invention.

As previously described by Landers et al (Landers C J, Cohavy O, Misra R, Yang H, Lin Y C, Braun J, Targan S R. Selected loss of tolerance evidenced by Crohn's disease-associated immune responses to auto- and microbial antigens. Gastroenterology 2002; 123:689-99.), homogeneous groups of CD patients based on selective antibody responses to specific microbial antigens and associated clinical features were defined. Thus far, the largest subgroup of CD has been stratified based on expression of ASCA. Among patients selected for study based on their antibody profiles (Cohort 1), anti-CBir1 is expressed in both ASCA− negative (46%) and ASCA+ (60%) CD patients (FIG. 13). Anti-CBir1 is also expressed by patients who do not react to ASCA, OmpC, I2, or ANCA (40%) as well as those who express ASCA exclusively (33%) and anti-I2 exclusively (40%) (FIG. 14). Anti-CBir1 expression and magnitude increases among patients reactive to both I2 and OmpC (60%), and increases more among those patients reactive to I2, OmpC and oligomannan (87%) (FIG. 14). These results were confirmed in Cohort 2, in which the inventors found anti-CBir1 expression in 46% ($^{66}/_{144}$) of ASCA−, 64% (102/159) of ASCA+, and 38% ($^{23}/_{61}$) of seronegative CD patients. The frequency of anti-CBir1 expression increases as the number of positive antibody responses increases in patients with 0, 1, 2, and 3 antigens (FIG. 15, p<0.001). Thus, in both Cohort 1 and Cohort 2, anti-CBir1 expression is highest in sera from patients who react to all three other antigens, but is also found along with any other combination of 1, 2, or 3 antibody responses.

Antibodies to CBir1 and pANCA Expression

Figure 16:
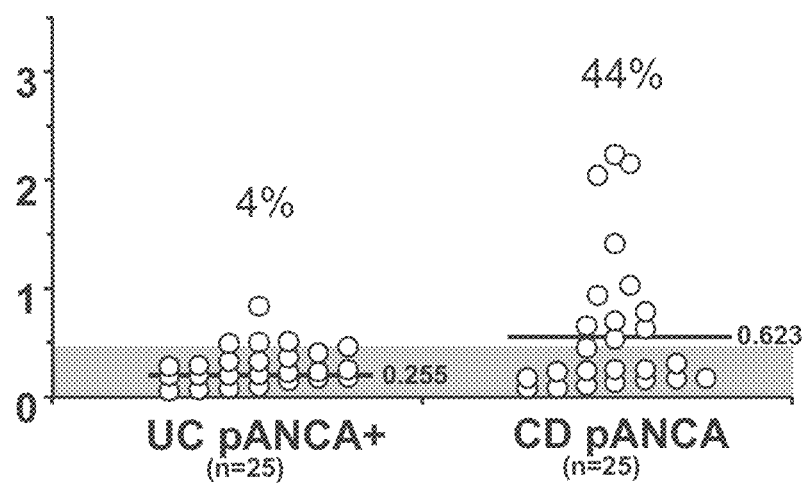
FIG. 16 shows that forty-four percent of pANCA-positive patients with Crohn's disease are also positive for anti-CBir1 and depicts the level of antibody response to CBir1 flagellin in pANCA+ UC vs pANCA+ CD subsets, in accordance with an embodiment of the present invention. The gray area indicates the negative range as defined by 2SD above the mean of the normal controls; lines indicate the median level for each group. The percentage of positive samples for each group is shown.

A small percentage of CD patients are solely pANCA-positive. pANCA is associated with ulcerative colitis, and in CD, pANCA marks for left-sided disease with ulcerative colitis-like features (Vasiliauskas E A, Plevy S E, Landers C J, Binder S W, Ferguson D M, Yang H, Rotter J I, Vidrich A, Targan S R. Perinuclear antineutrophil cytoplasmic antibodies in patients with Crohn's disease define a clinical subgroup. Gastroenterology 1996; 110:1810-9. Vasiliauskas E A, Kam L Y, Karp L C, Gaiennie J, Yang H, Targan S R. Marker antibody expression stratifies Crohn's disease into immunologically homogeneous subgroups with distinct clinical characteristics. Gut 2000; 47:487-96. Esters N, Vermeire S, Joossens S, Noman M, Louis E, Belaiche J, De Vos M, Van Gossum A, Pescatore P, Fiasse R, Pelckmans P, Reynaert H, Poulain D, Bossuyt X, Rutgeerts P. Serological markers for prediction of response to anti-tumor necrosis factor treatment in Crohn's disease. Am J Gastroenterol 2002; 97:1458-62. Peeters M, Joossens S, Vermeire S, Vlietinck R, Bossuyt X, Rutgeerts P. Diagnostic value of anti-*Saccharomyces cerevisiae* and antineutrophil cytoplasmic autoantibodies in inflammatory bowel disease. Am J Gastroenterol 2001; 96:730-4.). pANCA does not differentiate between UC and UC-like CD. Determine whether anti-CBir1 expression had any bearing on this subgroup was sought. Of the pANCA$^+$ patients with CD, 40-44% (Cohort 2 and Cohort 1, respectively) expressed anti CBir1 and none of other antibodies v. only 4% in pANCA$^+$ ulcerative colitis (FIG. 16). This difference stratifies another subgroup of CD with a potential pathophysiologically unique disease mechanism.

Crohn's Disease Phenotypic Associations with Anti-CBir1 Expression

It was previously determined that antibody responses to the microbial antigens, OmpC, I2, oligomannan and neutrophil nuclear antigen(s) is associated with anatomical location as well as disease expression (Vasiliauskas E A, Plevy S E, Landers C J, Binder S W, Ferguson D M, Yang H, Rotter J I, Vidrich A, Targan S R. Perinuclear antineutrophil cytoplasmic antibodies in patients with Crohn's disease define a clinical subgroup. Gastroenterology 1996; 110: 1810-9. Vasiliauskas E A, Kam L Y, Karp L C, Gaiennie J, Yang H, Targan S R. Marker antibody expression stratifies Crohn's disease into immunologically homogeneous subgroups with distinct clinical characteristics. Gut 2000; 47:487-96. Mow W S, Vasiliauskas E A, Lin Y C, Fleshner P R, Papadakis K A, Taylor K D, Landers C J, Abreu-Martin M T, Rotter J I, Yang H, Targan S R. Association of antibody responses to microbial antigens and complications of small bowel Crohn's disease. Gastroenterology 2004; 126:414-24. Arnott I D R, Landers C J, Nimmo E J, Drummond H E, Targan S R, Satsangi J. Reactivity to microbial components in Crohn's disease is associated with severity and progression. Am J Gastroenterol 2004; 99:2376-84.). Anti-CBir1 expression appears to be independently associated with CD. Therefore, to determine whether a clinical phenotype is independently associated with anti-CBir1 expression, the serotypically- and phenotypically-defined Cohort 2 was used to assess the overall and specific phenotypes associated with anti-CBir1 expression. It was found that 61% of patients with complicated (internal penetrating, fibrostenosing disease features, and those with or without history of surgery) were anti-CBir1+, compared to 42% of patients with inflammatory-only CD (p=0.002). Anti-CBir1 expression was positively associated with small bowel disease, fibrostenosing and internal penetrating disease (see Table 3), regardless of the presence of antibodies to 1, 2, or all 3 other antigens. Unlike some of the other antibody responses, anti-CBir1 expression was neither associated with small bowel surgery, nor was it negatively associated with the UC-like CD population. To further assess the independent relationship of anti-CBir1 expression to CD phenotypes, the inventors performed a multivariate logistic regression model analysis with the four CD-associated antibodies. The results in Table 4 show that anti-CBir1 expression is independently associated with small bowel, internal penetrating and fibrostenosing disease. Consistent with this finding is the lower frequency of anti-CBir1 expression in the cohort of patients treated with infliximab (30%, FIG. 11), among whom internal penetrating and fibrostenosing disease features would not be prevalent. Thus, anti-CBir1 expression is independently associated with CD, but also selects for a specific phenotype.

TABLE 3

Phenotypic Associations with anti-CBir1

| Phenotype | OR | CI | *P value |
|---|---|---|---|
| Small bowel disease | 2.16 | 1.22-3.30 | 0.009 |
| Fibrostenosis | 1.71 | 1.05-2.80 | 0.03 |
| Internal perforating disease | 2.01 | 1.22-3.30 | 0.006 |

OR = odds ratio
CI = confidence interval
*stratified Cochran-Mantel-Haenszel

TABLE 4

Clinical Features: Results of Multivariate Logistic Regression

| | Small Bowel Disease | Fibrostenosis | Internal Perforating | Small Bowel Surgery | UC-Like |
|---|---|---|---|---|---|
| Anti-CBir1 | 0.0099 | 0.0402 | 0.0093 | NS | NS |
| ASCA | 0.0194 | <0.0001 | 0.0009 | 0.0002 | <0.0001 |
| Anti-OmpC | NS | NS | 0.01 | NS | NS |
| Anti-I2 | NS | 0.0236 | NS | 0.0077 | NS |

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

Example 2

The inventors performed a genome-wide association study testing autosomal single nucleotide polymorphisms (SNPs) on the Illumina HumanHap300 Genotyping BeadChip. Based on these studies, the inventors found single nucleotide polymorphisms (SNPs) and haplotypes that are associated with increased or decreased risk for inflammatory bowel disease, including but not limited to CD and UC. These SNPs and haplotypes are suitable for genetic testing to identify at risk individuals and those with increased risk for complications associated with serum expression of Anti-Saccharomyces cerevisiae antibody, and antibodies to 12, OmpC, and Cbir. The detection of protective and risk SNPs and/or haplotypes may be used to identify at risk individuals, predict disease course and suggest the right therapy for individual patients. Additionally, the inventors have found both protective and risk allelic variants for Crohn's Disease and Ulcerative Colitis.

As disclosed herein, the inventors examined a case-control cohort consisting of 763 Crohn's Disease patients, 351 ulcerative colitis patients, and 254 control patients. The patients were genotyped using Illumina technology. SNPs were chosen to tag common Caucasian haplotypes using information from the Innate Immunity PGA.

NOD2: Serologic Analysis and Classification

Figure 17:
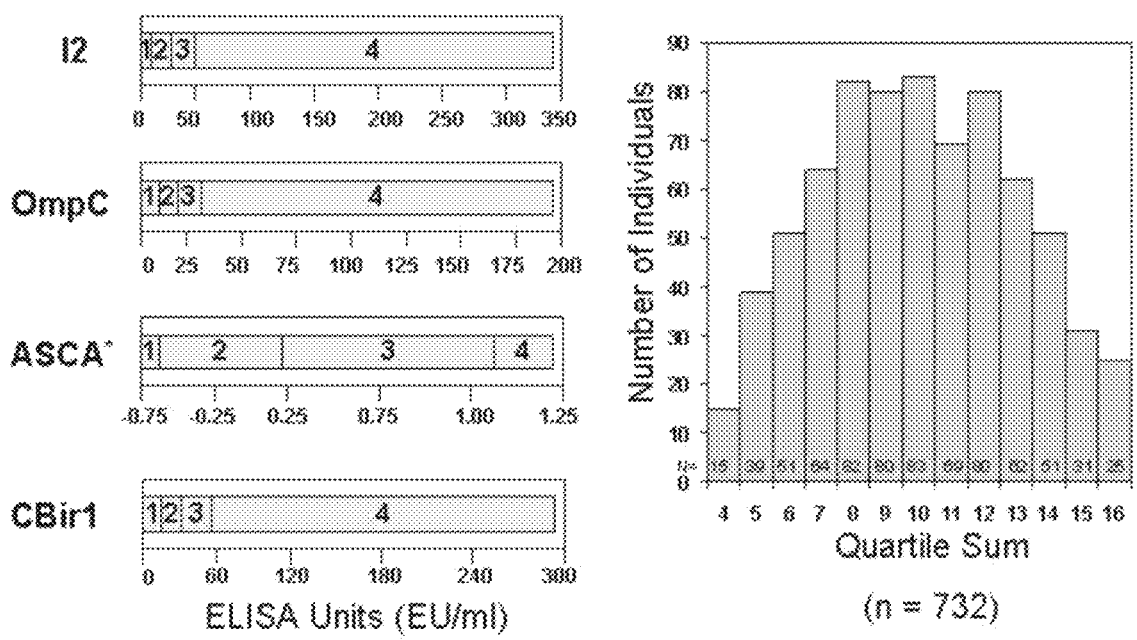
FIG. 17 depicts quartile analysis of the CD cohort for the 4 tested microbial antigens (ASCA, I2, OmpC, and CBir1). Reactivity to each antigen was divided into 4 quartiles and a value ascribed to a given individual based on their quartile of reactivity to each antigen (left panel). Quartile sums were calculated by the addition of the quartile value for each antigen (range, 4-16). The distribution of quartile sums is shown (right panel). Values for binding levels are in enzyme-linked immunosorbent assay units except for ASCA, which is presented in standardized format. Quartile sums were calculated similarly for unaffected relatives and healthy controls based on the distribution within each group (the quartile cut-off values and the distribution of quartile sums for the other two groups are not represented in this figure).

Sera were analyzed for expression of ASCA, anti-I2, anti-OmpC, in a blinded fashion by enzyme-linked immunosorbent assay (ELISA). Antibody levels were determined and results expressed as ELISA units (EU/ml) that are relative to a Cedars-Sinai laboratory (IgA-I2, IgA-OmpC) or a Prometheus Laboratory standard (San Diego, CA, IgA and IgG ASCA) derived from a pool of patient sera with well-characterized disease found to have reactivity to these antigens. Quantitation of IgG anti-Cbir1 reactivity was expressed in ELISA units derived based on a proportion of reactivity relative to a standardized positive control. As ASCA can be expressed in both an IgA and IgG class, positivity to ASCA was determined if either class of antibody was above the reference range. In determining a quantitative measure of ASCA, the reactivity was first log-transformed and standardized. The higher of two standardized units was then used to determine the quartile of reactivity. With the exception of determining variance (see statistical analysis), the magnitude of reactivity to the other three antigens was not standardized as each is represented by a single class of antibody. The magnitude of the serologic response to each antigen was divided into four equal quartiles in CD patients, unaffected relatives and healthy controls, evaluated as three separate cohorts, to determine quartile sum scores. FIG. 17 shows the patients with the serologic response to each antigen broken down by quartiles and assigned scores of 1-4 on the basis of their designated quartile. By adding individual quartile scores for each microbial antigen, a quartile sum (QS) (range, 4-16) was derived that represents the cumulative semi-quantitative immune response toward all 4 antigens. The quartile ranking reflects the pool of individuals under study (i.e. CD patient or unaffected relative or healthy control) and is not directly comparable between groups.

NOD2: Genotyping

Three NOD2 variants (R702W, G908R, and 1007fs), were adapted to the TaqMan MGB (Applied Biosystems, Foster City, CA) genotyping platform.

NOD2: Statistical Analysis

The inventors assessed the relationship between carriage of a NOD2, TLR2, TLR4, and TLR9 variant and collective sero-reactivity to microbial antigens both qualitatively and semi-quantitatively. The inventors then determined if any particular NOD2 variant was predominant and examined whether any particular antibody or combinations of antibodies was predominant in determining the relationship between NOD2 variants and sero-reactivity. The contribution of NOD2 to collective sero-reactivity was evaluated by calculating the percent of variance that could be attributed to the presence of NOD2 variants. Finally, the inventors examined whether the presence of a NOD2 variant was related to sero-reactivity to microbial antigens in unaffected relatives of CD patients and healthy controls.

To determine the significance of increasing frequency of carriage of any NOD2 variants with increasing numbers of qualitatively positive antibodies and with increasing quartile sum (range, 4-16), the Cochran-Armitage trend test was performed. To test for differences in the mean quartile sum between those individuals with no NOD2 variant versus those with any variant, the student's t-test was used since the distribution was approximately a normal distribution. One-way ANOVA analysis was done to test the linear trend of mean quartile sum among those with 0, 1, and 2 NOD2 variants. One-way ANOVA analysis was used to test for a difference in sero-reactivity associated with specific NOD2 variants and similarly when comparing mean quartile sum between differing TLR genotypes.

The non-parametric Mann-Whitney test was used to compare the level of seroreactivity between those individuals who carried versus those who did not carry a NOD2 variant for each antibody. To identify whether there is a significant difference in the frequency of carriage of a NOD2 variant among groups within each set with single, double and triple antibody positivity, chi-square analysis was performed.

To determine what proportion of the variation in the sero-reactivity to microbial antigens was attributable to the presence of a NOD2 variant, a coefficient of determination ($R^2$), defined as 1−SS (regression)/SS (total) in ANOVA was used. Sero-reactivity was defined, for this analysis, as the sum of the 4 standardized antibodies, where anti-OmpC= [log(anti-OmpC)-mean(log(anti-OmpC))]/SD(log(anti-OmpC)) and similarly for the other antibodies.

All analyses were performed using SAS computer software (version 8.2; SAS institute, Inc., Cary, North Carolina, USA, 1999).

NOD2

As disclosed herein, the inventors studied the serologic and genetic (NOD2) characteristics of a 732 patient cohort (Table 5). ASCA is detected in 50.4%, anti-I2 in 58.1%, anti-OmpC in 37.2% and anti-Cbir1 in 56.4% (Table 5). Simple heterozygosity for a disease-predisposing NOD2 variant is detected in 194 patients (26.5%), compound heterozygosity for two NOD2 variants is detected in 23 patients (3.1%), and homozygosity for two NOD2 variants is detected in 16 patients (2.2%) (Table 5).

TABLE 5

Serologic and Genetic (NOD2) Characteristics of the Crohn's Disease Patient Cohort

| Serologic and Genetic Characteristics | Cohort (n = 732) |
|---|---|
| Serological profile (%) | |
| ASCA positive (N3 = 369) | 50.4 |
| Anti-I2 positive (N = 425) | 58.1 |
| Anti-OmpC positive (N = 272) | 37.2 |
| Anti-CBir1 positive (N = 413) | 56.4 |
| NOD2 genotype for R702W, G908R, 1007fs (%) | |
| No mutations (N = 499) | 68.2 |
| Heterozygous (N = 194) | 26.5 |
| Compound heterozygous (N = 23) | 3.1 |
| Homozygous (N = 16) | 2.2 |

As disclosed herein, an example of a NOD2 genetic sequence is described as SEQ ID NO: 16. An example of a NOD2 peptide sequence is described herein as SEQ ID NO: 17. R702W, G908R, and 1007fs variant alleles are also described herein as SEQ ID NO: 18, SEQ ID NO: 19, and SEQ ID NO: 20, respectively, wherein the position of the variant allele is marked within the sequence listing as a letter other than A, C, G or T.

Figure 18:
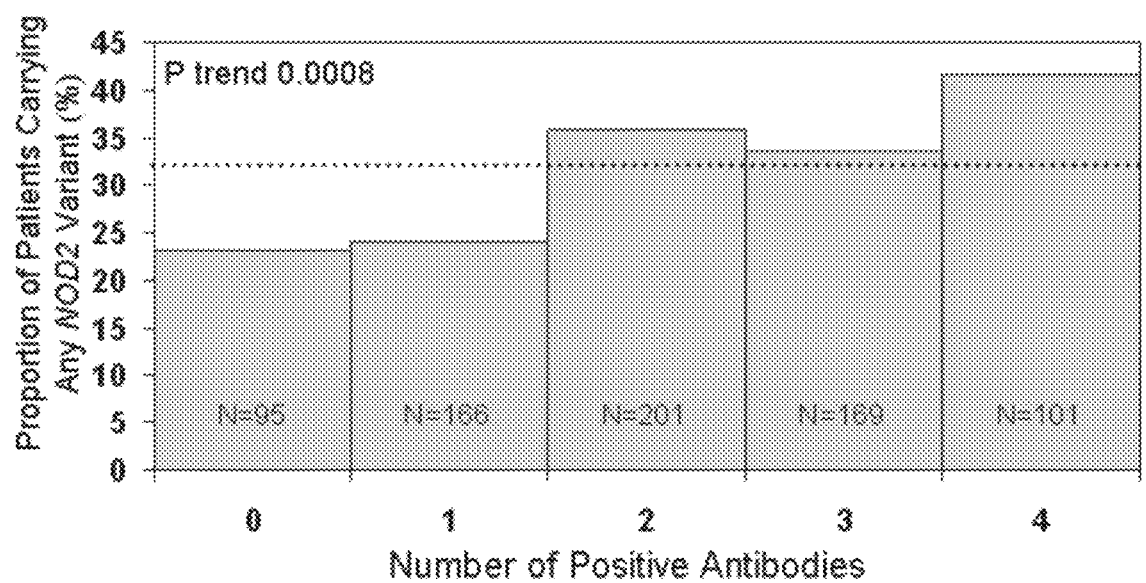
FIG. 18 depicts the frequency of carriage of any NOD2 variant increased with qualitative antibody reactivity, as represented by the antibody sum (number of positive antibodies, range 0-4). The dotted line represents the 31.8% frequency of carriage of at least one NOD2 variant, across the entire cohort.
Figure 19:
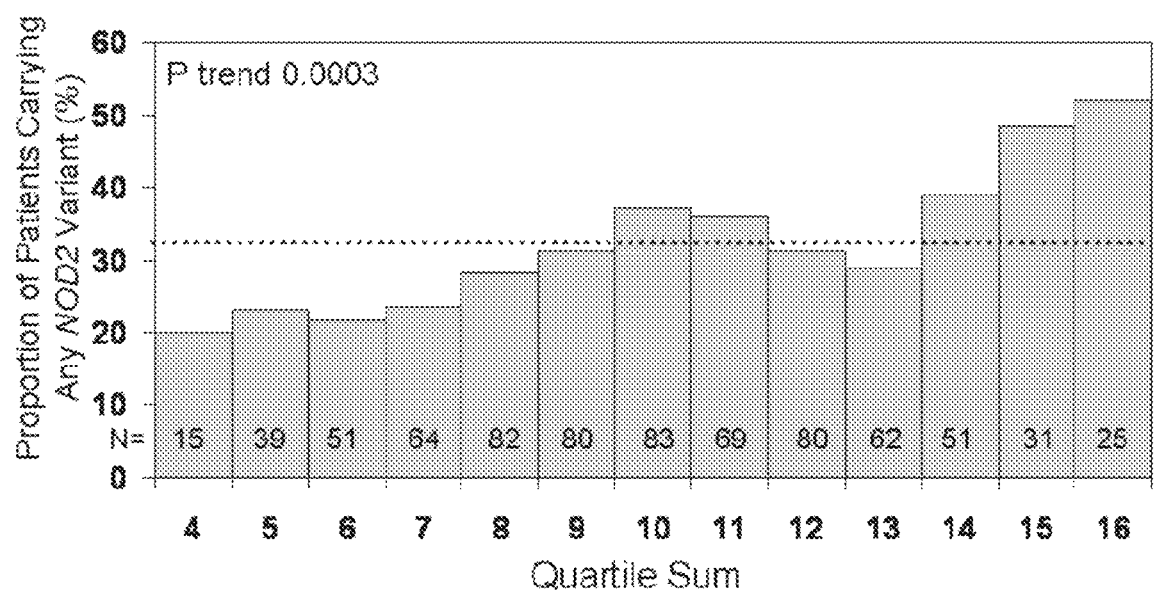
FIG. 19 depicts the frequency of carriage of any NOD2 variant increased with semiquantitative antibody reactivity, as represented by the quartile sum (range, 4-16). The dotted line represents the 31.8% frequency of carriage of at least one NOD2 variant, across the entire cohort.

As further disclosed herein, a Crohn's Disease patient cohort was divided into five groups based on the number of antibodies (from zero to four) for which they are qualitatively positive and the proportion of patients with NOD2 variant in each group is determined. NOD2 variants are present with increasing frequency in patients with reactivity to an increasing number of microbial antigens, especially when there is reactivity to two or more antibodies (FIG. 18). NOD2 variants are present in those with 0, 1, 2, 3 or 4 positive antibodies at a frequency of 23%, 24%, 36% and 42% respectively (P for trend=0.0008) (FIG. 18). NOD2 variants are present at increasing frequency in patients with increasing cumulative semi-quantitative immune response as reflected by individual quartile sums (P for trend 0.0003) (FIG. 19). As the serologic response is increased, either qualitatively (by number of positive antibodies) or semi-quantitatively (by magnitude of the cumulative serological response), the likelihood of a patient carrying a NOD2 variant is increased (FIGS. 18 and 19).

As further disclosed herein, the inventors compared the serologic response of patients carrying a NOD2 variant to those carrying no variant. In patients carrying any NOD2 variant, the mean number of positive antibodies is higher than in those carrying no variant (2.24+/− versus 1.92+/−1.24, respectively; P=0.0008) (Table 6). Patients carrying any NOD2 variant have a higher mean quartile sum than those carrying no variant (10.60+/−3.03 versus 9.72+/−3.01, respectively; P=0.0003) (Table 6).

TABLE 6

Cumulative Qualitative and Semi-Quantitative Sero-reactivity to Microbial Antigens According to NOD2 Variant Status in Crohn's Disease Patients

| | No NOD2 Variant (n = 499) | Any NOD2 Variant (n = 233) | P-value |
|---|---|---|---|
| Mean number of antibody positivity | 1.92 +/− 1.24 | 2.24 +/− 1.21 | 0.0008 |
| Mean quartile sum* | 9.72 +/− 3.01 | 10.60 +/− 3.03 | 0.0003 |

*Mean +/− Standard Deviation

Figure 20:
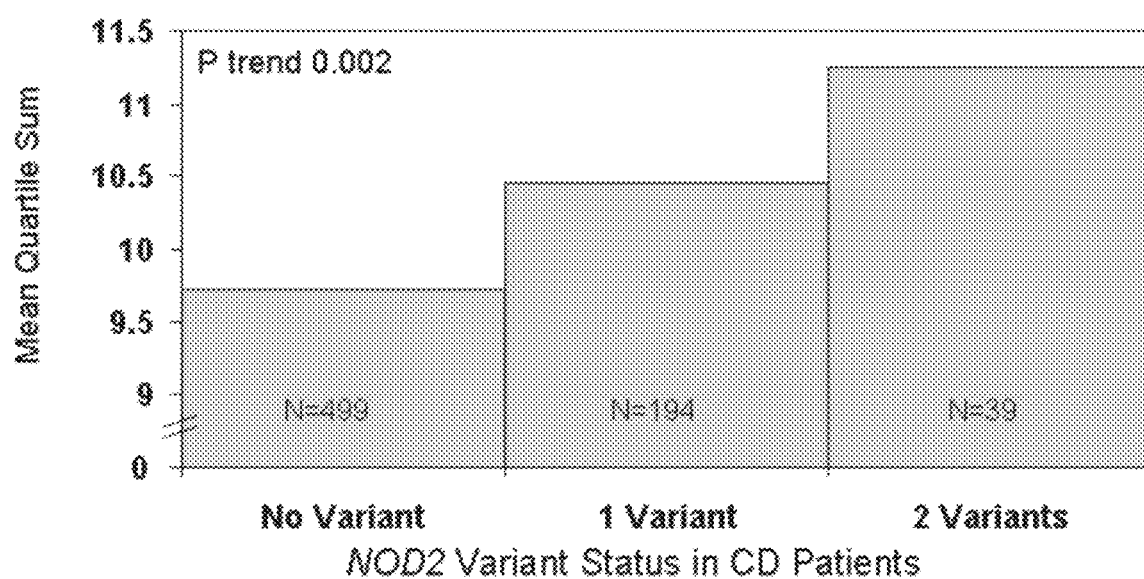
FIG. 20 depicts the cumulative semi-quantitative antibody reactivity, as represented by mean quartile sum, increased with increasing number of NOD2 variants by trend analysis (P=0.002).

As disclosed herein, the inventors compared the serologic response of patients with two defective alleles versus having only one. The mean quartile sum increases in parallel with increasing number of NOD2 variants (P trend=0.002) (FIG. 20).

As further disclosed herein, the inventors examined the absolute level of response to each antibody individually rather than collectively. For each of the four antibodies, the magnitude of sero-reactivity is higher when a NOD2 variant is present (Table 7).

TABLE 7

Median Sero-reactivity to Individual Microbial Antigens According to NOD2 Variant Status in Crohn's Disease Patients

| Antibody | Median seroreactivity in EU/ml* (range) No NOD2 Variant | Median seroreactivity in EU/ml* (range) Any NOD2 Variant | P-value |
|---|---|---|---|
| ASCA* | 0.032 (−1.40-2.31) | 0.620 (−1.26-2.57) | <0.0001 |
| Anti-I2 | 25.00 (0-248) | 27.56 (0-324) | 0.04 |
| Anti-Ompc | 16.32 (0-147) | 20.14 (0-203) | 0.03 |
| Anti-CBir1 | 28.36 (3.01-257) | 33.83 (0-280) | 0.01 |

Figure 21:
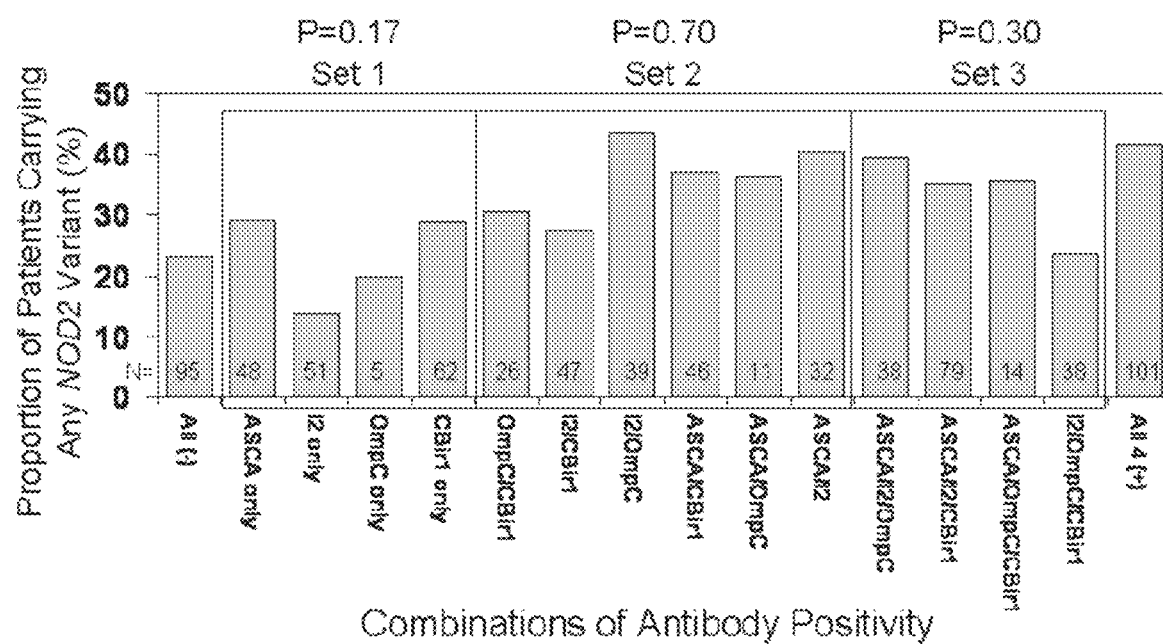
FIG. 21 depicts the cohort of CD patients divided into mutually exclusive groups based on all possible permutations of antibody positivity: no positive antibodies, single antibody positivity (4 groups in set 1), double antibody positivity (6 groups in set 2), and triple antibody positivity (4 groups in set 3), and all antibodies positive. Within each of the three sets, where the groups had the same number of antibody positivity, there was no statistically significant difference in the frequency of NOD2 variants among sets 1, 2, and 3, respectively.

*Sero-reactivity toward ASCA is expressed in standardized units with a mean of zero and a standard deviation of +/− one, thus a standardized unit may have a negative value As further disclosed herein, the inventors divided Crohn's Disease patients into 16 mutually exclusive groups based on all possible permutations of antibody positivity: no positive antibodies, single antibody positivity (4 groups in set 1), double antibody positivity (6 groups in set 2), triple antibody positivity (4 groups in set 3), and all antibodies positive. The inventors tested whether there is a significant difference among groups within each set where the groups had the same number of antibody positivity. There is no statistically significant difference in the frequency of NOD2 variants among groups within each set, and no single antibody or combination of antibody positivity is wholly responsible for the association between sero-reactivity and variant status (FIG. 21). As disclosed herein, the inventors discovered that the relationship between NOD2 variants and serologic response to microbial antigens reflects a cumulative effect rather than being driven by any particular antibody or antibody combination.

As further disclosed herein, the inventors calculated 2.7% as the proportion of variability in sero-reactivity that was attributable to the presence of a NOD2 variant.

Figure 22:
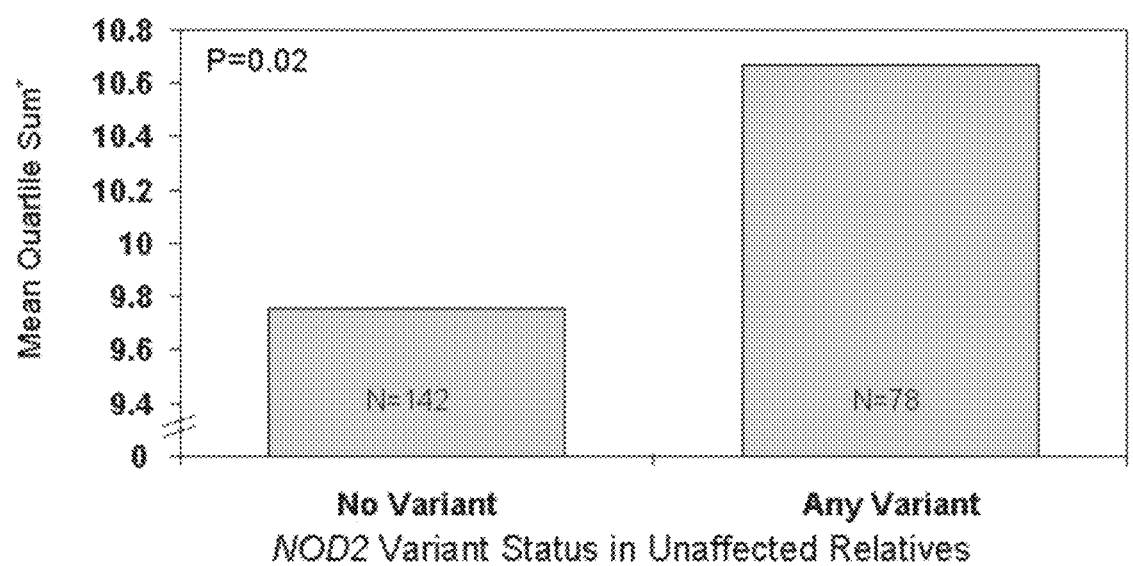
FIG. 22 depicts the cumulative semi-quantitative antibody reactivity in unaffected relatives of CD patients, as represented by mean quartile sum, was higher in individuals carrying any NOD2 variant than those carrying no variant (P=0.02). The quartile sum in unaffected relatives is based on quartiles of sero-reactivity within this cohort specifically and is not representative of the same magnitude of reactivity as an equivalent quartile sum value in a CD patient or a healthy control. No individuals carried two variants.
Figure 23:
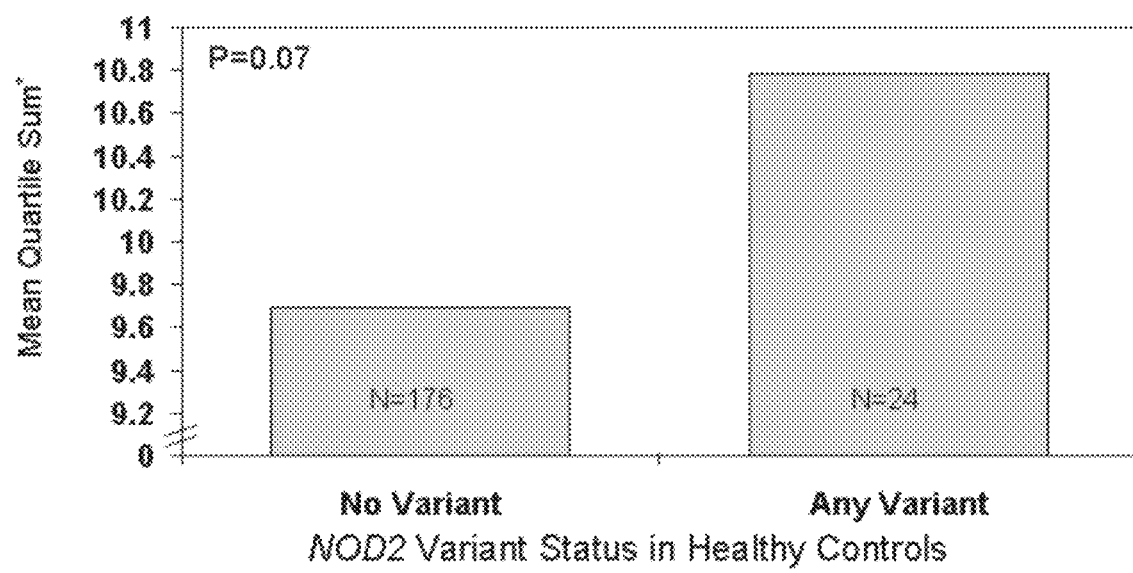
FIG. 23 depicts the cumulative semi-quantitative antibody reactivity in healthy controls, as represented by mean quartile sum, was numerically higher (though not achieving statistical significance) in individuals carrying any NOD2 variant than those carrying no variant (P=0.07). The quartile sum in healthy controls is based on quartiles of sero reactivity within this cohort specifically and is not representative of the same magnitude of reactivity as an equivalent quartile sum value in a CD patient or unaffected relative. No individuals carried two variants.

As further disclosed, a quartile sum was derived in Crohn's Disease patients, unaffected relatives, and healthy controls, based on the distribution of the magnitude of sero-reactivity within each cohort, with the same quartile sum in a Crohn's Disease patient or in a relative or healthy control not representative of the same absolute magnitude of response and not directly comparable. The magnitude of serologic response is significantly lower in unaffected relatives and healthy controls, compared to cases, and generally fell within the normal range. Sera was utilized from 220 unaffected relatives of Crohn's Disease patients (92% first degree). In the unaffected relatives the mean quartile sum in those individuals carrying any NOD2 variant is higher than those carrying no variant (10.67+/−2.73 vs. 9.75+/−2.52; P=0.02) (FIG. 22). Sera was utilized from 200 healthy controls. The mean quartile sum in healthy controls carrying any NOD2 variant is higher than healthy controls carrying no variant (n=176) (10.79+/−2.95 vs. 9.69+/−2.71; P=0.07) (FIG. 23).

NOD2 is a member of a family of intracellular cytosolic proteins important in mediating the host response to bacterial antigens and is found in epithelial cells of the small and large intestine as well as monocytes, macrophages, T and B cells, Paneth cells and dendritic cells (39-42). NOD2 senses MDP, a highly conserved component of bacterial peptidoglycan, which leads to the secretion of anti-bacterial substances such as alpha-defensins and the activation of nuclear factor kappa B (NF-kB) (43-44).

The inventors examined serologic and genetic data in 748 Crohn's Disease patients. ASCA and antibodies of I2, OmpC, and Cbir were measured by ELISA. Antibody sums (AS) and overall quartile sums (QS) (ranging from 4-16) of levels for all four antibodies were calculated as previously described (Mow et al Gastro 2004; 126:414). Genotyping (TaqmanMGB) was performed for 3 CD-associated variants of the NOD2 gene, R702W, G908R, and 1007fs.

ASCA was detected in 51%, anti-I2 in 58%, anti-OmpC in 38%, and anti-Cbir1 in 56%. 250 of 748 Crohn's Disease patients (33.4%) had at least one NOD2 variant; 206 (27.5%) having one and 44 (5.9%) having two. NOD2 variants were present at increasing frequency in patients with reactivity to increasing numbers of antigens. Variants were present in those with 0, 1, 2, 3, or 4 positive antibodies in 24%, 25%, 36%, 36%, and 46%, respectively (p for trend, 0.0001). NOD2 variants were present at increasing frequency in patients with increasing cumulative quantitative immune response as reflected by individual QS (p for trend, 0.0001). QS were also clustered into four groups by increasing cumulative quantitative immune response (group 1=4-6, group 2=7-9, group 3=10-13, and group 4=14-16). The frequency of having at least one NOD2 variant in each of the four groups was 22%, 29%, 35%, and 49% in groups 1, 2, 3, and 4, respectively (p for trend, 0.0001). The mean AS (number of positive antibodies) and QS was higher for patients with at least one NOD2 variant versus those with no variant (2.28+/−1.21 and 10.70+/−2.99 vs. 1.90+/−1.23 and 9.68+/−2.97, respectively. P, 0.0001).

Individuals with Crohn's disease who have variants of the NOD2 gene as a marker of abnormal innate immunity are more likely to have an increased adaptive immune response to multiple enteric organisms. The data provides a pathophysiologic link to similar findings in rodent mucosal inflammation. This allows disease relevant crossover genetic and functional studies.

TLR8

The inventors examined a case-control cohort consisting of 763 Crohn's Disease patients, 351 ulcerative colitis patients, and 254 control patients. The patients were genotyped using Illumina technology. SNPs were chosen to tag common Caucasian haplotypes using information from the Innate Immunity PGA.

Both a "risk" and a "protective" TLR8 haplotype were associated with CD in females (risk haplotype (H3): 18% of CD subjects had H3 compared with 8.9% of control subjects; protective haplotype (H2): 59% of CD subjects had H2 compared to 72% of control subjects). No significant association with TLR8 and CD in males was observed. H2 was also associated with UC in females (59% of UC females had H2 compared with 72% of controls, p=0.024) as well as males (32% of UC males had H2 compared with 47% of controls, p=0.009).

TLR8 haplotypes as described herein utilize data from the published Innate Immunity PGA collaboration.

TABLE 8

The odds ratio for CD and UC in females increased progressively as a factor of haplotype combinations from protective to risk.

| Odds Ratio | H2/H2 | H2/no H3 | Other | H3 positive | P value* |
|---|---|---|---|---|---|
| CD | 0.4 | 0.7 | 1 | 2 | 0.0002 |
| UC | 0.5 | 0.78 | 1 | 2.2 | 0.0032 |
| IBD | 0.43 | 0.7 | 1 | 2.1 | 0.0002 |

(*Mantel-Haenszel)

TLR8 is an X-linked IBD susceptibility gene, with common haplotypes predisposing and protecting. The associations further emphasize the importance of gene variation in innate immunity as genetic determinants, not only of CD, but of UC as well.

TLR2

The inventors studied if the relationship between variants in innate immune receptors and sero-reactivity to microbial antigens differed in Jewish (J) versus non-Jewish (NJ) patients with CD. Sera from 731 CD patients (282 J, 449 NJ) was tested for ASCA, anti-I2, anti-OmpC, and anti-CBir1 by ELISA while DNA was tested for five TLR2, two TLR4, and two TLR9 variants. The magnitude of responses to microbial antigens was examined according to variant status. Overall quartile sums (QS) (ranging from 4-16) of levels for all four antibodies were calculated as previously described (Mow et al Gastro 2004; 126:414).

There is no association between any TLR4 or 9 variant and sero-reactivity to microbial antigens in Jewish or non-Jewish patients with CD. There is an association between the non-synonymous, non-conservative P631H variant of TLR2 and ASCA positivity in Jewish patients (OR 2.75, p for interaction=0.01). There is an association between the P631H variant of TLR2 and cumulative quantitative response to microbial antigens in Jewish patients with CD. QS were clustered into four groups by increasing cumulative quantitative immune response (group 1=4-6, group 2=7-9, group 3=10-13, and group 4=14-16). The frequency of carriage of the P631H variant of TLR2 increased in parallel with QS cluster in Jewish patients; 2.86%, 3.70%, 7.02%, and 13.46% in groups 1, 2, 3, and 4, respectively (p for trend=0.03). No similar association is found in non-Jewish patients; 7.14%, 10.42%, 6.67%, and 5.45% in groups 1,2,3, and 4, respectively (p for trend=0.40).

Jewish, but not non-Jewish patients with CD who carry the P631H variant of TLR2 have increased sero-reactivity to microbial antigens. The data adds evidence to the paradigm that, in CD, innate immune defects lead to enhanced adaptive immune response to microbial antigens. The differential response to the same genetic variant in two different populations shows a possible gene-gene interaction consistent with the multigenic nature of CD.

Example 3

Increased Immune Reactivity Predicts Aggressive Complicating Crohn's Disease in Children Crohn's disease (CD) is a heterogeneous disorder characterized by diverse clinical phenotypes (inflammatory, fibrostenosing [FS], internal penetrating [IP]) that appear to be influenced by genetic and immune factors. Children frequently manifest an aggressive disease course, and the ability to identify those at risk for complicated disease at diagnosis would be invaluable in guiding initial therapy.

The inventors examined the association of serological immune responses and CARD15 with CD phenotype in a large well-characterized pediatric collaborative cohort. Sera were collected from 797 prospectively followed pediatric CD cases and tested for immune responses to microbial antigens: anti-Cbir1 (flagellin), anti-outer membrane protein C (anti-OmpC) and anti-*Saccharomyces-cerevisiae* (ASCA) using ELISA. Genotyping (TaqmanMGB) was performed for 3 CD-associated variants of CARD15 (SNPs 8, 12, 13). Disease phenotypes were determined blinded to genotype and immune responses. Associations between immune responses, CARD15 and clinical phenotype were evaluated.

CARD15 variants and immune responses were present in 34% and 78%, respectively. Small bowel (SB) location, IP and/or FS disease behavior were present in 68% (n=542) and 20% (n=152) of children after a median follow-up of 31 months. The odds of developing IP and/or FS disease were highest in patients positive for all 3 immune responses (Table 9). The highest level for each individual antibody was associated with IP and/or FS with the odds being highest when using the sum of all immune response levels (Table 10). Multivariate analysis confirmed the Anti-OmpC (p<0.0002) and anti-Cbir1 (p=0.005) association with IP as well as ASCA (p=0.02) and anti-Cbir1 (p=0.04) with FS. CARD15 was associated with small bowel disease (OR=1.7; p<0.0001) only, not with disease behavior. The rate of complicated CD increases in children as the number and magnitude of immune reactivity increases. Baseline immune response assessment may identify children at risk for complicating IP/FS phenotypes, for whom early, aggressive immunomodulatory therapy could be of benefit.

TABLE 9

Qualitative Analysis

| | ASCA Odds Ratio (OR); p value | Anti-OmpC OR; p value | Anti-Cbir1 OR; p value | Antibody Sum (ASCA+, OMPC+, Cbir1+) OR: p value |
|---|---|---|---|---|
| SB | 2.9; p < 0.0001 | NS | 1.6; p = 0.002 | 2.8; p < 0.0001 |
| FS | 2.4 p < 0.0001 | 2.7; p < 0.0001 | 2.0; p = 0.002 | 6.1; p < 0.0001 |
| IP | 2.3; p = 0.002 | 3.7; p < 0.001 | 2.3; p = 0.003 | 9.5; p < 0.0001 |

TABLE 10

Quantitative Analysis

| | ASCA OR; p value | Anti-OmpC OR; p value | Anti-Cbir1 OR; p value | Quartile Sum OR; p value |
|---|---|---|---|---|
| SB | 3.5; p < 0.0001 | NS | 1.8; p = 0.003 | 3.5; p < 0.0001 |
| FS | 2.6; p = 0.0001 | 3.5; p < 0.0001 | 3.7; p < 0.0001 | 12.5; p < 0.0001 |
| IP | 2.1; p = 0.006 | 3.5; p = 0.0001 | 3.9; p = 0.002 | 8.5; p < 0.0001 |

Serum Immune Responses Predict Rapid Disease Progression Among Children with Crohn's Disease: Immune Responses Predict Disease Progression Crohn's disease (CD) is a heterogeneous disorder characterized by diverse clinical phenotypes. Childhood-onset CD has been described as a more aggressive phenotype. Genetic and immune factors may influence disease phenotype and clinical course. The inventors examined the association of immune responses to microbial antigens with disease behavior and prospectively determined the influence of immune reactivity on disease progression in pediatric CD patients.

Sera were collected from 196 pediatric CD cases and tested for immune responses: anti-I2, anti-outer membrane protein C (anti-OmpC), anti-Cbir1 flagellin (anti-CBir1), and anti-*Saccharomyces-cerevisiae* (ASCA) using ELISA. Associations between Immune responses and clinical phenotype were evaluated.

Fifty-eight patients (28%) developed internal penetrating and/or stricturing (IP/S) disease after a median follow-up of 18 months. Both anti-OmpC (p<0.0006) and anti-12 (p<0.003) were associated with IP/S disease. The frequency of IP/S disease increased with increasing number of immune responses (p trend=0.002). The odds of developing IP/S disease were highest in patients positive for all four immune responses (OR (95% CI): 11 (1.5-80.4); p=0.03). Pediatric CD patients positive for ≥1 immune response progressed to IP/S disease sooner after diagnosis as compared to those negative for all immune responses (p<0.03).

The presence and magnitude of Immune responses to microbial antigens are significantly associated with more aggressive disease phenotypes among children with CO. This demonstrates that the time to develop a disease complication in children is significantly faster in the presence of immune reactivity, thereby predicting disease progression to more aggressive disease phenotypes among pediatric CD patients.

Serum Immune Responses Predict Rapid Disease Progression Among Children with Crohn's Disease: Immune Responses Predict Disease Progression: Patient Population Pediatric CD patients were enrolled from participating sites of the Western Regional Pediatric IBD Research Alliance. In order to be eligible, all CD patients must have undergone complete colonoscopy with ileal intubation or complete colonoscopy and small bowel follow through. A diagnosis of CD for this study required at least two of the following: (1) history of abdominal pain, weight loss, short stature, malaise, rectal bleeding, or diarrhea; (2) characteristic endoscopic findings of discontinuous ulcerations, cobblestoning, fistula, or severe perianal disease; (3) radiologic features of stricture, fistula, or evidence of cobblestoning, or ulceration of the mucosa; (4) macroscopic appearance at laparotomy of typical bowel wall induration, mesenteric lymphadenopathy, or serosal involvement showing creeping fat, or other inflammatory changes; (5) histopathology showing transmural inflammatory cell infiltrate or epithelial granulomas and absence of identifiable infectious agents (16). Blood for serological analysis was drawn at each of the participating sites and sent via overnight FedEx to the Genotyping Core Facility of the Medical Genetics Institute/GCRC and the Immunobiology Institute at Cedars-Sinai Medical Center (CSMC). This study was approved by the Ethics Review Board at each participating site.

Serum Immune Responses Predict Rapid Disease Progression Among Children with Crohn's Disease: Immune Responses Predict Disease Progression: Data Collection Subjects and their families completed patient demographic forms at the time of blood draw and physicians completed clinical information forms in reference to both date of diagnosis and date of last follow-up. Once collected, all data were then transferred and stored in a secure relational (Oracle) database for analysis. For the purpose of this study, key variables included date of diagnosis, age at diagnosis, date of last follow-up and duration of disease as of last follow-up, ethnicity, family history, disease location, disease behavior, granulomas, and surgical procedures.

Serum Immune Responses Predict Rapid Disease Progression Among Children with Crohn's Disease: Immune Responses Predict Disease Progression: Phenotype All phenotype assessments were performed by clinical investigators blinded to genetic and immune response analysis and based on the following uniform definitions:

Disease location at diagnosis was defined by the extent of the disease involvement at the time of initial presentation. Disease extent was based on endoscopic, histologic, and radiographic evidence of inflammation.

Disease location as of last follow-up was defined by the maximal extent of the disease involvement at the point of last follow-up or before a patient underwent first resection. Other than anal/perianal disease, location change was documented when clinically indicated investigations were performed anytime from diagnosis until the date of last follow-up. For the purpose of analysis, disease location as of last follow-up was used for all genotype/immune response-phenotype associations.

There were five disease locations that patients were categorized into (1) small bowel only: disease of the small bowel proximal to the cecum and distal to the ligament of treitz; (2) large bowel only: any colonic location between the cecum and rectum with no small bowel disease; (3) small and large bowel: disease of the small bowel and any location between the cecum and rectum; (4) upper digestive tract disease involving at least one of the following sites: esophagus, stomach. and duodenum; (5) anal: perianal and anal lesions including skin tags and anal ulcers. Patients could have been in more than one category such that patients with small and/or large bowel disease may also have concomitant upper tract and/or anal disease.

Disease behavior at diagnosis was defined by the behavior of the disease at presentation.

Disease behavior as of last follow-up was defined by the disease behavior observed as of last follow-up. At both time points, data may have been obtained after a patient underwent a surgical resection, as reliable data are often obtained at the time of surgery for defining complicated disease behaviors.

Disease behavior was divided into two broad categories: noncomplicating and complicating disease behaviors. Noncomplicating behavior referred to uncomplicated inflammatory disease without evidence of stricturing or penetrating disease behaviors (nonpenetrating nonstricturing [NPNS]). Complicating behaviors referred to penetrating and stricturing disease. (1) Stricturing disease was defined as the occurrence of constant luminal narrowing demonstrated by radiologic, endoscopic, or surgical examination combined with pre-stenotic dilatation and/or obstructive signs or symptoms. (2) Penetrating disease was defined as either IP if patients had evidence of entero-enteric or entero-vesicular fistulae, intraabdominal abscesses, or intestinal perforation, or perianal penetrating (PP) if patients developed either perianal fistulae or abscesses or recto-vaginal or ano-vaginal fistulae.

For the purpose of analysis, stricturing and IP complications were grouped into one outcome. PP and patients without complications (NPNS) comprised the other two comparison groups.

Serum Immune Responses Predict Rapid Disease Progression Among Children with Crohn's Disease: Immune Responses Predict Disease Progression: Immune Responses All blood samples were taken at the time of consent and enrollment. Sera were analyzed for expression of ASCA, antiOmpC, anti-12, and anti-CBir1 antibodies in a blinded fashion by ELISA. Analysis and IgG and IgA ASCA were performed at Cedars-Sinai Medical Center or Prometheus Laboratories using the same technology. All assays for anti-OmpC, anti-I2, and anti-CBir1 were performed at Cedars-Sinai. Antibody levels were determined and results expressed as ELISA units (EU/mL), which are relative to a Cedars-Sinai Laboratory (IgA-I2, IgA-OmpC, and IgG CBir1) or a Prometheus Laboratories Standard (IgA and IgG ASCA), which is derived from a pool of patient sera with well-characterized disease found to have reactivity to this antigen.

Serum Immune Responses Predict Rapid Disease Progression Among Children with Crohn's Disease: Immune Responses Predict Disease Progression: Statistical Analysis To determine the associations between disease phenotype characteristics and antibody responses toward microbial antigens, univariate analyses using chi-squared tests were performed. Odds ratios (OR) and 95% confidence intervals were calculated to compare the odds of positive serum reactivity toward the microbial antigens (CBir1, I2. OmpC. and ASCA) in the group of patients with a certain disease characteristic with the group of patients without such a characteristic. Quantitative comparison of immune response levels between groups (IP/S+vs IP/S−) for each antibody was performed using nonparametric Wilcoxin rank test. Multivariate analysis with logistic regression modeling was also performed to determine the primary associations among qualitative serological responses with disease phenotypes. To compare the length of time to the development of a disease complication between groups, Kaplan-Meier estimator of survival probability was calculated to construct survival curves. The log-rank test was used to test if the survival curves were significantly different between subgroups of patients. All analyses were performed by using Statistical Analysis Software (Version 8.02. SAS Institute, Inc., Cary NC).

Serum Immune Responses Predict Rapid Disease Progression Among Children with Crohn's Disease: Patient Population Results A total of 196 pediatric CD patients were eligible for analysis. Eighty-five percent (168/196) were Caucasians and 28% were of Jewish background. The median age at diagnosis was 12 yr (1-18) and the median age at study was 13 yr (4-19). The cohort comprised 47% males and 53% females. A positive family history of IBD was reported in 29% of patients.

Serum Immune Responses Predict Rapid Disease Progression Among Children with Crohn's Disease: Clinical Phenotypes Results A total of 38 (19%) patients had either a stricturing and/or penetrating complication at the time of diagnosis. After a median follow-up time (median disease duration as of last follow-up) of 18 months (1-200), the total number of pediatric CD patients who experienced a disease complication increased to 58 (30%). Table 11 details the clinical phenotypes of the pediatric CD cohort. Of the 35 patients with internal penetrating and/or stricturing (IP/S) disease, 18 had isolated stricturing disease, 11 had IP and 6 had both complications. Thirty-two of the 58 patients (55%) underwent a combined total of 53 surgeries related to disease complications, 38 (72%) of which were small bowel surgeries for IP/S disease complications. The remaining surgeries were for perianal perforating diseases. All but two patients (15/17) with IP disease and 45% of patients with isolated stricturing disease underwent small bowel surgery as of last follow-up.

TABLE 11

Clinical Phenotypes in Pediatric CD Cohort

| Clinical Phenotype | N (%) |
|---|---|
| Disease location | |
| Small bowel only | 24 (12.2) |
| Large bowel only | 51 (26.0) |
| Small and large bowel | 120 (61.2) |
| and/or upper tract | 78 (39.8) |
| and/or anal disease | 39 (19.9) |
| Disease behavior at diagnosis | |
| Non-penetrating non-stricturing | 158 (80.6) |
| Internal penetrating and/or stricturing | 21 (10.7) |
| Perianal penetrating only | 17 (8.7) |
| Disease behavior as of last follow up | |
| Non-penetrating non-stricturing | 138 (70.4) |
| Internal penetrating and/or stricturing | 35 (17.9) |
| Perianal penetrating only | 23 (11.7) |

Serum Immune Responses Predict Rapid Disease Progression Among Children with Crohn's Disease: Immune Responses Results Serum was collected at a median of 9.4 months (0-211.7) after diagnosis, 18% of patients ($35/196$) had serum collected at the time of diagnosis or within 1 month of diagnosis and 33% ($64/196$) within 3 months of diagnosis. A total of 77.0% of patients were positive for at least one immune response, 23.7% of which were positive for a combination of any two immune responses. 16.4% of patients were positive for all three responses, and 3.4% were positive for al 1 four responses. ASCA anti-12, anti-OmpC, and anti-CBir1 were present in 43%, 26%, 22%, and 53%, respectively.

Serum Immune Responses Predict Rapid Disease Progression Among Children with Crohn's Disease: Immune Responses and CD Phenotypes Results Presence and magnitude of immune responses influence disease behavior. A statistically significant association was not found for any of the immune responses with family history, ethnicity, or the presence of granulomas. ASCA was the only antibody significantly associated with small bowel disease location; yet was not associated with disease behavior. Both anti-12 (p=0.0034) and anti-OmpC (p=0.0006) were associated with complicating disease behaviors, more specifically IP/S disease. The frequency of isolated perianal perforating disease was similar between immune response groups (±) for all four antibodies. In addition to the qualitative associations observed for anti-OmpC and anti-I2, the magnitude of the immune response to OmpC and I2 also had an association with internal perforation and/or stricturing disease (p=0.008 and p=0.002 for anti-OmpC and anti-I2, respectively). The anti-OmpC association continued to be significant in the multivariate logistic regression, which showed that anti-OmpC (p<0.02) was independently associated with IP/S disease. ASCA, anti-I2, and anti-Cbir1 did not show any independent association with disease behavior.

Cumulative influence of immune responses on disease behavior. Individually there is a clear association with individual immune responses I2 and OmpC with IP/S. The inventors then examined whether there was a cumulative influence of immune responses on disease behavior and determined if the odds of having complicating IP/S disease were greater in the presence of multiple immune responses. As demonstrated, the frequency of IP/S disease significantly increased (p trend=0.002) as the number of immune responses increased. The OR demonstrate that the odds of having IP/S disease was significantly increased in children positive for a combination of any three immune responses (OR [95° C.I]; OR=5.5 [1.3-23.6]; p=0.02) and even more so in children positive for all four immune responses (OR

[95% CI]; OR=11.0 [1.5-80.4]; p=0.03) as compared to those patients negative for all immune responses (baseline group).

Serum Immune Responses Predict Rapid Disease Progression Among Children with Crohn's Disease: Disease Progression Results Based on the cross-sectional data, immune responses are associated with the presence of disease complications. For the second aim of the study, the inventors set out to examine whether seropositive patients (≥1 immune response) have a greater risk to progress to IP/S as compared to seronegative patients (0 immune responses). The inventors used a longitudinal study to answer this question which included only those patients who did not have IP/S at diagnosis (NPNS±PP) and continued to be uncomplicated (NPNS±PP) at the time the serum was collected for immune response measurement so that we could be certain that when clinically recognizable IP/S occurred it was after the sera were collected for antibody measurement. The median time from diagnosis to serum draw was 9.2 months (0-142.3). Among those who developed IP/S (10/167) during the follow-up, the median time from diagnosis to the onset of IP/S was 48 months. As of last follow-up, 8.2% (⅚7) of the seropositive group had IP/S versus only 2.9% (2./70) in the seronegative group. Because longer disease duration increases the chance of developing IP/S and not all patients are followed for the same amount of time, the inventors performed survival analysis to take the length of follow-up into consideration. The inventors first evaluated survival with OmpC, I2, and ASCA. Given the same length of follow-up, among those patients positive for at least one serology, more progressed to IP/S than those negative for the three serologies (p=0.03). Saying it differently, those patients positive for at least one serology progressed to IP/S faster than those negative for all three serologies. We then examined whether the addition of Cbir1 changed the survival outcome. Of significance is that the two patients who developed IP/S in the presumptive seronegative group, when measuring I2, OmpC, and ASCA only, were actually CBir1 positive. The inventors have fewer patients followed out long enough in those who had all four antibodies measured. Thus, when the inventors have adequate such numbers these anti-CBIR positive patients would be reclassified to the seropositive group. As of last follow-up, all seronegative patients remained complication free.

Serum Immune Responses Predict Rapid Disease Progression Among Children with Crohn's Disease: Conclusion The inventors have demonstrated that immune reactivity to specific microbial antigens is associated with complicating disease behaviors. This study demonstrates that immune responses to an increasing number of microbial antigens are associated with complicating IP/S disease behaviors in pediatric CD patients. Moreover, disease progression to a more aggressive disease phenotype in children is accelerated in the presence of immune reactivity. Serum immune responses predict a more rapid disease progression from uncomplicated to complicated disease.

CARD8: A Novel Association with Childhood-Onset Ulcerative Colitis (UC)

CARD proteins play an important role in apoptosis and cytokine regulation, including NfKB, processes which are important in the pathogenesis of IBD. CARD15/NOD2 was the first novel gene reported to confer Crohn's disease (CD) susceptibility and influence disease phenotype. CARD4 has not been found to be associated with CD. McGovern et al reported a significant CD association with the CARD8/TUCAN/CARDINAL gene toured at 19q13.3 in adult patients.

The inventors investigated the association of the CARD8-T10C polymorphism with susceptibility to UC and CD in children. DNA was collected from 342 subjects (75 CD trios, 39 UC trios). Both parents and the affected child were genotyped for 3 allelic variants of the CARD15 gene (R702W. G908R, 1007insC, also referred to as SNP 8, 12 and 13) as an association control and 1 variant of the CARD gene (T10C) using Taqman technology. The transmission disequilibrium test (TDT) was used to test association with either UC or CD using GENEHUNTER 2.0.

CARD8 allele T was present in 63% of CD patients and 77% of UC patients. CARD15 frequency (any variant) was 25% and 11% in CD and in UC, respectively. Similar frequencies were observed for parents for both genes. As expected, transmission distortion was seen for all CARD15 variants in CD, but not in UC. No association was observed between CARD8 and CD, however, in contrast, TDT showed a highly significant association with UC, with over transmission of the CARD8 common allele (Table 12).

This shows a CARD8 association with childhood-onset UC. The over transmission of the common allele in this analysis is similar to that which is seen with PPARgamma in type 2 diabetes and the insulin gene polymorphism in type 1 diabetes. These findings are in contrast to the adult CD association showing different mechanisms for pediatric IBD.

TABLE 12

TDT Analysis

| | CARD8 T allele | | | CARD13 SNP 8,12,13 | | |
|---|---|---|---|---|---|---|
| | TRANSMITTED | NOT TRANSMITTED | pvalue | TRANSMITTED | NOT TRANSMITTED | pvalue |
| CD (a = 75) | 37 | 33 | NS | 30 | 21 | 0.003 |
| UC (n = 39) | 23 | 8 | 0.007 | 4 | 7 | NS |

Antibodies to a Novel Flagellin (CBIR1) Adds Clinical Utility to the Diagnosis and Differentiation of Pediatric IBD Approximately ⅔ of IBD patients are positive for antibodies to microbial and auto-antigens. A novel antibody, anti-Cbir1, may have unique diagnostic properties and phenotypic associations in children. The inventors examined the added utility of anti-Cbir1 in the diagnosis and differentiation of pediatric IBD patients as compared to previously defined antibodies: ASCA, OmpC, I2 and pANCA.

Sera from 331 pediatric IBD patients (111 UC, 220 CD) were tested by ELISA for anti-OmpC, anti-I2, ASCA, anti- Cbir1 and pANCA. Quantitative and qualitative expression of antibody markers was evaluated. Anti-Cbir1 was present in 55% of CD vs. 15% of UC (p<0.001). 41% of anti-Cbir1 (+) UC patients were also positive for >1 CD-related antibody. Anti-Cbir1 was present in 53% of ASCA(−) CD patients and in 52% (31/60) of patients negative for all antibodies. The most Cbir1 reactive CD subset was OmpC+/I2+(74% median=49) and least reactive was ASCA+(56%, median=31). 13.5% of pANCA (+) only UC patients were anti-CBir1 (+) as compared to 35% of pANCA(+) only CD patients (p=0.03). Both pANCA and anti-Cbir1 levels were higher in pANCA (+) CD vs. UC (median pANCA: 46.6 vs. 70.0: p=0.003, and median anti-Cbir1: 21 vs. 12 p<0.0001).

Anti-Cbir1 increased detection of CD cases negative for all other antibodies. Cbir1 reactivity added to the differentiation of pANCA+CD from pANCA+UC and can minimize misdiagnosed CD colitis patients. Both the presence and magnitude of anti-Cbir1 reactivity adds to the clinical utility of presently known antibodies in pediatric IBD.

Increased Immune Reactivity Predicts Aggressive Complicating Crohn's Disease in Children The inventors determined whether immune responses and/or CARD15 variants are associated with complicated disease phenotypes and predict disease progression. Sera were collected prospectively from 796 pediatric CD cases and tested for anti-Cbir1 (flagellin), anti-outer membrane protein C (anti-OmpC), anti-*Saccharomyces-cerevisiae* (ASCA) and perinuclear anti-neutrophil cytoplasmic antibody (pANCA) using ELISA. Genotyping (TaqmanMGB) was performed for 3 CARD15 variants (SNPs 8, 12, 13). Associations between immune responses (antibody sum (AS) and quartile sum score (QSS), CARD15, and clinical phenotype were evaluated. All phenotype assessments were performed by clinical investigators blinded to genetic and immune response analysis.

32% of patients developed at least one disease complication within a median of 32 months and 18% underwent surgery. 73% of patients were positive for at least 1 immune response. The frequency of IP, S and surgery significantly increased (p trend <0.0001 for all 3 outcomes) with increasing AS and QSS. 9% of seropositive groups had IP/S vs. 2.9% in the seronegative group (p=0.01). 12% of seropositive groups underwent surgery vs. 2% in the seronegative group (p=0.0001). The highest AS group and QSS group demonstrated the most rapid disease progression (p<0.0001). Increased hazard ratio was observed for AS group 3 (7.8 [2.2-28.7] p<0.002 and QSS group 4 (11.0 [1.5, 83.0] p<0.02).

The inventors found that the rate of complicated CD increases in children as the number and magnitude of immune reactivity increases. Disease progression is significantly faster in children expressing immune reactivity. Baseline immune response assessment predict children at risk for complicating IP/S phenotypes, in whom early effective therapy would be of benefit.

Increased Immune Reactivity Predicts Aggressive Complicating Crohn's Disease in Children: Patient Population Pediatric CD patients were enrolled from 21 participating sites of the Western Regional Pediatric IBD Research Alliance, The Pediatric IBD Collaborative Research Group and the Wisconsin Pediatric IBD Alliance.

In order for pediatric CD patients to be eligible, all CD patients must have undergone complete colonoscopy with ileal intubation or complete colonoscopy and small bowel follow through. A diagnosis of CD was based on standard diagnostic criteria. Blood for serological analysis was drawn and sent to The Immunobiology Institute at Cedars-Sinai Medical Center (CSMC) for all sites in the Western Regional and Wisconsin Alliance. Serological analyses were run at Prometheus Laboratories (San Diego, CA) for all patients drawn at sites of the Pediatric IBD Collaborative Research Group. Genotyping was performed by the Genotyping Core Facility of the Medical Genetics Institute/GCRC at CSMC for all Western Regional sites, at the Children's Hospital of Wisconsin (SK) for the Wisconsin Alliance, and at Prometheus Laboratories for all sites of The Pediatric IBD Collaborative Research Group.

Increased Immune Reactivity Predicts Aggressive Complicating Crohn's Disease in Children: Disease Location Disease location was defined by the extent of the disease involvement at the time of initial presentation. Disease extent was based on endoscopic, histologic and radiographic evidence of inflammation.

There were 5 disease locations that patients were categorized into: 1) Small bowel only: disease of the small bowel proximal to the cecum and distal to the ligament of treitz; 2) Large bowel only: any colonic location between cecum and rectum with no small bowel disease; 3) Small and large bowel: disease of the small bowel and any location between cecum and rectum; 4) Upper digestive tract: disease involving at least one of the following sites: esophagus, stomach, duodenum; 5) Anal: perianal and anal lesions including skin tags and anal ulcers. Patients could have been in more than one category such that patients with small and/or large bowel disease may also have concomitant upper tract and/or anal disease.

Increased Immune Reactivity Predicts Aggressive Complicating Crohn's Disease in Children: Disease Behavior Disease behavior at diagnosis was defined by the behavior of the disease at presentation. Disease behavior as of last follow-up was defined by the disease behavior observed as of last follow-up. At both time points, data may have been obtained after a patient underwent a surgical resection, as reliable data is often obtained at the time of surgery for defining complicated disease behaviors.

Disease behavior was divided into 2 broad categories: non-complicating and complicating disease behaviors: non-complicating behavior: referred to uncomplicated inflammatory disease without evidence of stricturing or penetrating disease behaviors (non-stricturing non-penetrating [NPNS]). Complicating behaviors referred to penetrating and stricturing disease. 1) Stricturing disease (S): was defined as the occurrence of constant luminal narrowing demonstrated by radiologic, endoscopic or surgical examination combined with pre-stenotic dilatation and/or obstructive signs or symptoms. 2) Penetrating disease: was defined as either internal penetrating (IP) if patients had evidence of entero-enteric or entero-vesicular fistulae, intra-abdominal abscesses or intestinal perforation or perianal penetrating (PP) if patients developed either perianal fistulae or abscesses or recto-vaginal or ano-vaginal fistulae.

Increased Immune Reactivity Predicts Aggressive Complicating Crohn's Disease in Children: Immune Responses All blood samples were taken at the time of consent and enrollment. Sera were analyzed for expression of pANCA, ASCA, anti-OmpC, and anti-CBir1 antibodies in a blinded fashion by ELISA. Serological analyses were performed at CSMC or Prometheus Laboratories using the same technology. Antibody levels were determined and results expressed as ELISA units (EU/ml), which are relative to a Cedars-Sinai Laboratory or a Prometheus Laboratories Standard which is derived from a pool of patient sera with well-characterized disease found to have reactivity to this antigen.

Increased Immune Reactivity Predicts Aggressive Complicating Crohn's Disease in Children: Definitions of Immune Responses The following definitions were used for all analyses involving ASCA, anti-OmpC and anti-CBir1 immune responses. pANCA was analyzed separately given that pANCA has been shown to be negatively associated with the majority of disease phenotypes except large bowel disease location.

Antibody sum (AS): number of positive antibodies per individual: 0, or 1 or 2, or 3 positive.

Antibody Quartile Score: quartile score for each antibody level (<25%=1, 25-50%=2, 51%-<75%=3, 75%-100%=4).

Quartile Sum Score (QSS): sum of quartiles score for all 3 antibodies (ASCA (A or G, anti-OmpC and anti-CBir1). Minimum score of 3 (all antibodies had a quartile score of 1) and maximum score of 12 (all antibodies had a quartile score of 4).

Quartile Sum Score (QSS) Group: In order to minimize the number of patient subsets i.e quartile sum score 3-12, the inventors regrouped patients based on a range of quartile sum scores: Quartile sum score 3-5=group 1, 6-7=group 2, 8-9=group 3 and 10-12=group 4.

Increased Immune Reactivity Predicts Aggressive Complicating Crohn's Disease in Children: Genotyping Three single nucleotide polymorphisms (SNP's) in the CARD15 gene have been associated with CD. CARD15 SNP's R675W (rs2066844, CEPH-IBD1-snp8), G881R (rs2066845, CEPH-MD1-snp12), and 3020insC (rs2066847, CEPH-MD1-snp13) were adapted to the TaqMan MGB genotyping platform following the manufacturer's instructions and using PrimerExpress design software (Applied Biosystems, Foster City, CA). The TaqMan MGB platform is a two-probe, 5'-exonuclease PCR assay that employs a minor groove binder on the 3'-end of the probes in order to give greater allele discrimination.

Increased Immune Reactivity Predicts Aggressive Complicating Crohn's Disease in Children: Statistical Analysis To determine the associations between disease phenotype characteristics and antibody responses toward microbial antigens, univariate analyses using $\chi^2$ tests were performed. Odds ratios (OR) and 95% confidence intervals were calculated to compare the odds of positive serum reactivity (antibody sum, quartile sum score, quartile sum score group) towards the microbial antigens (CBir1, OmpC, and ASCA) in the group of patients with a certain disease characteristic with the group of patients without such a characteristic. For the OR calculations the minimum antibody sum of 0, the minimum quartile sum score of 3 and the minimal quartile sum score group 1 were set as baseline, i.e. OR of 1.0 Quantitative comparison of immune response levels between groups (IP/S+vs. IP/S−) for each antibody was performed using non-parametric Wilcoxin Rank test. Stepwise multivariable analysis using logistic regression modeling was also performed to determine the primary associations among qualitative serological responses with disease phenotypes. To compare the length of time to the development of a disease complication between groups, Kaplan-Meier estimator of survival probability was calculated to construct survival curves. The log-rank test was used to test if the survival curves were significantly different between subgroups of patients. The hazard ratio (HR) of occurrence of complication or surgery among patients who were sera positive compared to those who were sera negative as well as who were in higher antibody sum or quartile sum group compared to those who were in baseline group were estimated from Cox's proportional hazards model and adjusted for all other covariates. All HRs were expressed as a point estimate with 95% confidence interval. Patients who only had sera data after the occurrence of complications or surgery were not included in the survival analysis. Age at diagnosis and gender were included as covariates in all the multivariable analyses. The OR/HR for age at diagnosis was explained as the times of odds/hazards increase (e.g. OR-1) per one year older at diagnosis. All analyses were performed by using Statistical Analysis Software (Version 9.1; SAS Institute, Inc., Cary, NC).

Increased Immune Reactivity Predicts Aggressive Complicating Crohn's Disease in Children: Patient Demographics A total of 796 pediatric CD patients were eligible for analysis. Eighty-seven percent ($^{694}/_{796}$) were Caucasians and 28% were of Jewish background. The median age at diagnosis was 12 [0.6-18] years and the median disease duration as of last follow up was of 32 [1-235] months. The cohort was comprised of 56% males and 44% females.

Increased Immune Reactivity Predicts Aggressive Complicating Crohn's Disease in Children: Clinical Phenotypes A total of 236 (30.3%) patients presented with ($^{96}/_{796}$ [12%]) or developed ($^{140}/_{796}$[18%]) at least one disease complication within the median follow up time of 32 months: 116 stricturing disease, 70 internal penetrating, and 115 perianal penetrating disease. Ten patients had all 3 complications and 45 had a combination of 2 of the 3 complications. One hundred and forty patients (18%) underwent a CD related surgery of which 89 were small bowel resections. Of the remaining surgeries: a total of 42 were involving perianal penetrating disease; 24 patients underwent colectomy and 3 patients a limited colonic resection. Fifteen patients had more than one surgery.

Increased Immune Reactivity Predicts Aggressive Complicating Crohn's Disease in Children: Immune Response and Genotype Frequencies Serum was collected at the time of diagnosis or within 1 month of diagnosis in 18% ($^{146}/_{796}$) of patients and 30% ($^{241}/_{796}$) within 3 months of diagnosis. The remaining patients had serum collected greater than 3 months from time of diagnosis. A total 73% of patients were positive for at least one microbial driven immune response (ASCA, anti-OmpC or anti-Cbir1), 27% of whom were positive for a combination of any 2 of these immune responses and 8% of patients were positive for all 3 responses. ASCA, anti-OmpC, anti-CBir1 and pANCA were present in 45%, 18%, 52%, and 19% respectively. NOD2/CARD15 (any variant) was observed in 34% of patients (25% heterozygote and 9% homozygote or compound heterozygote).

Increased Immune Reactivity Predicts Aggressive Complicating Crohn's Disease in Children: Cross Sectional Analyses Univariate analysis of immune responses and NOD2/CARD15 genotype demonstrated that NOD2/CARD15 (all variants individually or any variant) was only associated with small bowel disease location (OR [95% CI]1.9 [1.4-2.7] p<0.0001) and had no association with disease behavior. ASCA was associated with small bowel disease (2.9 [2.1-4.0] P<0.0001) and perianal disease (1.5 [1.1-2.2] <0.02). C Bir1 was also associated with small bowel disease (1.6 [1.2-2.3] p=0.002) and OmpC had no significant association with any disease location. pANCA was associated with large bowel disease (4.0 [1.8-8.8] p<0.0001). ASCA, anti-CBir1 and anti-OmpC were negatively associated with non-penetrating non stricturing disease (NPNS); in contrast all showed a positive association with complicating disease and surgery. The odds of having internal penetrating (IP), perianal penetrating (PP), stricturing (S) disease and surgery were highest in the presence of anti-OmpC. As disclosed herein, there was a cumulative influence of number of immune responses (antibody sum) as well as the magnitude of the immune response (quartile sum score group) on disease behavior. The frequency of internal penetrating, stricturing disease and surgery significantly increased (p trend <0.0001) as the number of immune responses increased (antibody sum 0-3) and magnitude of immune response (quartile sum score group 1-4) increased. The odds ratios for the 3 disease behaviors and surgery associated with antibody sum and quartile sum score groups are disclosed herein.

Multivariable analysis confirmed the association of small bowel location with ASCA (OR [95% CI]:2.3 [1.6-3.2]; p<0.0001), anti-CBir1 (OR 1.5 [1-1.2]; p=0.03), pANCA (OR: 0.6 [0.4-0.9]; p=<0.007); and NOD2/CARD15 (OR; 1.7 [1.1-2.4]; p=0.007). Large bowel location was associated with pANCA (OR: 2.8 [1.4-5.4]; p<0.004). Results of the multivariable analysis for the independent associations with disease behavior and surgery are disclosed herein. All individual antibodies were included in the model as well as a single unit change in antibody quartile sum score as a co-variable (e.g. increase in score of 3 to 4). There was a significant association seen with quartile sum score change and complicating disease behaviors as well as surgery, such that for each unit of quartile sum increase the OR increased by 1.3 for internal penetrating and stricturing disease and 1.2 for surgery. The difference between a score of the minimum 3 and the maximum score of 12 equates to an OR of 10.6 $(=1.3)^9$ and 5.2 $(=1.2)^9$, respectively. Quartile sum score was not independently associated with small bowel disease location as compared to the presence of the individual antibodies as noted above. These results show that disease location is associated more so with the presence of the immune responses and less so by the antibody levels, whilst disease behavior and surgery are more significantly associated with the magnitude of the immune response. Additional independent associations were found between female gender and older age at diagnosis.

Increased Immune Reactivity Predicts Aggressive Complicating Crohn's Disease in Children: Predictors of Disease Progression The inventors' cross-sectional data demonstrate that both single and multiple immune responses are associated with the presence of disease complications and surgery. For the second aim of the study, the inventors set out to examine whether seropositive patients (1, 2, or 3 positive for ASCA, anti-OmpC and/or anti-CBir1) had a greater risk to progress to internal penetrating and/or stricturing (IP/S) disease as well as to surgery, as compared to seronegative patients (0 such immune responses). The inventors used a longitudinal study to answer this question which included only those patients who did not have IP/S or surgery at diagnosis (NPNS+/−PP) and continued to have uncomplicated disease status at the time the serum was collected for immune response measurement. Thus the inventors could be certain that in these individuals, when clinically recognizable IP/S or surgery occurred, it did so after the serum was collected. A total of 536 patients met these inclusion criteria. The median time from diagnosis to serum draw was 10 [0-211] months for the 536 patients included in the prospective analysis. A total of 90 of the entire prospective cohort of patients (n=536) developed IP/S in follow up; however 59% (53 patients) were eliminated from this analysis as they had immune responses collected after the complication occurred. Among the 37 patients who developed IP/S during the follow-up after serum was drawn, the median [range] time from diagnosis to the onset of IP/S was 26 [4-108] months. Thirty two of the 363 seropositive patients (9%) had IP/S vs. only 2.9% ($5/173$). in the seronegative group (p=0.01). Among the 61 patients who underwent surgery (any CD related surgery after serum was drawn) the median [range] time from diagnosis to surgery was 30 [1-105] months. Twelve percent ($57/464$) of the seropositive (at least one positive) patients had undergone surgery vs. only 2% ($4/189$) in the seronegative group (p=0.0001). Because longer disease duration increases the chance of developing IP/S as well as surgery, and not all patients were followed for the same amount of time, we performed survival analysis to take the length of follow-up into consideration. The Kaplan-Meier survival analysis, followed by the log-rank test for the different antibody sum and quartile sum score group comparisons, showed that overall survival times for IP/S and CD-related surgery were significantly lower for those positive for immune responses, and this was true when both the quantity of immune responses and magnitude of those responses were assessed. The first analyses examined antibody sum: 0 vs. 1 vs. 2 vs. 3 and time to development of IP and/or S as well as time to surgery. Given the same length of follow up, among those patients with antibody sum greater than 1, more progressed to IP/S than those negative for all 3 or positive for only 1 antibody (p=<0.0001). In other words, those patients positive for at least 2 immune responses (antibody sum 2 or 3) progressed to IP/S faster that those negative for all or positive for only 1 antibody. The group positive for all 3 antibodies demonstrated the most rapid disease progression with a median [range] time to disease progression of 20 [4-65] months. The same rapid progression to surgery was seen among the higher antibody sum group. Like antibody sum, those patients in the highest quartile sum score group (group 4=Quartile sum score 10-12) progressed faster to IP/S and surgery and the median [range] time to IP/S and surgery was 21[4-65] months and 27 [1-93] months, respectively. The survival curves were very similar when evaluating intestinal resection only (n=48) as compared to any CD surgery (n=61) (Log Rank: p<0.0001 for the 4 antibody sum groups and p=0.001 when comparing survival among the 4 quartile sum groups). The most conservative way to evaluate the predictive abilities of immune response was to limit inclusion in the survival analysis to only patients whose serum was drawn before a complication or surgery. The inventors also performed survival analysis on all 90 patients who developed IP and/or S in follow up regardless of when serologies were drawn. For both antibody sum and quartile sum score group, the results showed a significantly higher number of patients progressing to complication faster in the face of seropositivity.

The predictive ability of immune responses for rapid progression to the first IP/S or surgical event was further evaluated by fitting Cox-proportional hazards models. OmpC (HR [95% CI]; p value) (2.4[1.2-4.9]; p=0.01) and CBir1 (2.5[1.2-5.2]; p<0.02), but not ASCA, were associated with increased hazard of IP/S, as was older age at diagnosis (1.2 [1.1-1.3]; p=0.004). Lower hazards were observed with pANCA positivity (0.16 [0.04-0.70]; p<0.02). Antibody sums 2 and 3 as well as quartile sum score groups 3 and 4 were associated with an increased hazard for developing disease complications (IP/S). Hazard Ratios for all CD related surgeries as well as for intestinal resections only were calculated controlling for both disease location and disease complication (IP, S and PP). OmpC was associated with increased hazard of any CD related surgery (2.2 [1.3-3.8;] p=0.004 or intestinal resection surgery (3.5 [1.9-

6.4]; p=0.001). The Cox proportional hazard model also tested the predictive ability of antibody sum groups and quartile sum score groups for surgery. Results of any CD related surgery are disclosed herein. When examining intestinal resection surgery, an increased hazard was observed for antibody sum 3 (7.8 [2.2-28.7]; p<0.002 and quartile sum score group 4 (11.0 [1.5-83.0]; p<0.02).

Example 4

The inventors investigated the role genetic variants in the gene JAK3 may have in the development of Crohn's Disease. The inventors performed an antibody genome wide association study using patients diagnosed with Crohn's Disease, and found an association of JAK3 variants with expression of anti-I2 and ASCA for Crohn's Disease. The results of these studies are described in Tables 13-31 herein.

Results demonstrating the association of anti-I2 as positive/negative expression with JAK3 SNP rs2302600 (SEQ ID NO: 37) as a result of GWAS. Mantel-Haenszel Chi-Square statistics for the degree of freedom (DF), value and probability of anti-I2 antibody expression associated with genotype alleles AA, CA and CC for SEQ ID NO: 37 at the JAK3 genetic locus (Table 13).

TABLE 13

JAK3 variant (rs2302600) associated with anti-I2 expression (positive/negative)

| | rs2302600 | | |
|---|---|---|---|
| I2_P(I2_P) | AA | CA | CC |
| Positive | 76 | 64 | 19 |
| | 47.8 | 40.25 | 11.95 |
| negative | 54 | 24 | 7 |
| | 63.53 | 28.24 | 8.24 |
| Statistic | DF | Value | Prob |
| Mantel-Haenszel Chi-Square | 1 | 4.5573 | 0.0328 |

Results demonstrating the association of anti-I2 with JAK3 SNP rs2302600 (SEQ ID NO: 37) under dominant genetic model (Table 14).

TABLE 14

JAK3 variant (rs2302600) associated with anti-I2 expression under dominant genetic model

| | rs2302600_dom | | |
|---|---|---|---|
| I2_P(I2_P) | 0 | 1 | Total |
| Positive | 76 | 83 | 159 |
| | 47.8 | 52.2 | |
| negative | 54 | 31 | 85 |
| | 63.53 | 36.47 | |
| Statistic | DF | Value | Prob |
| Chi-Square | 1 | 5.5062 | 0.0189 |

Results demonstrating the association of ASCA with JAK3 SNP rs2302600 (SEQ ID NO: 37) under dominant genetic model (Table 15).

TABLE 15

JAK3 variant (rs2302600) associated with ASCA expression under dominant genetic model

| | rs2302600_dom | | |
|---|---|---|---|
| ASCA | 0 | 1 | Total |
| Positive | 76 | 80 | 156 |
| | 48.72 | 51.28 | |
| negative | 55 | 36 | 91 |
| | 60.44 | 39.56 | |
| Statistic | DF | Value | Prob |
| Chi-Square | 1 | 3.1704 | 0.075 |

Results demonstrating the association of JAK3 variant rs2302600 (SEQ ID NO: 37) with anti-I2 level in Crohn's Disease patients (Table 16).

TABLE 16

JAK3 variant (rs2302600) associated with anti-I2 level

Analysis Variable: I2VALUE I2 VALUE

| rs2302600_dom | N Obs | N | Median |
|---|---|---|---|
| 0 | 132 | 130 | 26.745 |
| 1 | 116 | 114 | 37.559 |

P = 0.03

Results demonstrating the association of JAK3 variant rs2302600 (SEQ ID NO: 37) with ASCA level in Crohn's Disease patients (Table 17).

TABLE 17

JAK3 variant (Rs2302600) associated with ASCA level

Analysis Variable: ascalev

| rs2302600_dom | N Obs | N | Median |
|---|---|---|---|
| 0 | 132 | 131 | 0.3021 |
| 1 | 116 | 116 | 0.6011 |

P = 0.02

Results demonstrating the association of ASCA as positive/negative expression with JAK3 SNP rs3212741 (SEQ ID NO: 38) as a result of GWAS. Mantel-Haenszel Chi-Square statistics for the degree of freedom (DF), value and probability of ASCA antibody expression associated with genotype alleles CC, TC, and TT for SEQ ID NO: 38 at the JAK3 genetic locus (Tableb18).

TABLE 18

JAK3 variant (rs3212741) associated with ASCA expression (positive/negative)

| | rs3212741 | | |
|---|---|---|---|
| ASCA | CC | TC | TT |
| Positive | 113 | 40 | 2 |
| | 72.9 | 25.81 | 1.29 |
| negative | 54 | 34 | 2 |
| | 60 | 37.78 | 2.22 |
| Statistic | DF | Value | Prob |
| Mantel-Haenszel Chi-Square | 1 | 4.2511 | 0.0392 |

Results demonstrating the association of JAK3 SNP rs3212741 (SEQ ID NO: 38) under dominant genetic model (Table 19).

TABLE 19

JAK3 variant (rs3212741) associated with ASCA expression under dominant genetic model

| ASCA | rs3212741_dom 0 | 1 | Total |
|---|---|---|---|
| Positive | 113 | 42 | 155 |
|  | 72.9 | 27.1 |  |
| negative | 54 | 36 | 90 |
|  | 60 | 40 |  |
| Statistic | DF | Value | Prob |
| Chi-Square | 1 | 4.3684 | 0.0366 |

Results demonstrating the association of JAK3 variant rs3212741 (SEQ ID NO: 38) with ASCA level in Crohn's Disease patients (Table 20).

TABLE 20

JAK3 variant (rs3212741) associated with ASCA level
Analysis Variable: ascalev

| rs3212741_dom | N Obs | N | Median |
|---|---|---|---|
| 0 | 167 | 167 | 0.561 |
| 1 | 79 | 78 | 0.281 | p = 0.06

TABLE 21

JAK3 variant rs2302600 association with OmpC (positive/negative)

| OMPC_P(OMPC_P) | rs2302600 AA | CA | CC |
|---|---|---|---|
| Positive | 52 | 36 | 13 |
|  | 51.49 | 35.64 | 12.87 |
| negative | 78 | 52 | 13 |
|  | 54.55 | 36.36 | 9.09 |
| Statistic | DF | Value | Prob |
| Mantel-Haenszel Chi-Square | 1 | 0.6027 | 0.4375 |

TABLE 22

JAK3 variant rs2302600 association with Cbir (positive/negative)

| cbir_p | rs2302600 AA | CA | CC |
|---|---|---|---|
| Positive | 76 | 51 | 16 |
|  | 53.15 | 35.66 | 11.19 |
| negative | 52 | 36 | 10 |
|  | 53.06 | 36.73 | 10.2 |
| Statistic | DF | Value | Prob |
| Mantel-Haenszel Chi-Square | 1 | 0.0102 | 0.9196 |

TABLE 23

JAK3 variant rs2302600 association with ASCA (positive/negative)

| ASCA | rs2302600 AA | CA | CC |
|---|---|---|---|
| Positive | 76 | 62 | 18 |
|  | 48.72 | 39.74 | 11.54 |
| negative | 55 | 27 | 9 |
|  | 60.44 | 29.67 | 9.89 |
| Statistic | DF | Value | Prob |
| Mantel-Haenszel Chi-Square | 1 | 2.2129 | 0.1369 |

TABLE 24

JAK3 variant rs2302600 association with OmpC in dominant genetic model

| OMPC_P(OMPC_P) | rs2302600_dom 0 | 1 | Total |
|---|---|---|---|
| Positive | 52 | 49 | 101 |
|  | 51.49 | 48.51 |  |
| negative | 78 | 65 | 143 |
|  | 54.55 | 45.45 |  |
| Statistic | DF | Value | Prob |
| Chi-Square | 1 | 0.2227 | 0.637 |

TABLE 25

JAK3 variant rs2302600 association with Cbir in dominant genetic model

| cbir_p | rs2302600_dom 0 | 1 | Total |
|---|---|---|---|
| Positive | 76 | 67 | 143 |
|  | 53.15 | 46.85 |  |
| negative | 52 | 46 | 98 |
|  | 53.06 | 46.94 |  |
| Statistic | DF | Value | Prob |
| Mantel-Haenszel Chi-Square | 1 | 0.0002 | 0.9896 |

TABLE 26

JAK3 variant rs3212741 association with OmpC (positive/negative)

| OMPC_P(OMPC_P) | rs3212741 CC | TC | TT |
|---|---|---|---|
| Positive | 73 | 27 | 1 |
|  | 72.28 | 26.73 | 0.99 |
| negative | 93 | 45 | 3 |
|  | 65.96 | 31.91 | 2.13 |
| Statistic | DF | Value | Prob |
| Mantel-Haenszel Chi-Square | 1 | 1.2813 | 0.2577 |

TABLE 27

JAK3 variant rs3212741 association with anti-I2 (positive/negative)

| I2_P(I2_P) | rs3212741 CC | TC | TT |
|---|---|---|---|
| Positive | 111 | 44 | 4 |
|  | 69.81 | 27.67 | 2.52 |
| negative | 55 | 28 | 0 |
|  | 66.27 | 33.73 | 0 |

TABLE 27-continued

JAK3 variant rs3212741 association with anti-I2 (positive/negative)

| | rs3212741 | | |
|---|---|---|---|
| I2_P(I2_P) | CC | TC | TT |
| Statistic | DF | Value | Prob |
| Mantel-Haenszel Chi-Square | 1 | 0.0227 | 0.8803 |

TABLE 28

JAK3 variant rs3212741 association with anti-Cbir (positive/negative)

| | rs3212741 | | |
|---|---|---|---|
| cbir_p | CC | TC | TT |
| Positive | 104 | 36 | 2 |
| | 73.24 | 25.35 | 1.41 |
| negative | 60 | 35 | 2 |
| | 61.86 | 36.08 | 2.06 |
| Statistic | DF | Value | Prob |
| Mantel-Haenszel Chi-Square | 1 | 3.2641 | 0.0708 |

TABLE 29

JAK3 variant rs3212741 association with anti-OmpC in dominant genetic model

| | rs3212741_dom | | |
|---|---|---|---|
| OMPC_P(OMPC_P) | 0 | 1 | Total |
| Positive | 73 | 28 | 101 |
| | 72.28 | 27.72 | |
| negative | 93 | 48 | 141 |
| | 65.96 | 34.04 | |
| Statistic | DF | Value | Prob |
| Chi-Square | 1 | 1.091 | 0.2962 |

TABLE 30

JAK3 variant rs3212741 association with anti-I2 in dominant genetic model

| | rs3212741_dom | | |
|---|---|---|---|
| I2_P(I2_P) | 0 | 1 | Total |
| Positive | 111 | 48 | 159 |
| | 69.81 | 30.19 | |
| negative | 55 | 28 | 83 |
| | 66.27 | 33.73 | |
| Statistic | DF | Value | Prob |
| Chi-Square | 1 | 0.3184 | 0.5726 |

TABLE 31

JAK3 variant rs3212741 association with anti-Cbir in dominant genetic model

| | rs3212741_dom | | |
|---|---|---|---|
| cbir_p | 0 | 1 | Total |
| Positive | 104 | 38 | 142 |
| | 73.24 | 26.76 | |
| negative | 60 | 37 | 97 |
| | 61.86 | 38.14 | |
| Statistic | DF | Value | Prob |
| Chi-Square | 1 | 3.4684 | 0.0626 |

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

What is claimed is:

1. A process for predicting IBD susceptibility in a subject, comprising:
   providing a sample from the subject;
   assaying the sample to detect risk and/or protective variants in genes selected from the group consisting of: CARD 8, TLR8, TLR2 and JAK3;
   assaying the sample to detect risk serological factors selected from the group consisting of: anti-CBir1, pANCA, anti-OmpC, ASCA and anti-I2; and
   determining that the subject has increased susceptibility to IBD if one or more risk variants and/or risk serological factors are present and the protective variants are absent or determining that the subject has a decreased susceptibility to IBD if one or more protective variants are present and the risk variants and/or risk serological factors are absent,
   wherein IBD comprises Crohn's disease (CD) and ulcerative colitis (UC).

2. A process for selecting a therapy for a subject with IBD comprising:
   providing a sample from the subject;
   assaying the sample to detect risk and/or protective variants selected from the group consisting of: CARD 8, TLR8, TLR2 and JAK3;
   assaying the sample to detect risk serological factors selected from the group consisting of: anti-CBir1, pANCA, anti-OmpC, ASCA and anti-I2; and
   determining that the subject has IBD if one or more risk variants and/or risk serological factors are present and the protective variants are absent or determining that the subject does not have IBD if one or more protective variants are present and the risk variants and/or risk serological factors are absent; and
   selecting a therapy for the subject with IBD;
   wherein IBD comprises Crohn's Disease (CD) and ulcerative colitis (UC).

* * * * *

SEQUENCE LISTING

<160> NUMBER OF SEQ ID NOS: 38

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cacaatcaca acatctaccc ag                                             22

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttactgtaag agctgaagta caccctg                                        27

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caattacata tgcatcacca tcaccatcac gtagtacagc acaatc                   46

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atagactaag cttactgtaa gagctgaagt acaccctg                            38

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caattacata tgcatcacca tcaccatcac gtagtacagc acaatttaca ggc           53

<210> SEQ ID NO 6
<211> LENGTH: 38
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 6
atagactaag cttactgtaa gagctgaagt acaccctg                              38

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atagactaag cttaagaaac cttcttgata gcgccag                               37

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagactgaat tctagtccat agcgtcaacg ttctttgtgt c                          41

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caattacata tgcatcacca tcaccatcac aagatgaact tccatgtagg tgc             53

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caattacata tgcatcacca tcaccatcac gtagtacagc acaatc                     46

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atagactaag cttactgtaa gagctgaagt acaccctg                              38

<210> SEQ ID NO 12
<211> LENGTH: 53
<212> TYPE: DNA
<213> ORGANISM: Artificial Sequence
<220> FEATURE:
<223> OTHER INFORMATION: Description of Artificial Sequence: Synthetic

```
                                    primer

<400> SEQUENCE: 12
caattacata tgcatcacca tcaccatcac gtagtacagc acaatcttag agc            53

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atagactaag cttagaggct gaaatcaatg tcctcg                              36

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atagactaag cttaatgtgc tgaaagatat cttgtcac                            38

<210> SEQ ID NO 15
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caattacata tgcatcacca tcaccatcac ttcagcctcc atgtaggtgc agatgc        56

<210> SEQ ID NO 16
<211> LENGTH: 4485
<212> TYPE: DNA
<213> ORGANISM: Homo sapiens

<400> SEQUENCE: 16
gtagacagat ccaggctcac cagtcctgtg ccactgggct tttggcgttc tgcacaaggc    60
ctacccgcag atgccatgcc tgctccccca gcctaatggg ctttgatggg ggaagagggt   120
ggttcagcct ctcacgatga ggaggaaaga gcaagtgtcc tcctcggaca ttctccgggt   180
tgtgaaatgt gctcgcagga ggcttttcag gcacagagga ccagctggt cgagctgctg    240 gtctcagggt ccctggaagg cttcgagagt gtcctggact ggctgctgtc ctgggaggtc   300
ctctcctggg aggactacga gggcttccac ctcctgggcc agcctctctc ccacttggcc   360
aggcgccttc tggacaccgt ctggaataag ggtacttggg cctgtcagaa gctcatcgcg   420
gctgcccaag aagcccaggc cgacagccag tcccccaagc tgcatggctg ctgggacccc   480
cactcgctcc acccagcccg agacctgcag agtcaccggc cagccattgt caggaggctc   540
cacagccatg tggagaacat gctggacctg gcatgggagc ggggtttcgt cagccagtat   600
gaatgtgatg aaatcaggtt gccgatcttc acaccgtccc agagggcaag aaggctgctt   660
gatcttgcca cggtgaaagc gaatggattg gctgccttcc ttctacaaca tgttcaggaa   720
ttaccagtcc cattggccct gcctttggaa gctgccacat gcaagaagta tatggccaag   780
```

```
ctgaggacca cggtgtctgc tcagtctcgc ttcctcagta cctatgatgg agcagagacg    840
ctctgcctgg aggacatata cacagagaat gtcctggagg tctgggcaga tgtgggcatg    900
gctggacccc cgcagaagag cccagccacc ctgggcctgg aggagctctt cagcacccct    960
ggccacctca atgacgatgc ggacactgtg ctggtggtgg gtgaggcggg cagtggcaag   1020
agcacgctcc tgcagcggct gcacttgctg tgggctgcag ggcaagactt ccaggaattt   1080
ctctttgtct tcccattcag ctgccggcag ctgcagtgca tggccaaacc actctctgtg   1140
cggactctac tctttgagca ctgctgttgg cctgatgttg gtcaagaaga catcttccag   1200
ttactccttg accaccctga ccgtgtcctg ttaacctttg atggctttga cgagttcaag   1260
ttcaggttca cggatcgtga acgccactgc tccccgaccg accccacctc tgtccagacc   1320
ctgctcttca accttctgca gggcaacctg ctgaagaatg cccgcaaggt ggtgaccagc   1380
cgtccggccg ctgtgtcggc gttcctcagg aagtacatcc gcaccgagtt caacctcaag   1440
ggcttctctg aacagggcat cgagctgtac ctgaggaagc gccatcatga gcccggggtg   1500
gcggaccgcc tcatccgcct gctccaagag acctcagccc tgcacggttt gtgccacctg   1560
cctgtcttct catggatggt gtccaaatgc caccaggaac tgttgctgca ggagggggg    1620
tccccaaaga ccactacaga tatgtacctg ctgattctgc agcattttct gctgcatgcc   1680
accccccag actcagcttc ccaaggtctg gacccagtc ttcttcgggg ccgcctcccc    1740
accctcctgc acctgggcag actggctctg tggggcctgg gcatgtgctg ctacgtgttc   1800
tcagcccagc agctccaggc agcacaggtc agccctgatg acatttctct tggcttcctg   1860
gtgcgtgcca aggtgtcgt gccagggagt acggcgcccc tggaattcct tcacatcact   1920
ttccagtgct tctttgccgc gttctacctg gcactcagtg ctgatgtgcc accagctttg   1980
ctcagacacc tcttcaattg tggcaggcca ggcaactcac caatggccag gctcctgccc   2040
acgatgtgca tccaggcctc ggagggaaag gacagcagcg tggcagcttt gctgcagaag   2100
gccgagccgc acaaccttca gatcacagca gccttcctgg cagggctgtt gtcccgggag   2160
cactggggcc tgctggctga gtccagaca tctgagaagg ccctgctccg cgccaggcc    2220
tgtgcccgct ggtgtctggc ccgcagcctc cgcaagcact ccactccat cccgccagct   2280
gcaccgggtg aggccaagag cgtgcatgcc atgcccgggt tcatctggct catccggagc   2340
ctgtacgaga tgcaggagga gcggctggct cggaaggctg cacgtggcct gaatgttggg   2400
cacctcaagt tgacattttg cagtgtgggc cccactgagt gtgctgccct ggcctttgtg   2460
ctgcagcacc tccggcggcc cgtggccctg cagctggact acaactctgt gggtgacatt   2520
ggcgtggagc agctgctgcc ttgccttggt gtctgcaagg ctctgtattt gcgcgataac   2580
aatatctcag accgaggcat ctgcaagctc attgaatgtg ctcttcactg cgagcaattg   2640
cagaagttag ctctattcaa caacaaattg actgacggct gtgcacactc catggctaag   2700
ctccttgcat gcaggcagaa cttcttggca ttgaggctgg ggataacta catcactgcc    2760
gcgggagccc aagtgctggc cgaggggctc cgaggcaaca cctccttgca gttcctggga   2820
ttctggggca acagagtggg tgacgagggg gcccaggccc tggctgaagc cttgggtgat   2880
caccagagct tgaggtggct cagcctggtg ggaacaaca ttggcagtgt gggtgcccaa    2940
gccttggcac tgatgctggc aaagaacgtc atgctagaag aactctgcct ggaggagaac   3000
catctccagg atgaaggtgt atgttctctc gcagaaggac tgaagaaaaa ttcaagtttg   3060
aaaatcctga agttgtccaa taactgcatc acctacctag gggcagaagc cctcctgcag   3120
gcccttgaaa ggaatgacac catcctggaa gtctggctcc gagggaacac tttctctcta   3180
```

-continued

```
gaggaggttg acaagctcgg ctgcagggac accagactct tgctttgaag tctccgggag    3240
gatgttcgtc tcagtttgtt tgtgagcagg ctgtgagttt gggccccaga ggctgggtga    3300
catgtgttgg cagcctcttc aaaatgagcc ctgtcctgcc taaggctgaa cttgttttct    3360
gggaacacca taggtcacct ttattctggc agaggaggga gcatcagtgc cctccaggat    3420
agacttttcc caagcctact tttgccattg acttcttccc aagattcaat cccaggatgt    3480
acaaggacag cccctcctcc atagtatggg actggcctct gctgatcctc ccaggcttcc    3540
gtgtgggtca gtgggccca tggatgtgct tgttaactga gtgccttttg gtggagaggc     3600
ccggcctctc acaaaagacc ccttaccact gctctgatga agaggagtac acagaacaca    3660
taattcagga agcagctttc cccatgtctc gactcatcca tccaggccat tcccgtctc     3720 tggttcctcc cctcctcctg gactcctgca cacgctcctt cctctgaggc tgaaattcag    3780
aatattagtg acctcagctt tgatatttca cttacagcac ccccaaccct ggcacccagg    3840
gtgggaaggg ctacaccta gcctgccctc ctttccggtg tttaagacat ttttggaagg     3900
ggacacgtga cagccgtttg ttccccaaga cattctaggt ttgcaagaaa aatatgacca    3960
cactccagct gggatcacat gtggactttt atttccagtg aaatcagtta ctcttcagtt    4020
aagcctttgg aaacagctcg acttaaaaaa gctccaaatg cagctttaaa aaattaatct    4080
gggccagaat tcaaacggc ctcactaggc ttctggttga tgcctgtgaa ctgaactctg      4140
acaacagact tctgaaatag acccacaaga ggcagttcca tttcatttgt gccagaatgc    4200
tttaggatgt acagttatgg attgaaagtt tacaggaaaa aaaattaggc cgttccttca    4260
aagcaaatgt cttcctggat tattcaaaat gatgtatgtt gaagcctttg taaattgtca    4320
gatgctgtgc aaatgttatt attttaaaca ttatgatgtg tgaaaactgg ttaatattta    4380
taggtcactt tgttttactg tcttaagttt atactcttat agacaacatg gccgtgaact    4440
ttatgctgta ataatcaga ggggaataaa ctgttgagtc aaaac                     4485
```

<210> SEQ ID NO 17
<211> LENGTH: 1040
<212> TYPE: PRT
<213> ORGANISM: Homo sapiens

<400> SEQUENCE: 17

```
Met Gly Glu Glu Gly Gly Ser Ala Ser His Asp Glu Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140
```

```
Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
            195                 200                 205

Pro Leu Ala Leu Pro Leu Glu Ala Ala Thr Cys Lys Lys Tyr Met Ala
210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Pro Pro Gln Lys Ser
            260                 265                 270

Pro Ala Thr Leu Gly Leu Glu Glu Leu Phe Ser Thr Pro Gly His Leu
            275                 280                 285

Asn Asp Asp Ala Asp Thr Val Leu Val Val Gly Glu Ala Gly Ser Gly
290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
            355                 360                 365

Asp His Pro Asp Arg Val Leu Leu Thr Phe Asp Gly Phe Asp Glu Phe
370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
            435                 440                 445

Glu Gln Gly Ile Glu Leu Tyr Leu Arg Lys Arg His His Glu Pro Gly
            450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
            515                 520                 525

Asp Ser Ala Ser Gln Gly Leu Gly Pro Ser Leu Leu Arg Gly Arg Leu
            530                 535                 540

Pro Thr Leu Leu His Leu Gly Arg Leu Ala Leu Trp Gly Leu Gly Met
545                 550                 555                 560
```

-continued

```
Cys Cys Tyr Val Phe Ser Ala Gln Gln Leu Gln Ala Ala Gln Val Ser
                565                 570                 575

Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
            595                 600                 605

Phe Phe Ala Ala Phe Tyr Leu Ala Leu Ser Ala Asp Val Pro Pro Ala
610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
        675                 680                 685

Leu Leu Ala Glu Cys Gln Thr Ser Glu Lys Ala Leu Leu Arg Arg Gln
690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
            755                 760                 765

Leu Thr Phe Cys Ser Val Gly Pro Thr Glu Cys Ala Ala Leu Ala Phe
770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
            915                 920                 925

Leu Arg Trp Leu Ser Leu Val Gly Asn Asn Ile Gly Ser Val Gly Ala
        930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
```

Asn Cys Ile Thr Tyr Leu Gly Ala Glu Ala Leu Leu Gln Ala Leu Glu
        980                 985                 990
                995                1000               1005

Arg Asn Asp Thr Ile Leu Glu Val Trp Leu Arg Gly Asn Thr Phe
    1010                1015                1020

Ser Leu Glu Glu Val Asp Lys Leu Gly Cys Arg Asp Thr Arg Leu
    1025                1030                1035

Leu Leu
    1040

<210> SEQ ID NO 18
<211> LENGTH: 601
<212> TYPE: DNA
<213> ORGANISM: Homo sapiens

<400> SEQUENCE: 18
cttcacatca ctttccagtg cttctttgcc gcgttctacc tggcactcag tgctgatgtg      60
ccaccagctt tgctcagaca cctcttcaat tgtggcaggc aggcaactc accaatggcc     120
aggctcctgc ccacgatgtg catccaggcc tcggagggaa aggacagcag cgtggcagct     180
ttgctgcaga aggccgagcc gcacaacctt cagatcacag cagccttcct ggcagggctg     240
ttgtcccggg agcactgggg cctgctggct gagtgccaga catctgagaa ggccctgctc     300
yggcgccagg cctgtgcccg ctggtgtctg gcccgcagcc tccgcaagca cttccactcc     360
atcccgccag ctgcaccggg tgaggccaag agcgtgcatg ccatgcccgg gttcatctgg     420
ctcatccgga gcctgtacga gatgcaggag gagcggctgg tcggaaggc tgcacgtggc     480
ctgaatgttg ggcacctcaa gttgacattt gcagtgtgg ccccactga gtgtgctgcc     540
ctggcctttg tgctgcagca cctccggcgg cccgtggccc tgcagctgga ctacaactct     600
g                                                                    601

<210> SEQ ID NO 19
<211> LENGTH: 601
<212> TYPE: DNA
<213> ORGANISM: Homo sapiens

<400> SEQUENCE: 19
ctcttgtcag tgagttcctg tccttaaggg ttagggctgg gtagccctct actattctct      60
aagtctgtaa tgtaaagcca ctgaaaactc ttgggttaag tttggccatc ccacccaaaa    120
gatggaggca ggtccacttt gctgggacca ggagccccag tgaggccact ctgggattga    180
gtggtcctgc ccctctggct gggactgcag agggaggagg actgttagtt catgtctaga    240
acacatatca ggtactcact gacactgtct gttgactctt ttggccttt cagattctgg    300
sgcaacagag tgggtgacga gggggcccag gccctggctg aagccttggg tgatcaccag    360
agcttgaggt ggctcaggta agcttcagag tctatcctgc agttttcttg gggagatcag    420
gtgaagaggg aggagctggg gccagttctg aaggtctttg aactttatt ctaccccaca    480
atgttaggca atggagtaag gaaaaaagac cattggattt caagagagga cactcgagtc    540
tttctgggtg acttggaaat gtccttgtc ctctcagggt tttgatacag tatctgtaaa    600
t                                                                    601

<210> SEQ ID NO 20
<211> LENGTH: 330
<212> TYPE: DNA
<213> ORGANISM: Homo sapiens

```
<220> FEATURE:
<221> NAME/KEY: modified_base
<222> LOCATION: (142)..(142)
<223> OTHER INFORMATION: a, c, t, or g

<400> SEQUENCE: 20
gactggctaa ctcctgcagt ctctttaact ggacagtttc aagaggaaaa ccaagaatcc      60
ttgaagctca ccattgtatc ttcttttcca ggttgtccaa taactgcatc acctacctag     120
gggcagaagc cctcctgcag gnccctggaa aggaatgaca ccatcctgga agtctggtaa     180
ggcccctggg caggcctgtt ttagctctcc gaacctcagt ttttctatct gtaaaatggg     240
gtgacgggag agaggaatgg cagaattttg aggatcccct ctgattctga cattcagtga     300
gaatgattct gcatgtgaag gatctgattc                                      330

<210> SEQ ID NO 21
<211> LENGTH: 25000
<212> TYPE: DNA
<213> ORGANISM: Homo sapiens

<400> SEQUENCE: 21
atggccctct tcaaatcttc tccatgccaa gccccgggcc tcaaatctag caggttgttc      60 ttgtgcttt ccaacagccc tcatatattt gaatcaatta tccccaacat cttcccacat     120
attttcagca tttggtactg atccctctac cagatgccct gtcccaaca agcagcctcg     180 cctcctatat ctgcccacca atggatgcgt cctcaaattc tgtcctctct acatcaaaca     240
tgttttatgt caccgactte atcatcatca tctcacaaaa cccagattct ttcctcacag     300
agcctatctg cattcgttct cattccaagg agaggtggcc cttcccttcc taaattgcaa     360
gcccacccac cactgcccct ggttcattca ctttccctac ttgggaaagc ggctccatga     420
ggttgactct gtccgttgca catgtgacca ctcttctcca cctgccggc ttttcctcct     480 cacttgaaca cacttctttt aaaattatct tccctccaaa gatgtttgtc gcagcattgt     540 ttgtaattc aaaaaattag acaagcaca atgccaatc aatagaggat tcattaagca     600
aaataccaca tgcataaccg gctacagaac acagccactg aaaaaaaaga acaagcagaga     660 tctgcatatc caaaccagaa tgctagctgg aaaaaaaaaa tgatgcagaa tagcacgtat     720
catgtgaact cagttttcaa aaagaattct gtacgtaatt atatgtcagt atatacatag     780
gaaaaatctt gaagaacata taccaaacca ttaacaatgg tcaactctga ggagtggaat     840
ttggagagct ttcatctgat gtgttctaca ttcctttatt gggatattta ggaccatgta     900
ataacattat actcagaaaa attttatata caaaagaaac ttcccttaat tctatcaata     960
tcatcctctg tttcccttta attttcacca acatccatcc atccatccat ccattcgtcc    1020
ccatccattt tcaccaacat ccatgtgtaa gaccaggctg gatggataca acagcccttg    1080
ggctcaaaac ttgtacagtc tggtgaatgt aacacggagc caccaaaatg tcatccagca    1140
gagaaagtgg caagtacgac agagctttcc gttcagatcc aagctttgct gctgaatttg    1200
ggtaaatgac tgagcccttta tgagcctgtt tcctcctctg aaaatgggga ttatagtaac    1260
aagcagagag aacaggagtg gtgggtgggt agcgccttaa gtaggtgttg gtgcagagga    1320
ctccatccca tctgggccac agaccatcag gaggcacgtg gggacttggg acaaagaaa    1380 acaagcagcc catatctgcc ggcaggacct ggcaaagtgg gcgtgacacc aacaagttgc    1440
atcccagagg tgaccacaaa gcgcccagga tttgcaaagc taaggtcaag tggaggcagg    1500
aggagacagt ttcaggaaac acctgtggcc tatctcaccc gtgtcttccc tggccaggga    1560
```

```
agggcagccg cttaaagggg ccaagggaag ctgcagcgtg gctcctaaac atggacgcac    1620
agtagctgtc ctctcaggag ctctgcaccc ccacttaaaa ccaggatcac aagagatttg    1680
tgtaaaggaa gcctcttgtg catttcttca tctgaatcgt tgacttaaaa gtttcttcca    1740
cgtaagtcct ttcactttag cttttgtatat atttagcatt gatttcacaa caaacaactg    1800
attccaggca cttggtgttt tcccagacct tgagcttttt ccagggttgc acgttatttc    1860
catatgtggt acttcgcggc agccccagta tggggaagcc atttgctgcc ttatgaattg    1920
tctggtcatc cactcgagag gaaagggctg tgtccagggc tggggaaggc cccaagagtg    1980
gttcttcagg cctactgttg gcaacagccc aggaatgtgt gaagtctgta acaacaagcg    2040
tagtaataat aattccagct ctgctagttg aacgctcact ttgtgccagc tacttttcta    2100
agagttccac gatatgaaca atttaatcct caaagccaac atctgagaaa gatactacta    2160
ttcttatccc aatttgacag atgagaaaac taaggctcag agaggcttgt ctgctggtga    2220
tttgtgtgtc tgggaagtgc acgttgtctg gcaggcttgc ctggcagaag cggttcatga    2280
caggtcttct ccattttgga atcaagatct gtgtcagcat ggatggcaag gggaagagta    2340
aggaaagatt ggtctaggag atgcccagga gcttttggcc tcacagtgca gggtggggag    2400
agcagacctg gccaccaagg accagtttct gggcttgggc agaagccaat catctggcta    2460
ctttacaagc agatggagct tcttcctctc agtaaccttc ctgccctggt gtcaattcca    2520 tttttcatttt catctttat ggtactggtt gtgtggagaa aactgaaggc tcatttggta    2580
taagtaagta actcattttt atgagtttgc ttgacataga tactagactg tatgtgtgta    2640
tatatacata taaacatgca tatgtacata aaaatatat atatatcata tatacatgat    2700
gatacacaca cacacacaca cacacacaca cacacatata tatatatacg tatacaagca    2760
tgctttacaa ggccaattga ctggtctaca attggctgac acttggtggc ctagaagcca    2820
gggtatgtga gtctcgcttt tctagaaagc tgacaaactc tccagttcca aggatccttg    2880
ctcagtcaac ggctggaagt cattttact tcgctgtttt ttgtttgttt gtttgtttgt    2940 tttttagac aaagtctcat tctgtcaccc aggctagagt gcagtggcac tatcatggct    3000
cactgcaatc tccacctcct gggctcaagc gatcctccca cctcagccac ccgagtaact    3060
gggactacag gtgcacacca ccatgcctgg ctaatttttg tatttttta gagacaaggt    3120 tttgccatgt tgcccgggtt ggtctcaaac ccctgagcac aagtgatcct cctgcctcgg    3180
cctctacaaa gtgctggaat tacaggtgtg agccactgca ctcgatccat tcttacttac    3240
tttctttact ttatttccaa gcaaatgttt ggagggaaac caagagactt ggatgcggcc    3300
agccgaggcc tttgggttta caatcacaaa tgttttggt ttgcccatga aggcccaggc    3360
tgcactctct gatgtcacag gaatcacctc tcaaaccatg caccaggtct tgaattccct    3420
tagggtgtga tctttagagg tccatctagg tatacccacc caagccattc tttgactgct    3480
gacaggcctt ccttcataac aaggtgttcc acagtccatt tatatatgga tgtcatctct    3540 gcccacctg ctgccaattt ggttttctcc cactcctggg gtgtaaggca agatgaaaca    3600
tatcacatcc cgttctaaac tttattcttg tggccagggg tcagcaaact ttttctgtaa    3660
agggccagat ggcaaatatc ttaggtttta caggccaaga agcaaatttg gcatattatg    3720
tagctactta tatagtaaaa taaaaatttc cacaattatg taattgatga aactcaaaat    3780
gtaataataa taatcgaagg cagttttttt gtagtatagg tttaataatg agaagaatgg    3840
aatcattttt ggaggtgcta acattctgct tggttggaat ttaaagttag tgttctgtat    3900
cagcaaatcc attgccaatg ttcatctaaa aatgttttca cttctgggcc ggatttcgtt    3960
```

```
caaaggctgc agtttgctga cctctgctct tggttacacc ttttgaggcc cttgctctcc    4020
gagcataaaa tggaatccat ttatcagact aaatcgggaa gattaaattt tccagcctca    4080
cgaatgctca gccattgact cactcgttca tacaatgaac actcattgag cttatactac    4140
atgccaggtg ctggaggagg catggggcgc ccaggagaaa gatgctcgct ttgcggccac    4200
agcccagtgg gagggagacc catacctacc ggtgctgtct cagaaacttg tggaacaaag    4260
atgaagcaat gttcatgtta ttcgcctaca tctgtgaatt acacaaggaa gacgagtttg    4320
agaaatccga agttcagtac aaatttatgg taactttttt aaaaaagaat acactgaagt    4380
tttcttagtg aatggaataa tgttcccttt ttctcccctg tacacacaaa tacacaaaaa    4440
ctaacaaaaa tacgtcgtgt gtgtctgatt tgggttgtat ttaaatcatt tcataaatga    4500
cttttttccca taacttcagt ttcaaagttt taaagcacag tcaattaatg atttggcaac    4560
agctaagaaa tcacaagttc ccttcttttc atgtaaactt ctgtaaaaca cacgctacgt    4620
tctgctgatg gtaaatagag ccatttcagg aagttagcca gtttctcttc tcggccacct    4680
cctgcataga gggtaccatt ctgcgctgct gcaagttacg gaatgaaaaa ttagaacaac    4740
agaaacatgg taagccactt ctatttcttt agcaaagctt tccaacagaa tatgggtttt    4800
ctgacccaga atctgggtt ggtggcaaat ggtgtgagcc tagaaagtaa taaatgggca    4860
aataaggata aaaattaaag atcgaaacaa ctgtaaatgc aggtaaagcg gcttgctatg    4920
atctttaatt tgtgcacacg ttagtataaa ggaattagag agtaaatttt gaaaatcaaa    4980
tgcagtgatg atcttactaa tttgacagg aaaataagaa aatttcaagt tagaaattga    5040
actgaaaata ttacttactg gccctaccag agacaatatc ctcttccaga acaacagggt    5100
tggaagagaa ggtgagggaa atattcttcc tttgctattt ctgtagaaaa ggacaaactc    5160
tcttccttca catacatagg tcaattgcta gatcctagtg aagcctgagc ttaacctact    5220
gttggaggct taaagttcga cattaattgc tacttttctt ggtcagagtt ttaaataatt    5280
aggttggtac aaaaaactgt gattactttt ccaccaacct aataacatgc tacaatttct    5340
gtaattatta ttttcactg tcaagacata gcaggtggtc cgttttgtt attgtcaaga    5400
actgtcagac taaaaatgaa cttttacactt cttttttaaat gatacatttt ctagaaaatt    5460
caatgaggtt taagagcaat tgaaaagtct gatttcaaga gagtctcatc caaaatgtac    5520
tatatatttt tcccccaaagt ccttggagtt aattttgaca acaatttaaa gtacacttaa    5580
gtcttttgaa gttaatgggt ctgccacccca ggttggagtg cagtggcgtg atctcagctc    5640
actgcaacct ccgcctcccg ggttcaagcg attctcctgc ctcaacctcc caagtagctg    5700
ggactacagg tgtgtgccac cacgcctggc taattttgt attttagta gagacggggt    5760
ttctccatgt tggccaggct ggtctcgaac tcctgacctc aggtgatccg cctgtctcag    5820
cctcccaaag tgctgggatt acaggcatga gccaccgcgc ccggcctgaa gttaattttt    5880
atcccacct aatgttcatt atggatcttg aaggtaaatt aattctgcac taaaattta    5940
caatgcttta caaaatgact gtaggtggcc catatggaat tcggtcaact gggccaatga    6000
cacatatggg attgcagttg aaattatcca attcctactt gatatttgta agctgctgtg    6060
atagccagta taattgtact gtaagaatgt ggtaaatagc cggggcccgg tggctcacgc    6120
ctataatccc agcactttgg gaagccgacg tgggcggatc acttgaggtc agtaggtaga    6180
gaccagcccg gtcaacacgg caaaacctcg tctctactaa aaatacaaaa attagccagg    6240
tgtggtggta cgcacctgta gtcccagcta ctcaggaggc tgaggcagga gaatcgcttg    6300
```

```
agcccatgag gtggatgttg cagtgagcaa agatcgcacc attgtactcc agcctgggca    6360
acggagtaag actctgtttc aaaacaacaa caacaacaac aacaacagat tggtaaatag    6420
agtaataata aaatcaaatt aaacttgcaa aaaatggcca ctttgctccc actggtggcc    6480
aatggaggtc aaggacctgg ctgacctcct gcctaaaggc agaggttgtt agccttcgca    6540
atggactcaa atcagagggg gagctttcaa aactcctgct gcccagactg aaccccagat    6600
caatgaaacc aaaatctctg gatacagggc ttggcatttg tagcttttag agttcctaag    6660
tatctctact gtgcagccaa agttaagaat cagtgcctta gaacatcaac agttttttgg    6720
tccttttgtt aaaaagcaca gtccgttttt ttaggtggct agaaatgctc caggaagagc    6780
tgaaatgtat ttaccagcca ccttggtttg attttagaaa gcaaaataga agttctaagt    6840
atgctttctc tgaaaagctg agactgcaga taagagtgag ggcagttgat ggagttcatt    6900
ctcctctttc aatcactgct tctcatcctt tcattataat aatctaagaa tctcagagat    6960
tatgaaagag aaagcagtct tatggaagac cccagactca cagaatatta gggtgtgttt    7020
cacagggaag gatgtcatta cccacagtta gtctttgaaa cgcagttgga cattatttgt    7080
aagtgcatca tagtgtcgcc tccaggttcc attgagggga acgtcattcc aatgcaacat    7140
ctctgagttc atctgggtta ttaaatgggg ttgagggatt tgttattttt aaattagtag    7200
ccccaattta ggactactca agaccatagg acaagcctgt ccaaccctcg gcctgcgggc    7260
tgcatatggc cgaggacagc tttgaatgca gcccaagaca aattcataaa ctttctgaaa    7320
atattatgca tttgttttt agcccatcag ctactgttag tgttagtgta ttttatgtgt    7380
ggcccaagac aattcttctt cttccagtgt ggcccagaga agctgaaaga ttggacaccc    7440
ctgctataag acacagtaat ataaatacat aacctgtggt tctggattgg cattagcaga    7500
tacaggctgt gttgattttg cagaaagtta caaagagctg ctagttggtg tgtatgtcta    7560
aaatcagtag atttcctgtg gttctaagga atgacaaaga atctggaagt tctctgtggt    7620
agcctgctca gtgcagaaag ggaacgtgga aaatccgcca ccagcatttg agtcttggag    7680
gttccacata gggctatcag gtctctgctg atcactgaaa ccagatcatg gccaactagc    7740
cccttggctt cagccctccc aattcattaa ctactcaggt aaatctaggg tcactttcaa    7800
ctctaccacc taccatctga gtgaccttga aaacattcat ctctctgagc tcaggtccc     7860 atgtctgtaa agcaggggcc tcatggactt ctttgggttt ttttgttttt gttttttgttt   7920 ctgaggatta aacaaatgct ccctacccta tttcccagca tccagtaaca cagttttca     7980 tatttttgtg tatgttaagt caggaccat ctctttaatg ataagtgcac ttaatgtggt    8040
catgttttct tttgtcttcc aaagctgtta gtgaatccat tgaatttggg atgggtaaaa    8100
taaagtatct attattaatt gtaaattttca tctaaagtga caaatcctac ctgcataacc    8160
atttcttaat ttcctttcat catgtatcag tggtcaacat tgttaactgc gaatgaatca    8220
gaatccatca aaaattagaa ctatttccag tctggcaaaa attcagctct ggttgaatcc    8280
aaacattgtg ctgaagcagc taagtaattc aactgaggag attaattaca tgttataatc    8340
aataggttct cttgacactt cagtgttagg gaacatcagc aagacccatc caggagacc     8400 ttgaaggaag cctttgaaag ggagaatgaa ggagtcatct ttgcaaaata gctcctgcag    8460
cctgggaaag gagactaaaa aggtaaaaag ctgttaattc caggaagaca gctttacgcc    8520
cctcccagac cacctgcact gcacactacg tggaatttat tttagtctca catggcagcg    8580
tccctacctt tgtgcccaca catctggtct ccgcctggc tgcagccctc cccttcaggc     8640
gaattctggg tgtgtcctat ctgctcattg caactcccag cgaatgagtt ttcagcgaag    8700
```

```
gcagactttc tgacctgttc ttcaaactgc actggtcttt taaaaacgtg tttggtggcc    8760
atcagcatcc aatttcagaa gaaagatttg ggtgaggact gagagaggct gttgttgttg    8820
tgctgtctgt ttccttcaga atctgcagaa gaaaattggc aggtcatgta ctgtggacct    8880
aaccaaagga caaatgatgt atggaaaata gaaaaactgt tgtgaaattg cttcctcatt    8940
agcaataact gtatttggca gggagaggag aagttgggca cattttttt tcttttttt    9000 ttcatgattc atacgttttc tttaaagaag tgggttttgc ttttcactgg gtgctctaag    9060
acaaccccag tgaaagatct ggaccacgaa gacccagtca tcctcataag ggtgttcatt    9120
gcagcaagct caagggcatg ccaggcaaag gccttttttc tggcagcttg aacttgtctc    9180
agcagagggt ttcacagaac aactgtcatt tacctgttct ctgctcttac ttgattcgtt    9240
tcccaggact gctgaaacaa agtaccacaa acttggtgga tcaaaacagc agaaatatat    9300
cctctcacag ttctggaaac cacaagtcag aaaccaatgt gttgttggca gggttggttc    9360
cttcttaagg ggctagaggg aaaatctgtt tcatgctcct ctcccagctt ctggtggtag    9420
ctagcaattc ttgatgctct ctggcttgcc gctgcatctc tctagccttc acctctcctc    9480
atgtgggtgg ccttctttcc tgtgtgtcta tttccaaatt ccccttttct tataagggga    9540
ccagttattg gatcagggcc caccttaatt cagtagatcc cattttaact tgatgacatc    9600
agcaaagtcc aaataaggtt gtattcacag gtaccagggg ttagaacttc aagttatcta    9660
ttaggggaca caattcaacc taaaaactcc ccttttttga ttctctattc tgccacttct    9720
actcaatcca ggttcttcac ttcatcagct cccaatctaa tacttatctt atttctagta    9780
agcatctctt ccttatctta actggtccct ggggcctggc ccgagcccca ttataccatc    9840
agctgttgac atcaagggtg gacttctctt tcggcacaga aggcacaggg ctgtaggctt    9900
cagccttctc tgctttgctc tgccccatct actgttcatc cacctgcttt ccattttgct    9960
aaactttgta gaaaattctt gtcagctgtt gtctcctcct acactttctt tgatcttaga   10020
ggattctatt cttttactat ggctttaatc ggagcacccg actgttaggt tcaaccaaca   10080
gaagttggtt gtgctctctc actctttctt tctctctctc tctctttctc tctatttgca   10140
tagtggtatt ttttttttcc tctattttat tggcagaatt gccatttctc taagttattg   10200
tagagttgct gtttctctat tttatttgca tatttctctt ctgccaggct ggattgtttc   10260
tattgattgg ttctgctgta atgagggtga cttctcatta gtatccttct cacttcatct   10320
gggaccagat gcccttgat atccttttgg agccacaact tttggtagtc agaggcatgg   10380
gtgtggctca aaggaagaac ttggctcaga aggtgcagct cttgctgggc ctttggtctc   10440
tgctctgtct tctgagatca gtggctgctg ggacctgggg ttcccccatg ccgggcatgg   10500
tcacacagca ctcctatgga cttgagcaga gcaccctgca aagtgagcat agcaatcca   10560 ttccaactct gtgcagtcct gcacggaata tagaaggtgg agcaatgaca gtctccccaa   10620
cttctctgca agcaacctgc tcaccatttc ttgcccttcc catttatgta cttttcaaaa   10680
tcaggttatt tggaatttgt cgactcatgt ttcttacttc agtacttttt tgggagggca   10740
gcattagaaa cctcaaactc ttaactaaaa aatgtctttg ggaatgttct ggccattttc   10800
atggcccaca atttgcttta agctgcttta gactctccca gaggctattt tcatcccgaa   10860
agaacagagc agagctcaaa agactccagt tttggtctct agcagcccct agaggatttc   10920
cccctcaatt cctctctgcc ttgtatgaaa tagaattgga tttgaaatcg gatgttgagg   10980
ccttacctcc aggctagtga ggccacacaa gatggatcct ctggaccgc ccaagtgtcc   11040
```

```
acctaaacat gagttaccaa ctaacaatgt tttgtttagc atgcaaaggg agtggtctgg   11100
aatctggcct tgccctgaca tattctcctt gggccttttt aaaaaaataa tttgtgttaa   11160
tctgtagtta aaaattataa taaggacctg acaaacacta cctcagtcag atgatcaagg   11220
tacacataaa tagtgaaagt catgttgata gcatgcaccc ttcatatgat atggctagaa   11280
tggccctgca cttctgtgat cttcctcccc tagactcatc agctcgatct aatcataaca   11340
aaagcatcag ataagtcccc gcccagggac attctacata accatttccc ttcccagtta   11400 tattttttctc cacaatactt tccaccatct aacattctat ctttcaaaat gggcaagtat   11460
tttagcctgg tttgttcatt gttttatctg caactcaaat acagttcctg aaataaaata   11520
tctgcctaat aaatatttaa tgaatgaatg aatatagcat tgccttatcc gtttaattgc   11580
cacatggtat ttcattgtgt gaacataata tcgtttattt acccagacta ctactcatag   11640
gcatttagat tatttccggt cttttgctat tgctaacagc ctttgcaatg aacatccttg   11700
tatacagaca tttgcatata tgagggtgtg tctttaggat ctacttctag aattgaaatt   11760
gccaactcca agtatatgtt tccaattgtg atagatatta cacattaccc tccatcttag   11820
aggtggtgtt aatttagatt cctgccagca aaatttaaga gtgtttgttt ccccatatcc   11880
tcaactgcct aacagaatca gtgaaaaatg gtatgacagt gtaattttttg agtgaggttg   11940 agtatctttt cctatgcttt aagagcaatt tatgtttcct ttttatgtga actgtctgtt   12000
aatatatttt ttcaatttttt ctattgggtt atttgtctttt tcattaatgc atatacctgt   12060
tacatattta taccaagtat gtattaaata ctaacatatt gatgaaacag agcaaaaagc   12120 ctagaaaatag atccaaataa cagaagagtt agtatgtgat acaggaagcc tataaaatca   12180
gtgagcaaaa gaccatccaa ttaataacgt tagggtaaat gggtctccat ttagaaaaaa   12240
ataatgtggg tctacacctc acattttata cctaaacaat tccagtggga taagaaaatg   12300
aaatcataaa aaattactag gaaaaagatg agaaaattgt tcataaaact gaagtgtgga   12360 agatcccttta tgccttacac tgccctgagt gatctcattc atacccatgg cttcaattgt   12420
catgaatccc aaattcattc ctctgtcaga actctcttct gagcttcaga cccacatact   12480
cagctgccta ctggacacct ctacttgaat atcacaaact caactcaaaa gcaaacctgt   12540
caaatttaat tactagtagc cctaccccaa acaatcttcc tgctcagtga atgacaccca   12600
tccctccagg tgcacagacc aggaacctag aagtcactct gattgcatcc ctctccctca   12660
caacctctac ctcccttttat tcatccattg ctatgtctct caaatgtacc tcccaaatat   12720
ctcttgaacg cgttctttttc tatctctatt gccaccaccc tagttcaaac tcccatcatc   12780
tcatgactga agttctgtgc cctcttgcca gtgaacactg tagaatcaat ctaaacatgg   12840
tgccaccctg cttaaaaacc ttcaaaggct cacatcactt ctcagatgaa gagattgggg   12900
agacgttggt aataggacac aaaatttcag ttaggcagga ggaaaaagtt ctattgaaga   12960
actctattgt acaatatggt gactatagtt aataacaaca tattatacac ttgaaaatca   13020
ctaagagagt ccatttttaag tgttctcatg accaaaaaat gataagtata tgaggtaatg   13080
catatgtgaa ttagcttgac tgaggcattc tacatgtata catatttcga aacatcatgt   13140
tgtacatcat aaatgcatac acttttttagt tgtcaattta attaatatttt tttaaaccta   13200 ctctggcctt tttttccttt tttgagacgg gtggtctctg tccccccatgc tagagtgcag   13260 tgcgcaatca tggctcactg cagcctccac ctcccagtct caggcgattc tccagtctca   13320
gcctcccaag tagctgggac cacaagcatg agccaccatg cccgctatt  tgttttttgta   13380 ttttttgtag agatgggatc tcgccacatg gcccagtctg gtgtccaact cctgagctcc   13440
```

```
agtgatccac ctgcctcagc ttcccaaact gctgggatta caggcgtgag ccactgtgcc   13500
tggtccactc tggtctttac tcaagtccct ggctttctct cagtctctta aacttatgtg   13560
cttagtaaga tgaggactga aaaatgtcca cagaacatag tgacatggag atactgagaa   13620
cctcaacgac atctccatta gccacttcct ctgtgccatt ccagtcctct gggcccact    13680 gtggcaagca gtcctaccat ggcaaacatg aaagctgatg tgccttgtct tagacccaca   13740
ccatatctct ctgaattcct gtcccagggc ttctctggag gtacagcctg ggaaactcac   13800
gggaatagac acagggcctt tgcacatgct gctcccttt  cctgaaaaat cctttgaca    13860 tcttggttgt gccttacaca tgcctactca accttaggat tgcagttcag gtttcactcc   13920
tttttttttt ttcttttga dacggagttt cactcttgtt gcccaggctg gagtgcaatg    13980
gtgtgatcct ggctcaccac aacctctgcc tcctgggttc aagtgattct cctgcctcaa   14040
cctcctgagt agctgggatt atagtcatgc accaccacgc ccagctaatt ttgtattttt   14100
agtagagaca gtgtttctct atgttggcca ggctggtctc gaactcccga cctcaggtga   14160
tcggcccgcc tcggcctagg ttccacttct ttatggaaat cttccccagt tgccttgact   14220
aggccaaagt cccctcttct taggctctta cagtgtcatg cacttctttt ttatcacagt   14280
gtaaaccttg taatgttgtg tttaagtcat atctgttgta cccatgagac tgggagccaa   14340
ttcatatatt gtgagtgtaa tcgaacagac ttcccaggcc acccactagc taatcaaggc   14400
agggatgagt ccggaaagtg actttgaaat ctagcaatgt tggaacttgg aaatcacaca   14460
ggctgagatc tgctcaggtg cctgaacaaa tatagcattg cctgtggcgt ctccctcaaa   14520
gtgccttgca tgtctgagcc ccgttgcccc ttcctttggt gtgcctgtgt ctcccggtac   14580
agatgtgaag cctggagacc tgtggctgcc tctgcaggag ctccatgttt tcaagccata   14640
aatcatctta gaattcatag catctagata tattagtttt ctattactgc agaacaaatc   14700
gctcccaaat gtagaggctt caaagaatgc ccattgattg gccttaattt ctgtaagtta   14760
gaatctgggc aggtttgcct gagttctcca ctccaagtct cataaagcca agctgggctg   14820
tcatctggag gctctgagta aaaatttgtt tccaggttca tccagattgt caggtgattt   14880
cagttccttg cagttgttgt tcgactcact accccaccac caccccgaaa acctcatttc   14940
cttgctagct gcctgcagag agccactctc agcttccaca ggctgcttgc attccttgtt   15000
gtggggccgc tacctcctca agccagaaat agggcatcca gttcttctca tgcatcctac   15060
ccctctgact tttccttctg ccgataacca gaaaaaacgt tccgccttca aacgctcgta   15120
tgattagact aagcccatcc agataaaattc ccatatgcca tatactataa tgtcatcaca   15180
gcagtaatac ccgggacaaa attcatgggg gtcatcttaa aattctgcct atcacaccag   15240
gtatagtaga ggcttgtttt agtgcaagtt aaacattaag cagcaacatc acgatagtgc   15300
tgcatttgaa aataactact agcaactgaa catgtctggg agttctgctc cactttaatt   15360
tccatctcaa aaggagctgg gttttccttg gctgttacaa atgggcaata atgattgagc   15420
ttaagaataa tcaatgtcca cataaaaatc ttttataaca tagtgagagt gtgacatata   15480
aaggtgttag ttcaccggcc ctaaatttta ggagaatttt taaaaaggca cttatctggt   15540
ttaatccata ataaagacat gagttgggct ttagtgaaaa atctaggctg gtttctgtgt   15600
tcagtgaaag aagatttgag agttctctta attacaaccc ttgatcaaac ctaccacatt   15660
aatctgttta ttgcattgta tggttaccaa aagtgatata ttcagccctc tatttattaa   15720
gaaacagtta cagaaagtga ggcactctcc tgtgttactg agggtgcata aaaatataaa   15780
```

```
gcaccatgtg tcttccctag agaagtttca aaactagcaa gcaaatagct attaatgcta   15840
atgtttgtgt gatagggaac atatgagtag taattattcc acaaacaatt ttttgagtgc   15900
tgtttacatt tgaggcacag ttcaggcacg aggatttcaa aaggagattg tgtagcatga   15960
tggcttgtta aaaatatgat tttggaatca gatttgctca agtcccagtg ctacagcata   16020
ccatccttca aaaaggtact taagtctctg agtttgtttt ctcatctgca aaatataaat   16080
aataagagga cctactgcgt catgttcttg tgagcattaa tgtgggtgat gaaatgttta   16140
tgaagcactt agcacaatac ctgacatttt gtttgttatt attatcaaca taaagtgccc   16200
actttccagt catgcaagaa gaaaacataa tatatgtcac catagaagta tagaacaatt   16260
gtgggaaata ccagtaagag agatatagct gtataaataa ggtaaagatg actgcctaga   16320
agatctagga tgataccata ttagaagttg catctgaact ctccttgggg actggccaaa   16380
gtttcatcaa gtgtcatgtc agtaggttgg tgctataaat atatagcttg caaagctata   16440
gacttactat aaaccatagc tgtggtccag cttagactca ttatggtggt ggagtatctt   16500
gattaatggc ctctgcagaa gcttcccagg tcttctcatc atcataatct cagatagctt   16560
catcttcaac ttcctttttt ttgttgtttt tgagacaggg tctcactctg tcatccagga   16620
tggagtgcag tggcacaatc atggctcact gcagcctcga cctcaggagc tcaagccatc   16680
ctcccacttc agcctcccga gtagttggga ctacaggcat gcaccactac gcccggctaa   16740
ttttttcatt ttttttgtaga gtcagggtct ccctatgctg cccagtctgg tctcaaactc   16800
ctgggctcaa accatctttc cacctcggcc tcccaaaatg ttgggattac aggtgtgagc   16860
caccacacac agcccatctt caacttcttt tagcaccatg aagctgaaca tagtaaaaaa   16920
gtaaaatcat tctggaccta atctgatgca atttatttaa ttgttaagtg aatgcacaca   16980
tcaaaattca tacaagtatg gggcagcgct gctaatttat ttacaaaaca cctggcaaat   17040
actgctactc taatactgtg cttccacttt tgatttttcct taggaaaaca tgttccttca   17100
gtcgtcaatg ctgacctgca ttttcctgct aatatctggt tcctgtgagt tatgcgccga   17160
agaaaatttt tctagaagct atccttgtga tgagaaaaag caaaatgact cagttattgc   17220
agagtgcagc aatcgtcgac tacaggaagt tccccaaacg gtgggcaaat atgtgacaga   17280
actagacctg tctgataatt tcatcacaca cataacgaat gaatcatttc aagggctgca   17340
aaatctcact aaaataaatc taaaccacaa ccccaatgta cagcaccaga acggaaatcc   17400
cggtatacaa tcaaatggct tgaatatcac agacggggca ttcctcaacc taaaaaacct   17460
aagggagtta ctgcttgaag acaaccagtt accccaaata ccctctggtt tgccagagtc   17520
tttgacagaa cttagtctaa ttcaaaacaa tatatacaac ataactaaag agggcatttc   17580
aagacttata aacttgaaaa atctctattt ggcctggaac tgctatttta acaaagtttg   17640
cgagaaaact aacatagaag atggagtatt tgaaacgctg acaaatttgg agttgctatc   17700
actatctttc aattctcttt cacacgtgcc acccaaactg ccaagctccc tacgcaaact   17760
ttttctgagc aacacccaga tcaaatacat tagtgaagaa gatttcaagg gattgataaa   17820
tttaacatta ctagatttaa gcgggaactg tccgaggtgc ttcaatgccc catttccatg   17880
cgtgccttgt gatggtggtg cttcaattaa tatagatcgt tttgcttttc aaaacttgac   17940
ccaacttcga tacctaaacc tctctagcac ttccctcagg aagattaatg ctgcctggtt   18000
taaaaatatg cctcatctga aggtgctgga tcttgaattc aactatttag tgggagaaat   18060
agcctctggg gcatttttaa cgatgctgcc ccgcttagaa atacttgact tgtcttttaa   18120
ctatataaag gggagttatc cacagcatat taatatttcc agaaacttct ctaaactttt   18180
```

```
gtctctacgg gcattgcatt taagaggtta tgtgttccag gaactcagag aagatgattt    18240
ccagcccctg atgcagcttc caaacttatc gactatcaac ttgggtatta attttattaa    18300
gcaaatcgat ttcaaacttt tccaaaattt ctccaatctg gaaattattt acttgtcaga    18360
aaacagaata tcaccgttgg taaaagatac ccggcagagt tatgcaaata gttcctcttt    18420
tcaacgtcat atccggaaac gacgctcaac agattttgag tttgacccac attcgaactt    18480
ttatcatttc acccgtcctt taataaagcc acaatgtgct gcttatggaa aagcttaga    18540
tttaagcctc aacagtattt tcttcattgg gccaaaccaa tttgaaaatc ttcctgacat    18600
tgcctgttta aatctgtctg caaatagcaa tgctcaagtg ttaagtggaa ctgaattttc    18660
agccattcct catgtcaaat atttggattt gacaaacaat agactagact ttgataatgc    18720
tagtgctctt actgaattgt ccgacttgga agttctagat ctcagctata attcacacta    18780
tttcagaata gcaggcgtaa cacatcatct agaatttatt caaaatttca caatctaaa    18840
agttttaaac ttgagccaca acaacattta tactttaaca gataagtata acctggaaag    18900
caagtccctg gtagaattag ttttcagtgg caatcgcctt gacattttgt ggaatgatga    18960
tgacaacagg tatatctcca ttttcaaagg tctcaagaat ctgacacgtc tggatttatc    19020
ccttaatagg ctgaagcaca tcccaaatga agcattcctt aatttgccag cgagtctcac    19080
tgaactacat ataaatgata atatgttaaa gttttttaac tggacattac tccagcagtt    19140
tcctcgtctc gagttgcttg acttacgtgg aaacaaacta ctcttttaa ctgatagcct    19200
atctgacttt acatcttccc ttcggacact gctgctgagt cataacagga tttcccacct    19260
accctctggc tttctttctg aagtcagtag tctgaagcac ctcgatttaa gttccaatct    19320
gctaaaaaca atcaacaaat ccgcacttga aactaagacc accaccaaat tatctatgtt    19380
ggaactacac ggaaacccct ttgaatgcac ctgtgacatt ggagatttcc gaagatggat    19440
ggatgaacat ctgaatgtca aaattcccag actggtagat gtcatttgtg ccagtcctgg    19500
ggatcaaaga gggaagagta ttgtgagtct ggagctaaca acttgtgttt cagatgtcac    19560
tgcagtgata ttattttct tcacgttctt tatcaccacc atggttatgt tggctgccct    19620
ggctcaccat ttgtttact gggatgtttg gtttatatat aatgtgtgtt tagctaaggt    19680
aaaaggctac aggtctcttt ccacatccca aactttctat gatgcttaca tttcttatga    19740
caccaaagat gcctctgtta ctgactgggt gataaatgag ctgcgctacc accttgaaga    19800
gagccgagac aaaaacgttc tcctttgtct agaggagagg gattgggatc cgggattggc    19860
catcatcgac aacctcatgc agagcatcaa ccaaagcaag aaaacagtat tgttttaac    19920
caaaaaatat gcaaaagct ggaactttaa aacagctttt tacttggctt gcagaggct    19980
aatggatgag aacatggatg tgattatatt tatcctgctg gagccagtgt tacagcattc    20040
tcagtatttg aggctacggc agcggatctg taagagctcc atcctccagt ggcctgacaa    20100
cccgaaggca gaaggcttgt tttggcaaac tctgagaaat gtggtcttga ctgaaaatga    20160
ttcacggtat aacaatatgt atgtcgattc cattaagcaa tactaactga cgttaagtca    20220
tgatttcgcg ccataataaa gatgcaaagg aatgacattt ctgtattagt tatctattgc    20280
tatgtaacaa attatcccaa aacttagtgg tttaaaacaa cacatttgct ggcccacagt    20340
ttttgagggt caggagtcca ggcccagcat aactgggtcc tctgctcagg gtgtctcaga    20400
ggctgcaatg taggtgttca ccagagacat aggcatcact ggggtcacac tcatgtggtt    20460
gttttctgga ttcaattcct cctgggctat tggccaaagg ctatactcat gtaagccatg    20520
```

```
cgagcctctc ccacaaggca gcttgcttca tcagagctag caaaaaagag aggttgctag      20580
caagatgaag tcacaatctt ttgtaatcga atcaaaaaag tgatatctca tcactttggc      20640
catattctat ttgttagaag taaaccacag gtcccaccag ctccatggga gtgaccacct      20700
cagtccaggg aaaacagctg aagaccaaga tggtgagctc tgattgcttc agttggtcat      20760
caactatttt cccttgactg ctgtcctggg atggcctgct atcttgatga tagattgtga      20820
atatcaggag gcagggatca ctgtggacca tcttagcagt tgacctaaca catcttcttt      20880
tcaatatcta agaactttg ccactgtgac taatggtcct aatattaagc tgttgtttat       20940
atttatcata tatctatggc tacatggtta tattatgctg tggttgcgtt cggttttatt      21000
tacagttgct tttacaaata tttgctgtaa catttgactt ctaaggttta gatgccattt      21060
aagaactgag atggatagct tttaaagcat cttttacttc ttaccatttt ttaaaagtat      21120
gcagctaaat tcgaagcttt tggtctatat tgttaattgc cattgctgta aatcttaaaa      21180
tgaatgaata aaaatgtttc attttacaag aggagtgtat gataaatata tcatagagaa      21240
attggtcttt aatataaaag aaattgccat atacactgaa ttttttcaga actcttttta      21300
aaaaactatt tggtagaaat caaaggggaa gcagttttca tgacactttt actttaagat      21360
acttattaat agataaattc tatcttgatt ccctactcag aagacataaa gtcagaatgc      21420
ctggctgttg gtagccttg tgcaattccc ccaaatgaaa caactttggc aaccctttcc       21480
acttctactg tccccttggt tcctctgcat cagtccatag catcctctat ccagtatgaa      21540
tcttgagata tctaatgaaa tttacctgag aataactaga aattatccaa gcataagaaa      21600
aggaagttgc ttcagaatga aaagaagata aacctccaat ataccatctt tccttttag       21660 ttaaatctta cagcatgagt tacctttaa tatgtgcttc taagaaactg accaaaataa       21720
tgtgtcatag tgttatttaa tacgcacaaa gtggaaagca gtgcaagttt gccaaggaca      21780
atttaatttt gtcacattgc atgctgtttt gtgaccatga agagtttata caaagatgtt      21840
tatgcttgtg cttgttgagg tatagggaca aatatctaaa agcaagatca gatgggtgtg      21900
gtatctcaca cctataatcc ttggattaaa atctacctca attgtaggac taccagttga      21960
accacatgct tcccactgcc ctcagcaaag ggcaccttag ttagaggaaa ggtagagcct      22020
ttctatggag gaggaatttg tgaggtttga gttttatcag ctacctggga gtcagaccct      22080
gatagattct ccttcacact ccctggacct tttcctgcca agtggaggct ctcactcaga      22140
ggaaatctcc attcttttga tgcaggtcat tcatactcag atattctgca ctgttcaagc      22200
aataaaaatt gaatgagcac ctattatgta caccagttgg cactgtgtca aaatgtactt      22260
gtgcagagac cttggatcat tggtgacagg tcttcttctc ctctgcattt ttctcaagac      22320
caggcctcag tgtagcatgt ttccatggag tgaaagaggg gaaggaagag tgggctttgg      22380
aaagtggcag ctgtgtcata gcagtcagcc tctgtgtatg tgaaggactt tccagagccc      22440
ccccactaaa gcctccatgc tcctcctggg actgccacag ttcttgaaac tatccataca      22500
gtcttcatga gttatttta atttttttt cttcttttct ctttcctcct tttcccttt         22560 tccccactcc ctagttagat ctttaaaaat gcaattgtaa cctttatctt cccttcacca      22620
gacactccct acagggcaag cttatgtata cgcttaccta aaagctccag agccagaaat      22680
ctctcccact cgggg actgc tcaagagac agcagtcaat ttacaaccta aagcatgccc      22740
acaacaaaac tctctcccac ctggaggata tcttgaggca atggtcactt tacaacctag      22800
ttctgcctgc aatggcacca gctcaaccac ctggtacata agacacaaaa gcaagttgca      22860
tagacctcac cttctcactc ccttccctgc atgccattaa tgccaactcc cccttttaaaa     22920
```

```
gcccctgctt tctgccccaa aagcaaagtg ataccattaa agtcaggagc ctatacttct   22980 tcccctaag  ctaatttttg gaataaaagt cattttattg agaacctcca taaactgttg    23040
gtgggaatat aaattagtaa accatgatgg agaacagttt ggagtttcct caagaaacta   23100
aaaatcgaat taccatatga cccagcaatc ccactgctgg gtatacaccc aaaagaaagg   23160
aagtaattat attgaagaga tatctgcact cccatgtttg ctgcagcact gtttacaata   23220
gctgagattt gcagcaacct aagtgtctat caacagatga atggataaag aaaatgtggt   23280
acacatacaa aatggagtac tagtcagcca taaaaagaat gagatcctgt catttgcaac   23340
aacatggatg gaactggagg tcattatgtt aagtgaaata agccagacac agaaagacaa   23400
atatcaaatg ttctcactta tttgtgggat ctaaaaatta aaacaattca actcatggac   23460
atagagagta gaaggatggt taccagaggc tgggagggga agtggaagct aggggaggtg   23520
gggatggtta atgggtacaa aaaaatagaa agaatgaatt agatctacta tttgatagca   23580
caacagagtg actatagtca ataataattt aactgtactt tttaaaaata acaaaaatcg   23640
tgtaattgga ctgtttataa ctcaaagaat aaatgcttga ggggatggat atcccattct   23700
ccatgatgtg attacccatt gcatgtatca aaacatctcg tgtaccccct aaatatatac   23760
acctactatg tatccacaaa aactaaaaat aaaattttgt ttaaaaagtc actttcttta   23820
taccacatct caccccttgtt aattggactc tgcgaggggt gaacaactgg acctgtgatt   23880
cagttaaaat tagatcctca ggcaccttct gttgagaaag aataggtctc aaatgttgca   23940
aatctctttt acctttctca aggttctagc ctctcctatc accaatttag gtaagaatat   24000
aaaatcatca ggcctgtgtt acctcaacta tcttcctctt tgatccaaaa cgtatactta   24060
gtggacaaag cttttttgga caactaatat gtgctaagtc ttaaggtggg ttcagaaatg   24120
gccaggatcc atcaactaat caatggataa ataaaatgtg atctatccat acaatggaat   24180
attattcagc cataaaatgt aatgaagcac taatactatg atgcaacatg gatgaacttt   24240
gaaaacatca tgctaataga ccaataacag gctctgaaat tgtggcaata atcaatagct   24300
tgctaaccaa aaagagtcca ggaccagatg gattcacagc cgaattctac cagaggtaca   24360
aggaggaact ggtaccattc cttctgaaac tattccaatc aatagaaaaa gagggggatcc   24420 tccctaactc attttatgag gccagagtca tcctgatacc aaagccgggc agagacacaa   24480
ccaagaaaga gaattttaga ccaatatcct tgatgaacat tgatgcaaaa atcctcaata   24540
aaatactggc aaaccgaatc cagcagcaca tcaaaaagct tatgcaccat gatcaagtgg   24600
gcttcatccc tgggatgcaa ggctggttca atatatgcaa atcaataaac gtaatccagc   24660
atataaacag aaccaaagac aaaaaccaca tgattatctc aatagatgca gaaaaggcct   24720
ttgacaaaat tcaacagcct ttcatgctaa aaactctcaa taattaggt attgatggga   24780 tgtatctcaa aataataaga gctatctatg accaacccac agccagtatc atactgaatg   24840
ggcaaaaact ggaagcattc cctttgaaaa ctggcacaag acagggatgc cctctctcac   24900
cactcctatt caacatagtg ttggaagttc tggccaaggc aattaggcag gagaaggaaa   24960
taaagggtat tcaattagga aaagaggaag tcaaattgtc                          25000
```

<210> SEQ ID NO 22
<211> LENGTH: 1041
<212> TYPE: PRT
<213> ORGANISM: Homo sapiens

<400> SEQUENCE: 22

```
Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Glu Asn Phe Ser Arg
            20                  25                  30

Ser Tyr Pro Cys Asp Glu Lys Lys Gln Asn Asp Ser Val Ile Ala Glu
            35                  40                  45

Cys Ser Asn Arg Arg Leu Gln Glu Val Pro Gln Thr Val Gly Lys Tyr
    50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
                100                 105                 110

Gly Leu Asn Ile Thr Asp Gly Ala Phe Leu Asn Leu Lys Asn Leu Arg
            115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
            195                 200                 205

Ser Phe Asn Ser Leu Ser His Val Pro Pro Lys Leu Pro Ser Ser Leu
    210                 215                 220

Arg Lys Leu Phe Leu Ser Asn Thr Gln Ile Lys Tyr Ile Ser Glu Glu
225                 230                 235                 240

Asp Phe Lys Gly Leu Ile Asn Leu Thr Leu Leu Asp Leu Ser Gly Asn
            245                 250                 255

Cys Pro Arg Cys Phe Asn Ala Pro Phe Pro Cys Val Pro Cys Asp Gly
            260                 265                 270

Gly Ala Ser Ile Asn Ile Asp Arg Phe Ala Phe Gln Asn Leu Thr Gln
    275                 280                 285

Leu Arg Tyr Leu Asn Leu Ser Ser Thr Ser Leu Arg Lys Ile Asn Ala
    290                 295                 300

Ala Trp Phe Lys Asn Met Pro His Leu Lys Val Leu Asp Leu Glu Phe
305                 310                 315                 320

Asn Tyr Leu Val Gly Glu Ile Ala Ser Gly Ala Phe Leu Thr Met Leu
                325                 330                 335

Pro Arg Leu Glu Ile Leu Asp Leu Ser Phe Asn Tyr Ile Lys Gly Ser
            340                 345                 350

Tyr Pro Gln His Ile Asn Ile Ser Arg Asn Phe Ser Lys Leu Leu Ser
            355                 360                 365

Leu Arg Ala Leu His Leu Arg Gly Tyr Val Phe Gln Glu Leu Arg Glu
    370                 375                 380

Asp Asp Phe Gln Pro Leu Met Gln Leu Pro Asn Leu Ser Thr Ile Asn
385                 390                 395                 400

Leu Gly Ile Asn Phe Ile Lys Gln Ile Asp Phe Lys Leu Phe Gln Asn
            405                 410                 415

Phe Ser Asn Leu Glu Ile Ile Tyr Leu Ser Glu Asn Arg Ile Ser Pro
```

```
                420             425             430
Leu Val Lys Asp Thr Arg Gln Ser Tyr Ala Asn Ser Ser Phe Gln
        435             440             445
Arg His Ile Arg Lys Arg Ser Thr Asp Phe Glu Phe Asp Pro His
        450             455             460
Ser Asn Phe Tyr His Phe Thr Arg Pro Leu Ile Lys Pro Gln Cys Ala
465             470             475             480
Ala Tyr Gly Lys Ala Leu Asp Leu Ser Leu Asn Ser Ile Phe Phe Ile
                485             490             495
Gly Pro Asn Gln Phe Glu Asn Leu Pro Asp Ile Ala Cys Leu Asn Leu
                500             505             510
Ser Ala Asn Ser Asn Ala Gln Val Leu Ser Gly Thr Glu Phe Ser Ala
                515             520             525
Ile Pro His Val Lys Tyr Leu Asp Leu Thr Asn Asn Arg Leu Asp Phe
                530             535             540
Asp Asn Ala Ser Ala Leu Thr Glu Leu Ser Asp Leu Glu Val Leu Asp
545             550             555             560
Leu Ser Tyr Asn Ser His Tyr Phe Arg Ile Ala Gly Val Thr His His
                565             570             575
Leu Glu Phe Ile Gln Asn Phe Thr Asn Leu Lys Val Leu Asn Leu Ser
                580             585             590
His Asn Asn Ile Tyr Thr Leu Thr Asp Lys Tyr Asn Leu Glu Ser Lys
                595             600             605
Ser Leu Val Glu Leu Val Phe Ser Gly Asn Arg Leu Asp Ile Leu Trp
                610             615             620
Asn Asp Asp Asp Asn Arg Tyr Ile Ser Ile Phe Lys Gly Leu Lys Asn
625             630             635             640
Leu Thr Arg Leu Asp Leu Ser Leu Asn Arg Leu Lys His Ile Pro Asn
                645             650             655
Glu Ala Phe Leu Asn Leu Pro Ala Ser Leu Thr Glu Leu His Ile Asn
                660             665             670
Asp Asn Met Leu Lys Phe Phe Asn Trp Thr Leu Leu Gln Gln Phe Pro
                675             680             685
Arg Leu Glu Leu Leu Asp Leu Arg Gly Asn Lys Leu Leu Phe Leu Thr
                690             695             700
Asp Ser Leu Ser Asp Phe Thr Ser Ser Leu Arg Thr Leu Leu Leu Ser
705             710             715             720
His Asn Arg Ile Ser His Leu Pro Ser Gly Phe Leu Ser Glu Val Ser
                725             730             735
Ser Leu Lys His Leu Asp Leu Ser Ser Asn Leu Leu Lys Thr Ile Asn
                740             745             750
Lys Ser Ala Leu Glu Thr Lys Thr Thr Lys Leu Ser Met Leu Glu
                755             760             765
Leu His Gly Asn Pro Phe Glu Cys Thr Cys Asp Ile Gly Asp Phe Arg
                770             775             780
Arg Trp Met Asp Glu His Leu Asn Val Lys Ile Pro Arg Leu Val Asp
785             790             795             800
Val Ile Cys Ala Ser Pro Gly Asp Gln Arg Gly Lys Ser Ile Val Ser
                805             810             815
Leu Glu Leu Thr Thr Cys Val Ser Asp Val Thr Ala Val Ile Leu Phe
                820             825             830
Phe Phe Thr Phe Phe Ile Thr Thr Met Val Met Leu Ala Ala Leu Ala
                835             840             845
```

```
His His Leu Phe Tyr Trp Asp Val Trp Phe Ile Tyr Asn Val Cys Leu
    850                 855                 860
Ala Lys Val Lys Gly Tyr Arg Ser Leu Ser Thr Ser Gln Thr Phe Tyr
865                 870                 875                 880
Asp Ala Tyr Ile Ser Tyr Asp Thr Lys Asp Ala Ser Val Thr Asp Trp
                885                 890                 895
Val Ile Asn Glu Leu Arg Tyr His Leu Glu Glu Ser Arg Asp Lys Asn
            900                 905                 910
Val Leu Leu Cys Leu Glu Glu Arg Asp Trp Asp Pro Gly Leu Ala Ile
        915                 920                 925
Ile Asp Asn Leu Met Gln Ser Ile Asn Gln Ser Lys Lys Thr Val Phe
    930                 935                 940
Val Leu Thr Lys Lys Tyr Ala Lys Ser Trp Asn Phe Lys Thr Ala Phe
945                 950                 955                 960
Tyr Leu Ala Leu Gln Arg Leu Met Asp Glu Asn Met Asp Val Ile Ile
                965                 970                 975
Phe Ile Leu Leu Glu Pro Val Leu Gln His Ser Gln Tyr Leu Arg Leu
            980                 985                 990
Arg Gln Arg Ile Cys Lys Ser Ser  Ile Leu Gln Trp Pro Asp Asn Pro
        995                 1000                1005
Lys Ala  Glu Gly Leu Phe Trp  Gln Thr Leu Arg Asn  Val Val Leu
    1010                 1015                 1020
Thr Glu  Asn Asp Ser Arg Tyr  Asn Asn Met Tyr Val  Asp Ser Ile
    1025                 1030                 1035
Lys Gln  Tyr
    1040

<210> SEQ ID NO 23
<211> LENGTH: 801
<212> TYPE: DNA
<213> ORGANISM: Homo sapiens

<400> SEQUENCE: 23
acaggtgtga gccactgcac tcgatccatt cttacttact ttctttactt tatttccaag    60
caaatgtttg gagggaaacc aagagacttg gatgcggcca gccgaggcct tgggtttac    120
aatcacaaat gttttggtt tgcccatgaa ggcccaggct gcactctctg atgtcacagg    180
aatcacctct caaaccatgc accaggtctt gaattccctt agggtgtgat ctttagaggt    240
ccatctaggt atacccaccc aagccattct ttgactgctg acaggccttc cttcataaca    300
aggtgttcca cagtccattt atatatggat gtcatctctg cccaccctgc tgccaatttg    360
gttttctccc actcctgggg tgtaaggcaa gatgaaacat rtcacatccc gttctaaact    420
ttattcttgt ggccaggggt cagcaaactt tttctgtaaa gggccagatg gcaaatatct    480
taggttttac aggccaagaa gcaaatttgg catattatgt agctacttat atagtaaaat    540
aaaaatttcc acaattatgt aattgatgaa actcaaaatg taataataat aatcgaaggc    600
agttttttg tagtataggt ttaataatga gaagaatgga atcatttttg gaggtgctaa    660
cattctgctt ggttggaatt taagttagt gttctgtatc agcaaatcca ttgccaatgt    720
tcatctaaaa atgttttcac ttctgggccg gatttcgttc aaaggctgca gtttgctgac    780
ctctgctctt ggttacacct t                                              801

<210> SEQ ID NO 24
<211> LENGTH: 801
```

```
<212> TYPE: DNA
<213> ORGANISM: Homo sapiens

<400> SEQUENCE: 24
aaaaatttcc acaattatgt aattgatgaa actcaaaatg taataataat aatcgaaggc      60
agttttttg tagtataggt ttaataatga gaagaatgga atcattttg gaggtgctaa       120
cattctgctt ggttggaatt taaagttagt gttctgtatc agcaaatcca ttgccaatgt    180
tcatctaaaa atgttttcac ttctgggccg gatttcgttc aaaggctgca gtttgctgac    240
ctctgctctt ggttacacct tttgaggccc ttgctctccg agcataaaat ggaatccatt    300
tatcagacta aatcgggaag attaaatttt ccagcctcac gaatgctcag ccattgactc    360
actcgttcat acaatgaaca ctcattgagc ttatactaca ygccaggtgc tggaggaggc    420
atggggcgcc caggagaaag atgctcgctt tgcggccaca gcccagtggg agggagaccc    480
atacctaccg gtgctgtctc agaaacttgt ggaacaaaga tgaagcaatg ttcatgttat    540
tcgcctacat ctgtgaatta cacaaggaag acgagtttga gaaatccgaa gttcagtaca    600
aatttatggt aactttttta aaaagaata cactgaagtt ttcttagtga atggaataat     660
gttccctttt tctcccctgt acacacaaat acacaaaaac taacaaaaat acgtcgtgtg    720
tgtctgattt gggttgtatt taaatcattt cataaatgac ttttttccat aacttcagtt    780
tcaaagtttt aaagcacagt c                                              801

<210> SEQ ID NO 25
<211> LENGTH: 801
<212> TYPE: DNA
<213> ORGANISM: Homo sapiens

<400> SEQUENCE: 25 acccataacct accggtgctg tctcagaaac ttgtggaaca agatgaagc aatgttcatg     60
ttattcgcct acatctgtga attacacaag gaagacgagt ttgagaaatc cgaagttcag    120
tacaaatttta tggtaacttt tttaaaaaag aatacactga agttttctta gtgaatggaa    180
taatgttccc ttttctccc ctgtacacac aaatacacaa aaactaacaa aaatacgtcg     240
tgtgtgtctg atttgggttg tatttaaatc atttcataaa tgacttttttc ccataacttc   300
agtttcaaag ttttaaagca cagtcaatta atgatttggc aacagctaag aaatcacaag    360
ttcccttctt ttcatgtaaa cttctgtaaa acacacgcta sgttctgctg atggtaaata    420
gagccatttc aggaagttag ccagtttctc ttctcggcca cctcctgcat agagggtacc    480
attctgcgct gctgcaagtt acggaatgaa aaattagaac aacagaaaca tggtaagcca    540
cttctatttc tttagcaaag ctttccaaca gaatatgggg tttctgaccc agaaatctgg    600
gttggtggca atggtgtga gcctagaaag taataaatgg gcaaataagg ataaaaatta     660
aagatcgaaa caactgtaaa tgcaggtaaa gcggcttgct atgatctta atttgtgcac     720
acgttagtat aaaggaatta gagagtaaat tttgaaaatc aaatgcagtg atgatcttac    780
taatttggac aggaaaataa g                                              801

<210> SEQ ID NO 26
<211> LENGTH: 801
<212> TYPE: DNA
<213> ORGANISM: Homo sapiens

<400> SEQUENCE: 26
aatgttcatg ttattcgcct acatctgtga attacacaag gaagacgagt ttgagaaatc     60
```

```
cgaagttcag tacaaattta tggtaacttt tttaaaaaag aatacactga agttttctta    120
gtgaatggaa taatgttccc ttttctccc ctgtacacac aaatacacaa aaactaacaa    180
aaatacgtcg tgtgtgtctg atttggttg tatttaaatc atttcataaa tgacttttc     240 ccataacttc agtttcaaag ttttaaagca cagtcaatta atgatttggc aacagctaag    300
aaatcacaag ttcccttctt ttcatgtaaa cttctgtaaa acacacgcta cgttctgctg    360
atggtaaata gagccatttc aggaagttag ccagtttctc ytctcggcca cctcctgcat    420
agagggtacc attctgcgct gctgcaagtt acggaatgaa aaattagaac aacagaaaca    480
tggtaagcca cttctatttc tttagcaaag ctttccaaca gaatatgggg tttctgaccc    540
agaaatctgg gttggtggca atggtgtga gcctagaaag taataaatgg gcaaataagg     600
ataaaaatta aagatcgaaa caactgtaaa tgcaggtaaa gcggcttgct atgatcttta    660
atttgtgcac acgttagtat aaaggaatta gagagtaaat tttgaaaatc aaatgcagtg    720
atgatcttac taatttggac aggaaaataa gaaaatttca agttagaaat tgaactggaa    780
atattactta ctggccctac c                                               801

<210> SEQ ID NO 27
<211> LENGTH: 801
<212> TYPE: DNA
<213> ORGANISM: Homo sapiens

<400> SEQUENCE: 27
atggtaactt ttttaaaaaa gaatacactg aagttttctt agtgaatgga ataatgttcc     60 cttttctcc cctgtacaca caatacaca aaaactaaca aaaatacgtc gtgtgtgtct     120
gatttgggtt gtatttaaat catttcataa atgactttt cccataactt cagtttcaaa    180
gttttaaagc acagtcaatt aatgatttgg caacagctaa gaaatcacaa gttcccttct    240
tttcatgtaa acttctgtaa aacacacgct acgttctgct gatggtaaat agagccattt    300
caggaagtta gccagtttct cttctcggcc acctcctgca tagagggtac cattctgcgc    360
tgctgcaagt tacggaatga aaaattagaa caacagaaac rtggtaagcc acttctattt    420
ctttagcaaa gctttccaac agaatatggg gtttctgacc cagaaatctg ggttggtggc    480
aaatggtgtg agcctagaaa gtaataaatg gcaaataag gataaaaatt aaagatcgaa     540
acaactgtaa atgcaggtaa agcggcttgc tatgatcttt aatttgtgca cacgttagta    600
taaaggaatt agagagtaaa ttttgaaaat caaatgcagt gatgatctta ctaatttgga    660
caggaaaata gaaaatttca agttagaaat tgaactgga atattactt actgccccta     720 ccagagacaa tatcctcttc cagaacaaca gggttggaag agaaggtgag ggaaatattc    780
ttcctttgct atttctgtag a                                               801

<210> SEQ ID NO 28
<211> LENGTH: 201
<212> TYPE: DNA
<213> ORGANISM: Homo sapiens

<400> SEQUENCE: 28
ctgaagttaa ttttatacc cacctaatgt tcattatgga tcttgaaggt aaattaattc      60
tgcactaaaa ttttacaatg ctttacaaaa tgactgtagg yggcccatat ggaattcggt    120
caactgggcc aatgacacat atgggattgc agttgaaatt atccaattcc tacttgatat    180
ttgtaagctg ctgtgatagc c                                               201
```

```
<210> SEQ ID NO 29
<211> LENGTH: 801
<212> TYPE: DNA
<213> ORGANISM: Homo sapiens

<400> SEQUENCE: 29
caacagtttt ttggtccttt tgttaaaaag cacagtccgt tttttaggt ggctagaaat      60
gctccaggaa gagctgaaat gtatttacca gccaccttgg tttgatttta gaaagcaaaa     120
tagaagttct aagtatgctt tctctgaaaa gctgagactg cagataagag tgagggcagt    180
tgatggagtt cattctcctc tttcaatcac tgcttctcat cctttcatta taataatcta    240
agaatctcag agattatgaa agagaaagca gtccttatgga agaccccaga ctcacagaat   300
attagggtgt gtttcacagg gaaggatgtc attacccaca gttagtcttt gaaacgcagt    360
tggacattat ttgtaagtgc atcatagtgt cgcctccagg wtccattgag gggaacgtca    420
ttccaatgca acatctctga gttcatctgg gttattaaat ggggttgagg gatttgttat    480
ttttaaatta gtagcccccaa tttaggacta ctcaagacca taggacaagc ctgtccaacc   540
ctcggcctgc gggctgcata tggccgagga cagctttgaa tgcagcccaa gacaaattca   600
taaacttcct gaaatatta tgcatttgtt ttttagccca tcagctactg ttagtgttag    660
tgtatttat gtgtggccca agacaattct tcttcttcca gtgtggccca gagaagctga    720
aagattggac cccctgcta taagacacag taatataaat acataacctg tggttctgga   780
ttggcattag cagatacagg c                                            801

<210> SEQ ID NO 30
<211> LENGTH: 801
<212> TYPE: DNA
<213> ORGANISM: Homo sapiens

<400> SEQUENCE: 30
ctttgaatgc agcccaagac aaattcataa actttctgaa aatattatgc atttgttttt     60
tagcccatca gctactgtta gtgttagtgt attttatgtg tggcccaaga caattcttct    120
tcttccagtg tggcccagag aagctgaaag attggacacc cctgctataa gacacagtaa    180
tataaataca taacctgtgg ttctggattg gcattagcag atacaggctg tgttgatttt    240
gcagaaagtt acaaagagct gctagttggt gtgtatgtct aaaatcagta gatttcctgt    300
ggttctaagg aatgacaaag aatctggaag ttctctgtgg tagcctgctc agtgcagaaa    360
gggaacgtgg aaaatccgcc accagcattt gagtcttgga rgttccacat agggctatca    420
ggtctctgct gatcactgaa accagatcat ggccaactag cccccttggct tcagccctcc    480
caattcatta actactcagg taaatctagg gtcactttca actctaccac ctaccatctg    540
agtgaccttg aaaacattca tctctctgag cctcaggtcc catgtctgta aagcaggggc    600
ctcatggact tctttgggtt tttttgtttt tgttttgtt tctgaggatt aaacaaatgc     660
tccctaccct atttcccagc atccagtaac acagttttc atattttgt gtatgttaag     720
tcaggaccca tctctttaat gataagtgca cttaatgtgg tcatgttttc ttttgtcttc   780
caaagctgtt agtgaatcca t                                            801

<210> SEQ ID NO 31
<211> LENGTH: 801
<212> TYPE: DNA
<213> ORGANISM: Homo sapiens

<400> SEQUENCE: 31
```

```
cataacctgt ggttctggat tggcattagc agatacaggc tgtgttgatt ttgcagaaag    60
ttacaaagag ctgctagttg gtgtgtatgt ctaaaatcag tagatttcct gtggttctaa   120
ggaatgacaa agaatctgga agttctctgt ggtagcctgc tcagtgcaga aagggaacgt   180
ggaaaatccg ccaccagcat ttgagtcttg gaggttccac atagggctat caggtctctg   240
ctgatcactg aaaccagatc atggccaact agccccttgg cttcagccct cccaattcat   300
taactactca ggtaaatcta gggtcacttt caactctacc acctaccatc tgagtgacct   360
tgaaaacatt catctctctg agcctcaggt cccatgtctg yaaagcaggg gcctcatgga   420
cttctttggg ttttttttgtt tttgttttg tttctgagga ttaaacaaat gctccctacc   480
ctatttccca gcatccagta acacagtttt tcatattttt gtgtatgtta agtcaggacc   540
catctcttta atgataagtg cacttaatgt ggtcatgttt tcttttgtct tccaaagctg   600
ttagtgaatc cattgaattt gggatgggta aaataaagta tctattatta attgtaaatt   660
tcatctaaag tgacaaatcc tacctgcata accatttctt aatttccttt catcatgtat   720
cagtggtcaa cattgttaac tgcgaatgaa tcagaatcca tcaaaaatta gaactatttc   780
cagtctggca aaaattcagc t                                             801

<210> SEQ ID NO 32
<211> LENGTH: 21803
<212> TYPE: DNA
<213> ORGANISM: Homo sapiens

<400> SEQUENCE: 32
cggaggcagc gagaaagcgc agccaggcgg ctgctcggcg ttctctcagg tgactgctcg    60
gagttctccc aggtacgtcg tgcgctcccc actcgtgtgg tctctctgca cccttcctg    120 gggtcgggtc gggcaggggc ggaggggagc cgcagcccgg tcacgggctc tggggaaccc   180
gggctcccgt tcggctgcac ctgggcccct agctcctgtc cgggcgggga tagcgggaag   240
cgcaccaggc ccccgggacg ccggtgcttc tttgcacggc ccagcgcggg aatgtggaca   300
ccagcgaagc cggctcaggt cggccctcgg gagaagcagg ggctacacgg aaagggagcc   360
cgagggtcct gcagagcccg aggtcgggac cccgcgcgtg cagtgccaat gggctgcggc   420
tgggctgagc gcccttccaa ccttgcaggc cccggggggg ttgccgcgga gagcttccgc   480
tggggctccg ggcctctggc cgccacctcc ctcgggaggc cgaggggggc ggtgccccg    540 gcccggccct cccgcttccc tcacggcctg gccctcccgc ttccctgatt cccggtaggg   600
tcgctctccc cgcctcctgg cccctcttgg ctcggatgac aaagattggg taaaggcttt   660
caacgagcta gcgtctggca gggggtgtgt cctcgctcac tggttactgc taggacggag   720
cttggatttt ggtcaccgtg gctcagaggt gggaaaggtt ccgtgctctg ggtctgtcca   780
ggaccctggc tccctaaccc aagtctgacc tctgctccct ggcaggcttc gccccacctc   840
tgcgttcctt cattcttagg atgtgtgagt taggtctctg attagaaaac aacttacagc   900
gtttaagcaa agtcgagtcc ttcaagtaag aatgctttga agtgcccttt acaacttctt   960
caacttctat aaatatgaac ttgtgtttag aacttaaatg caagccagga aagtctttt   1020 cctgtttgaa agagagagaa agagagagaa agaggtgatt ggaagtggtg ggtggggcg   1080 gagaaagaga aggagagtaa tctgggtgta gacaactcaa agtttgctga gatgactta   1140 atcttttgac tctgttatta agattttac caaagagcaa ctgtagctat ggtggcctga   1200
cttgaaggga cagaccaaac aaacaacaaa acacaaaaca aaacaaacaa acaacaaaag   1260
caagagcaga aactattgga aaatgattta ttcaccaata ttttaaaggt tcttcctgtt   1320
```

```
ctaagcaagg aacatcttta agttctttat aatgtaccca ttttacattt acaaaaactg  1380
ccagaagttg acagcatgtt ttgggggttt ctaagctatc agttaatttt ttggggtaca  1440
gttttattga taaactaaca gagtagaaaa aatctaatgg aatacccca aatttaaaag  1500 agggcaagaa aagagagaca atagaacata aaacaaatgg gacaagaata aagtacatag  1560
ttgtcacagt cccttgggtg ctgctgtaac aaaatacctg agactgggta atttacaaag  1620
aacagaaatt tatccattca tggttctgga gtctgggaag tccaagattg aagggctgca  1680
tctggtgagg gtcatctggc tacattataa catgatggaa agcatcacat ggtgagagag  1740
agcaagagag gacagaactt actttttataa caaactcatt ctcacaataa actgctccct  1800
tggtgataac attaatccat ttatgagggt acagccttca taacctaatc acctcttaaa  1860
aggttccacc tctcagctcg cagtgagccg agatcatgcc actgcactcc agcctgggtg  1920
acagagcgag actctgtctc aaaacaaaca aacaaacaaa aattccacct ctcaacactg  1980
ttgcattgaa gatgaaattt ccaatacatg agctttgggg cacacattca aaccatagca  2040
atagttcaat tactttaaag cccaaaatgt cagtaattat attaaatgca atttaataca  2100
tcagtaacta aatgagatag actaaatttt atgataatca gactaatatt atcagactag  2160
acttcaaaac aacccaacaa tcatatgctg tttacaagag acacatttat ggatactaaa  2220
aggtataaag tgaacagatg caaccattta tcaaaagaaa gctgttgtgg caatattact  2280
attagacaaa atagaattag gaaaaaaatc ataactgtag ataaacgttt cactaagtta  2340
aaggtttcac tgagaagaaa taaaaatttt gaatttataa gtacttataa caacattaag  2400
aaactagaaa atagaaaaag aatagagcca aattgactga actagaaaaa tagaaaattc  2460
atagaaaaat ccacaatcat agtgggagat tttatcatac atctctcagt aactgataga  2520
aaaaccagac aaaaatcaat aaggataaag aaaatgcgaa cacaatgtag ttcacataag  2580
gaacctatac tacttccaac agcagctgaa atcacagagc atacttaaaa tctgaccata  2640
tactggctca tagagtaaat tgcaatacat tttaaagaat ttaaatcata cagaatatgt  2700
cttctgacca taatgcaatt aaagtagaaa agaacagaaa aacttataga aaattctcat  2760
atatttggaa attagtaaat ttctaaataa cccatgggtc aaaaaataat cagaatgaaa  2820
atcagaaaat atttttaatg acttatgaaa aaaattacat ataaaaactt gtcagatgca  2880
cctaaactgt tgcttaaagg aaacttacaa ccttaagtgc atatattaga aatgaagagt  2940
gacgaaaaat gaatgagcaa gcaaatacct taaaaactgg aaaaggaata gtaaaataaa  3000
tccagagaaa tcgaacagg ggaaataata atataagaat agaaattaat gtgctagaaa  3060
ataggggatc tatcaagtca gaagttgatt ttttgaaaat gctaataaaa atgatgaacc  3120
tctggcaaga caataaaagc tggtacaaat aactcatcta aggaataaaa ttgaggacct  3180
ctcttttgtt aaatgacata agcaggaggc cattatcctg agactgtctc tacactttga  3240
gttcttacat aataaactgc aacctaattt agtatactac ataaacaaac tgaaacctaa  3300
cttaggagct ttttttttgt aattaatagc taaatttcca ccaaatcata aatagccaag  3360
ctttagccaa tcacaggcag ccaactgatc agactatgcc caaacaaggt aaatgcctat  3420
tacaccatac ccaataagg cagactccta gctgaagcca atcaggtgat tactatgctc  3480
ttgtgtttgg cctataaaag ctcactgctc acactgttgg atgctctctg aaacttttgt  3540
gaatctgagt gctgcctgat tcatgaatca ttctttgcta aaataaactc tgtcaaattt  3600
aatttgtctg aagtttctct tttaacagtg tttggtgttg caagcaggat ccaaaggaga  3660
```

```
cctatagtga ctcccaggag ctcttagtga ccaagtgaag gtacctgtgg ggctcattgt    3720
gcccattgct ctttcactgc tttcaactgg tagttgtggg taagttcctg ctcagacttg    3780
agcactatac atttgcattt tcagctctct gactttattt gagcaattct ttgatggatt    3840
ggctccagaa ttggattgga ttcagtgaag aaactgaaac tggactggtg ctctaggagg    3900
cctcaagtag ataaggttac tagaagacag ggaatcctgg gcttatctgg atttaaggag    3960
tctacaactc catctgcaac tccagccgat tcatttata agaattatgg accaagaacc    4020
tgtgcttttc tagagaaatg tgtgagcctt actaaaggta acttagaatt acaatggact    4080
gctgagacca gctcggtcgt ggagacccta acccagcagc gctagaggaa tcaaagacac    4140
acacacagaa atgtagagtg tggagtggga atcagggga ctcacagcct tcagagctga    4200
gagcccctaa cagagattta cccacatatt tactgacagc aagccagtga taagcattat    4260
cgctatagat tatagattaa ctaaaagtat tccttacagg aaacaaaggg atgggccgaa    4320
acaaagggat aggctctggc tagatgtctg cagcaggaac acgtccttaa ggcacagatt    4380
gctcatgcta ttgttgtggc ttaggaacac gttaagcggt tttctgccct gggtgggcca    4440
ggtgttcctt gccctcattc cagtaaaccc acaaccttca gcgtgggcgt catggctgtc    4500
acaaacatgt cacagtgctg cagagatttt gtttatggcc aaatctgggg ctagtttatg    4560
gccaggtttg ggagcctgtt cccacatgtc ccccttttt gttttgcaaa gcaataaaag    4620
caaaggcagc tttgtcacag tgagctactt cttgcaggag tcgggattcg catatgcata    4680
ctatacaaag acaaacaaca cagattaaaa gcacaaccat cattgaaatc acagagcttc    4740
caagtgtctt tatctatttt aatgggttaa tcactgctaa tctgtctgca gctccttcaa    4800
gcactccagt tcctggcatt aaggtctggt gtgcctggaa tgctttaaat atttgttctt    4860
ttaatattgc aatatggaaa gacaagtttg tagagtgtct tctaggtgct tttttattct    4920
ttcctgaatt tggtcttatt taagagccat taatagtttc cacaaatcct tatgtttagc    4980
tcctacagcg ggccatatca tttgagggtg aggtgccact ataccatcat gtttccagat    5040
aataggaact cttgccatat ttcttgctat ttctaccatc tgaccatttt gtttagacca    5100
gctaaacata gtgtggccat ggcacgcaga ctgagaggtg caatttaagc taaacatccc    5160
cttaggggac caatcaataa tgattccata ggaatcactg cgcagcacct ctgcctattc    5220
tgcaatgcaa tcttcccaaa caagtatgtt cattatttct ggccaggtcc aattctgttt    5280
acaaataggt ttttgagggc aatatgcctc aattatagaa acagatttat tatggtaaat    5340
actgagatca gaaagcatgt gtaactgtgt catagaatga ttacatccag gcattattgc    5400
cagccaagat tgataaatat gcccaataag tataattgtt ctctgtgtta gcccttgttg    5460
aaggaatact aatggcaatg gtgatcactg ctatcatagc tatcattaaa ttactcattg    5520
tgactggttg tcccactttc ctcaggtttt cttccaccct ctatggcagt tcttgatct     5580 gtccccaggt agatggctgt gtttgatggt tgttgctcgt gatagtttgg gtcctcctca    5640
gcatcagtct cgacatggct gcaaccagag ggtcctcggg atcctcccag aatctcttcc    5700
ttggcatctg gctcatgata aggtttcagg tgtcttgatg gtatccaaat cagctattga    5760
ttctggcctg gagaaacaca agcataacct ctaccccaag ttattatttt acctatttcc    5820 caacttttg ttgtcagatc tctgcaccaa gccagttgtt ctgcttctgt ttttgcagct     5880
ggtttctgta gatgctcttc agctgctgat agcatctggc ctttaggcag gctcaaaaaa    5940
tttaaagtca ttaatgctag attcagttgt atatggggtg tcctgtaatc cctgtttccc    6000 cttttttgctt ttgcaactgc tgtttcaggg agagattcat tctttctaca atggtttgtc    6060
```

```
cttgagaatt atatgggatg ccagtaatgt gtttaatatt ccatatagag aaaaatgtag    6120
ctagagcttg gctagtatag cctggggcat tatctgtttt aacagaagtt ggaattccta    6180
tcaccacaaa acactgcaaa aggtgatgct taacacatgc agtctcctga ttggcatgta    6240
gcccagacaa agtgagaaaa ggtgtccaca catacatgta cataagctag tctcccaaac    6300
gagggaacgt gtgacatcca tttgctaaag ataattaggt tccaatcctc gaggattaac    6360
tcctcctgtt aaagatgagg aatgcaccat ttggcaagtt gggcatcact ggataatagc    6420
tttagcttct ttccaggtac tgttatatct gcatttgaga ccagaggcat aacatgggt     6480 taaattgtga aagtgtctag cattagatat tgcagtagca actaggcgat cagccatttg    6540
attcccttca gttaaaggtc ctggaagagg tgtatgagcc ctaatgtgag tgatgtaaaa    6600
agggtgcatt ctactcctaa atgctgtttg caattgggta aataaagtca tcagttgttc    6660
atctgtatga agtcataact gagcattttc aattaattgt atggaatgaa ccacatagga    6720
agaatcagaa atcacattaa taggcatatc aaaagcagtc aatacctcaa ttacagctaa    6780
agctccactt tttgagctga agtatagggc gtgtgaaaaa ctttacctttt tgatccagaa    6840 taagaggctt taccattaca agacccatct gtaaaaacat tctcagcacc ttcagttggt    6900
ttaaatttag ttattttggg gagaatccaa ttagttaatt tcaaaaattg aaataatttc    6960
attttaggaa aatgattatc aagaataccc acaaagtcag ctaaatgggt ttgccaagta    7020
agactattta tagaagcttg ctgtatttgt gcctttgtga gagggacaat aattttttcca    7080 ggatcatatc catgtaattt aacaatccga attctcccat ttcttatcat cgtagccatt    7140
tgatccaaat aaggagttag agtctgtgaa ttagtatgtg aagaaaaag ccactgtaca     7200 aagtcttgct cttatacaat aacaccagta agtgaatgct gagttggaaa aattagcaaa    7260
tctagggtct ttttttggatc tattctattt atttgagatt tatggatttg cttttttgatt   7320 agctgcagct ctgcctcagc ttcttttgtt aattgctgag ggctaatgag actaggatct    7380
cctctaagga tagaaaatag attactcagg gcataggtgg gaatgcctag agcaggtcat    7440
atccgattaa tgtcccctag taattttga aagtcattta atgttttcaa ttgatcccta     7500
cgtatagtta cttttctgtgg cacaatggta gtgtcattta ctaaggtccc caagtaggag   7560
taaggagtag tagtctgaat tttgtcagga gctatataat taaactggca tgagaaatcg    7620
agttttgcaa gtgatcataa cattggagta atatttcttg agtgggggca gcacaaagta    7680
tattatccat ataatgaata atgtaacact gtgaaaattt tttacgagta ggttcaattg    7740
cttgcccttc ataagtctgg caaattttttg aactgtttca catgccttgt agcaacactt   7800
tccaatacaa atgctttagt atgctgcagg ttttttactg caggaattgt aaatgcaaac    7860
agttcacagc cttgctcagc taaggggata gtaaagaaac agtcttttaa atttatgact    7920
attaaaggcc aattttttgg aatcatagca gaagaaggca gtcccggctg caatgtcccc    7980
ataggttgta taactgaatt aatggctctt aagtcagtta acattctgca tttacctgat    8040 ttttttcttaa ttacaaaaac tggagaattc caaggggaaa atgttgagct atgtgtcctt    8100
tttctaattg ttcagcaact aagtcctcta aagcctccag tttctcttta ctcagcagcc    8160
attgtgctat ccaaattggc ttatctgtta accattttaa aggtatatag gttctggagg    8220
cttaacaatg gccaccatca aaaatgatat cctaaacctt ggtgggaact ttgtcttttcc    8280 gcttgaagca tttccttcaa agcttgcaaa ttttttccta gtcccatacc agggacatac    8340
cccatttcat gcatcatatg ttgactttga gggctgtata attattctgg aattagaact    8400
```

```
tgtgatcccc attgttgtaa taaatctctt ccctataaat ttataggtac agaagttata    8460
attttttgta tagtcccagg ttgtccattg ggcccttcac aatgcaaaat ataactactt    8520
tgatatactt taagggcttt accaactcca actatgttaa attgagcagg ttgaattgac    8580
catgcagatg gccagtgctg tacagaaatg attgaaatgt ccgctcctgt atctaccaaa    8640
cttttaaatt tctttccctg aatagttatt tcaccagtag gatgtttatc agtaatttga    8700
ttcacccaat aagctgcttt gccttgttta tttgtgcttc caaatcttcc tgttcattta    8760
atttcacttt tccccatttc cacatatggc ataatcagga gctgtgctat atgctctcct    8820
ggctctgctt tccagggaac agaagtagat ataacaattt gaatttcccc tttgtaatct    8880
gaatcaatga ctcctgtttg tacttgcacg ccttttaaat ttaaactaga cctacctaga    8940
agtaatccta ccatccccgc tggcatcatc tgactggaga cagcaacctt ctttaacagt    9000
cccattacaa aaggagaacc tgttccatat ggattaatag cttgtttaaa ttctttgagt    9060
aatttaaaag gaaaaggctc aaatgtagct ataatatttc cctgttgatc tacggggtat    9120
attctaacag ggaactgcta agcctctata tcaccctctc ttctaacttg ctgaattcct    9180
ggctgaatag aactgagagt ggtcgctcga ggtgctgctc agtcactggg gcgactactt    9240
tttgcccagt gtcctctgga aaagaaagat ctggaggatc aggctactct tttgcttcga    9300
aataatgagg gggtgcagaa gggtagggac aaacctctcc ctcctttgcc actttagctt    9360
tagctggcaa acaaacctgc tctgtcacct cttctgttac ttcattatac tttccttcct    9420
cctcatcttt agtgtgaaaa ggttccaagg tggaatgagc tagagcccac acttgcccat    9480
tgttaccctg atgcttccga gctccccttc ttactcacca tggggattgc ttaagagtac    9540
tcgggtatcc tccagctttg ttccacgttt tccaaccatt gctccagcga gccttcatcc    9600
tgggtttgag tccccacgtt gggcgccact tgccgagacc agctcggtcg tggagaccct    9660
aacccagcag tgctagagga attaaagaca cacacagaa acatagagt gtggagtggg    9720
aaatcagggg attcacagcc ttcagagctg agagccctga acagagattt acccacgtat    9780
ttattgacag caagccggtg ataagcatta tttctgtaga ttatagatta actaaaagta    9840
ttccttacag gaaacaaagg gatgggccaa aacaaagcga tgggctctgg ctagatatct    9900
gcagcaggaa cacgtcctta aggcacagat cgctcatgct attgtttgtg gcttaggaat    9960
gccttaagtg gttttccatc ttgggtggac caggtgttcc ttgccctcat tccagtaaac   10020
ccacaacctt cagtgtgggc gtcatggcca tcacaaacat gtcacagtgc tgcagagatt   10080
ttgtttatgg caagatctgg ggccagttta tggccagatt tgagggcctg ttcccaacag   10140
tggacaaaga agaaaagctg cttaaggcaa acaggcacat atttttaaa gctacaatag   10200
ctagacaaac taagagaatc ctgtgtatgt tttacttttg tatttttatt tttaatattt   10260
gtggatacat agtagatgta tatatttatg gggcacttga gatattttga tacaggcata   10320
caatggataa taataacatc acggtaaaag gggtatccat tacctcaagc atttatcctt   10380
tctttgtgtt ataaacaatc caattaaacc ttttatcata aaatgtacaa taatgttgac   10440
tgtggtcacc ctgttttgct atcaaagaat aaatcttatt cattttatct aagtatattt   10500
gtgtacccat taaccatccc agtccccctg ctcctccaac tacacttccc agcctctgtt   10560
aaccatcatt ctactctctt atctccatga gttcaattgt tttaatttgt agctcccaca   10620
aataagcgag aacatgggat gtttgtcttt ctgtgcctta tttcacttaa cataatatcc   10680
tccagttcca tccatgttgt tatatgacag aatttcattc tttcttatgg ctgaatagta   10740
ccccattgta tatatatacc acattttctt tatccattca tgtgtaggtg gacacttgga   10800
```

```
ttgcttctag atcttggcta ctgtgaatag tgcagcacta acatgggcg tgcagatatc    10860 tccttgatat attgattcc tttattttgg gtatatacct agcagtggga ttgctggatt     10920
gtgtggtagc tctactgtta gtcttttgag gaacctccaa attgttctcc atagtggttg   10980
tactaattta cattcccaac caacaacagt gtacaggggc ctgttttctc cacatccttg    11040
cagcattttt attgcctgtc ttttggataa aagccatttt aactggggtg aaatgatatc   11100
tcattgtagt tttgattagc atttctctga tgatcattga tgttgagcac cttttatat    11160 atctgtttgc cattcatgtg ccttctttg agaaatgtct atttagatct tttgcccatt    11220
taaaaaattg gattattaga ttttttcct attgagttat ttgatctcct tatatattct    11280
ggttattaat ccccttcaa atggatagtt tgtgaatatt ttctcccatt ctgtgtattg    11340
cctctgcact tgttgatta tttaatttgc tatgcagaaa cttttaact tgatgtgatc     11400 ccttttgctc attttgctt tggttgccta tgcttgtggg gtatgactta agaaatcttt    11460
gcccagacca atgtcatgga gagttttctt aatgttttct tttaatagtt tcatagttg    11520 atgtcttaga tttaagtctt taatctattt tgttttatt tttgtatatg gcaagatata   11580
ggggtctagt ttcttccgca tatggatatc tacttttccc agtaccattt gttgaagaga    11640
ctgtcctttc tgcaatgtat gttcttgaca cttttattga aaatgaattc actgtagatg   11700
tgtggatttg tttctgggtt ctctattctg ttctgttgtt ctgtgtgtct gtttttatgc   11760
cagtaccatt ctgtttttagt tactatagct ctgtagtata attttaagtc agataatgtg   11820
attcctccag ttttgttctt tttgctcaga atagctctgg ctattctggg tcttttgtgg   11880
tttcatgtaa attttaggat tatatttat taacatattt ctgtgaagaa tgtcattggt   11940
attttgatag gaactgcatt aaatctatag attgctttgg gtagtaagga tatttaaca    12000 atattgattt ttccaatcca tgaacatgga atatctttcc attttttggt gtcctcttta    12060
atttcttgca tcagtgttta tagtgtttct ttcatcagtg tttatagttt tcattgtaga    12120
gatcttttac tccttgatt aagtttattc ctgggtattt tatttgtagc tgttgtagac    12180
gagattacta tcttgatttc tttttcagat tgttcactgt tggcatatac aaatgctact    12240
gatttttgta tgttgatttt gtatactaca attcactga atttgcttat tacagagaga    12300
ctaaagatag ttaggtccat taccaaatgt gttttctgtc acattgaaaa attataccat    12360
gagaaggcac atgcttctag taattacagt tcatagatat gtcaatgtac agaatgctgg    12420
tgtgacagtt cacaattgtt tgctttatag ttttcactgg aaattaaatt actaagggta    12480
aagtaatccc agcactgtgg gaagctgagg caggatgatt gcttaatgcc aggagtttga    12540
gaccagctgg ggcaatgtag catgagccca tctacaaaaa aaaaaaggaa ttctaattaa    12600
tatgtggtac tagaattacc agaaataata agggaaacaa ctcggaaaag aaggtaagat    12660
gtgttttggg taagaacagc tataaagtat gagggggatgt tttgttttgt taaggaaaaa   12720
ataaaataat atttgtccta aagtagaatg cctggttgtt aagacaatga gaaagagaaa    12780
gagtatagaa gaaaaactga atggatataa gaaagttgta gaaggttgtg ggataggaat    12840
cctggaaagg gaattttata tgtgatcaaa ctaagatttg aagaaaattc taagtttttt    12900
tttaaaaaaa ttgagcatga atatcaaaaa catactgaca cagaactaga aatttgtcct    12960
ctatgttaaa acaacaaggt tttcttggag tattggtctg ctcttaataa gaaattgaaa    13020
gacttttctt tacctgctaa gtaattggcc taggaaatga agattctgtg ttttattgag    13080
ataatttatt gtgcttcatg ttgtctttat tagatctttg actgcctcag agacctgagt    13140
```

```
tcaccttatt aaaagagaaa gagtttctac aattatgtgg ctttctttat ttgcctttga    13200
agtcttttac caatcactct agttaaatga ataaatattg tttcataggg acctgtgatc    13260
ctattttaat cagatatttt aaaccttttg atattttga cttctcaaaa tcaaattcta    13320
aattaaaacc ttttgacgtt gaacaaactt tggaagcttc tagatgggct tctggaatat    13380
ctcaaaagaa attgttttct ctcctgataa aaagagaga tattaaacta attgggctta    13440
tttgatatgt tatattgcat gggaagaatt gttaaattat aagtgatgct gaactttctt    13500
taagtcatat tgtatgggta tgttattaat atgtgcttca gaaattatat gaaattctta    13560
gaaaccagat agtcgtggta taatactatc agccaaaatt ctaattatcg tgaaatatta    13620
tgtgttgcag aagtaataca atttccttat caattgcatt attgtgaact ctcatcatat    13680
ctttaaccaa gtccatttta agctttgtca tctacaaaga gtcacttgtt ttactctggt    13740
actttccgga acactgtgaa aaacaattat ataaagggtg tggacctata agacaaacaa    13800
ccaaacaaaa atcgtaaagt gttcttttaa aagattcgtg gaaaggactc tgataagtac    13860
aggtttctga taactttaag atcatactac tggactgggt aagaatttcc agaactctag    13920
caaagaagtg gattggttca taaaactgcc aacccaacat gaagcagaat aagaattaat    13980
tgaataccag ggaaatgctt tggcagattt tcatgctaag tcagccagta ctgaaattgt    14040
taagatatgc aatttgaaag aacactataa tattcatctg aatcaaatta tctatgataa    14100
cctatttaaa tgaacagcat catgcacctg aattggagaa acaaaactga tatttaaaat    14160
gatataaatt tagtgttaaa tgtggcctca tggatcagac agctatctgg tcctttctga    14220
gtccatatag ctgccattat taaaagttct gcactctatg actcatcaca gaatagataa    14280
cgtgaaatta tgaaaaaata ttggtgttat gactgttcta aaattgctaa aatggcttat    14340
aatcaatgtt tggtttgtca aatccacaat ttttataaga taataaaaac ctcagttggt    14400
acatttccac catccactgg actatttgaa catttacaga tggattgcat tcagttgcct    14460
cattgggaat ctgcaggaaa cttaagtaaa tgctggatat gtcatgttga accaaatact    14520
aatatgcttt taaagatctt ctaattcacc ctatagcaga tttcactgat attccaagtg    14580
tgactacctg ttcaaattgc acatctggtc tttctatagg gttaggcttt ttgagtcaca    14640
tattcagatt tcatgtttaa agctaacagt agacaaaaca tataggagag gctttacagt    14700
taaattattc cagaaactga ataataaaac caaaaggaga gataattaga cagtttgtag    14760
acgaattcat aaccctaatt ctctaattgt tggtagcctc cattgatgat aattaatagt    14820
ggagccttag ataaatacta ctattgcttc cccgttgatg accectgtag cacacagtgt    14880 cccacaggga actgtctctt gtgcccctct agcatatatt tttatctatg aaggatttaa    14940
ctatcaatca taggcacagg caactccatg tcccagtcag taggaaataa gaagtcagtg    15000
tggattaggg attctaacag taccactgtc actccataac caactgaaaa tttgacattg    15060
ttctatacct cttaatttgc actatggtat aaaaaggaac tttctagcag gtacgaatcc    15120
ctctaaatgg gcatcttttg ttcaaatgct ccttccctgg cttggaataa atgtaaatga    15180
ggttatgatt agaaatcccc ttcaaacatt agctactaca gctcactcta ctgcaaaggc    15240
tatatagttg cccagtgaag ttctctaaat tctcttgcta agtttctttt aaataacagg    15300
attgccttga actatctgtt ggtttgtagt ggggcagggg gtgtgatagg ggacactgtg    15360
tataatagct aatacatcct actgcacttg cataaaggaa tctgttataa agaaaatgaa    15420
ataaaggtat aaaagttggc aagaagaaaa ccatcattat gtcttgagga tgattgggga    15480
tacagaaaat gagaagaatc cacaaactat tagaattact aagttaattt agcaaggttg    15540
```

```
ctcaatgcat ggtcagtata caaaatttaa ttgaatttct acatatatgt atatgccata   15600
ttgtgttaga ttgttttgca ttgctataag ggaatacctg aagctgggta atttataaag   15660
aaaagaggct tatttggctc atggttctgc aggctgtaca agcatggcac tagcatctgt   15720
ttgaccttag gaagccttta ctcatggtgg aagaaggggg agcaggcatg tcatatagtg   15780
agagagggag tgagagggag ggagcaagag tgaagggga ggtcccagac tcttttaaa    15840 taacctgaaa tcctgtgaac agagtgaaaa ctaacttatt accatgaaga gcacaccaag   15900
ccattcatga ggggtatacc ttcatgaccc aaacgctttc caccaggtcc taccttcaac   15960 actgggatc acatttcaac atgagatttg gagaggacaa acatccaaat catatcacat    16020
atataaatat gtaaaactat tttaaatgtt tttaaagtat cgaatagaaa taaatctcac   16080
aaaatatgct taagaacttt aagcaaaaac cataaaatac tattgtgata agttaaagaa   16140
gacctaaata aatggagaga tctgtcatgc tcatggattg gaagattcaa tactgtaatg   16200
atatgaatag ttcccaaatt gttctataga ttcaaaacat tgccagttaa aatctcagtg   16260
gactttgttt tttttgaaact gacaagctga ttctgccatt tataataata ttcaaagggg  16320
caagaataac caagacacat ttgaagaaga acaaggagga agaagaacgt atttgaagaa   16380
gaataaggaa ctctattaag tgtatatctc ctatatattg agatacacat ttgaaataca   16440
tctatcacct agatattgag atatattata catttaatat agtgtgttgc tggtataggg   16500
atagacaaat gaacattgga tcagaatagc actgaaacaa gatctacccc tatatgggca   16560
tgtccctatt aacaaaaaaa tattgttgat tatttcctca agtgatctg taaaaaacaa    16620 gttaattgaa catccatatg ggaaaaagt gaatccttct gctacctcaa atatcaaccc    16680
caggtagatt atagatctaa aagtgaaagg caaagcaata aagattttag aaaataacaa   16740
agagaatatc tttatgaaaa tacaggaaat atttttaaaaa taggctagaa aactcactat  16800
taaaatatat aaaatataag aacatctgtt catcaaaagt actatagttt gaatagcagt   16860
gtctcctcca aaattcatat tgaaacttaa tccccattgt aacagtacta atcctaaaac   16920
taagtattaa gaggtgtgac ctgtgggaag tgactaagtc atgaggggtc tttcctcagg   16980
tatgggatta gcatccttat aaaaggcctt gagatggaat gtagtgcccc cttgccctct   17040
tgcgttctcc catgtgagga cacagcaaca aggcaccatc ttggaaggag agaagccc    17100 tcaccagaca acagtgcaca tgccttgatc ttagacttcc cagcctccag agctataata   17160
aatacatttc tgttctttat aaattacttg gtctctggta ttttgttaca gaagcactaa   17220
tggactaaga caaaaagatt ccattatgaa agtgaaaagg caaccgcaga gtggcagaag   17280
cttttggaga tgatgaatat gtttacttcc tggattgcgg tgatgatacc atgagtgtat   17340
acatatgtgt gtatacataa tgtatacaaa ttgtgttcat tgattatgta cagtttcttt   17400
gtataccaat tataccttaa taaagctaag gaaaaaaaaa agaaaatcca gaataaatat   17460
gcatggtatg acccatttat ttaaaaaaaa aagagggaa tgcgaagcag tggttttggt    17520
gcgaacacaa aaattctggc ttcaacagca tttaaattcc caaaccaagc atgtttgtgt   17580
tttaattctt tgtggccata aattgtacag ctcaggcctt tatagtctct cagattctgt   17640
gaatgtgggg aattagtttt actcataaaa agttttgttc ttggggataa attttttaaa   17700 aaaattttg tatagttagc acactgagaa aatacagaca aaggcataca gatgcaagaa    17760
atgaggtagc tgaatagacc aaagaatgat atagggccca gaaggtaggc aaagagaaag   17820
ttgttgggtt tatggttaca agtaaactag cagttgtggt gcagatagtt ttatttcccc   17880
```

```
cacattaatc tgaacagccc atccagactt aaacactgct ttttgcattt acttctaggc    17940
aggaagacag ggttctgatg gtgtgagtct ccttcaactc agcaaaccac cttggtctgc    18000
ctcgagtttc caacacccct cctgcctgct agtgataggt gtgaggcagg ttgatgaaca    18060
tggaactttt ttcttttggt cccaaagcat gctactcctg gagtttcatt cagtgaatga    18120
gaactatagt ttggttctgt gagatctcta tgaatcaagg cggccactga agcggagaaa    18180
agaaatgctt aaatgttaag aaagtttgaa gtgcagaaaa aggtgattgt aaatccatat    18240
ggttaagctt agcccatttc ttaaaaggct tgattgctca ttcctccatt cattgattta    18300
ctcactcttc caatccatgt tattgagtct tgctctgtaa ttccggatgg ttgtgctttt    18360
aagtactgca tagtggttgt atgtctgtgt tagcattgct gaatgtatca gggaattcat    18420 tttttatcc ccattcattc gttccattca tctgtttctc tctctctctc tctttgtgtg    18480
tgtgtgtgtg tgtgtgtgtg tgtgtgtgtg tgtgtgtgtt atgcctagaa aacatttctc    18540
aagaattaga attacgatat gctgtcaaac acaatgactt atttgaacct cttttatttg    18600
taggttgaag cactggacaa tgccacatac tttgtggatg gtgtgggtct tggggtcat    18660 catcagcctc tccaaggaag aatcctccaa tcaggcttct ctgtcttgtg accgcaatgg    18720
tatctgcaag ggcagctcag gatctttaaa ctccattccc tcagggctca cagaagctgt    18780
aaaaagcctt gacctgtcca acaacaggat cacctacatt agcaacagtg acctacagag    18840
gtgtgtgaac ctccaggctc tggtgctgac atccaatgga attaacacaa tagaggaaga    18900
ttctttttct tccctgggca gtcttgaaca tttagactta tcctataatt acttatctaa    18960
tttatcgtct tcctggttca agccccttc ttctttaaca ttcttaaact tactgggaaa    19020
tccttacaaa acctagggg aaacatctct ttttctcat ctcacaaaat tgcaaatcct    19080
gagagtggga aatatggaca ccttcactaa gattcaaaga aaagattttg ctggacttac    19140
cttccttgag gaacttgaga ttgatgcttc agatctacag agctatgagc caaaaagttt    19200
gaagtcaatt cagaatgtaa gtcatctgat ccttcatatg aagcagcata ttttactgct    19260
ggagattttt gtagatgtta caagttccgt ggaatgtttg gaactgcgag atactgattt    19320
ggacactttc cattttcag aactatccac tggtgaaaca aattcattga ttaaaaagtt    19380
tacatttaga aatgtgaaaa tcaccgatga agtttgttt caggttatga aacttttgaa    19440
tcagatttct ggattgttag aattagagtt tgatgactgt acccttaatg gagttggtaa    19500
ttttagagca tctgataatg acagagttat agatccaggt aaagtggaaa cgttaacaat    19560
ccggaggctg catattccaa ggttttactt atttttatgat ctgagcactt tatattcact    19620
tacagaaaga gttaaaagaa tcacagtaga aaacagtaaa gttttttctgg ttccttgttt    19680 actttcacaa catttaaaat cattagaata cttggatctc agtgaaaatt tgatggttga    19740
agaatacttg aaaaattcag cctgtgagga tgcctggccc tctctacaaa ctttaattt    19800 aaggcaaaat catttggcat cattggaaaa aaccggagag actttgctca ctctgaaaaa    19860
cttgactaac attgatatca gtaagaatag ttttcattct atgcctgaaa cttgtcagtg    19920
gccagaaaag atgaaatatt tgaacttatc cagcacacga atacacagtg taacaggctg    19980
cattcccaag acactggaaa ttttagatgt tagcaacaac aatctcaatt tattttcttt    20040
gaatttgccg caactcaaag aactttatat ttccagaaat aagttgatga ctctaccaga    20100
tgcctccctc ttacccatgt tactagtatt gaaaatcagt aggaatgcaa taactacgtt    20160
ttctaaggag caacttgact catttcacac actgaagact ttggaagctg gtggcaataa    20220
cttcatttgc tcctgtgaat tcctctcctt cactcaggag cagcaagcac tggccaaagt    20280
```

```
cttgattgat tggccagcaa attacctgtg tgactctcca tcccatgtgc gtggccagca    20340
ggttcaggat gtccgcctct cggtgtcgga atgtcacagg acagcactgg tgtctggcat    20400
gtgctgtgct ctgttcctgc tgatcctgct cacggggtc ctgtgccacc gtttccatgg     20460
cctgtggtat atgaaaatga tgtgggcctg gctccaggcc aaaaggaagc ccaggaaagc    20520
tcccagcagg aacatctgct atgatgcatt tgtttcttac agtgagcggg atgcctactg    20580
ggtggagaac cttatggtcc aggagctgga gaacttcaat ccccccttca agttgtgtct    20640
tcataagcgg gacttcattc ctggcaagtg gatcattgac aatatcattg actccattga    20700
aaagagccac aaaactgtct ttgtgctttc tgaaaacttt gtgaagagtg agtggtgcaa    20760
gtatgaactg gacttctccc atttccgtct ttttgatgag aacaatgatg ctgccattct    20820
cattcttctg gagcccattg agaaaaaagc cattccccag cgcttctgca agctgcggaa    20880
gataatgaac accaagacct acctggagtg gcccatggac gaggctcagc gggaaggatt    20940
ttgggtaaat ctgagagctg cgataaagtc ctaggttccc atatttaaga ccagtctttg    21000
tctagttggg atctttatgt cactagttat agttaagttc attcagacat aattatataa    21060
aaactacgtg gatgtaccgt catttgagga cttgcttact aaaactacaa aacttcaaat    21120
tttgtctggg gtgctgtttt ataaacatat gccagattta aaaattggtt tttggttttt    21180
ctttttctta tgagataacc atgatcataa gtctattact gatatctgaa tatagtccct    21240
tggtatccaa gggaattggt tgcaggatcc tcgtggatat caaaattcat agatgatcaa    21300
gtcccttata agagtggcat agtatttgca tataacctgt gtacattctc ctgtatactt    21360
taaatcatct ctagattact tatgataccc aatacaatgt aaatactatg taaatagttg    21420
tactgtcttt ttatttatat tattattgtt atttttatt ttcaaaattt ttaaaacata    21480
cttttgatcc acagttggtt gacttcatgg atgcagaacc catggatata gagggccaac    21540
tgtaatctgt agcaactggc ttagttcatt aggaaacagc acaaatgaac ttaagattct    21600
caatgactgt gtcattcttt cttcctgcta agagactcct ctgtggccac aaaaggcatt    21660
ctctgtccta cctagctgtc acttctctgt gcagctgatc tcaagagcaa caaggcaaag    21720
tatttggggc actccccaaa acttgttgct attcctagaa aaaagtgctg tgtatttcct    21780
attaaacttt acaggatgag aaa                                            21803
```

<210> SEQ ID NO 33
<211> LENGTH: 201
<212> TYPE: DNA
<213> ORGANISM: Homo sapiens

<400> SEQUENCE: 33

```
ctgttcctgc tgatcctgct cacggggtc ctgtgccacc gtttccatgg cctgtggtat      60
atgaaaatga tgtgggcctg gctccaggcc aaaaggaagc mcaggaaagc tcccagcagg    120
aacatctgct atgatgcatt tgtttcttac agtgagcggg atgcctactg ggtggagaac    180
cttatggtcc aggagctgga g                                               201
```

<210> SEQ ID NO 34
<211> LENGTH: 784
<212> TYPE: PRT
<213> ORGANISM: Homo sapiens

<400> SEQUENCE: 34

```
Met Pro His Thr Leu Trp Met Val Trp Val Leu Gly Val Ile Ile Ser
1               5                   10                  15
```

```
Leu Ser Lys Glu Glu Ser Ser Asn Gln Ala Ser Leu Ser Cys Asp Arg
            20              25                  30

Asn Gly Ile Cys Lys Gly Ser Ser Gly Ser Leu Asn Ser Ile Pro Ser
            35              40                  45

Gly Leu Thr Glu Ala Val Lys Ser Leu Asp Leu Ser Asn Asn Arg Ile
 50              55                  60

Thr Tyr Ile Ser Asn Ser Asp Leu Gln Arg Cys Val Asn Leu Gln Ala
 65              70                  75                  80

Leu Val Leu Thr Ser Asn Gly Ile Asn Thr Ile Glu Glu Asp Ser Phe
            85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
            115                 120                 125

Leu Asn Leu Leu Gly Asn Pro Tyr Lys Thr Leu Gly Glu Thr Ser Leu
            130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
            195                 200                 205

Gln His Ile Leu Leu Leu Glu Ile Phe Val Asp Val Thr Ser Ser Val
            210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
            290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
            355                 360                 365

Glu Asn Leu Met Val Glu Glu Tyr Leu Lys Asn Ser Ala Cys Glu Asp
            370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430
```

```
Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
450                 455                 460

Ser Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
            515                 520                 525

Glu Ala Gly Gly Asn Asn Phe Ile Cys Ser Cys Glu Phe Leu Ser Phe
530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
            595                 600                 605

Cys His Arg Phe His Gly Leu Trp Tyr Met Lys Met Met Trp Ala Trp
610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
            675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
            755                 760                 765

Ala Gln Arg Glu Gly Phe Trp Val Asn Leu Arg Ala Ala Ile Lys Ser
770                 775                 780

<210> SEQ ID NO 35
<211> LENGTH: 5059
<212> TYPE: DNA
<213> ORGANISM: Homo sapiens

<400> SEQUENCE: 35
ctggttctca acttctttg aaataatgtt catagagaag gagggctgtc tgagattcga      60
gggaaacaag ctctcaggac ttccggtcgc catgatggct gtgggcggta aacgcggtta     120
gtgcaagcat ctgggccatc ttcaatggta aaaaagatac agtaaagaca taaataccac    180
```

```
atttgacaaa tggaaaaaaa ggagtgtcca gaaaagagta gcagcagtga ggaagagctg    240
ccgagacggg tatacaggga gctaccctgt gtttctgaga ccctttgtga catctcacat    300
tttttccaag aagatgatga gacagaggca gagccattat tgttccgtgc tgttcctgag    360
tgtcaactat ctgggggga cattcccagg agacatttgc tcagaagaga atcaaatagt     420
ttcctcttat gcttctaaag tctgttttga gatcgaagaa gattataaaa atcgtcagtt    480 tctgggcct gaaggaaatg tggatgttga gttgattgat aagagcacaa acagatacag     540
cgtttggttc cccactgctg gctggtatct gtggtcagcc acaggcctcg gcttcctggt    600
aagggatgag gtcacagtga cgattgcgtt tggttcctgg agtcagcacc tggccctgga    660
cctgcagcac catgaacagt ggctggtggg cggccccttg tttgatgtca ctgcagagcc    720
agaggaggct gtcgccgaaa tccacctccc ccacttcatc tccctccaag gtgaggtgga    780
cgtctcctgg tttctcgttg cccattttaa gaatgaaggg atggtcctgg agcatccagc    840
ccgggtggag ccttctatg ctgtcctgga aagccccagc ttctctctga tgggcatcct     900
gctgcggatc gccagtggga ctcgcctctc catccccatc acttccaaca cattgatcta    960 ttatcaccc cacccgaag atattaagtt ccacttgtac cttgtcccca gcgacgcctt      1020
gctaacaaag gcgatagatg atgaggaaga tcgcttccat ggtgtgcgcc tgcagacttc    1080 gccccaatg gaaccctga ctttggttc cagttatatt gtgtctaatt ctgctaacct       1140
gaaagtaatg cccaaggagt tgaaattgtc ctacaggagc cctggagaaa ttcagcactt    1200
ctcaaaattc tatgctgggc agatgaagga acccattcaa cttgagatta ctgaaaaaag    1260
acatgggact ttggtgtggg atactgaggt gaagccagtg gatctccagc ttgtagctgc    1320 atcagccct cctcctttct caggtgcagc ctttgtgaag gagaaccacc ggcaactcca     1380
agccaggatg ggggacctga aggggtgct cgatgatctc caggacaatg aggttcttac     1440
tgagaatgag aaggagctgg tggagcagga aaagacacgg cagagcaaga atgaggcctt    1500
gctgagcatg gtggagaaga aggggacct ggccctggac gtgctcttca gaagcattag     1560
tgaaagggac ccttacctcg tgtcctatct tagacagcag aatttgtaaa atgagtcagt    1620
taggtagtct ggaagagaga atccagcgtt ctcattggaa atggataaac agaaatgtga    1680
tcattgattt cagtgttcaa gacagaagaa gactgggtaa catctatcac acaggctttc    1740
aggacagact tgtaacctgg catgtaccta ttgactgtat cctcatgcat tttcctcaag    1800
aatgtctgaa gaaggtagta atattccttt taaattttt ccaaccattg cttgatatat     1860
cactatttta tccattgaca tgattcttga gacccagga taaggacat ccggataggt      1920 gtgtttatga aggatgggc ctggaaaggc aacttttcct gattaatgtg aaaaataatt     1980
cctatggaca ctccgtttga agtatcacct tctcataact aaaagcagaa aagctaacaa    2040
aagcttctca gctgaggaca ctcaaggcat acatgatgac agtcttttt tttttgtat      2100 gttaggactt taacacttta tctatggcta ctgttattag aacaatgtaa atgtatttgc    2160
tgaaagagag cacaaaaatg ggagaaaatg caaacatgag cagaaaatat tttcccactg    2220
gtgtgtagcc tgctacaagg agttgttggg ttaaatgttc atggtcaact ccaaggaata    2280
ctgagatgaa atgtggtaaa tcaactccac agaaccacca aaaagaaaat gagggtaatt    2340
cagcttattc tgagacagac attcctggca atgtaccata caaaaaataa gccaactctg    2400
acatttggat tctaccatag actctgtcat tttgtagcca tttcagctgt cttttgatta    2460
atgttttcgt ggcacacata tttccatcct tttatgttta atctgtttaa aacaagttcc    2520
```

```
tagtagacac catctggttg agtcagtttt ttttatggtg tattttgaac ccattctgat    2580
agtctctttt aactggaaga tttcaattac ttacgttaat gtaattatta atatgttagg    2640
atttatcctc agtcagccag tttgttatgt cttttctatt ctactgttat cacatttgta    2700
ccacttaaag tggaatctag gcactttatc accatttaga tcctattacc ttttctcatc    2760
taggatatag ttatcttcta cataatcttt ctgtatctta aaacccatca ataaattatt    2820
atatattttc tacttttaat cactcagaag atttaaaaaa ctcatgagaa gagtaatctg    2880
ttatgttttt ccagatattt accatttctg ttgctcttcc ttcattattt tccaaatttc    2940
gttctgcaaa tttccacttc ttctgataga cgttttttag ttcttttaga gtggttctga    3000
taggtacaga ttctcttatt ttttgcttcc tctgaggaca tcttttttctc accttcattc    3060 tcagtgatgt tttttgcttg tagtatttt agttgacatt gttttctgtt cagcagtttc    3120
cttttagctt ccgtatttcc tgatgagaaa tctgcagtca ttcaaattgt tgtttccctg    3180
tatgtagtgt gtcattttc tgtcagattt caaggtattt atcttttagtt tttagccatt    3240 tcattatgtt ggggatgagt ttccttgttt tattcccttt ggaatttgct ccaattcata    3300
aatttgcagt tttatgtctt ttaccaaact tagaggtttt cagcctaatt tctaaaaata    3360 cttttttatta gcctgatttt catctttata ggaaatagtt taagtgatga caagttccaa    3420
tagcttatat gcccagaagg ccttcaaaat aagaatttttg aaagaataca gaaaacaaac    3480
ttttatatcc ttctcatgtc ttctactgta aaattcatat gctttgctac tctaaaccta    3540
gtttgaaatc aacagtcttg agaatagatg aaaattttga tgaatagtgg aattctttta    3600
aatgaaaacc tcttacatgt gattttcctt gccatctaga aataaaccat agtatttatg    3660
ttgaatcaat caatattata ttttgttttt ttcctcctct tctgagactc ttattgtgga    3720
aatgttagac ttttatgttt tcctaaatgt ccctgatatt ctactattt agaacatctt    3780 ttcattttttt ccattattct gattgggtaa ttttaatttg tctatttttca aatttgctgg    3840 agtgttcacc tgttgttgtc tgtgtcgtcc cactgagtgc attcaccacc ttttaaattt    3900
tggtcactgt atgtatcagt tctaaaattt ccattttgtt ctctatattt taaatttctt    3960
ggcttatatt ctattttcct gcaaatgtgt cagcatttgc ttgtttgagc ttttttttttt    4020 tcaagacagg gtctcaactc tgttacccag gctggagtgc agtggtgcga tctcagctca    4080
ctgcaacctc tgcctcctgg ttcaagcgat tattgtgcct cagcctcctg agtagctggg    4140
attacaggca tgcaccacca cagcccagct aattttttgt atttttagta gagacagagt    4200
tttgctatgt tggccaggct ggttttgaac tcctggcctc aagtgatcca cccacctcag    4260
cctcccaaag tgctgggatt acaggccact acacctggca catttgagta ttttttttttt    4320 ttttttttttt ttgagatgga gtctcgctct gtcatctagg ctggagtgca gtggtgtgat    4380
ctcagctcac tgcagcctct gtctcccggg ctcaagcgat tctcttgcct cagcctcctg    4440
agtagctagg actacaggtg catgccaaca cgcccggcta atttttttaa aaatatttt    4500 tagtagagac agggtttcac cattttggcc aggatggtct cgatctcctg acctcatgat    4560
ccacccgcct cggccttcca aagtgctggg attacaggca tgagccaccg tgcctggcct    4620
catttgagta ttttttataat gtctctttta aagtctttgt cagataattc cactgtacat    4680
gttattcagt gtttggtgtc cactgagttg tcatttgcca gacaagtgga gattttttgca    4740 gctcatcctt gtattctcag tagttccgat atgtaccctc gacatgtgaa tgttatctta    4800
tgagactctg ttttatttgt atccaacaga agatgtttat tatttatttg gctttctgtg    4860
aactgaggtc ttaatatcag ctcatttttaa aagtctttgc agtggtattc ggatctatcc    4920
```

| | |
|---|---:|
| tgtgtgtgcc tatgagattg ggtgcagtgt atcctgttag ctccattctc agggcgtttg | 4980 |
| aatgtgaatt aggaccagcg caatgaatgc tcaagttggg gttgggcgtt agaattcata | 5040 |
| aaagtctttta tatgctcag | 5059 |

<210> SEQ ID NO 36
<211> LENGTH: 1466
<212> TYPE: DNA
<213> ORGANISM: Homo sapiens

<400> SEQUENCE: 36

| | |
|---|---:|
| ctcaggaccc cactgtggcc ttcagcctca tcatcagcca gtttcctaga gaattaggtt | 60 |
| ggttttatgt attgagtaac agcttaacca ataacccact ggtcttcgat tgcattgctc | 120 |
| attgcctttt tgtgtatagg ttctctagac acctccatgg aagaaaacct cattgcttaa | 180 |
| ggtttgtttc aaaaatttct ggattcattg ctagtattgc ataagctcat tcattctccc | 240 |
| ctgagttcga tgaaaaacac ccaaattcct ctaattctca tgttcctctg tgatattgag | 300 |
| acacagcgtc caatagtttt ccaacggaat agcttttctt acctgggaat gtcccccca | 360 |
| gatagttgac actcaggaac agcacggawc aataatggct ctgcctctgt ctcatcatct | 420 |
| tcttggaaaa aatgtgagat gtcacaaagg gtctcagaaa cacagggtag ctccctgtat | 480 |
| accctggaaa acaacaacag aatttttact atgaatataa ggtaggtgcc tgatgatagc | 540 |
| ataggctgtg caggaagatt ttatgttaat agccatagac tcaatatttt atcttaggga | 600 |
| agtcattcct caggcccta cgactccatc tcacctctca gactcccatg actctttctt | 660 |
| acatctcatt atgttaaatt taactggctc tctgtttccc actatatgct gctctttcca | 720 |
| tcctaggaag cagacgtcag tcagttctca acatctagca tttgccacaa acattggttt | 780 |
| cataataggt caacaagtat gttgacctat ataaccttgc taagaatttt agggaaagga | 840 |
| tgagattcct aatttgtagt ctcccttcat ccataattgg tgcccgagag aataggaccc | 900 |
| taaaatgatt gggattgcag ggcattagtg agattgggca tgttttataa gaacccatgg | 960 |
| aacagttatc tcctcttctc ccttctgcct gcaaatggtg agaggggttg cataaagcaa | 1020 |
| caaaaatgct cacagaaaaa gaaaattatg gatattgtac acactttctt ttcccatcaa | 1080 |
| ggatccttat tcagatatgg aacatgagag tcctatgcta gatccttttc tcttcttcat | 1140 |
| ttttgaaggc ttggtgctgt cctcctatgg ctggcaggaa tcaagattga ggttaggagt | 1200 |
| gatggagtgt cctttatgcc aagatattca atggccaata tgacagccac tagccacacc | 1260 |
| tgcctattta catttagttt taaattgtta aatgtgaaaa tcagttcctc ctttgaagta | 1320 |
| gccatatttc aagtgctcaa aagccacacg tggctcttgc ctgccaccat gtaagacatg | 1380 |
| cctttgctcc tcctttgact tctgccatga tggtgaggcc tccccagcca cgtgaaacta | 1440 |
| aaagaattt tctgggtaat ggacat | 1466 |

<210> SEQ ID NO 37
<211> LENGTH: 601
<212> TYPE: DNA
<213> ORGANISM: Homo sapiens

<400> SEQUENCE: 37

| | |
|---|---:|
| gcgccagctg gcttgcccga gaccccggcc caatctacag actgggaaac tgaggctagc | 60 |
| cctgcggcgc tcacctcagc agggcaggca ggaggcgccg gcagcctctg gccctcctcc | 120 |
| agcagttcca agaggcggca gagggcgggg acatcccgct cacatcccat catccgcagg | 180 |

-continued

```
aactcctgga gccaaggagg agcgcatgtg gtgggggagg agcctccgtg ggtggagggg      240
gaggggccac ccgtggtggg ggtaggggcc atctgtgatg gagcggggag gggctgcctg      300
maccgtgaag gggtcagaaa ggtgaggaag cgtcctcccc actggggcct atgatgctgg      360
gaccaggtga ccccatgcta aagagggacg caggcgcaga caggttggag attggccacg      420
aggggcgtgg agggagaaga aggctggggg ctctgggaag ccgactcacg gccgaggggc      480
tgcagctttt gtcgcagtag gtgaagagct cgtacaggac gacccccgaag ctccagacgt     540 ctgactggcg agagaagatg ttgtccgaga gggattcggg ggcatacctg gagaggggac      600
a                                                                      601

<210> SEQ ID NO 38
<211> LENGTH: 511
<212> TYPE: DNA
<213> ORGANISM: Homo sapiens

<400> SEQUENCE: 38
gcccggctat tttttttgta ttttcagtag cgacggggtt tcacggtgtt agccaggatg       60
gtgttgatct cctgacctcg tgatccacct gcctcggcct cccaaaatgc tgggattaca      120
ggcgtgagcc acggcgcctg gcccatggct gattttataa atgggggggag ggtgtcacct    180 ggcaaggatc ccagggctac agaggtacct gaatttgagc ccaggtctct ctgtcttctt     240
ctatctctga ctcctyccca ttccctctca ccttccccca cagtctggac tttgccatca     300
acaagctcaa gactgggggc tcacgtcctg gctcctatgt tctccgccgc agcccccagg    360
actttgacag cttcctcctc actgtctgtg tccaggtcgg tctactgcta gggtgggtag     420
tggagggctg cctggaggag gtgacgtttg aattgagatt taaaagatca gtcagcattt     480
ggttcctgaa gaataggagg gaaaagacac c                                    511
```